(12) United States Patent
Ruiz-Opazo et al.

(10) Patent No.: US 11,236,169 B2
(45) Date of Patent: Feb. 1, 2022

(54) ANTI-DESPR MONOCLONAL ANTIBODY TARGETED THERAPY AND IMAGING FOR CANCER AND STROKE

(71) Applicant: TRUSTEES OF BOSTON UNIVERSITY, Boston, MA (US)

(72) Inventors: Nelson Ruiz-Opazo, Westwood, MA (US); Victoria L. M. Herrera, Westwood, MA (US); Francis Joseph Carr, Balmedie (GB)

(73) Assignee: TRUSTEES OF BOSTON UNIVERSITY, Boston, MA (US)

( * ) Notice: Subject to any disclaimer, the term of this patent is extended or adjusted under 35 U.S.C. 154(b) by 0 days.

(21) Appl. No.: 16/263,202

(22) Filed: Jan. 31, 2019

(65) Prior Publication Data

US 2019/0153106 A1    May 23, 2019

Related U.S. Application Data

(62) Division of application No. 15/245,853, filed on Aug. 24, 2016, now Pat. No. 10,202,457.

(60) Provisional application No. 62/208,937, filed on Aug. 24, 2015.

(51) Int. Cl.
    *C07K 16/28*     (2006.01)
    *A61P 35/00*     (2006.01)
    *A61K 39/00*     (2006.01)

(52) U.S. Cl.
    CPC .......... *C07K 16/2863* (2013.01); *A61P 35/00* (2018.01); *A61K 2039/505* (2013.01); *C07K 2317/21* (2013.01); *C07K 2317/24* (2013.01); *C07K 2317/34* (2013.01); *C07K 2317/52* (2013.01); *C07K 2317/53* (2013.01); *C07K 2317/56* (2013.01); *C07K 2317/76* (2013.01); *C07K 2317/92* (2013.01)

(58) Field of Classification Search
    CPC .......... A61K 2039/505; C07K 16/2863; C07K 2317/76; C07K 2317/24; C07K 2317/34; C07K 2317/21; C07K 2317/52; C07K 2317/53; C07K 2317/56; C07K 2317/92
    See application file for complete search history.

(56) References Cited

U.S. PATENT DOCUMENTS

| | | | |
|---|---|---|---|
| 4,867,973 | A | 9/1989 | Goers |
| 5,969,098 | A | 10/1999 | Brittain |
| 7,504,490 | B1 | 3/2009 | Weinstock |
| 8,956,609 | B2 | 2/2015 | Herrera et al. |
| 2009/0028852 | A1 | 1/2009 | Herrera |
| 2009/0215680 | A1 | 8/2009 | Caboche et al. |
| 2009/0317836 | A1 | 12/2009 | Kuhn |
| 2011/0313229 | A1 | 12/2011 | Sugaya |
| 2013/0022551 | A1 | 1/2013 | Ruiz-Opazo |
| 2013/0177500 | A1 | 7/2013 | Ruiz-Opaz |
| 2014/0186344 | A1 | 7/2014 | Herrera |
| 2016/0108124 | A1 | 4/2016 | Ruiz-Opazo et al. |
| 2017/0058036 | A1 | 3/2017 | Ruiz-Opazo et al. |
| 2017/0253657 | A1 | 3/2017 | Constantin |

FOREIGN PATENT DOCUMENTS

| | | | |
|---|---|---|---|
| WO | 2003002144 A1 | 1/2003 | |
| WO | 2006055665 A2 | 5/2006 | |
| WO | 2007102354 A2 | 9/2007 | |
| WO | 2010114801 A1 | 10/2010 | |
| WO | 2012012750 A1 | 1/2012 | |
| WO | WO-2012012750 A1 * | 1/2012 | .............. A61P 27/06 |
| WO | 2013112467 A1 | 8/2013 | |
| WO | 2016127255 A1 | 8/2016 | |

OTHER PUBLICATIONS

MacCallum et al. Antibody-antigen Interactions: Contact Analysis and Binding Site Topography. Journal of Molecular Biology, 262: 732-745, 1996 (Year: 1996).*
Casset et al. A peptide mimetic of an anti-CD4 monoclonal antibody by rational design. Biochemical and Biophysical Research Communications, 307:198-205, 2003 (Year: 2003).*
Vajdos et al. Comprehensive Functional Maps of the Antigen binding Site of an Anti-ErbB2 Antibody Obtained with Shotgun Scanning Mutagenesis. Journal of Molecular Biology, Jul. 5, 2002;320(2):415-28 (Year: 2002).*
Paul. Fundamental Immunology, 3rd Edition, Raven Press, New York, Chapters, pp. 292-295, 1993 (Year: 1993).*
MacCallum et al. Journal of Molecular Biology, 262:732-745, 1996 (Year: 1996).*
Casset et al. Biochemical and Biophysical Research Communications, 307:198-205, 2003 (Year: 2003).*
Vajdos et al. Journal of Molecular Biology, Jul. 5, 2002;320(2):415-28 (Year: 2002).*
Sela-Culang et al. 2013 The structural basis of antibody-antigen recognition; Frontiers in Immunology 4(302):1-13 (Year: 2013).*
Ferrara et al. mABs, 2015; 7(1): 32-41 (Year: 2015).*
Goel et al. J Immunol 2004; 173:7358-7367 (Year: 2004).*

(Continued)

*Primary Examiner* — Vanessa L. Ford
*Assistant Examiner* — Sandra E Dillahunt
(74) *Attorney, Agent, or Firm* — Nixon Peabody LLP; Ronald I. Eisenstein; Nicole D. Kling

(57) ABSTRACT

Provided herein are novel compositions comprising anti-DEspR antibodies and fragments thereof derived from 6G8G7 and 7C5B2 anti-DEspR variant antibodies, including fully human, composite engineered human, humanized, monoclonal, and polyclonal anti-DEspR antibodies and fragments thereof, and methods of their use in a variety of therapeutic applications. The compositions comprising the anti-DEspR antibodies and fragments thereof described herein are useful in diagnostic and imaging methods, such as DEspR-targeted molecular imaging of angiogenesis, and for companion diagnostic and/or in vivo non-invasive imaging and/or assessments.

9 Claims, 54 Drawing Sheets
(39 of 54 Drawing Sheet(s) Filed in Color)
Specification includes a Sequence Listing.

(56) References Cited

OTHER PUBLICATIONS

Lescar et al. JBC 1995; 270(30):18067-18076 (Year: 1995).*
Lloyd et al. Protein Engineering, Design & Selection, 2009; 22(3):159-168 (Year: 2009).*
Edwards et al. Journal of Molecular Biology, 2003; 334:103-118 (Year: 2003).*
Abdollahi et al., "Evading tumor evasion: current concepts and perspectives of anti-angiogenic cancer therapy", Drug Resist Updat 13(1-2) 16-28 (2010).
Bergers et al., "Modes of resistance to anti-angiogenic therapy", Nat Rev Cancer 8(8) 592-603 (2008).
Brown et al., "Tolerance of single, but not multiple, amino acid replacements in antibody VH CDR 2: a means of minimizing B cell wastage from somatic hypermutation?", J Immunol 156(9) 3285-3291 (1996).
Carmeliet et al., "Abnormal blood vessel development and lethality in embryos lacking a single VEGF allele", Nature 380(6573) 435-439 (1996).
Carmeliet et al., "Angiogenesis in life, disease and medicine", Nature 438(7070) 932-936 (2005).
Casset et al., "A peptide mimetic of an anti-CD4 monoclonal antibody by rational design", Biochem Biophys Res Commun 307(1) 198-205 (2003).
Clouthier et al., "Cranial and cardiac neural crest defects in endothelin-A receptor-deficient mice", Development 125(5)813-824(1998).
Colman et al., "Effects of amino acid sequence changes on antibody-antigen interactions", Res Immunol 145(1) 33-36 (1994).
Cools-Lartigue et al., "Neutrophil extracellular traps in cancer progression." Cellular and Molecular Life Sciences 71(21):4179-4194 (2014).
Drawford et al., "Chapter 6. Mouse models to investigate anti-cancer effects of VEGF inhibitors", Methods Enzymol 445: 125-139 (2008).
Decano et al., "Dual enothelin-1/VEGFsp receptor (DEspR) roles in adult angiogenesis in despr+/- knockout micr and carotid artery disease rat model", Manuscript submitted to Circulation. (2010).
Decano et al., "Early-life sodium exposure unmasks susceptibility to stroke in hyperlipidemic, hypertensive heterozygous Tg25 rats transgenic for human cholesteryl ester transfer protein", Circulation 119(11) 1501-1509 (2009).
Decano et al., "Molecular imaging of vasa vasorum neovascularization via DEspR-targeted contrast-enhanced ultrasound microimaging in transgenic atherosclerosis rat model", Mol Imaging Biol 13(6) 1096-1106 (2011).
Ebos et al., "Accelerated metastasis after short-term treatment with a potent inhibitor of tumor angiogenesis", Cancer Cell 15(3) 232-239 (2009).
Edwards et al., "Regulation of neutrophil apoptosis by Mcl-1." Biochemical Society Transactions 32:489-492 (2004).
El Kebir et al., "Modulation of neutrophil apoptosis and the resolution of inflammation through β2 integrins." Frontiers in Immunology 4(6) (2013).
El Kebir et al., "Targeting neutrophil apoptosis for enhancing the resolution of inflammation." Cells 2(2):330-348 (2013).
Fadini et al.,"A perspective on NETosis in diabetes and cardiometabolic disorders." Nutrition, Metabolism and Cardiovascular Diseases 26(1):1-8 (2016).
Ferrara et al., "Heterozygous embryonic lethality induced by targeted inactivation of the VEGF gene", Nature 380 (6573)439-442 (1996).
Ferrara et al., "Pathways mediating VEGF-independent tumor angiogenesis", Cytokine Growth Factor Rev 21(1) 21-26 (2010).
Gamicia et al., "Neutrophil extracellular traps in sepsis." Shock 42(4):286-294 (2014).
Gattinoni et al., "Ventilator-induced lung injury: the anatomical and physiological framework." Critical Care Medicine 38(10):S539-S548 (2010).

GenBank, dual endothelial-1 (VEGRsp)/angiotension II receptor [*Homo sapiens*], NCBI Locus ABP04239, AC ABP04236 GI: 144954326 (2008).
Gloriosso et al., "Association of ATP1A1 and dear single-nucleotide polymorphism haplotypes with essential hypertension: sex-specific and haplotype-specific effects", Circ Res 100(10) 1522-1529 (2007).
Hanahan et al., "Hallmarks of cancer: the next generation", Cell 144(5) 646-674 (2011).
Herrera et al., "Analysis of gender-specific atherosclerosis susceptibility in transgenic[hCETP]25DS rat model", Atherosclerosis 17791) 9-18 (2004).
Herrera et al., "Confirmation of translatability and functionality certifies the dual endothelinl/VEGFsp receptor (DEspR) protein." BMC Molecular Biology 17(1):15 (2016).
Herrera et al., "DEspR roles in tumor vasculo-angiogenesis, invasiveness, CSC-survival and anoikis resistance: a common receptor coordinator'paradigm " PloS One 9(1):e85821 (2014).
Herrera et al., "Embryonic lethality in Dear gene-deficient mice: new player in angiogenesis", Physiol Genomics 23 (3) 257-268 (2005).
Herrera et al., "Sex-specific hippocampus-dependent cognitive deficits and increased neuronal autophagy in DEspR haploinsufficiency in mice", Physiol Genomics 35(3) 316-329 (2008).
Lin et al., "Origins of circulating endothelial cells and endothelial outgrowth from blood", J Clin Invest 105(1) 71-77 (2000).
Loges et al., "Mechanisms of resistance to anti-angiogenic therapy and development of third-generation anti-angiogenic drug candidates", Genes Cancer 1(1) 12-25 (2010).
MacCallum et al., "Antibody-antigen interactions: contact analysis and binding site topography", J Mol Biol 262(5) 732-745 (1996).
Michaud et al., "Mechanisms of ventilator-induced lung injury: the clinician's perspective." Critical Care 7(3):209-2010 (2003).
Paez-Ribes et al., "Antiangiogenic therapy elicits malignant progression of tumors to increased local invasion and distant metastasis", Cancer Cell 15(3) 220-231 (2009).
Paul, "Fundamental Immunology", Third Edition, Raven Press, New York, Chapter 8, 292-295 (1993).
Rudikoff et al., "Single amino acid substitution altering antigen-binding specificity", Proc Natl Acad Sci USA 79(6) 1979-1983 (1982).
Ruiz-Opazo et al., "Molecular characterization of a dual endothelin-1/Angiotensin II receptor", Mol Med 4(2) 96-108 (1998).
Swami et al., "Multipotent tumour endothelial cells", Nature Reviews Cancer 8(11) 2008.
Thalin et al., "NETosis promotes cancer-associated arterial microthrombosis presenting as ischemic stroke with troponin elevation." Thrombosis Research 139:56-64 (2016).
UniProt Submission B0L3A2_Human [Retrieved from Internet Feb. 7, 2017; <http://www.uniprot.org/uniprot/B0L3A2.txt?version=11>] (2008).
Vajdos et al., "Comprehensive functional maps of the antigen-binding site of an anti-ErbB2 antibody obtained with shotgun scanning mutagenesis", J Mol Biol 320(2) 415-428 (2002).
Wong et al., "Diabetes primes neutrophils to undergo NETosis, which impairs wound healing." Nature Medicine 21 (7):815-819 (2015).
Yang et al., "Identification of local and circulating cancer stem cells in human liver cancer", Hepatolofy 47(3) 919-928 (2008).
Fridlender et al. "Transcriptomic Analysis Comparing Tumor-Associated Neutrophils with Granulocytic Myeloid-Derived Suppressor Cells and Normal Neutrophils." PLoS One 7(2): e31524 (2012).
Narasaraju et al., "Neutrophils as Possible Therapeutic Targets in Severe Influenza Pneumonia." Journal of Infectious Pulmonary Diseases 2(2):1-3 (2016).
Templeton et al. "Prognostic Role of Neutrophil-to-Lymphocyte Ratio in Solid Tumors: A Systematic Review and Meta-Analysis." JNCI: Journal of the National Cancer Institute 106(6): 1-11 (2014).
McCarthy. "Antiangiogenesis drug promising for metastatic colorectal cancer." The Lancet 361(9373): 1959 (2003).

(56) References Cited

OTHER PUBLICATIONS

Edwards et al. "The remarkable flexibility of the human antibody repertoire; isolation of over one thousand different antibodies to a single protein, BLyS." Journal of molecular biology 334(1): 103-118 (2003).
Ferrara et al. "Recombinant renewable polyclonal antibodies." MAbs. 7(1): 32-41 (2015).
Goel et al. "Plasticity within the antigen-combining site may manifest as molecular mimicry in the humoral immune response." The Journal of Immunology 173(12): 7358-7367 (2004).
Lescar et al. "Crystal structure of a cross-reaction complex between Fab F9. 13.7 and guinea fowl lysozyme." Journal of Biological Chemistry 270(30): 18067-18076 (1995).
Lloyd et al. "Modelling the human immune response: performance of a 1011 human antibody repertoire against a broad panel of therapeutically relevant antigens" Protein Engineering, Design & Selection 22(3): 159-168 (2009).
Yipp et al. "NETosis: how vital is it?." Blood 122(16): 2784-2794 (2013).

* cited by examiner

1C. H&E section show hemorrhagic infarct

1B. H&E section confirm hemorrhages 1A. brain surface showing hemorrhages.

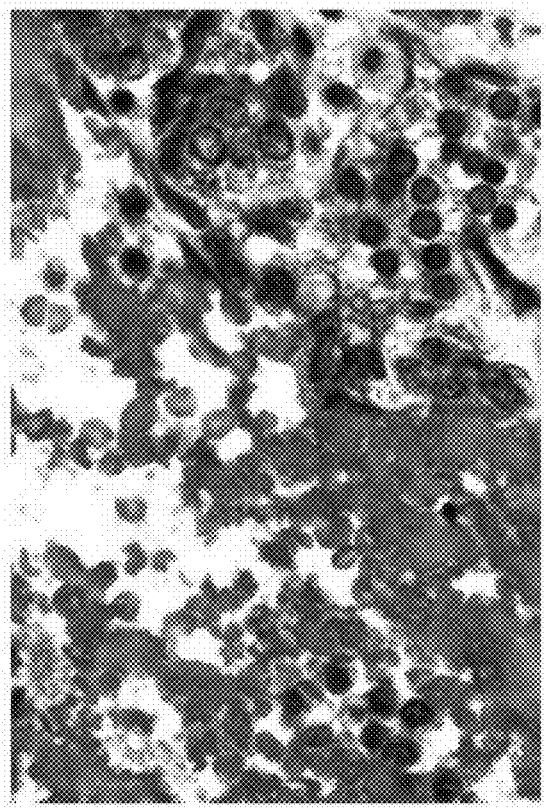
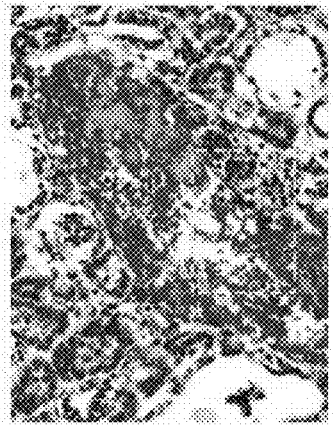
FIG. 6A
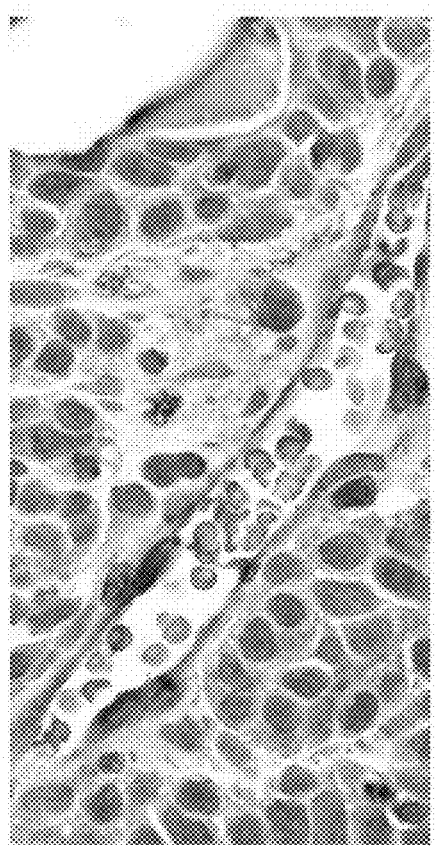
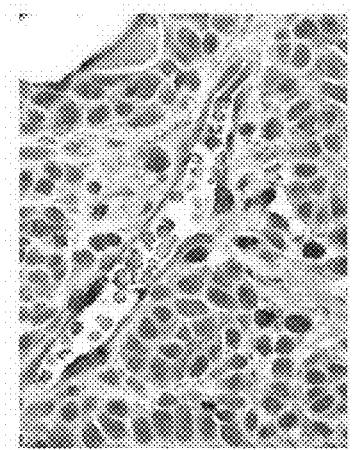
FIG. 6B

FIG. 8B Western blot analysis of pulldown products from U87 cells was first probed with 6g8g7, then stripped, re-exposed to confirm no residual signal, then probed with 5g12e8 mAb.

FIG. 23
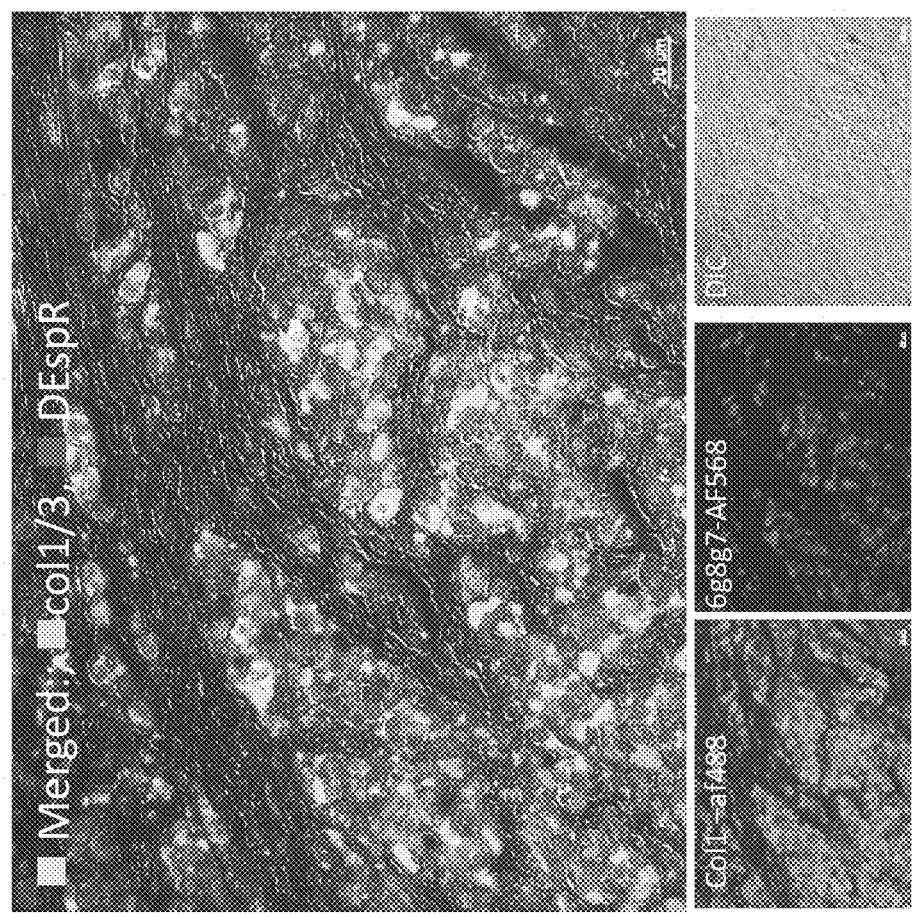
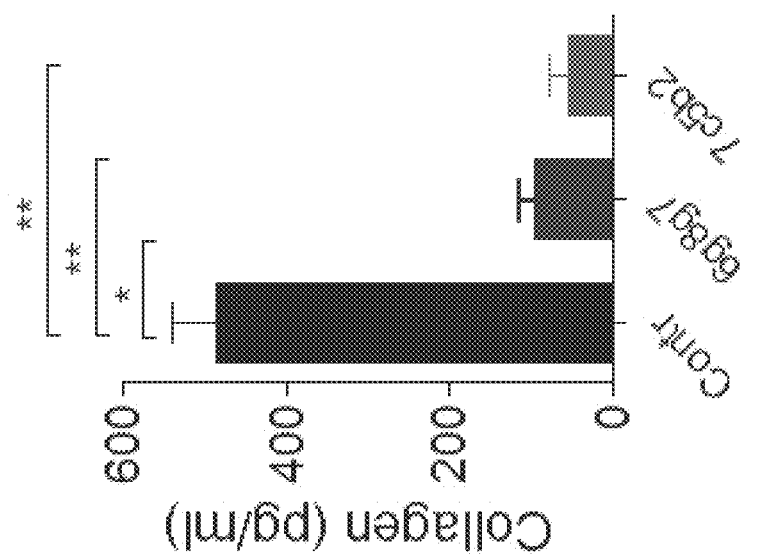

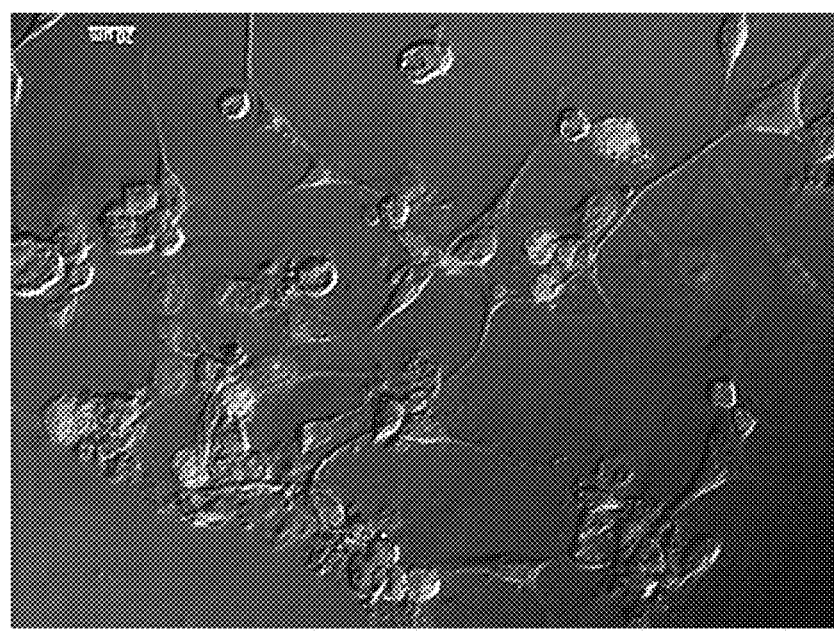
FIG. 25
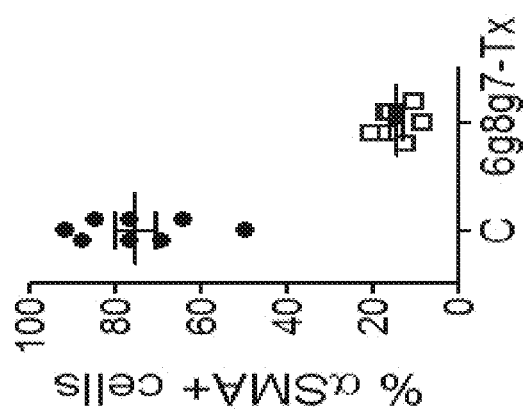
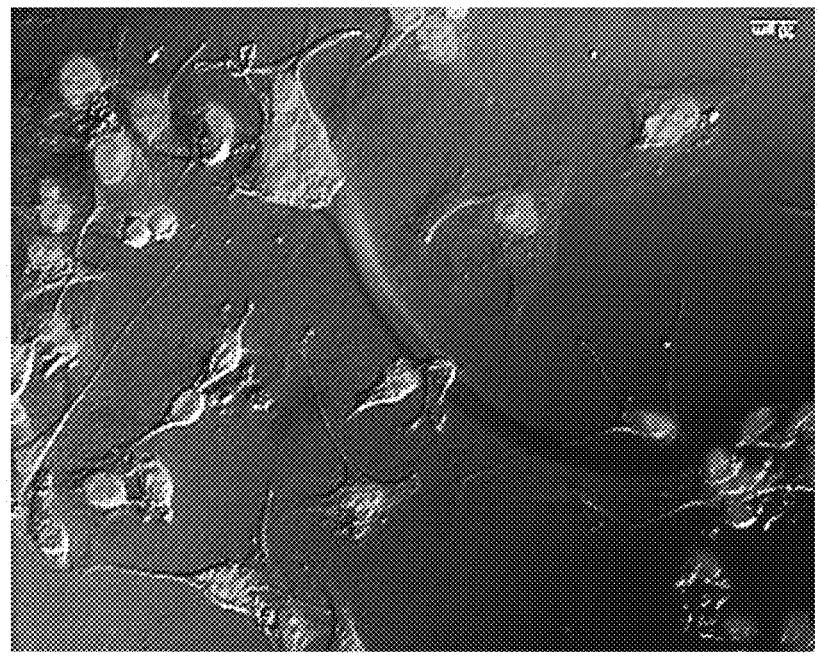

ARMS assay specific for spliced DEspR-RNA 270-bp amplicon (red arrow) spanning the spliced exon-to-exon junction confirms presence of spliced DEspR-RNA in Panc1 (lane 1) and U87 (lane 2) CSCs.

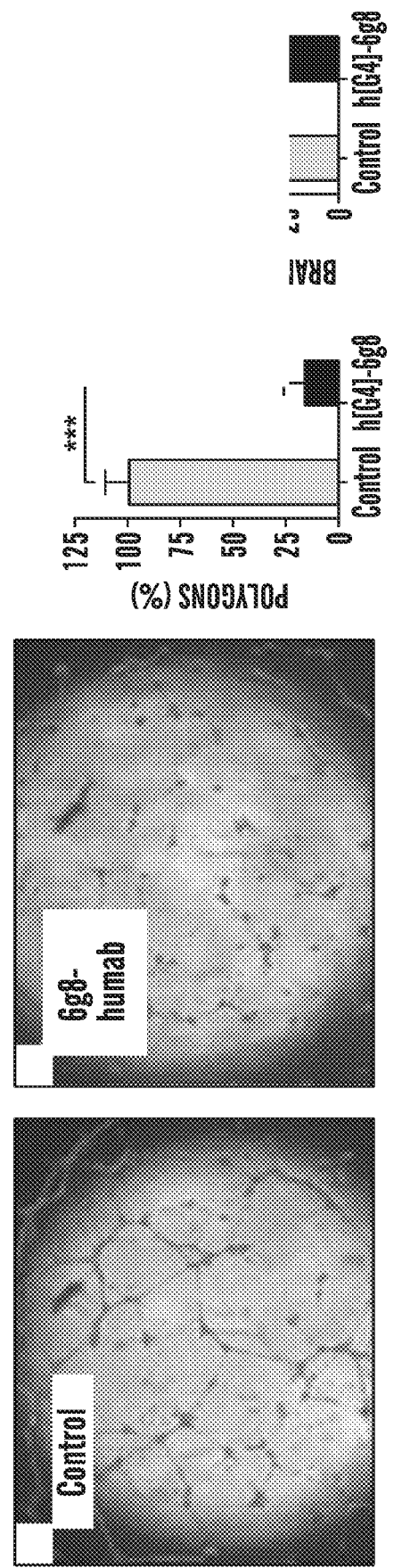

41A

41B

43A

43B

44B

Single dose target-bioeffects on myeloperoxidase (MPO): a human stroke biomarker released by activated neutrophils

44A

Single dose attains plasma levels > EC50 for inhibition of activated neutrophils: similar profile for 6g8 and 10a3 mumabs

45B

45A

Live cell imaging of Panc1 tumor cells

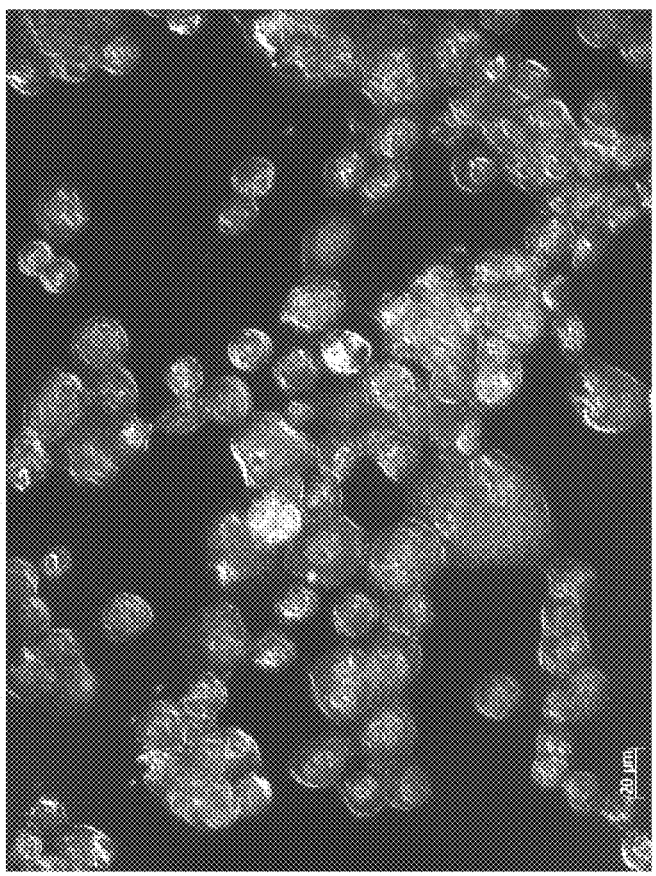
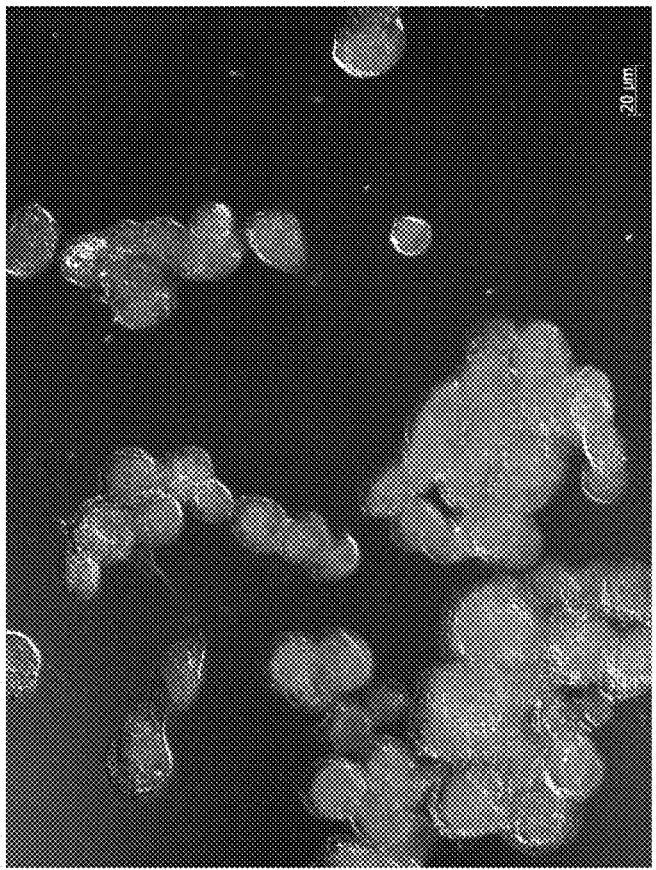
FIG. 50

SEQUENCE LISTING

```
<160> NUMBER OF SEQ ID NOS: 71

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Ser Asn Glu Met Lys Ser Arg Trp Asn Trp Gly Ser
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Glu Met Lys Ser Arg Trp Asn Trp Gly Ser
1               5                   10

<210> SEQ ID NO 3
<211> LENGTH: 85
<212> TYPE: PRT
<213> ORGANISM: Homo sapiens

<400> SEQUENCE: 3

Met Thr Met Phe Lys Gly Ser Asn Glu Met Lys Ser Arg Trp Asn Trp
1               5                   10                  15

Gly Ser Ile Thr Cys Ile Ile Cys Phe Thr Cys Val Gly Ser Gln Leu
            20                  25                  30

Ser Met Ser Ser Ser Lys Ala Ser Asn Phe Ser Gly Pro Leu Gln Leu
        35                  40                  45

Tyr Gln Arg Glu Leu Glu Ile Phe Ile Val Leu Thr Asp Val Pro Asn
    50                  55                  60
```

```
Tyr Arg Leu Ile Lys Glu Asn Ser His Leu His Thr Thr Ile Val Asp
 65                  70                  75                  80

Gln Gly Arg Thr Val
                85
```

<210> SEQ ID NO 4
<211> LENGTH: 26
<212> TYPE: PRT
<213> ORGANISM: Homo sapiens

<400> SEQUENCE: 4

```
Met Asn Phe Leu Leu Ser Trp Val His Trp Ser Leu Ala Leu Leu Leu
 1               5                  10                  15

Tyr Leu His His Ala Lys Trp Ser Gln Ala
                20                  25
```

<210> SEQ ID NO 5
<211> LENGTH: 408
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

```
ggatcccaag tgcagctgca ggagtcagga cctggcctgg tggcgccctc acagagcctg      60
tccatcacat gcaccgtctc agggttctca ttaaccggct atggtgtaaa ctgggttcgc     120
cagcctccag aaagggtct ggaatggctg gaatgatttt gggatgatgg aagcacagac      180
tataattcag ctctcaaatc cagactgatc atcaccaagg acaactccag gagccaagtt    240
ttcttaaaaa tgaacagtct gcaaactgat gacacagcca ggtactactg tgccagagac    300
ccagtatagg tccatttcta tgctatggac tactggggtc aaggaacctc agtcaccgtc    360
tcctcagcca aaacgacacc cccatctgtc tatggtggcg gtggttct               408
```

<210> SEQ ID NO 6
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

```
Gly Ser Gln Val Gln Leu Gln Glu Ser Gly Pro Gly Leu Val Ala Pro
 1               5                  10                  15

Ser Gln Ser Leu Ser Ile Thr Cys Thr Val Ser Gly Phe Ser Leu Thr
                20                  25                  30

Gly Tyr Gly Val Asn Trp Val Arg Gln Pro Pro Gly Lys Gly Leu Glu
            35                  40                  45

Trp Leu Gly Met Ile Trp Asp Asp Gly Ser Thr Asp Tyr Asn Ser Ala
    50                  55                  60

Leu Lys Ser Arg Leu Ile Ile Thr Lys Asp Asn Ser Arg Ser Gln Val
 65                  70                  75                  80

Phe Leu Lys Met Asn Ser Leu Gln Thr Asp Asp Thr Ala Arg Tyr Tyr
                85                  90                  95

Cys Ala Arg Asp Pro Val Val His Phe Tyr Ala Met Asp Tyr Trp Gly
            100                 105                 110
```

Gln Gly Thr Ser Val Thr Val Ser Ser Ala Lys Thr Thr Pro Pro Ser
            115                 120                 125
Val Tyr Gly Gly Gly Ser
        130                 135

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Tyr Gly Val Asn
1               5

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Met Ile Trp Asp Asp Gly Ser Thr Asp Tyr Asn Ser Ala Leu Lys Ser
1               5                   10                  15

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asp Pro Val Val His Phe Tyr Ala Met Asp Tyr
1               5                   10

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Phe Ser Leu Thr Gly Tyr Gly
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ile Trp Asp Asp Gly Ser Thr
1               5

<210> SEQ ID NO 12
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12

```
ggatccgaag ttcagctgca ggagtctgga ggtggcctgg tgcagcctgg aggatccctg      60
aaactctcct gtgcagcctc aggattcgat tttagtagat actggatgag ttgggtccgg     120
caggctccag ggaaaggact agaatggatt ggagaaatta atccagatag cagtacgata     180
aactatacgc catctctaaa ggataaattc atcatttcta gagacaccgc caaaaaaact     240
ctgtacctgc aaatgagcaa agtgagatca gaggacacag ccctttatta ctgtgcaaga     300
catggtagag gtatggacta ctggagtcaa ggaacctcag tcaccgtctc ctcagccaaa     360
acgacacccc catctgtcta tggtggcggt ggttct                                396
```

<210> SEQ ID NO 13
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gly Ser Glu Val Gln Leu Gln Glu Ser Gly Gly Gly Leu Val Gln Pro
1               5                   10                  15

Gly Gly Ser Leu Lys Leu Ser Cys Ala Ala Ser Gly Phe Asp Phe Ser
            20                  25                  30

Arg Tyr Trp Met Ser Trp Val Arg Gln Ala Pro Gly Lys Gly Leu Glu
        35                  40                  45

Trp Ile Gly Glu Ile Asn Pro Asp Ser Ser Thr Ile Asn Tyr Thr Pro
    50                  55                  60

Ser Leu Lys Asp Lys Phe Ile Ile Ser Arg Asp Thr Ala Lys Lys Thr
65                  70                  75                  80

Leu Tyr Leu Gln Met Ser Lys Val Arg Ser Glu Asp Thr Ala Leu Tyr
                85                  90                  95

Tyr Cys Ala Arg His Gly Arg Gly Met Asp Tyr Trp Ser Gln Gly Thr
            100                 105                 110

Ser Val Thr Val Ser Ser Ala Lys Thr Thr Pro Pro Ser Val Tyr Gly
        115                 120                 125

Gly Gly Gly Ser
    130

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Tyr Trp Met Ser
1               5

```
<210> SEQ ID NO 15
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Glu Ile Asn Pro Asp Ser Ser Thr Ile Asn Tyr Thr Pro Ser Leu Lys
1               5                   10                  15
Asp

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

His Gly Arg Gly Met Asp Tyr
1               5

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Phe Asp Phe Ser Arg Tyr Trp
1               5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ile Asn Pro Asp Ser Ser Thr Ile
1               5

<210> SEQ ID NO 19
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
caggtgcagc tgaaggagtc aggacctggc ctggtggcgc cctcacagag cctgtccatc      60
acatgcactg tctcaggatt ctcattaaaa agttatgctg taagctgggt tcgccagcct     120
ccaggaaagg gtctggagtg gctgggagta atctggggtg acgggagcac agattatcat     180
tcagctctca tatccagact gagcatcagt aaggataact ccaagagcca attttcttca     240
agactgaaca gtctgcaaac tgatgacaca gccacgtatt actgtgccag aggaactggg     300
acggggtttg cttactgggg ccaggggact ctggtcactg tctctgca                  348
```

```
<210> SEQ ID NO 20
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Lys Ser Tyr
            20                  25                  30

Ala Val Ser Trp Val Arg Gln Pro Pro Gly Lys Gly Leu Glu Trp Leu
        35                  40                  45

Gly Val Ile Trp Gly Asp Gly Ser Thr Asp Tyr His Ser Ala Leu Ile
    50                  55                  60

Ser Arg Leu Ser Ile Ser Lys Asp Asn Ser Lys Ser Gln Phe Phe Leu
65                  70                  75                  80

Arg Leu Asn Ser Leu Gln Thr Asp Asp Thr Ala Thr Tyr Tyr Cys Ala
                85                  90                  95

Arg Gly Thr Gly Thr Gly Phe Ala Tyr Trp Gly Gln Gly Thr Leu Val
            100                 105                 110

Thr Val Ser Ala
        115

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ser Tyr Ala Val Ser
1               5

<210> SEQ ID NO 22
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Val Ile Trp Gly Asp Gly Ser Thr Asp Tyr His Ser Ala Leu Ile Ser
1               5                   10                  15

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Thr Gly Thr Gly Phe Ala Tyr
1               5
```

```
<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Phe Ser Leu Lys Ser Tyr Ala
1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ile Trp Gly Asp Gly Ser Thr Asp
1               5

<210> SEQ ID NO 26
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
ggtggcggtg gttctgatat tgtgctcaca caaactaacc aaatcatgtc cgcatcagta      60
ggagaccggg tcagtgtcac ctgcaaggcc agtcagaatg tggatagtaa tgtggcctgg     120
tatcaacaga aacctggaca ttctcccaaa gcactaattt attcggcatc ctaccggtac     180
agtagagtcc ctgatcgcat cacaggcagt ggatctggga cagatttcac tctcaccatc     240
accaatgtgc agtctaaaga cttggcagac tatttctgtc agcaatatca cagctatcct     300
cttctcgcgt tcggtgctgg gaccaagctg gagctgaaac gggctgatgc tgcaccaact     360
gtatccctcg ag                                                         372

<210> SEQ ID NO 27
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gly Gly Gly Gly Ser Asp Ile Val Leu Thr Gln Thr Asn Gln Ile Met
1               5                   10                  15

Ser Ala Ser Val Gly Asp Arg Val Ser Val Thr Cys Lys Ala Ser Gln
                20                  25                  30

Asn Val Asp Ser Asn Val Ala Trp Tyr Gln Gln Lys Pro Gly His Ser
            35                  40                  45

Pro Lys Ala Leu Ile Tyr Ser Ala Ser Tyr Arg Tyr Ser Arg Val Pro
        50                  55                  60

Asp Arg Ile Thr Gly Ser Gly Ser Gly Thr Asp Phe Thr Leu Thr Ile
65                  70                  75                  80
```

Thr Asn Val Gln Ser Lys Asp Leu Ala Asp Tyr Phe Cys Gln Gln Tyr
            85                  90                  95

His Ser Tyr Pro Leu Leu Ala Phe Gly Ala Gly Thr Lys Leu Glu Leu
            100                 105                 110

Lys Arg Ala Asp Ala Ala Pro Thr Val Ser Leu Glu
        115                 120

<210> SEQ ID NO 28
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Lys Ala Ser Gln Asn Val Asp Ser Asn Val Ala
1               5                   10

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ser Ala Ser Tyr Arg Tyr Ser
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gln Gln Tyr His Ser Tyr Pro
1               5

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gln Asn Val Asp Ser Asn
1               5

<210> SEQ ID NO 32
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ser Ala Ser
1

```
<210> SEQ ID NO 33
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
ggtggcggtg gttctgacat tgtgatcaca cagtctaacg caatcatgtc tgcatctcca     60
ggggagaagg tcaccataac ctgcagtgcc agctcaagtg taagtttcat gcactggttc    120
cagcagaagc caggcacttc tcccaaactc tggatttata gcacatccaa cctggcttct    180
ggagtccctg ctcgcttcag tggcagtgga tctgggacct cttactctct cacaatcagc    240
cgaatggagg ctgaagatgc tgccacttat tactgccagc aaaggagtag ttacccactc    300
acgttcggtg ctgggaccaa gctggagctg aaacgggctg atgctgcacc aactgtatcc    360
ctcgag                                                               366

<210> SEQ ID NO 34
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Gly Gly Gly Gly Ser Asp Ile Val Ile Thr Gln Ser Asn Ala Ile Met
1               5                   10                  15

Ser Ala Ser Pro Gly Glu Lys Val Thr Ile Thr Cys Ser Ala Ser Ser
            20                  25                  30

Ser Val Ser Phe Met His Trp Phe Gln Gln Lys Pro Gly Thr Ser Pro
        35                  40                  45

Lys Leu Trp Ile Tyr Ser Thr Ser Asn Leu Ala Ser Gly Val Pro Ala
    50                  55                  60

Arg Phe Ser Gly Ser Gly Ser Gly Thr Ser Tyr Ser Leu Thr Ile Ser
65                  70                  75                  80

Arg Met Glu Ala Glu Asp Ala Ala Thr Tyr Tyr Cys Gln Gln Arg Ser
                85                  90                  95

Ser Tyr Pro Leu Thr Phe Gly Ala Gly Thr Lys Leu Glu Leu Lys Arg
            100                 105                 110

Ala Asp Ala Ala Pro Thr Val Ser Leu Glu
        115                 120

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ser Ala Ser Ser Ser Val Ser Phe Met His
1               5                   10

<210> SEQ ID NO 36
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 36

Ser Thr Ser Asn Leu Ala Ser
1               5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gln Gln Arg Ser Ser Tyr Pro
1               5

<210> SEQ ID NO 38
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ser Ser Val Ser Phe
1               5

<210> SEQ ID NO 39
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ser Thr Ser
1

<210> SEQ ID NO 40
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
ggtggcggtg gttctgatat tgtgctcaca cagactcaca aattcctgct tgtatcagca      60
ggagacagga ttaccataac ctgcaaggcc agtcagagtg tgagtaatga tgtagcttgg     120
taccaacaga agccagggca gtctcctaaa ctgctgatat actatgcatc caatcgctac     180
actggagtcc ctgatcgctt cactggcagt ggatatggga cggatttcac tttcaccatc     240
agcactgtgc aggctgatga cctggcagtt tatttctgtc aacaggatta tagctccccg     300
ttcacgttcg gagggggggac caagctggaa ataaaacggg ctgatgctgc accaactgta     360
tccctcgag                                                              369
```

```
<210> SEQ ID NO 41
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gly Gly Gly Ser Asp Ile Val Leu Thr Gln Thr His Lys Phe Leu Leu
1               5                   10                  15

Val Ser Ala Gly Asp Arg Ile Thr Ile Thr Cys Lys Ala Ser Gln Ser
            20                  25                  30

Val Ser Asn Asp Val Ala Trp Tyr Gln Gln Lys Pro Gly Gln Ser Pro
        35                  40                  45

Lys Leu Leu Ile Tyr Tyr Ala Ser Asn Arg Tyr Thr Gly Val Pro Asp
    50                  55                  60

Arg Phe Thr Gly Ser Gly Tyr Gly Thr Asp Phe Thr Phe Thr Ile Ser
65                  70                  75                  80

Thr Val Gln Ala Asp Asp Leu Ala Val Tyr Phe Cys Gln Gln Asp Tyr
                85                  90                  95

Ser Ser Pro Phe Thr Phe Gly Gly Gly Thr Lys Leu Glu Ile Lys Arg
            100                 105                 110

Ala Asp Ala Ala Pro Thr Val Ser Leu Glu
        115                 120

<210> SEQ ID NO 42
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Lys Ala Ser Gln Ser Val Ser Asn Asp Val Ala
1               5                   10

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Tyr Ala Ser Asn Arg Tyr Thr
1               5

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gln Gln Asp Tyr Ser Ser Pro Phe Thr
1               5
```

```
<210> SEQ ID NO 45
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gln Ser Val Ser Asn Asp
1               5

<210> SEQ ID NO 46
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Tyr Ala Ser
1

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gln Gln Asp Tyr Ser Ser Pro
1               5

<210> SEQ ID NO 48
<211> LENGTH: 17
<212> TYPE: PRT
<213> ORGANISM: Homo sapiens

<400> SEQUENCE: 48

Met Asn Phe Leu Leu Ser Trp Val His Trp Ser Leu Ala Leu Leu Leu
1               5                   10                  15

Tyr

<210> SEQ ID NO 49
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
gatgttgtga tgacccaaac tccactctcc ctgcctgtca gtcttggaga tcaagcctcc      60
atctcttgca gatctagtca gagccttgta cacagtaatg aaacaccta tttacattgg     120 tacctgcaga agccaggcca gtctccaaag ctcctgatct acaaagtttc caaccgattt     180
tctggggtcc cagacaggtt cagtggcagt ggatcaggga cagatttcac actcaagatc     240
agccgagtgg aggctgagga tctgggaatt tatttctgct ctcaatgtac acatattccg     300
tggacgttcg gtggaggcac caacctggaa atcaaa                              336
```

```
<210> SEQ ID NO 50
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Phe Cys Ser Gln Cys
                85                  90                  95

Thr His Ile Pro Trp Thr Phe Gly Gly Gly Thr Asn Leu Glu Ile Lys
            100                 105                 110

<210> SEQ ID NO 51
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Arg Ser Ser Gln Ser Leu Val His Ser Asn Gly Asn Thr Tyr Leu His
1               5                   10                  15

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Lys Val Ser Asn Arg Phe Ser
1               5

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ser Gln Cys Thr His Ile Pro Trp Thr
1               5

<210> SEQ ID NO 54
<211> LENGTH: 348
<212> TYPE: DNA
<213> ORGANISM: Artificial Sequence
```

<220> FEATURE:
<223> OTHER INFORMATION: Description of Artificial Sequence: Synthetic
      polynucleotide

<400> SEQUENCE: 54

```
gaggtgcagc tggtggagtc cggcggcggc ctggtgcagc ccggcggctc cctgcgcctg      60
tcctgcgccg cctccggctt caccttctcc cgctactgga gtcctgggt gcgccaggcc     120 cccggcaagg gcctggagtg gatcggcgag atcaacccg actcctccac catcaactac     180
accccctccc tgaaggaccg cttcaccatc tcccgcgaca ccgccaagaa gtccctgtac     240
ctgcagatgt ccaaggtgcg ctccgaggac accgccctgt actactgcgc ccgccacggc     300
cgcggcatgg actactggtc ccagggcacc tccgtgaccg tgtcctcc                  348
```

<210> SEQ ID NO 55
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Thr Pro Ser Leu
    50                  55                  60

Lys Asp Arg Phe Thr Ile Ser Arg Asp Thr Ala Lys Lys Ser Leu Tyr
65                  70                  75                  80

Leu Gln Met Ser Lys Val Arg Ser Glu Asp Thr Ala Leu Tyr Tyr Cys
                85                  90                  95

Ala Arg His Gly Arg Gly Met Asp Tyr Trp Ser Gln Gly Thr Ser Val
            100                 105                 110

Thr Val Ser Ser
        115
```

<210> SEQ ID NO 56
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56

```
gacatcgtgc tgacccagtc ccccgacatc ctgtccgtgt ccctgggcga gcgcgccacc      60
gtgaactgca aggcctccca gaacgtggac tccaacgtgg cctggtacca gcagaagccc     120
ggccaccccc ccaagctgct gatctactcc gcctcctacc gctactcccg cgtgcccgac     180
cgcatctccg gctccggctc cggcaccgac ttcaccctga ccatctccaa cctgcaggcc     240
gaggacgtgg ccgtgtacta ctgccagcag taccactcct accccctgct ggccttcggc     300
gccggcacca agctggagct gaagcgcgcc gacgccgccc cc                        342
```

```
<210> SEQ ID NO 57
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Asp Ile Val Leu Thr Gln Ser Pro Asp Ile Leu Ser Val Ser Leu Gly
1               5                   10                  15

Glu Arg Ala Thr Val Asn Cys Lys Ala Ser Gln Asn Val Asp Ser Asn
            20                  25                  30

Val Ala Trp Tyr Gln Gln Lys Pro Gly His Pro Pro Lys Leu Leu Ile
        35                  40                  45

Tyr Ser Ala Ser Tyr Arg Tyr Ser Arg Val Pro Asp Arg Ile Ser Gly
    50                  55                  60

Ser Gly Ser Gly Thr Asp Phe Thr Leu Thr Ile Ser Asn Leu Gln Ala
65              70                  75                  80

Glu Asp Val Ala Val Tyr Tyr Cys Gln Gln Tyr His Ser Tyr Pro Leu
                85                  90                  95

Leu Ala Phe Gly Ala Gly Thr Lys Leu Glu Leu Lys Arg Ala Asp Ala
            100                 105                 110

Ala Pro

<210> SEQ ID NO 58
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58
gacatcgtgc tgacccagtc ccccgacatc ctgtccgtgt ccctgggcga gcgcgccacc      60
gtgaactgca aggcctccca gaacgtggac tccaacgtgg cctggtacca gcagaagccc     120
ggccaccccc ccaagctgct gatctactcc gcctcctacc gctactcccg cgtgcccgac     180
cgcatctccg gctccggctc cggcaccgac ttcaccctga ccatctccaa cctgcaggcc     240
gaggacctgg ccgactactt ctgccagcag taccactcct accccctgct ggccttcggc     300
gccggcacca agctggagct gaagcgcgcc gacgccgccc cc                        342

<210> SEQ ID NO 59
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Asp Ile Val Leu Thr Gln Ser Pro Asp Ile Leu Ser Val Ser Leu Gly
1               5                   10                  15

Glu Arg Ala Thr Val Asn Cys Lys Ala Ser Gln Asn Val Asp Ser Asn
            20                  25                  30

Val Ala Trp Tyr Gln Gln Lys Pro Gly His Pro Pro Lys Leu Leu Ile
        35                  40                  45

Tyr Ser Ala Ser Tyr Arg Tyr Ser Arg Val Pro Asp Arg Ile Ser Gly
    50                  55                  60
```

Ser Gly Ser Gly Thr Asp Phe Thr Leu Thr Ile Ser Asn Leu Gln Ala
 65                  70                  75                  80

Glu Asp Leu Ala Asp Tyr Phe Cys Gln Gln Tyr His Ser Tyr Pro Leu
                 85                  90                  95

Leu Ala Phe Gly Ala Gly Thr Lys Leu Glu Leu Lys Arg Ala Asp Ala
             100                 105                 110

Ala Pro

<210> SEQ ID NO 60
<211> LENGTH: 1413
<212> TYPE: DNA
<213> ORGANISM: Homo sapiens

<400> SEQUENCE: 60

| | | | | | |
|---|---|---|---|---|---|
| atggacccca | agggcagcct | gagctggaga | atcctgctgt | tcctgagcct | ggccttcgag | 60 |
| ctgagctacg | gcgaggtgca | gctggtggag | tccggcggcg | gcctggtgca | gcccggcggc | 120 |
| tccctgcgcc | tgtcctgcgc | cgcctccggc | ttcaccttct | cccgctactg | gatgtcctgg | 180 |
| gtgcgccagg | cccccggcaa | gggcctggag | tggatcggcg | agatcaaccc | cgactcctcc | 240 |
| accatcaact | acacccctc | cctgaaggac | cgcttcacca | tctcccgcga | caccgccaag | 300 |
| aagtccctgt | acctgcagat | gtccaaggtg | cgctccgagg | acaccgccct | gtactactgc | 360 |
| gcccgccacg | gcgcggcat | ggactactgg | tcccagggca | cctccgtgac | cgtgtcctcc | 420 |
| gctagcacca | agggccccag | cgtgttccct | ctggccccca | gcagcaagag | caccagcggc | 480 |
| ggaaccgccg | ccctgggctg | cctggtgaag | gactacttcc | ccgagcccgt | gaccgtgtcc | 540 |
| tggaacagcg | gcgctctgac | cagcggagtg | cacaccttcc | ctgccgtgct | gcagagcagc | 600 |
| ggcctgtact | ccctgagcag | cgtggtgacc | gtgcccagca | gcagcctggg | cacccagacc | 660 |
| tacatctgca | acgtgaacca | caagccctcc | aacaccaagg | tggacaagaa | ggtggagcct | 720 |
| aagagctgcg | acaagaccca | cacctgccct | ccctgccccg | ccccgagct | gctgggcgga | 780 |
| cccagcgtgt | tcctgttccc | tcccaagccc | aaggacaccc | tgatgatcag | ccgcaccccc | 840 |
| gaggtgacct | gcgtggtggt | ggacgtgagc | cacgaggacc | ccgaggtgaa | gttcaactgg | 900 |
| tacgtggacg | gcgtggaggt | gcacaacgcc | aagaccaagc | ctcgggagga | gcagtacaac | 960 |
| tccacctacc | gcgtggtgag | cgtgctgacc | gtgctgcacc | aggactggct | gaacggcaag | 1020 |
| gagtacaagt | gcaaggtgag | caacaaggcc | ctgcccgctc | catcgagaa | gaccatcagc | 1080 |
| aaggccaagg | gccagccccg | ggagcctcag | gtgtacaccc | tgccccccag | ccgcgacgag | 1140 |
| ctgaccaaga | accaggtgag | cctgacctgc | ctggtgaagg | gcttctaccc | ctccgacatc | 1200 |
| gccgtggagt | gggagagcaa | cggccagcct | gagaacaact | acaagaccac | ccctcccgtg | 1260 |
| ctggacagcg | acggcagctt | cttcctgtac | agcaagctga | ccgtggacaa | gtcccggtgg | 1320 |
| cagcagggca | acgtgttcag | ctgcagcgtg | atgcacgagg | ccctgcacaa | ccactacacc | 1380 |
| cagaagagcc | tgagcctgag | ccccggatag | taa | | | 1413 |

<210> SEQ ID NO 61
<211> LENGTH: 469
<212> TYPE: PRT
<213> ORGANISM: Homo sapiens

```
<400> SEQUENCE: 61

Met Asp Pro Lys Gly Ser Leu Ser Trp Arg Ile Leu Leu Phe Leu Ser
1               5                   10                  15

Leu Ala Phe Glu Leu Ser Tyr Gly Glu Val Gln Leu Val Glu Ser Gly
            20                  25                  30

Gly Gly Leu Val Gln Pro Gly Ser Leu Arg Leu Ser Cys Ala Ala
        35                  40                  45

Ser Gly Phe Thr Phe Ser Arg Tyr Trp Met Ser Trp Val Arg Gln Ala
50                  55                  60

Pro Gly Lys Gly Leu Glu Trp Ile Gly Glu Ile Asn Pro Asp Ser Ser
65                  70                  75                  80

Thr Ile Asn Tyr Thr Pro Ser Leu Lys Asp Arg Phe Thr Ile Ser Arg
                85                  90                  95

Asp Thr Ala Lys Lys Ser Leu Tyr Leu Gln Met Ser Lys Val Arg Ser
            100                 105                 110

Glu Asp Thr Ala Leu Tyr Tyr Cys Ala Arg His Gly Arg Gly Met Asp
        115                 120                 125

Tyr Trp Ser Gln Gly Thr Ser Val Thr Val Ser Ser Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Leu Gly Thr Gln Thr Tyr Ile Cys Asn
210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
        290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
        370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415
```

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly
465

<210> SEQ ID NO 62
<211> LENGTH: 1404
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62

```
atggacccca agggcagcct gagctggaga atcctgctgt tcctgagcct ggccttcgag      60
ctgagctacg gcgaggtgca gctggtggag tccggcggcg gcctggtgca gcccggcggc     120
tccctgcgcc tgtcctgcgc cgcctccggc ttcaccttct cccgctactg gatgtcctgg     180
gtgcgccagg cccccggcaa gggcctggag tggatcggcg agatcaaccc cgactcctcc     240
accatcaact acacccectc cctgaaggac cgcttcacca tctcccgcga caccgccaag     300
aagtccctgt acctgcagat gtccaaggtg cgctccgagg acaccgccct gtactactgc     360
gcccgccacg gccgcggcat ggactactgg tcccagggca cctccgtgac cgtgtcctcc     420
gctagcacca agggccccag cgtgtttcct ctcgctccct gcagccggag cacatccgag     480
agcaccgctg ctctgggctg tctcgtgaag gactacttcc ctgaacccgt caccgtcagc     540
tggaatagcg gcgccctgac atccggcgtc cacacattcc ccgctgtcct gcagagcagc     600
ggcctgtaca gcctgagctc cgtggtcacc gtgcctagca gcagcctggg aacaaagacc     660
tacacctgca acgtggacca taagccctcc aacaccaagg tggacaagcg ggtggaatcc     720
aagtatggac cccctgtcc tccttgccct gctcctgaat ttctcggagg ccctccgtc      780 ttcctgtttc cccccaagcc caaggacacc ctgatgatct cccggacacc cgaagtcacc     840
tgcgtcgtgg tggatgtcag ccaggaagat cccgaggtgc agttcaactg gtacgtggac     900
ggagtggagg tgcataacgc caaaaccaag cccagggaag agcagttcaa cagcacctat     960
cgggtcgtgt ccgtgctcac cgtcctgcat caggattggc tcaacggcaa ggagtacaag    1020
tgcaaggtgt ccaacaaggg cctgcccccc tccatcgaga gaccatctc caaggctaag     1080 ggccaacctc gggagcccca agtgtatacc ctccctccca gccaggagga gatgaccaag    1140
aatcaagtga gcctgacctg cctcgtgaag ggattttacc cctccgacat cgctgtggaa    1200
tgggaaagca atggccaacc tgagaacaac tacaagacca cccccccgt gctggactcc      1260 gatggctcct tcttcctgta cagcaggctg accgtggaca atcccggtg caagaggga     1320 aacgtgttca gctgctccgt gatgcacgag gctctccaca ccactacac ccagaagagc      1380 ctctccctga gcctcggcta gtaa                                            1404
```

<210> SEQ ID NO 63
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 63

Met Asp Pro Lys Gly Ser Leu Ser Trp Arg Ile Leu Leu Phe Leu Ser
1               5                   10                  15

Leu Ala Phe Glu Leu Ser Tyr Gly Glu Val Gln Leu Val Glu Ser Gly
            20                  25                  30

Gly Gly Leu Val Gln Pro Gly Gly Ser Leu Arg Leu Ser Cys Ala Ala
        35                  40                  45

Ser Gly Phe Thr Phe Ser Arg Tyr Trp Met Ser Trp Val Arg Gln Ala
50                  55                  60

Pro Gly Lys Gly Leu Glu Trp Ile Gly Glu Ile Asn Pro Asp Ser Ser
65                  70                  75                  80

Thr Ile Asn Tyr Thr Pro Ser Leu Lys Asp Arg Phe Thr Ile Ser Arg
                85                  90                  95

Asp Thr Ala Lys Lys Ser Leu Tyr Leu Gln Met Ser Lys Val Arg Ser
            100                 105                 110

Glu Asp Thr Ala Leu Tyr Tyr Cys Ala Arg His Gly Arg Gly Met Asp
        115                 120                 125

Tyr Trp Ser Gln Gly Thr Ser Val Thr Val Ser Ser Ala Ser Thr Lys
130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Lys Thr Tyr Thr Cys Asn
210                 215                 220

Val Asp His Lys Pro Ser Asn Thr Lys Val Asp Lys Arg Val Glu Ser
225                 230                 235                 240

Lys Tyr Gly Pro Pro Cys Pro Pro Cys Pro Ala Pro Glu Phe Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser Gln
        275                 280                 285

Glu Asp Pro Glu Val Gln Phe Asn Trp Tyr Val Asp Gly Val Glu Val
290                 295                 300

His Asn Ala Lys Thr Lys Pro Arg Glu Glu Gln Phe Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Gly Leu Pro Ser Ser Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Gln Glu Glu Met Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415
```

```
Val Leu Asp Ser Asp Gly Ser Phe Phe Leu Tyr Ser Arg Leu Thr Val
            420                 425                 430

Asp Lys Ser Arg Trp Gln Glu Gly Asn Val Phe Ser Cys Ser Val Met
        435                 440                 445

His Glu Ala Leu His Asn His Tyr Thr Gln Lys Ser Leu Ser Leu Ser
    450                 455                 460

Leu Gly
465

<210> SEQ ID NO 64
<211> LENGTH: 708
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64
atggagaccg acaccctgct gctctgggtg ctgctgctct gggtgcccgg ctccaccgga      60
gacatcgtgc tgacccagtc ccccgacatc ctgtccgtgt ccctgggcga gcgcgccacc     120
gtgaactgca aggcctccca gaacgtggac tccaacgtgg cctggtacca gcagaagccc     180
ggccaccccc ccaagctgct gatctactcc gcctcctacc gctactcccg cgtgcccgac     240
cgcatctccg gctccggctc cggcaccgac ttcaccctga ccatctccaa cctgcaggcc     300
gaggacgtgg ccgtgtacta ctgccagcag taccactcct acccctgct ggccttcggc      360 gccggcacca gctggagct gaagcggacc gtggccgccc ccagcgtgtt catcttccct     420
cccagcgacg agcagctgaa gtctggcacc gccagcgtgg tgtgcctgct gaacaacttc     480
tacccccgcg aggccaaggt gcagtggaag gtggacaacg ccctgcagag cggcaacagc     540
caggagagcg tgaccgagca ggactccaag gacagcacct acagcctgag cagcaccctg     600
accctgagca aggccgacta cgagaagcac aaggtgtacg cctgcgaggt gacccaccag     660
ggactgtcta gccccgtgac caagagcttc aaccggggcg agtgctaa                  708

<210> SEQ ID NO 65
<211> LENGTH: 235
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Asp Ile Leu Ser
            20                  25                  30

Val Ser Leu Gly Glu Arg Ala Thr Val Asn Cys Lys Ala Ser Gln Asn
        35                  40                  45

Val Asp Ser Asn Val Ala Trp Tyr Gln Gln Lys Pro Gly His Pro Pro
    50                  55                  60

Lys Leu Leu Ile Tyr Ser Ala Ser Tyr Arg Tyr Ser Arg Val Pro Asp
65                  70                  75                  80

Arg Ile Ser Gly Ser Gly Ser Gly Thr Asp Phe Thr Leu Thr Ile Ser
                85                  90                  95

Asn Leu Gln Ala Glu Asp Val Ala Val Tyr Tyr Cys Gln Gln Tyr His
            100                 105                 110
```

```
Ser Tyr Pro Leu Leu Ala Phe Gly Ala Gly Thr Lys Leu Glu Leu Lys
            115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 66
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66
gacatcgtgc tgacccagtc ccccgacatc ctgtccgtgt ccctgggcga gcgcgccacc      60
gtgaactgca aggcctccca gaacgtggac tccaacgtgg cctggtacca gcagaagccc    120
ggccaccccc ccaagctgct gatctactcc gcctcctacc gctactcccg cgtgcccgac    180
cgcatctccg gctccggctc cggcaccgac ttcaccctga ccatctccaa cctgcaggcc    240
gaggacctgg ccgactactt ctgccagcag taccactcct accccctgct ggccttcggc    300
gccggcacca agctggagct gaagcgcgcc gacgccgccc ccaccgtgtc cctggag       357

<210> SEQ ID NO 67
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Asp Ile Val Leu Thr Gln Ser Pro Asp Ile Leu Ser Val Ser Leu Gly
1               5                   10                  15

Glu Arg Ala Thr Val Asn Cys Lys Ala Ser Gln Asn Val Asp Ser Asn
            20                  25                  30

Val Ala Trp Tyr Gln Gln Lys Pro Gly His Pro Pro Lys Leu Leu Ile
        35                  40                  45

Tyr Ser Ala Ser Tyr Arg Tyr Ser Arg Val Pro Asp Arg Ile Ser Gly
    50                  55                  60

Ser Gly Ser Gly Thr Asp Phe Thr Leu Thr Ile Ser Asn Leu Gln Ala
65                  70                  75                  80

Glu Asp Leu Ala Asp Tyr Phe Cys Gln Gln Tyr His Ser Tyr Pro Leu
                85                  90                  95
```

```
Leu Ala Phe Gly Ala Gly Thr Lys Leu Glu Leu Lys Arg Ala Asp Ala
            100                 105                 110
Ala Pro Thr Val Ser Leu Glu
        115

<210> SEQ ID NO 68
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 68

Phe Gly Xaa Gly
1

<210> SEQ ID NO 69
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(9)
<223> OTHER INFORMATION: Any amino acid

<400> SEQUENCE: 69

Cys Xaa Xaa Xaa Xaa Xaa Xaa Xaa Xaa
1               5

<210> SEQ ID NO 70
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Leu Glu Trp Ile Gly
1               5

<210> SEQ ID NO 71
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 71

Trp Gly Xaa Gly
1
```

ANTI-DESPR MONOCLONAL ANTIBODY TARGETED THERAPY AND IMAGING FOR CANCER AND STROKE

CROSS-REFERENCE TO RELATED APPLICATIONS

This application is a divisional application of U.S. application Ser. No. 15/245,853 filed on Aug. 24, 2016, now U.S. Pat. No. 10,202,457 issued on Feb. 12, 2019, which claims benefit under 35 U.S.C. § 119(e) of U.S. Provisional Application Ser. No. 62/208,937 filed on Aug. 24, 2015, the contents of which are herein incorporated by reference in their entirety.

GOVERNMENT SUPPORT

This invention was made with Government Support under Contract Nos. U54TR001012, HL058136, and AG032649 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Jan. 30, 2019, is named 701586-085062USD1_SL.txt and is 46,239 bytes in size.

FIELD OF THE INVENTION

This invention relates to monoclonal antibodies against the dual endothelin1/VEGF-signal peptide receptor, DEspR, and their use as therapeutics in the inhibition of tumor initiation or progression or spread or recurrence and therapy resistance in cancer, and in the inhibition of microvascular leakiness or disruption, and microbleeds such as occurs in, but not limited to, cancer and stroke, as well as diagnostic agents and targeting agents for molecular imaging and targeted delivery of other therapeutic agents.

BACKGROUND

Although targeted therapies have been tested, to date, there is no effective therapy to stop therapy-resistant tumor recurrence or reseeding. Single targeted therapy that can stop tumor "reseeding" of therapy-resistant tumors as seen in recurrent glioblastoma and in peritoneal carcinomatosis, such as occurs in pancreatic cancer, ovarian and gastric cancers provide a novel approach. Even if the primary tumors responded to current therapies, tumor recurrence usually results in therapy-resistant tumors—as seen in, for example, recurrent glioblastoma, pancreatic cancer, triple negative breast cancer (TNBC), and peritoneal carcinomatosis. Similarly, circulating tumor cells have been increasingly described, and serve as prognostic markers, but no therapy exists to inhibit them and prevent metastatic tumor initiation. Likewise, microvascular leakiness in tumors contributes to poor therapy delivery while facilitating egress of circulating tumor cells, but no significant therapy exists to address this. The basic rationale is that these cancer trends for recurrence can best be inhibited by a single-agent that can simultaneously inhibit tumor initiation, therapy resistance, and microvessel leakiness.

In parallel, there is no therapy for patients with microvessel leakiness, disruption, and/or microbleeds in the brain that progress to major bleeds as seen in ischemic stroke patients (post-ischemic hemorrhagic transformation or hemorrhagic conversion). In fact, a known complication of the FDA-approved thrombolytic tissue-plasminogen activator (TPA)-therapy for ischemic stroke when given late is hemorrhagic transformation. Once initiated, micro-to-macrobleed initiation-progression, or hemorrhagic transformation, leads to death even if the initiating ischemic insult is resolved by current stroke thrombolytic therapy. There too is no therapy for patients with brain microvessel leakiness, disruption, and/or microbleeds (detected on MRI) which are associated with subsequent pathologies, such as, but not limited to stroke. The basic rationale is that microvessel leakiness, microbleeds and progression to hemorrhagic transformation or other microbleed-associated pathologies can best be stopped or prevented by preventing development of microbleeds and their progression to macrobleeds—collectively represented by microvascular leakiness, loss of integrity, and neutrophil-mediated injury.

SUMMARY OF THE INVENTION

Described herein are novel compositions comprising isolated antibodies and antigen-binding fragments, including anti-DEspR antibodies and antigen-binding fragments thereof, derived from 6G8G7 and 7C5B2 anti-DEspR variant antibodies, including humanized, fully human, composite engineered human, and deimmunized (T cell epitope-depleted) monoclonal anti-DEspR antibodies and antigen-binding fragments thereof, and methods of their use in a variety of applications, including, anti-angiogenesis therapies and anti-tumor cell invasiveness relevant for treatment of cancer and/or metastasis and anti-angiogenesis approaches relevant to treatment of those vascular diseases where pathological angiogenesis plays a role in pathogenesis or progression such as in carotid artery disease, stroke, ischemic hemorrhagic transformation, cerebral microbleeds, stroke, hemorrhagic transformation, vasa vasorum neovascularization, and vulnerable plaque neovascularization.

Accordingly, provided herein, in some aspects is an isolated antibody or antigen-binding fragment thereof that has at least one of the following functional characteristics:
 a. an EC50 for binding to DEspR (dual endothelin/VEGF signal peptide receptor) of 12 µg/ml or less;
 b. an IC50 for inhibiting activated neutrophil survival or human angiogenesis of 3.0 µg/ml or less; or
 c. a $K_D$ for binding DEspR of 2.5 µg/ml or less.

In some embodiments of these aspects and all such aspects described herein, the isolated antibody or antigen-binding fragment thereof has an EC50 for binding to DEspR of 5 µg/ml or less.

In some embodiments of these aspects and all such aspects described herein, the isolated antibody or antigen-binding fragment thereof has an EC50 for binding to DEspR of 30 nM or less.

In some embodiments of these aspects and all such aspects described herein, the isolated antibody or antigen-binding fragment thereof, the IC50 for inhibiting activated neutrophil survival or human angiogenesis is 2.6 µg/ml or less.

In some embodiments of these aspects and all such aspects described herein, the isolated antibody or antigen-binding fragment thereof, a$K_D$ for binding DEspR is 1.5 µg/ml or less.

In some embodiments of these aspects and all such aspects described herein, the isolated antibody or antigen-binding fragment thereof has at least two of the functional characteristics.

In some embodiments of these aspects and all such aspects described herein, the isolated antibody or antigen-binding fragment thereof has all three of the functional characteristics.

In some embodiments of these aspects and all such aspects described herein, the isolated antibody or antigen-binding fragment thereof is a neutralizing antibody or a DEspR antagonist.

In some embodiments of these aspects and all such aspects described herein, the isolated antibody or antigen-binding fragment thereof specifically binds to an epitope of DEspR of SEQ ID NO: 1 or SEQ ID NO: 2.

In some embodiments of these aspects and all such aspects described herein, the isolated antibody or antigen-binding fragment thereof comprises one or more heavy and light chain complementarity determining regions (CDRs) selected from the group consisting of:
 a. a heavy chain CDR1 having the amino acid sequence of SEQ ID NO: 7, SEQ ID NO: 14, or SEQ ID NO: 21;
 b. a heavy chain CDR2 having the amino acid sequence of SEQ ID NO: 8, SEQ ID NO: 15, or SEQ ID NO: 22;
 c. a heavy chain CDR3 having the amino acid sequence of SEQ ID NO: 9, SEQ ID NO: 16, or SEQ ID NO: 23;
 d. a light chain CDR1 having the amino acid sequence of SEQ ID NO: 28, SEQ ID NO: 35, SEQ ID NO: 42, or SEQ ID NO: 51;
 e. a light chain CDR2 having the amino acid sequence of SEQ ID NO: 29, SEQ ID NO: 36, SEQ ID NO: 43, or SEQ ID NO: 52; and
 f. a light chain CDR3 having the amino acid sequence of SEQ ID NO: 30, SEQ ID NO: 37, SEQ ID NO: 44, or SEQ ID NO: 53.

In some embodiments of these aspects and all such aspects described herein, the isolated antibody or antigen-binding fragment thereof comprises one or more heavy chain complimentarity determining regions (CDRs) selected from the group consisting of:
 a. a heavy chain CDR1 having the amino acid sequence of SEQ ID NO: 7, SEQ ID NO: 14, or SEQ ID NO: 21;
 b. a heavy chain CDR2 having the amino acid sequence of SEQ ID NO: 8, SEQ ID NO: 15, or SEQ ID NO: 22;
 c. a heavy chain CDR3 having the amino acid sequence of SEQ ID NO: 9, SEQ ID NO: 16, or SEQ ID NO: 23;
and one or more light chain CDRs selected from the group consisting of:
 a. a light chain CDR1 having the amino acid sequence of SEQ ID NO: 28, SEQ ID NO: 35, SEQ ID NO: 42, or SEQ ID NO: 51;
 b. a light chain CDR2 having the amino acid sequence of SEQ ID NO: 29, SEQ ID NO: 36, SEQ ID NO: 43, or SEQ ID NO: 52; and
 c. a light chain CDR3 having the amino acid sequence of SEQ ID NO: 30, SEQ ID NO: 37, SEQ ID NO: 44, or SEQ ID NO: 53.

In some embodiments of these aspects and all such aspects described herein, the isolated antibody or antigen-binding fragment thereof comprises:
 a. a heavy chain CDR1 having the amino acid sequence of SEQ ID NO: 7;
 b. a heavy chain CDR2 having the amino acid sequence of SEQ ID NO: 8;
 c. a heavy chain CDR3 having the amino acid sequence of SEQ ID NO: 9;
 d. a light chain CDR1 having the amino acid sequence of SEQ ID NO: 28;
 e. a light chain CDR2 having the amino acid sequence of SEQ ID NO: 29; and
 f. a light chain CDR3 having the amino acid sequence of SEQ ID NO: 30.

In some embodiments of these aspects and all such aspects described herein, the isolated antibody or antigen-binding fragment thereof comprises:
 a. a heavy chain CDR1 having the amino acid sequence of SEQ ID NO: 7;
 b. a heavy chain CDR2 having the amino acid sequence of SEQ ID NO: 8;
 c. a heavy chain CDR3 having the amino acid sequence of SEQ ID NO: 9;
 d. a light chain CDR1 having the amino acid sequence of SEQ ID NO: 35;
 e. a light chain CDR2 having the amino acid sequence of SEQ ID NO: 36; and
 f. a light chain CDR3 having the amino acid sequence of SEQ ID NO: 37.

In some embodiments of these aspects and all such aspects described herein, the isolated antibody or antigen-binding fragment thereof comprises:
 a. a heavy chain CDR1 having the amino acid sequence of SEQ ID NO: 14;
 b. a heavy chain CDR2 having the amino acid sequence of SEQ ID NO: 15;
 c. a heavy chain CDR3 having the amino acid sequence of SEQ ID NO: 16;
 d. a light chain CDR1 having the amino acid sequence of SEQ ID NO: 42;
 e. a light chain CDR2 having the amino acid sequence of SEQ ID NO: 43; and
 f. a light chain CDR3 having the amino acid sequence of SEQ ID NO: 44.

In some embodiments of these aspects and all such aspects described herein, the isolated antibody or antigen-binding fragment thereof comprises:
 a. a heavy chain CDR1 having the amino acid sequence of SEQ ID NO: 21;
 b. a heavy chain CDR2 having the amino acid sequence of SEQ ID NO: 22;
 c. a heavy chain CDR3 having the amino acid sequence of SEQ ID NO: 23;
 d. a light chain CDR1 having the amino acid sequence of SEQ ID NO: 51;
 e. a light chain CDR2 having the amino acid sequence of SEQ ID NO: 52; and
 f. a light chain CDR3 having the amino acid sequence of SEQ ID NO: 53.

In some embodiments of these aspects and all such aspects described herein, the isolated antibody or antigen-binding fragment thereof is a chimeric, humanized, or composite human antibody or dual antibody or antigen-binding fragment thereof.

In some embodiments of these aspects and all such aspects described herein, the antibody fragment is a Fab fragment, a Fab' fragment, a Fd fragment, a Fd' fragment, a Fv fragment, a dAb fragment, a F(ab')2 fragment, a single chain fragment, a diabody, or a linear antibody.

Provided herein, in some aspects, is an isolated anti-DEspR antibody or antigen-binding fragment thereof that specifically binds to an epitope of DEspR (dual endothelin/VEGF signal peptide receptor) of SEQ ID NO: 1.

In some aspects, provided herein, is an isolated anti-DEspR antibody or antigen-binding fragment thereof that specifically binds to an epitope of DEspR (dual endothelin/VEGF signal peptide receptor) of SEQ ID NO: 2.

In some aspects, provided herein, is an isolated anti-DEspR antibody or antigen-binding fragment thereof that specifically binds to DEspR (dual endothelin/VEGF signal peptide receptor) comprising one or more heavy and light chain complimentarity determining regions (CDRs) selected from the group consisting of:
  a. a heavy chain CDR1 having the amino acid sequence of SEQ ID NO: 7, SEQ ID NO: 14, or SEQ ID NO: 21;
  b. a heavy chain CDR2 having the amino acid sequence of SEQ ID NO: 8, SEQ ID NO: 15, or SEQ ID NO: 22;
  c. a heavy chain CDR3 having the amino acid sequence of SEQ ID NO: 9, SEQ ID NO: 16, or SEQ ID NO: 23;
  d. a light chain CDR1 having the amino acid sequence of SEQ ID NO: 28, SEQ ID NO: 35, SEQ ID NO: 42, or SEQ ID NO: 51;
  e. a light chain CDR2 having the amino acid sequence of SEQ ID NO: 29, SEQ ID NO: 36, SEQ ID NO: 43, or SEQ ID NO: 52; and
  f. a light chain CDR3 having the amino acid sequence of SEQ ID NO: 30, SEQ ID NO: 37, SEQ ID NO: 44, or SEQ ID NO: 53.

In some embodiments of these aspects and all such aspects described herein, the isolated anti-DEspR antibody or antigen-binding fragment thereof comprises the heavy chain complimentarity determining regions (CDRs):
  a. a heavy chain CDR1 having the amino acid sequence of SEQ ID NO: 7, SEQ ID NO: 14, or SEQ ID NO: 21;
  b. a heavy chain CDR2 having the amino acid sequence of SEQ ID NO: 8, SEQ ID NO: 15, or SEQ ID NO: 22; and
  c. a heavy chain CDR3 having the amino acid sequence of SEQ ID NO: 9, SEQ ID NO: 16, or SEQ ID NO: 23

In some embodiments of these aspects and all such aspects described herein, the isolated anti-DEspR antibody or antigen-binding fragment thereof comprises the light chain complimentarity determining regions (CDRs):
  a. a light chain CDR1 having the amino acid sequence of SEQ ID NO: 28, SEQ ID NO: 35, SEQ ID NO: 42, or SEQ ID NO: 51;
  b. a light chain CDR2 having the amino acid sequence of SEQ ID NO: 29, SEQ ID NO: 36, SEQ ID NO: 43, or SEQ ID NO: 52; and
  c. a light chain CDR3 having the amino acid sequence of SEQ ID NO: 30, SEQ ID NO: 37, SEQ ID NO: 44, or SEQ ID NO: 53.

In some embodiments of these aspects and all such aspects described herein, the isolated anti-DEspR antibody or antigen-binding fragment thereof comprises the complimentarity determining regions (CDRs):
  a. a heavy chain CDR1 having the amino acid sequence of SEQ ID NO: 7, SEQ ID NO: 14, or SEQ ID NO: 21;
  b. a heavy chain CDR2 having the amino acid sequence of SEQ ID NO: 8, SEQ ID NO: 15, or SEQ ID NO: 22;
  c. a heavy chain CDR3 having the amino acid sequence of SEQ ID NO: 9, SEQ ID NO: 16, or SEQ ID NO: 23;
  d. a light chain CDR1 having the amino acid sequence of SEQ ID NO: 28, SEQ ID NO: 35, SEQ ID NO: 42, or SEQ ID NO: 51;
  e. a light chain CDR2 having the amino acid sequence of SEQ ID NO: 29, SEQ ID NO: 36, SEQ ID NO: 43, or SEQ ID NO: 52; and
  f. a light chain CDR3 having the amino acid sequence of SEQ ID NO: 30, SEQ ID NO: 37, SEQ ID NO: 44, or SEQ ID NO: 53.

In some embodiments of these aspects and all such aspects described herein, the isolated anti-DEspR antibody or antigen-binding fragment thereof comprises a heavy chain having the amino acid sequence of SEQ ID NO: 6, SEQ ID NO: 13, or SEQ ID NO: 20.

In some embodiments of these aspects and all such aspects described herein, the isolated anti-DEspR antibody or antigen-binding fragment thereof comprises a light chain having the sequence of SEQ ID NO: 27, SEQ ID NO: 34, SEQ ID NO: 41, or SEQ ID NO: 50.

Provided herein, in some aspects, is an isolated anti-DEspR antibody or antigen-binding fragment thereof that specifically binds DEspR (dual endothelin/VEGF signal peptide receptor) comprising:
  a. a heavy chain CDR1 having the amino acid sequence of SEQ ID NO: 7;
  b. a heavy chain CDR2 having the amino acid sequence of SEQ ID NO: 8;
  c. a heavy chain CDR3 having the amino acid sequence of SEQ ID NO: 9;
  d. a light chain CDR1 having the amino acid sequence of SEQ ID NO: 28;
  e. a light chain CDR2 having the amino acid sequence of SEQ ID NO: 29; and
  f. a light chain CDR3 having the amino acid sequence of SEQ ID NO: 30.

Provided herein, in some aspects, is an isolated anti-DEspR antibody or antigen-binding fragment thereof that specifically binds DEspR (dual endothelin/VEGF signal peptide receptor) comprising:
  a. a heavy chain CDR1 having the amino acid sequence of SEQ ID NO: 7;
  b. a heavy chain CDR2 having the amino acid sequence of SEQ ID NO: 8;
  c. a heavy chain CDR3 having the amino acid sequence of SEQ ID NO: 9;
  d. a light chain CDR1 having the amino acid sequence of SEQ ID NO: 35;
  e. a light chain CDR2 having the amino acid sequence of SEQ ID NO: 36; and
  f. a light chain CDR3 having the amino acid sequence of SEQ ID NO: 37.

Provided herein, in some aspects, is an isolated anti-DEspR antibody or antigen-binding fragment thereof that specifically binds DEspR (dual endothelin/VEGF signal peptide receptor) comprising:
  a. a heavy chain CDR1 having the amino acid sequence of SEQ ID NO: 7;
  b. a heavy chain CDR2 having the amino acid sequence of SEQ ID NO: 8;
  c. a heavy chain CDR3 having the amino acid sequence of SEQ ID NO: 9;
  d. a light chain CDR1 having the amino acid sequence of SEQ ID NO: 42;
  e. a light chain CDR2 having the amino acid sequence of SEQ ID NO: 43; and
  f. a light chain CDR3 having the amino acid sequence of SEQ ID NO: 44.

In some aspects, provided herein is an isolated anti-DEspR antibody or antigen-binding fragment thereof that specifically binds DEspR (dual endothelin/VEGF signal peptide receptor) comprising:
  a. a heavy chain CDR1 having the amino acid sequence of SEQ ID NO: 7;
  b. a heavy chain CDR2 having the amino acid sequence of SEQ ID NO: 8;

c. a heavy chain CDR3 having the amino acid sequence of SEQ ID NO: 9;
d. a light chain CDR1 having the amino acid sequence of SEQ ID NO: 51;
e. a light chain CDR2 having the amino acid sequence of SEQ ID NO: 52; and
f. a light chain CDR3 having the amino acid sequence of SEQ ID NO: 53.

In some aspects, provided herein is an isolated anti-DEspR antibody or antigen-binding fragment thereof that specifically binds DEspR (dual endothelin/VEGF signal peptide receptor) comprising:
a. a heavy chain CDR1 having the amino acid sequence of SEQ ID NO: 14;
b. a heavy chain CDR2 having the amino acid sequence of SEQ ID NO: 15;
c. a heavy chain CDR3 having the amino acid sequence of SEQ ID NO: 16;
d. a light chain CDR1 having the amino acid sequence of SEQ ID NO: 28;
e. a light chain CDR2 having the amino acid sequence of SEQ ID NO: 29; and
f. a light chain CDR3 having the amino acid sequence of SEQ ID NO: 30.

Provided herein, in some aspects, is an isolated anti-DEspR antibody or antigen-binding fragment thereof that specifically binds DEspR (dual endothelin/VEGF signal peptide receptor) comprising:
a. a heavy chain CDR1 having the amino acid sequence of SEQ ID NO: 14;
b. a heavy chain CDR2 having the amino acid sequence of SEQ ID NO: 15;
c. a heavy chain CDR3 having the amino acid sequence of SEQ ID NO: 16;
d. a light chain CDR1 having the amino acid sequence of SEQ ID NO: 35;
e. a light chain CDR2 having the amino acid sequence of SEQ ID NO: 36; and
f. a light chain CDR3 having the amino acid sequence of SEQ ID NO: 37.

Provided herein, in some aspects, is an isolated anti-DEspR antibody or antigen-binding fragment thereof that specifically binds DEspR (dual endothelin/VEGF signal peptide receptor) comprising:
a. a heavy chain CDR1 having the amino acid sequence of SEQ ID NO: 14;
b. a heavy chain CDR2 having the amino acid sequence of SEQ ID NO: 15;
c. a heavy chain CDR3 having the amino acid sequence of SEQ ID NO: 16;
d. a light chain CDR1 having the amino acid sequence of SEQ ID NO: 42;
e. a light chain CDR2 having the amino acid sequence of SEQ ID NO: 43; and
f. a light chain CDR3 having the amino acid sequence of SEQ ID NO: 44.

Provided herein, in some aspects, is an isolated anti-DEspR antibody or antigen-binding fragment thereof that specifically binds DEspR (dual endothelin/VEGF signal peptide receptor) comprising:
a. a heavy chain CDR1 having the amino acid sequence of SEQ ID NO: 14;
b. a heavy chain CDR2 having the amino acid sequence of SEQ ID NO: 15;
c. a heavy chain CDR3 having the amino acid sequence of SEQ ID NO: 16;
d. a light chain CDR1 having the amino acid sequence of SEQ ID NO: 51;
e. a light chain CDR2 having the amino acid sequence of SEQ ID NO: 52; and
f. a light chain CDR3 having the amino acid sequence of SEQ ID NO: 53.

Provided herein, in some aspects, is an isolated anti-DEspR antibody or antigen-binding fragment thereof that specifically binds DEspR (dual endothelin/VEGF signal peptide receptor) comprising:
a. a heavy chain CDR1 having the amino acid sequence of SEQ ID NO: 21;
b. a heavy chain CDR2 having the amino acid sequence of SEQ ID NO: 22;
c. a heavy chain CDR3 having the amino acid sequence of SEQ ID NO: 23;
d. a light chain CDR1 having the amino acid sequence of SEQ ID NO: 28;
e. a light chain CDR2 having the amino acid sequence of SEQ ID NO: 29; and
f. a light chain CDR3 having the amino acid sequence of SEQ ID NO: 30.

Provided herein, in some aspects, is an isolated anti-DEspR antibody or antigen-binding fragment thereof that specifically binds DEspR (dual endothelin/VEGF signal peptide receptor) comprising:
a. a heavy chain CDR1 having the amino acid sequence of SEQ ID NO: 21;
b. a heavy chain CDR2 having the amino acid sequence of SEQ ID NO: 22;
c. a heavy chain CDR3 having the amino acid sequence of SEQ ID NO: 23;
d. a light chain CDR1 having the amino acid sequence of SEQ ID NO: 35;
e. a light chain CDR2 having the amino acid sequence of SEQ ID NO: 36; and
f. a light chain CDR3 having the amino acid sequence of SEQ ID NO: 37.

Provided herein, in some aspects, is an isolated anti-DEspR antibody or antigen-binding fragment thereof that specifically binds DEspR (dual endothelin/VEGF signal peptide receptor) comprising:
a. a heavy chain CDR1 having the amino acid sequence of SEQ ID NO: 21;
b. a heavy chain CDR2 having the amino acid sequence of SEQ ID NO: 22;
c. a heavy chain CDR3 having the amino acid sequence of SEQ ID NO: 23;
d. a light chain CDR1 having the amino acid sequence of SEQ ID NO: 42;
e. a light chain CDR2 having the amino acid sequence of SEQ ID NO: 43; and
f. a light chain CDR3 having the amino acid sequence of SEQ ID NO: 44.

Provided herein, in some aspects, is an isolated anti-DEspR antibody or antigen-binding fragment thereof that specifically binds DEspR (dual endothelin/VEGF signal peptide receptor) comprising:
a. a heavy chain CDR1 having the amino acid sequence of SEQ ID NO: 21;
b. a heavy chain CDR2 having the amino acid sequence of SEQ ID NO: 22;
c. a heavy chain CDR3 having the amino acid sequence of SEQ ID NO: 23;
d. a light chain CDR1 having the amino acid sequence of SEQ ID NO: 51;

e. a light chain CDR2 having the amino acid sequence of SEQ ID NO: 52; and f. a light chain CDR3 having the amino acid sequence of SEQ ID NO: 53.

Provided herein, in some aspects, is an isolated anti-DEspR antibody or antigen-binding fragment thereof that specifically binds to DEspR (dual endothelin/VEGF signal peptide receptor) comprising one or more heavy chain complimentarity determining regions (CDRs) selected from the group consisting of:

a. a heavy chain CDR1 having the amino acid sequence of SEQ ID NO: 7;

b. a heavy chain CDR2 having the amino acid sequence of SEQ ID NO: 8; and c. a heavy chain CDR3 having the amino acid sequence of SEQ ID NO: 9.

Provided herein, in some aspects, is an isolated anti-DEspR antibody or antigen-binding fragment thereof that specifically binds to DEspR (dual endothelin/VEGF signal peptide receptor) comprising one or more heavy chain complimentarity determining regions (CDRs) selected from the group consisting of:

a. a heavy chain CDR1 having the amino acid sequence of SEQ ID NO:14;

b. a heavy chain CDR2 having the amino acid sequence of SEQ ID NO: 15; and c. a heavy chain CDR3 having the amino acid sequence of SEQ ID NO: 16.

Provided herein, in some aspects, is an isolated anti-DEspR antibody or antigen-binding fragment thereof that specifically binds to DEspR (dual endothelin/VEGF signal peptide receptor) comprising one or more heavy chain complimentarity determining regions (CDRs) selected from the group consisting of:

a. a heavy chain CDR1 having the amino acid sequence of SEQ ID NO: 21;

b. a heavy chain CDR2 having the amino acid sequence of SEQ ID NO: 22; and c. a heavy chain CDR3 having the amino acid sequence of SEQ ID NO: 23.

Provided herein, in some aspects, is an isolated anti-DEspR antibody or antigen-binding fragment thereof that specifically binds to DEspR (dual endothelin/VEGF signal peptide receptor) comprising one or more light chain complimentarity determining regions (CDRs) selected from the group consisting of:

a. a light chain CDR1 having the amino acid sequence of SEQ ID NO: 28;

b. a light chain CDR2 having the amino acid sequence of SEQ ID NO: 29; and c. a light chain CDR3 having the amino acid sequence of SEQ ID NO: 30.

Provided herein, in some aspects, is an isolated anti-DEspR antibody or antigen-binding fragment thereof that specifically binds to DEspR (dual endothelin/VEGF signal peptide receptor) comprising one or more light chain complimentarity determining regions (CDRs) selected from the group consisting of:

a. a light chain CDR1 having the amino acid sequence of SEQ ID NO: 35;

b. a light chain CDR2 having the amino acid sequence of SEQ ID NO: 36; and c. a light chain CDR3 having the amino acid sequence of SEQ ID NO: 37.

Provided herein, in some aspects, is an isolated anti-DEspR antibody or antigen-binding fragment thereof that specifically binds to DEspR (dual endothelin/VEGF signal peptide receptor) comprising one or more light chain complimentarity determining regions (CDRs) selected from the group consisting of:

a. a light chain CDR1 having the amino acid sequence of SEQ ID NO: 42;

b. a light chain CDR2 having the amino acid sequence of SEQ ID NO: 43; and c. a light chain CDR3 having the amino acid sequence of SEQ ID NO: 44.

Provided herein, in some aspects, is an isolated anti-DEspR antibody or antigen-binding fragment thereof that specifically binds to DEspR (dual endothelin/VEGF signal peptide receptor) comprising one or more light chain complimentarity determining regions (CDRs) selected from the group consisting of:

a. a light chain CDR1 having the amino acid sequence of SEQ ID NO: 51;

b. a light chain CDR2 having the amino acid sequence of SEQ ID NO: 52; and c. a light chain CDR3 having the amino acid sequence of SEQ ID NO: 53.

Provided herein, in some aspects, is an isolated anti-DEspR antibody or antigen-binding fragment thereof that specifically binds to DEspR (dual endothelin/VEGF signal peptide receptor) comprising a humanized variable heavy chain amino acid sequence of SEQ ID NO: 55.

Provided herein, in some aspects, is an isolated anti-DEspR antibody or antigen-binding fragment thereof that specifically binds to DEspR (dual endothelin/VEGF signal peptide receptor) comprising a humanized variable light chain amino acid sequence of SEQ ID NO: 57 or SEQ ID NO: 59.

Provided herein, in some aspects, is an isolated anti-DEspR antibody or antigen-binding fragment thereof that specifically binds to DEspR (dual endothelin/VEGF signal peptide receptor) comprising a humanized variable heavy chain amino acid sequence of SEQ ID NO: 55, and a humanized variable light chain amino acid sequence of SEQ ID NO: 57 or SEQ ID NO: 59.

Provided herein, in some aspects, is an isolated anti-DEspR antibody or antigen-binding fragment thereof that specifically binds to DEspR (dual endothelin/VEGF signal peptide receptor) comprising a humanized variable heavy chain IgG1 amino acid sequence of SEQ ID NO: 61.

Provided herein, in some aspects, is an isolated anti-DEspR antibody or antigen-binding fragment thereof that specifically binds to DEspR (dual endothelin/VEGF signal peptide receptor) comprising a humanized variable heavy chain IgG4 amino acid sequence of SEQ ID NO: 63.

Provided herein, in some aspects, is an isolated anti-DEspR antibody or antigen-binding fragment thereof that specifically binds to DEspR (dual endothelin/VEGF signal peptide receptor) comprising a humanized variable kappa light chain amino acid sequence of SEQ ID NO: 65.

Provided herein, in some aspects, is an isolated anti-DEspR antibody or antigen-binding fragment thereof that specifically binds to DEspR (dual endothelin/VEGF signal peptide receptor) comprising a humanized variable heavy chain IgG1 amino acid sequence of SEQ ID NO: 61 and a humanized variable kappa light chain amino acid sequence of SEQ ID NO: 65.

Provided herein, in some aspects, is an isolated anti-DEspR antibody or antigen-binding fragment thereof that specifically binds to DEspR (dual endothelin/VEGF signal peptide receptor) comprising a humanized variable heavy chain IgG4 amino acid sequence of SEQ ID NO: 63 and a humanized variable kappa light chain amino acid sequence of SEQ ID NO: 65.

In some embodiments of these aspects and all such aspects described herein, the anti-DEspR antibody or antigen-binding fragment thereof specifically binds to an epitope of SEQ ID NO: 1.

In some embodiments of these aspects and all such aspects described herein, the anti-DEspR antibody or antigen-binding fragment thereof specifically binds to an epitope of SEQ ID NO: 2.

In some embodiments of these aspects and all such aspects described herein, the antibody is a chimeric, humanized, or composite human antibody or dual antibody or antigen-binding fragment thereof.

In some embodiments of these aspects and all such aspects described herein, the antibody fragment is a Fab fragment, a Fab' fragment, a Fd fragment, a Fd' fragment, a Fv fragment, a dAb fragment, a F(ab')$_2$ fragment, a single chain fragment, a diabody, or a linear antibody.

In some embodiments of these aspects and all such aspects described herein, the isolated anti-DEspR antibody or antibody fragment thereof further comprises an agent conjugated to the anti-DEspR binding protein, antibody or antibody fragment, or antigen-binding portion thereof to form an immunoconjugate specific for DEspR.

In some embodiments of these aspects and all such aspects described herein, the agent conjugated to the binding protein, antibody or antibody fragment, or antigen-binding portion thereof thereof is a chemotherapeutic agent, a toxin, a radioactive isotope, a small molecule, an siRNA, a nanoparticle, or a microbubble.

In some aspects, provided herein are pharmaceutical compositions comprising any of the isolated anti-DEspR antibodies or antibody fragments thereof described herein and a pharmaceutically acceptable carrier.

In some aspects, provided herein is a method of inhibiting angiogenesis in a subject having a disease or disorder dependent or modulated by angiogenesis, the method comprising administering to a subject in need thereof a therapeutically effective amount of any of the pharmaceutical compositions described herein.

In some embodiments of these aspects and all such aspects described herein, the disease or disorder dependent or modulated by angiogenesis is a cancer or a tumor.

In some embodiments of these aspects and all such aspects described herein, the disease or disorder dependent or modulated by angiogenesis is selected from the group consisting of age-related macular degeneration, carotid artery disease, diabetic retinopathy, rheumatoid arthritis, neurodegenerative disorder, Alzheimer's disease, obesity, endometriosis, psoriasis, atherosclerosis, ocular neovascularization, neovascular glaucoma, osteoporosis, and restenosis.

In some aspects, provided herein is a method of inhibiting tumor cell invasiveness in a subject having a cancer or a tumor, the method comprising administering to a subject in need thereof a therapeutically effective amount of any of the pharmaceutical compositions described herein.

In some embodiments of this aspect and all such aspects described herein, the method further comprises the administration of one or more chemotherapeutic agents, angiogenesis inhibitors, cytotoxic agents, tumor-targeted therapies, immunotherapy, or anti-proliferative agents.

In some aspects, provided herein is a method of inhibiting tumor growth and reducing tumor size or tumor metastasis in a subject in need thereof by inhibiting DEspR expression and/or function in a cell, the method comprising administering to a subject in need thereof a therapeutically effective amount of any of the pharmaceutical compositions described herein.

In some embodiments of this aspect and all such aspects described herein, the DEspR expression and/or function is inhibited in a tumor cell, a tumor initiating cell, a cancer stem-like cell, a cancer stem cell, a metastatic tumor cell, an endothelial progenitor cell, an inflammatory cell, a tumor stromal cell, a tumor vasculature cell, or any combination thereof.

In some embodiments of this aspect and all such aspects described herein, the tumor vasculature cell is an endothelial cell, a pericyte, a smooth muscle cell, an adventitial cell, or any combination thereof.

In some aspects, provided herein is a method of inhibiting tumor therapy resistance, tumor initiation, and/or tumor recurrence by inhibiting DEspR expression and/or function in a cell, the method comprising administering to a subject in need thereof a therapeutically effective amount of any of the pharmaceutical compositions described herein.

In some embodiments of this aspect and all such aspects described herein, the DEspR expression and/or function is inhibited in a tumor cell, a tumor initiating cell, a cancer stem-like cell, a cancer stem cell, a metastatic tumor cell, or any combination thereof.

In some aspects, provided herein is a method of inhibiting cancer progression through promotion of autophagy of a cancer cell by inhibiting DEspR expression and/or function in a tumor cell, the method comprising administering to a subject in need thereof a therapeutically effective amount of any of the pharmaceutical compositions described herein.

In some embodiments of this aspect and all such aspects described herein, the DEspR expression and/or function is inhibited in a tumor cell, a tumor initiating cell, a cancer stem-like cell, a cancer stem cell, a metastatic tumor cell, or any combination thereof.

In some aspects, provided herein is a method of promoting autophagy or a reduction in accumulation of intracellular noxious substances or pathogens by inhibiting DEspR expression and/or function, the method comprising administering to a subject in need thereof a therapeutically effective amount of any of the pharmaceutical compositions described herein.

In some embodiments of this aspect and all such aspects described herein, the subject has Alzheimer's disease or Huntington's disease.

In some aspects, provided herein is a method of molecular imaging via targeting DEspR, the method comprising administering an effective amount of any of the pharmaceutical compositions described herein conjugated to a targeting moiety, and determining the presence or absence of the pharmaceutical composition conjugated to the targeting moiety using molecular imaging.

In some embodiments of this aspect and all such aspects described herein, the molecular imaging is contrast-enhanced ultrasound imaging, MRI (magnetic resonance imaging), near infrared imaging, or photoacoustics imaging.

In some embodiments of this aspect and all such aspects described herein, the targeting moiety is an antibody, a DEspR-binding peptide ligand, a small molecule, a nanoparticle, a polymer, an aptamer, or any combination thereof.

In some aspects, provided herein is a method for enhancing delivery of a therapeutic agent via DEspR-targeted sonoporation, the method comprising delivering an effective amount of any of the pharmaceutical compositions described herein and a therapeutic agent using targeted ultrasound delivery to a subject in need thereof, wherein delivery of the therapeutic agent is enhanced relative to delivering the therapeutic agent in the absence of the pharmaceutical composition.

In some embodiments of this aspect and all such aspects described herein, the therapeutic agent is a chemotherapeutic agent, a small molecule, a peptide, or an aptamer.

In some aspects, provided herein is a method for reducing toxicity of a therapeutic agent via DEspR-targeted sonoporation, the method comprising delivering an effective amount of any of the pharmaceutical compositions described herein and a therapeutic agent using targeted ultrasound delivery to a subject in need thereof, wherein toxicity of the therapeutic agent is reduced relative to delivering the therapeutic agent in the absence of the pharmaceutical composition.

In some embodiments of this aspect and all such aspects described herein, the therapeutic agent is a chemotherapeutic agent, a small molecule, a peptide, or an aptamer.

In some aspects, provided herein is a method for combining DEspR-targeted molecular imaging and DEspR-targeted delivery of a therapeutic agent, the method comprising administering to a subject an effective amount of a therapeutic agent and any of the pharmaceutical compositions described herein conjugated to a targeting moiety, and determining the presence or absence of the pharmaceutical composition conjugated to the targeting moiety using molecular imaging.

In some embodiments of this aspect and all such aspects described herein, the molecular imaging is contrast-enhanced ultrasound imaging, MRI (magnetic resonance imaging), near infrared imaging, or photoacoustics imaging.

In some embodiments of this aspect and all such aspects described herein, the therapeutic agent is a chemotherapeutic agent, a small molecule, a peptide, or an aptamer.

In some aspects, provided herein is a method of inhibiting tumor vascular leakiness by inhibiting DEspR expression and/or function in a cell, the method comprising administering to a subject in need thereof a therapeutically effective amount of any of the pharmaceutical compositions described herein.

In some embodiments of this aspect and all such aspects described herein, the DEspR expression and/or function is inhibited in a tumor cell, a tumor initiating cell, a cancer stem-like cell, a cancer stem cell, a metastatic tumor cell, an endothelial cell, an endothelial progenitor cell, a stromal cell, an inflammatory cell, or any combination thereof.

In some aspects, provided herein is a method of inhibiting peritoneal carcinomatosis by inhibiting DEspR expression and/or function in a cell, the method comprising administering to a subject in need thereof a therapeutically effective amount of any of the pharmaceutical compositions described herein.

In some embodiments of this aspect and all such aspects described herein, the DEspR expression and/or function is inhibited in a tumor cell, a tumor initiating cell, a cancer stem-like cell, a cancer stem cell, a metastatic tumor cell, an endothelial cell, an endothelial progenitor cell, a stromal cell, an inflammatory cell, a peritoneal mesothelial cell, or any combination thereof.

A method of inhibiting microvascular leakiness, microvascular disruption, microbleeds, or microvascular instability by inhibiting DEspR expression and/or function in a cell, the method comprising administering to a subject in need thereof a therapeutically effective amount of any of the pharmaceutical compositions described herein.

In some embodiments of this aspect and all such aspects described herein, the DEspR expression and/or function is inhibited in an endothelial cell, an endothelial progenitor cell, a pericyte, a vascular wall cell, a stromal cell, an inflammatory cell, or any combination thereof.

In some embodiments of this aspect and all such aspects described herein, the microvascular leakiness, microvascular disruption, microbleeds, or microvascular instability occurs in the brain.

In some aspects, provided herein is a method of inhibiting DEspR expression and/or function using VEGFsp-26 peptide with or without modifications that stabilize the peptide in vivo.

In some embodiments of this aspect and all such aspects described herein, the VEGFsp-26 peptide comprises SEQ ID NO: 47.

In some embodiments of this aspect and all such aspects described herein, the DEspR expression and/or function is inhibited in tumor cell, a tumor initiating cell, a cancer stem-like cell, a cancer stem cell, a metastatic tumor cell, an endothelial cell, an endothelial progenitor cell, a pericyte, a vascular wall cell, a stromal cell, an inflammatory cell, a peritoneal mesothelial cell, or any combination thereof.

In some aspects, provided herein is a method of stimulating DEspR expression and/or function using a VEGFsp-17 peptide with or without modifications that stabilize the peptide in vivo.

In some embodiments of this aspect and all such aspects described herein, the VEGFsp-17 peptide comprises SEQ ID NO: 48.

In some embodiments of this aspect and all such aspects described herein, wherein the DEspR expression and/or function is stimulated an endothelial cell, an endothelial progenitor cell, a pericyte, a vascular wall cell, a stromal cell, an inflammatory cell, or any combination thereof.

Definitions

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology, and molecular biology can be found in The Merck Manual of Diagnosis and Therapy, 19th Edition, published by Merck Sharp & Dohme Corp., 2011 (ISBN 978-0-911910-19-3); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, 4$^{th}$ ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

The term "DEspR binding protein construct" (or "DEspR binding protein") refers to a polypeptide that specifically binds to DEspR and is an Ig-like protein comprising one or more of the antigen binding portions described herein linked to a linker or an immunoglobulin constant domain. A binding protein can be a dual variable domain (DVD-Ig) binding protein. A "linker polypeptide" comprises two or more amino acid residues joined by peptide bonds and are used to link one or more antigen binding portions. Such linker polypeptides are well known in the art (see e.g., Holliger et al. (1993) Proc. Natl. Acad. Sci. USA 90: 6444-6448; Poljak (1994) Structure 2: 1121-1123). An immunoglobulin constant domain refers to a heavy or light chain constant domain. Human IgG heavy chain and light chain constant domain amino acid sequences are known in the art, (e.g., see SEQ ID NO: 197, 198, 199 and 200 of US Application 2016/0200813, which is incorporated herein in its entirety by reference for representative examples). In various embodiments, the binding proteins and antibodies disclosed herein can comprise any of the constant domains of SEQ ID NO: 197, 198, 199 and 200 of US Application 2016/0200813.

The term "antibody" broadly refers to any immunoglobulin (Ig) molecule and immunologically active portions of immunoglobulin molecules (i.e., molecules that contain an antigen binding site that immunospecifically bind an antigen) comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody formats are known in the art. Nonlimiting embodiments of which are discussed below, and include but are not limited to a variety of forms, including full length antibodies and antigen-binding portions thereof; including, for example, an immunoglobulin molecule, a monoclonal antibody, a chimeric antibody, a CDR-grafted antibody, a human antibody, a humanized antibody, a single chain antibody, a Fab, a F(ab'), a F(ab')2, a Fv antibody, fragments produced by a Fab expression library, a disulfide linked Fv, a scFv, a single domain antibody (dAb), a diabody, a multispecific antibody, a dual specific antibody, an anti-idiotypic antibody, a bispecific antibody, a functionally active epitope-binding fragment thereof, bifunctional hybrid antibodies (e.g., Lanzavecchia et al., Eur. J. Immunol. 17, 105 (1987)) and single chains (e.g., Huston et al., Proc. Natl. Acad. Sci. U.S.A., 85, 5879-5883 (1988) and Bird et al., Science 242, 423-426 (1988), which are incorporated herein by reference) and/or antigen-binding fragments of any of the above (See, generally, Hood et al., Immunology, Benjamin, N.Y., 2ND ed. (1984), Harlow and Lane, Antibodies. A Laboratory Manual, Cold Spring Harbor Laboratory (1988) and Hunkapiller and Hood, Nature, 323, 15-16 (1986), which are incorporated herein by reference). Antibodies also refer to immunoglobulin molecules and immunologically active portions of immunoglobulin molecules, i.e., molecules that contain antigen or target binding sites or "antigen-binding fragments." The antibody or immunoglobulin molecules described herein can be of any type (e.g., IgG, IgE, IgM, IgD, IgA and IgY), class (e.g., IgG1, IgG2, IgG3, IgG4, IgA1 and IgA2) or subclass of immunoglobulin molecule, as is understood by one of skill in the art. Furthermore, in humans, the light chain can be a kappa chain or a lambda chain.

In a full-length antibody, each heavy chain is comprised of a heavy chain variable domain (abbreviated herein as HCVR or $V_H$) and a heavy chain constant region. The heavy chain constant region is comprised of three domains: CH1, CH2, and CH3. Each light chain is comprised of a light chain variable domain (abbreviated herein LCVR as $V_L$) and a light chain constant region. The light chain constant region is comprised of one domain, CL. The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. This structure is well-known to those skilled in the art. The chains are usually linked to one another via disulfide bonds.

The term "Fc region" is used to define the C-terminal region of an immunoglobulin heavy chain, which may be generated by papain digestion of an intact antibody. The Fc region may be a native sequence Fc region or a variant Fc region. The Fc region of an immunoglobulin generally comprises two constant domains, a CH2 domain, and a CH3 domain, and optionally comprises a CH4 domain. Replacements of amino acid residues in the Fc portion to alter antibody effector function are known in the art (U.S. Pat. Nos. 5,648,260 and 5,624,821). The Fc portion of an antibody mediates several important effector functions, for example, cytokine induction, ADCC, phagocytosis, complement dependent cytotoxicity (CDC), and half-life/clearance rate of antibody and antigen-antibody complexes. In some cases these effector functions are desirable for therapeutic antibody but in other cases might be unnecessary or even deleterious, depending on the therapeutic objectives. Certain human IgG isotypes, particularly IgG1 and IgG3, mediate ADCC and CDC via binding to Fc.gamma.Rs and complement C1q, respectively. Neonatal Fc receptors (FcRn) are the critical components determining the circulating half-life of antibodies. In still another embodiment at least one amino acid residue is replaced in the constant region of the antibody, for example the Fc region of the antibody, such that effector functions of the antibody are altered.

The term "antigen-binding portion" of an antibody refers to one or more fragments of an antibody that retain the ability to specifically bind to an antigen (e.g., DEspR). Antigen-binding functions of an antibody can be performed by fragments of a full-length antibody. Such antibody fragment embodiments may also be incorporated in bispecific, dual specific, or multi-specific formats such as a dual variable domain (DVD-Ig) format; specifically binding to two or more different antigens (e.g., DEspR and a different antigen molecule). Examples of binding fragments encompassed within the term "antigen-binding portion" of an antibody include (i) a Fab fragment, a monovalent fragment consisting of the VL, VH, CL, and CH1 domains; (ii) a F(ab')$^2$ fragment, a bivalent fragment comprising two Fab fragments linked by a disulfide bridge at the hinge region; (iii) a Fd fragment consisting of the VH and CH1 domains;

(iv) a Fv fragment consisting of the VL and VH domains of a single arm of an antibody, (v) a dAb fragment (Ward et al. (1989) Nature, 341: 544-546; PCT Publication No. WO 90/05144), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see, for example, Bird et al. (1988) Science 242: 423-426; and Huston et al. (1988) Proc. Natl. Acad. Sci. USA 85: 5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see, for example, Holliger et al. (1993) Proc. Natl. Acad. Sci. USA 90: 6444-6448; Poljak (1994) Structure 2: 1121-1123); Kontermann and Dubel eds., Antibody Engineering, Springer-Verlag, N.Y. (2001), p. 790 (ISBN 3-540-41354-5). In addition single chain antibodies also include "linear antibodies" comprising a pair of tandem Fv segments (VH-CH1-VH-CH1) which, together with complementary light chain polypeptides, form a pair of antigen binding regions (Zapata et al. (1995) Protein Eng. 8(10): 1057-1062; and U.S. Pat. No. 5,641,870).

An immunoglobulin constant (C) domain refers to a heavy ($C_H$) or light ($C_L$) chain constant domain. Murine and human IgG heavy chain and light chain constant domain amino acid sequences are known in the art.

As used herein, an "anti-DEspR antibody" refers to an antibody that binds to DEspR with sufficient affinity and specificity. The antibody selected will normally have a binding affinity for DEspR, for example, the antibody can bind human DEspR protein with a $K_D$ value between $10^{-5}$ M to $10^{-10}$ M.

A DEspR binding protein, antibody, or antigen-binding portion thereof, may be part of a larger immunoadhesion molecule, formed by covalent or noncovalent association of the antibody antigen-binding portion with one or more other proteins or peptides. Examples of such immunoadhesion molecules include use of the streptavidin core region to make a tetrameric scFv molecule (Kipriyanov et al. (1995) Human Antibod. Hybridomas 6:93-101) and use of a cysteine residue, a marker peptide and a C-terminal polyhistidine tag to make bivalent and biotinylated scFv molecules (Kipriyanov et al. (1994) Mol. Immunol. 31:1047-1058). Antibody portions, such as Fab and F(ab').sub.2 fragments, can be prepared from whole antibodies using conventional techniques, such as papain or pepsin digestion, respectively, of whole antibodies. Moreover, antibodies, antigen-binding portions thereof, and immunoadhesion molecules can be obtained using standard recombinant DNA techniques. A DEspR binding protein, such as an antigen-binding portion of an antibody may also be part of a dual variable domain (DVD-Ig).

As used herein, the term "target" refers to a biological molecule (e.g., peptide, polypeptide, protein, lipid, carbohydrate) to which a polypeptide domain which has a binding site can selectively bind. The target can be, for example, an intracellular target (e.g., an intracellular protein target) or a cell surface target (e.g., a membrane protein, a receptor protein). Preferably, a target is a cell surface target, such as a cell surface protein.

As described herein, an "antigen" is a molecule that is bound by a binding site on a polypeptide agent, such as a binding protein, an antibody or antibody fragment, or antigen-binding fragment thereof. Typically, antigens are bound by antibody ligands and are capable of raising an antibody response in vivo. An antigen can be a polypeptide, protein, nucleic acid or other molecule. In the case of conventional antibodies and fragments thereof, the antibody binding site as defined by the variable loops (L1, L2, L3 and H1, H2, H3) is capable of binding to the antigen. The term "antigenic determinant" refers to an epitope on the antigen recognized by an antigen-binding molecule, and more particularly, by the antigen-binding site of said molecule.

The term "epitope" includes any polypeptide determinant capable of specific binding to an immunoglobulin or T-cell receptor. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. An epitope is a region of an antigen that is bound by a binding protein. An epitope may be determined by obtaining an X-ray crystal structure of an antibody:antigen complex and determining which residues on the antigen (DEspR) are within a specified distance of residues on the antibody of interest, wherein the specified distance is, 5 Å or less, e.g., 5 Å, 4 Å, 3 Å, 2 Å, 1 Å or any distance in between. In some embodiments, an "epitope" can be formed on a polypeptide (e.g., DEspR) both from contiguous amino acids, or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5, about 9, or about 8-10 amino acids in a unique spatial conformation. An "epitope" includes the unit of structure conventionally bound by an immunoglobulin $V_H/V_L$ pair. Epitopes define the minimum binding site for an antibody, and thus represent the target of specificity of an antibody. In the case of a single domain antibody, an epitope represents the unit of structure bound by a variable domain in isolation. The terms "antigenic determinant" and "epitope" can also be used interchangeably herein. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. In some embodiments, an epitope comprises of 8 or more contiguous or non-contiguous amino acid residues in the DEspR sequence in which at least 50%, 70% or 85% of the residues are within the specified distance of the antibody or binding protein in the X-ray crystal structure.

The terms "specificity" or "specific for" refers to the number of different types of antigens or antigenic determinants to which a binding protein, antibody or antibody fragment, or antigen-binding portion thereof as described herein can bind. The specificity of a binding protein, antibody or antibody fragment, or antigen-binding portion thereof can be determined based on affinity and/or avidity. The affinity, represented by the equilibrium constant for the dissociation ($K_D$) of an antigen with an antigen-binding protein, is a measure of the binding strength between an antigenic determinant and an antigen-binding site on the antigen-binding protein, such as a binding protein, antibody or antibody fragment, or antigen-binding portion thereof: the lesser the value of the $K_D$, the stronger the binding strength between an antigenic determinant and the antigen-binding molecule. Alternatively, the affinity can also be expressed as the affinity constant (KA), which is $1/K_D$). As will be clear to the skilled person, affinity can be determined in a manner known per se, depending on the specific antigen of interest. Accordingly, a binding protein, antibody or antibody fragment, or antigen-binding portion thereof as defined herein is said to be "specific for" a first target or antigen compared to a second target or antigen when it binds to the first antigen with an affinity (as described above, and suitably expressed, for example as a $K_D$ value) that is at least 10 times, such as at least 100 times, and preferably at least 1000 times, and up to 10000 times or more better than the affinity with which said amino acid sequence or polypeptide binds to another target or polypeptide.

Accordingly, as used herein, "selectively binds" or "specifically binds" or "specific binding" in reference to the interaction of an antibody, or antibody fragment thereof, or a binding protein described herein, means that the interaction is dependent upon the presence of a particular structure (e.g., an antigenic determinant or epitope or target) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody. In certain embodiments, a binding protein or antibody or antigen-binding fragment thereof that specifically binds to an antigen binds to that antigen with a $K_D$ greater than $10^{-6}$ M, $10^{-7}$ M, $10^{-8}$ M, $10^{-9}$ M, $10^{-10}$ M, $10^{-11}$M, $10^{-12}$ M, $10^{-13}$ M, $10^{-14}$ M. In other embodiments, a binding protein or antibody or antigen binding fragment thereof that specifically binds to an antigen binds to that antigen with a $K_D$ between $10^{-6}$ and $10^{-7}$M, $10^{-6}$ and $10^{-8}$ M, $10^{-6}$ and $10^{-9}$ M, $10^{-6}$ and $10^{-10}$ M, $10^{-6}$ and $10^{-11}$ M, $10^{-6}$ and $10^{-12}$M, $10^{-6}$ and $10^{-13}$M, $10^{-6}$ and $10^{-14}$M, $10^{-9}$ and $10^{-10}$ M, $10^{-9}$ and $10^{-11}$ M, $10^{-9}$ and $10^{-12}$M, $10^{-9}$ and $10^{-13}$M, $10^{-9}$ and $10^{-14}$M. In some embodiments, a binding protein or antibody or antigen-binding fragment thereof binds to an epitope, with a $K_D$ $10^{-5}$ M (10000 nM) or less, e.g., $10^{-6}$ M, $10^{-7}$ M, $10^{-8}$ M, $10^{-9}$ M, $10^{-10}$ M, $10^{-11}$ M, $10^{-12}$ M, or less. Specific binding can be influenced by, for example, the affinity and avidity of the polypeptide agent and the concentration of polypeptide agent. The person of ordinary skill in the art can determine appropriate conditions under which the polypeptide agents described herein selectively bind the targets using any suitable methods, such as titration of a polypeptide agent in a suitable cell binding assay. In certain embodiments, a binding protein or antibody or antigen-binding fragment thereof is said to "specifically bind" an antigen when it preferentially recognizes its target antigen in a complex mixture of proteins and/or macromolecules. Binding proteins, antibodies or antigen-binding fragments that bind to the same or similar epitopes will likely cross-compete (one prevents the binding or modulating effect of the other). Cross-competition, however, can occur even without epitope overlap, e.g., if epitopes are adjacent in three-dimensional space and/or due to steric hindrance.

Avidity is the measure of the strength of binding between an antigen-binding molecule (such as a binding protein, antibody or antibody fragment, or antigen-binding portion thereof described herein) and the pertinent antigen. Avidity is related to both the affinity between an antigenic determinant and its antigen binding site on the antigen-binding molecule, and the number of pertinent binding sites present on the antigen-binding molecule. Typically, antigen-binding proteins (such as a binding protein, antibody or antibody fragment, or antigen-binding portion thereof described herein) will bind to their cognate or specific antigen with a dissociation constant ($K_D$ of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e., with an association constant ($K_A$) of $10^5$ to $10^{12}$ liter/moles or more, and preferably $10^7$ to $10^{12}$ liter/moles or more and more preferably $10^8$ to $10^{12}$ liter/moles). Any $K_D$ value greater than $10^{-4}$ mol/liter (or any KA value lower than $10^4$ $M^{-1}$) is generally considered to indicate non-specific binding. The $K_D$ for biological interactions which are considered meaningful (e.g., specific) are typically in the range of $10^{-10}$ M (0.1 nM) to $10^{-5}$ M (10000 nM). The stronger an interaction is, the lower is its $K_D$. Preferably, a binding site on a binding protein, antibody or antibody fragment, or antigen-binding portion thereof described herein will bind to the desired antigen with an affinity less than 500 nM, preferably less than 200 nM, more preferably less than 10 nM, such as less than 500 pM. Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as other techniques as mentioned herein.

In some embodiments, an anti-DEspR binding protein, antibody or antibody fragment, or antigen-binding portion thereof described herein binds to DEspR, with a $K_D$ $10^{-5}$ M (10000 nM) or less, e.g., $10^{-6}$ M, $10^{-7}$ M, $10^{-8}$ M, $10^{-9}$ M, $10^{-10}$ M, $10^{-11}$ M, $10^{-12}$ M, or less. In some embodiments, where an antibody or antigen-binding fragment thereof is directed to an epitope or antigenic peptide, the antibody or antigen-binding fragment thereof can be referred to, for example, as an antibody or antigen-binding fragment thereof directed to or specific for SEQ ID NO: 1 or SEQ ID NO: 2.

The term "$K_{on}$" (also "Kon", "kon"), as used herein, is intended to refer to the on rate constant for association of a binding protein, antibody or antigen-binding fragment to an antigen to form an association complex, e.g., binding protein/antigen complex, as is known in the art. The "$K_{on}$" also is known by the terms "association rate constant", or "ka", as used interchangeably herein. This value indicates the binding rate of a binding protein to its target antigen or the rate of complex formation between an antibody and antigen as is shown by the equation below:

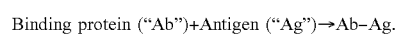

Binding protein ("Ab")+Antigen ("Ag")→Ab–Ag.

The term "$K_{off}$" (also "Koff", "koff"), as used herein, is intended to refer to the off rate constant for dissociation, or "dissociation rate constant", of a binding protein, antibody or antigen-binding fragment from an association complex (e.g., a binding protein/antigen complex) as is known in the art. This value indicates the dissociation rate of an antibody from its target antigen or separation of Ab-Ag complex over time into free binding protein and antigen as shown by the equation below:

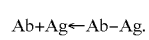

Ab+Ag←Ab–Ag.

The term "$K_D$" (also "$K_d$"), as used herein, is intended to refer to the "equilibrium dissociation constant", and refers to the value obtained in a titration measurement at equilibrium, or by dividing the dissociation rate constant (Koff) by the association rate constant (Kon). The association rate constant (Kon), the dissociation rate constant (Koff), and the equilibrium dissociation constant (K are used to represent the binding affinity of a binding protein to an antigen. Methods for determining association and dissociation rate constants are well known in the art. Using fluorescence-based techniques offers high sensitivity and the ability to examine samples in physiological buffers at equilibrium. Other experimental approaches and instruments such as a BIAcore® (biomolecular interaction analysis) assay can be used (e.g., instrument available from BIAcore International AB, a GE Healthcare company, Uppsala, Sweden). Additionally, a KinExA® (Kinetic Exclusion Assay) assay, available from Sapidyne Instruments (Boise, Id.) can also be used.

The term "antibody fragment," or "antigen-binding fragment" as used herein, refer to a protein fragment that comprises only a portion of an intact antibody, generally including an antigen binding site of the intact antibody and thus retaining the ability to bind antigen. Examples of antibody fragments encompassed by the present definition include: (i) the Fab fragment, having $V_L$, $C_L$, $V_H$ and $C_H1$ domains; (ii) the Fab' fragment, which is a Fab fragment having one or more cysteine residues at the C-terminus of the $C_H1$ domain; (iii) the Fd fragment having $V_H$ and $C_H1$ domains; (iv) the Fd' fragment having $V_H$ and $C_H1$ domains and one or more cysteine residues at the C-terminus of the $C_H1$ domain; (v) the Fv fragment having the $V_L$ and $V_H$ domains of a single arm of an antibody; (vi) the dAb fragment (Ward et al., Nature 341, 544-546 (1989)) which consists of a $V_H$ domain; (vii) isolated CDR regions; (viii) F(ab')$_2$ fragments, a bivalent fragment including two Fab' fragments linked by a disulphide bridge at the hinge region; (ix) single chain antibody molecules (e.g., single chain Fv; scFv) (Bird et al., Science 242:423-426 (1988); and Huston et al., PNAS (USA) 85:5879-5883 (1988)); (x) "diabodies" with two antigen binding sites, comprising a heavy chain variable domain ($V_H$) connected to a light chain variable domain ($V_L$) in the same polypeptide chain (see, e.g., EP 404,097; WO 93/11161; and Hollinger et al., Proc. Natl. Acad. Sci. USA, 90:6444-6448 (1993)); (xi) "linear antibodies" comprising a pair of tandem Fd segments ($V_H$-$C_H1$-$V_H$-$C_H1$) which, together with complementary light chain polypeptides, form a pair of antigen binding regions (Zapata et al. Protein Eng. 8(10):1057-1062 (1995); and U.S. Pat. No. 5,641,870).

The term anti-DEspR "antigen-binding fragment" refers to a protein fragment that comprises at least an antigen binding site of the intact antibody and thus retains the ability to bind a DEspR antigen or epitope. Non-limiting examples of antibody fragments encompassed by the term antigen-binding fragment include: (i) the Fab fragment, having $V_L$, $C_L$, $V_H$ and $C_H1$ domains; (ii) the Fab' fragment, which is a Fab fragment having one or more cysteine residues at the C-terminus of the $C_H1$ domain; (iii) the Fd fragment having $V_H$ and $C_H1$ domains; (iv) the Fd' fragment having $V_H$ and $C_H1$ domains and one or more cysteine residues at the C-terminus of the CH1 domain; (v) the Fv fragment having the $V_L$ and $V_H$ domains of a single arm of an antibody; (vi) the dAb fragment (Ward et al., Nature 341, 544-546 (1989)) which consists of a $V_H$ domain; (vii) isolated CDR regions; (viii) F(ab')$_2$ fragments, a bivalent fragment including two Fab' fragments linked by a disulphide bridge at the hinge region; (ix) single chain antibody molecules (e.g., single chain Fv; scFv) (Bird et al., Science 242:423-426 (1988); and Huston et al., PNAS (USA) 85:5879-5883 (1988)); (x) "diabodies" with two antigen binding sites, comprising a heavy chain variable domain ($V_H$) connected to a light chain variable domain ($V_L$) in the same polypeptide chain (see, e.g., EP 404,097; WO 93/11161; and Hollinger et al., Proc. Natl. Acad. Sci. USA, 90:6444-6448 (1993)); (xi) "linear antibodies" comprising a pair of tandem Fd segments ($V_H$-$C_H1$-$V_H$-$C_H1$) which, together with complementary light chain polypeptides, form a pair of antigen binding regions (Zapata et al. Protein Eng. 8(10):1057-1062 (1995); and U.S. Pat. No. 5,641,870).

An "Fv" fragment is an antibody fragment which contains a complete antigen recognition and binding site. This region consists of a dimer of one heavy and one light chain variable domain in tight association, which can be covalent in nature, for example in scFv. It is in this configuration that the three CDRS of each variable domain interact to define an antigen binding site on the surface of the $V_H$-$V_L$ dimer. Collectively, the six CDRS or a subset thereof confer antigen binding specificity to the antibody. However, even a single variable domain (or half of an Fv comprising only three CDRS specific for an antigen) has the ability to recognize and bind antigen, although usually at a lower affinity than the entire binding site.

The "Fab" fragment contains a variable and constant domain of the light chain and a variable domain and the first constant domain ($C_H1$) of the heavy chain. F(ab')$_2$ antibody fragments comprise a pair of Fab fragments which are generally covalently linked near their carboxy termini by hinge cysteines between them. Other chemical couplings of antibody fragments are also known in the art.

"Single-chain Fv" or "scFv" antibody fragments comprise the $V_H$ and $V_L$ domains of antibody, wherein these domains are present in a single polypeptide chain. Generally the Fv polypeptide further comprises a polypeptide linker between the $V_H$ and $V_L$ domains, which enables the scFv to form the desired structure for antigen binding. For a review of scFv, see Pluckthun in The Pharmacology of Monoclonal Antibodies, Vol 113, Rosenburg and Moore eds. Springer-Verlag, New York, pp. 269-315 (1994).

The term "monoclonal antibody" or "mAb" as used herein refers to an antibody obtained from a population of substantially homogeneous antibodies, i.e., the individual antibodies comprising the population are identical except for possible naturally occurring mutations that can be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen. The modifier "monoclonal" is not to be construed as requiring production of the antibody by any particular method. For example, the monoclonal antibodies to be used in accordance with the invention can be made by the hybridoma method first described by Kohler et al., Nature 256:495 (1975), or can be made by recombinant DNA methods (see, e.g., U.S. Pat. No. 4,816,567). The "monoclonal antibodies" can also be isolated from phage antibody libraries using the techniques described in Clackson et al., Nature 352:624-628 (1991) or Marks et al., J. Mol. Biol. 222:581-597 (1991), for example. A monoclonal antibody can be of any species, including, but not limited to, mouse, rat, goat, rabbit, and human monoclonal antibodies. Various methods for making monoclonal antibodies specific for DEspR as described herein are available in the art. For example, the monoclonal antibodies can be made using the hybridoma method first described by Kohler et al., Nature, 256:495 (1975), or by recombinant DNA methods (U.S. Pat. No. 4,816,567). "Monoclonal antibodies" can also be isolated from or produced using phage antibody libraries using the techniques originally described in Clackson et al., Nature 352:624-628 (1991), Marks et al., J. Mol. Biol. 222:581-597 (1991), McCafferty et al., Nature, 348:552-554 (1990), Marks et al., Bio/Technology, 10:779-783 (1992)), Waterhouse et al., Nuc. Acids. Res., 21:2265-2266 (1993), and techniques known to those of ordinary skill in the art.

The term "human antibody" includes antibodies having variable and constant regions derived from human germline immunoglobulin sequences. The human antibodies of the disclosure may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody" does not include antibodies in which CDR sequences derived from the germline of another mammalian species, such as a mouse, have been grafted onto human framework sequences.

The term "recombinant human antibody" includes all human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse) that is transgenic for human immunoglobulin genes, or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "chimeric antibody" refers to antibodies that comprise heavy and light chain variable domain sequences from one species and constant region sequences from another species, such as antibodies having murine heavy and light chain variable domains linked to human constant regions.

The term "CDR-grafted antibody" refers to antibodies that comprise heavy and light chain variable domain sequences from one species but in which the sequences of one or more of the CDR regions of VH and/or VL are replaced with CDR sequences of another species, such as antibodies having murine heavy and light chain variable domains in which one or more of the murine CDRs (e.g., CDR3) has been replaced with human CDR sequences.

The term "CDR" refers to the complementarity determining region within antibody variable sequences. There are three CDRs in each of the variable domains of the heavy chain and the light chain, which are designated CDR1, CDR2 and CDR3, for each of the variable domains. The term "CDR set" as used herein refers to a group of three CDRS that occur in a single variable domain capable of binding the antigen. The exact boundaries of these CDRS have been defined differently according to different systems. The system described by Kabat (Kabat et al., Sequences of Proteins of Immunological Interest, National Institutes of Health, Bethesda, Md. (1987) and (1991)) not only provides an unambiguous residue numbering system applicable to any variable domain of an antibody, but also provides precise residue boundaries defining the three CDRs. These CDRs may be referred to as Kabat CDRs. Chothia and coworkers (Chothia et al. (1987) J. Mol. Biol. 196: 901-917; and Chothia et al. (1989) Nature 342: 877-883) found that certain sub-portions within Kabat CDRS adopt nearly identical peptide backbone conformations, despite having great diversity at the level of amino acid sequence. These sub-portions were designated as L1, L2, and L3 or H1, H2, and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan et al. ((1995) FASEB J. 9:133-139) and MacCallum et al. ((1996) J. Mol. Biol. 262(5):732-745). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRS defined according to any of these systems, although exemplary embodiments use Kabat or Chothia defined CDRs.

The terms "Kabat numbering", "Kabat definitions", and "Kabat labeling" are used interchangeably herein. These terms, which are recognized in the art, refer to a system of numbering amino acid residues which are more variable (i.e., hypervariable) than other amino acid residues in the heavy and light chain variable domains of an antibody, or an antigen binding portion thereof (Kabat et al. (1971) Ann. NY Acad. Sci. 190:382-391; and Kabat et al. (1991) Sequences of Proteins of Immunological Interest, Fifth Edition, U.S. Department of Health and Human Services, NIH Publication No. 91-3242, which is also available on the world wide web, and is expressly incorporated herein in its entirety by reference. The "EU index as in Kabat" refers to the residue numbering of the human IgG1 EU antibody. As used herein, "Kabat sequence numbering" refers to numbering of the sequence encoding a variable region according to the EU index as in Kabat. In some embodiments, IMGT (INTERNATIONAL IMMUNOGENETICS INFORMATION SYSTEM) numbering of variable regions can also be used, which is the numbering of the residues in an immunoglobulin variable heavy or light chain according to the methods of the IIMGT, as described in Lefranc, M.-P., "The IMGT unique numbering for immunoglobulins, T cell Receptors and Ig-like domains", The Immunologist, 7, 132-136 (1999), and is expressly incorporated herein in its entirety by reference. As used herein, "IMGT sequence numbering" refers to numbering of the sequence encoding a variable region according to the IMGT. For the heavy chain variable domain, the hypervariable region ranges from amino acid positions 31 to 35 for CDR1, amino acid positions 50 to 65 for CDR2, and amino acid positions 95 to 102 for CDR3. For the light chain variable domain, the hypervariable region ranges from amino acid positions 24 to 34 for CDR1, amino acid positions 50 to 56 for CDR2, and amino acid positions 89 to 97 for CDR3.

The growth and analysis of extensive public databases of amino acid sequences of variable heavy and light regions over the past twenty years have led to the understanding of the typical boundaries between framework regions (FR) and CDR sequences within variable region sequences and enabled persons skilled in this art to accurately determine the CDRs according to Kabat numbering, Chothia numbering, or other systems. See, e.g., Martin, "Protein Sequence and Structure Analysis of Antibody Variable Domains," Chapter 31, In Antibody Engineering, (Kontermann and Dubel, eds.) (Springer-Verlag, Berlin, 2001), especially pages 432-433. A useful method of determining the amino acid sequences of Kabat CDRs within the amino acid sequences of variable heavy (VH) and variable light (VL) regions are known in the art, e.g., as follows:

To identify a CDR-L1 amino acid sequence: Starts approximately 24 amino acid residues from the amino terminus of the VL region; Residue before the CDR-L1 sequence is always cysteine (C); Residue after the CDR-L1 sequence is always a tryptophan (W) residue, typically Trp-Tyr-Gln (W-Y-Q), but also Trp-Leu-Gln (W-L-Q), Trp-Phe-Gln (W-F-Q), and Trp-Tyr-Leu (W-Y-L); Length is typically 10 to 17 amino acid residues. To identify a CDR-L2 amino acid sequence: Starts always 16 residues after the end of CDR-L1; Residues before the CDR-L2 sequence are generally Ile-Tyr (I-Y), but also Val-Tyr (V-Y), Ile-Lys (1-K), and Ile-Phe (1-F); Length is always 7 amino acid residues. To identify a CDR-L3 amino acid sequence: Starts always 33 amino acids after the end of CDR-L2; Residue before the CDR-L3 amino acid sequence is always a cysteine (C); Residues after the CDR-L3 sequence are always Phe-Gly-X-Gly (F-G-X-G) (SEQ ID NO: 68), where X is any amino acid; Length is typically 7 to 11 amino acid residues.

To identify a CDR-H1 amino acid sequence: Starts approximately 31 amino acid residues from amino terminus of VH region and always 9 residues after a cysteine (C); Residues before the CDR-H1 sequence are always Cys-X-X-X-X-X-X-X-X (SEQ ID NO: 69), where X is any amino acid; Residue after CDR-H1 sequence is always a Trp (W), typically Trp-Val (W-V), but also Trp-Ile (W-I), and Trp-Ala (W-A); Length is typically 5 to 7 amino acid residues. To identify a CDR-H2 amino acid sequence: Starts always 15 amino acid residues after the end of CDR-H1; Residues before CDR-H2 sequence are typically Leu-Glu-Trp-Ile-Gly (L-E-W-I-G) (SEQ ID NO: 70), but other variations also; Residues after CDR-H2 sequence are Lys/Arg-Leu/Ile/Val/Phe/Thr/Ala-Thr/Ser/Ile/Ala (K/R-L/I/V/F/T/A-T/S/I/A); Length is typically 16 to 19 amino acid residues. To identify a CDR-H3 amino acid sequence: Starts always 33 amino acid residues after the end of CDR-H2 and always 3 after a cysteine (C)' Residues before the CDR-H3 sequence are always Cys-X-X (C-X-X), where X is any amino acid, typically Cys-Ala-Arg (C-A-R); Residues after the CDR-H3 sequence are always Trp-Gly-X-Gly (W-G-X-G) (SEQ ID NO: 71), where X is any amino acid; Length is typically 3 to 25 amino acid residues.

As used herein, the term "canonical" residue refers to a residue in a CDR or framework that defines a particular canonical CDR structure as defined by Chothia et al. ((1987) J. Mol. Biol. 196: 901-917); and Chothia et al. ((1992) J. Mol. Biol. 227: 799-817), both are incorporated herein by reference). According to Chothia et al., critical portions of the CDRS of many antibodies have nearly identical peptide backbone confirmations despite great diversity at the level of amino acid sequence. Each canonical structure specifies primarily a set of peptide backbone torsion angles for a contiguous segment of amino acid residues forming a loop.

As used herein, "antibody variable domain" refers to the portions of the light and heavy chains of antibody molecules that include amino acid sequences of Complementarity Determining Regions (CDRs; i.e., CDR1, CDR2, and CDR3), and Framework Regions (FRs). Each heavy chain is composed of a variable region of the heavy chain ($V_H$ refers to the variable domain of the heavy chain) and a constant region of said heavy chain. The heavy chain constant region consists of three domains CH1, CH2 and CH3. Each light chain is composed of a variable region of said light chain ($V_L$ refers to the variable domain of the light chain) and a constant region of the light chain. The light chain constant region consists of a CL domain. The VH and VL regions can be further divided into hypervariable regions referred to as complementarity-determining regions (CDRs) and interspersed with conserved regions referred to as framework regions (FR). Each VH and VL region thus consists of three CDRS and four FRs that are arranged from the N terminus to the C terminus in the following order: FR1, CDR1, FR2, CDR2, FR3, CDR3, FR4. This structure is well known to those skilled in the art. According to the methods used herein, the amino acid positions assigned to CDRs and FRs can be defined according to Kabat (Sequences of Proteins of Immunological Interest (National Institutes of Health, Bethesda, Md., 1987 and 1991)). Amino acid numbering of antibodies or antigen binding fragments is also according to that of Kabat.

As used herein, the term "Complementarity Determining Regions" ("CDRs"), i.e., CDR1, CDR2, and CDR3) refers to the amino acid residues of an antibody variable domain the presence of which are necessary for antigen binding. Each variable domain typically has three CDR regions identified as CDR1, CDR2 and CDR3. Each complementarity determining region can comprise amino acid residues from a "complementarity determining region" as defined by Kabat (i.e., about residues 24-34 (L1), 50-56 (L2) and 89-97 (L3) in the light chain variable domain and 31-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" (i.e., about residues 26-32 (L1), 50-52 (L2) and 91-96 (L3) in the light chain variable domain and 26-32 (H1), 53-55 (H2) and 96-101 (H3) in the heavy chain variable domain; Chothia and Lesk J. Mol. Biol. 196:901-917 (1987)). In some instances, a complementarity determining region can include amino acids from both a CDR region defined according to Kabat and a hypervariable loop. For example, the CDRH1 of the heavy chain of antibody 4D5 includes amino acids 26 to 35.

As used herein, the term "CDR" refers to the complementarity determining region within antibody variable sequences. There are three CDRs in each of the variable regions of the heavy chain and of the light chain, which are designated CDR 1, CDR2 and CDR3, for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al, Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Each complementarity determining region may comprise amino acid residues from a "complementarity determining region" as defined by Kabat (i.e. about residues 24-34 (L1), 50-56 (L2) and 89-97 (L3) in the light chain variable domain and 31-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" (i.e. about residues 26-32 (L1), 50-52 (L2) and 91-96 (L3) in the light chain variable domain and 26-32 (H1), 53-55 (H2) and 96-101 (H3) in the heavy chain variable domain; Chothia and Lesk J. Mol. Biol. 196:901-917 (1987)). In some instances, a complementarity determining region can include amino acids from both a CDR region defined according to Kabat and a hypervariable loop. For example, the CDRH1 of the human heavy chain of antibody 4D5 includes amino acids 26 to 35. Chothia and coworkers (Chothia & Lesk, J. Mol. Biol, 196:901-917 (1987) and Chothia et al., Nature 342:877-883 (-1989)) found that certain sub-portions within Kabat CDRs adopt nearly identical peptide backbone conformations, in spite of great diversity at the level of amino acid sequence. These sub-portions were designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (FASEB). 9:133-139 (1995)) and MacCallum (J Mol Biol 262(5):732-45 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRS do not significantly impact antigen binding. The methods used herein may utilize CDRS defined according to any of these systems, although preferred embodiments use Kabat or Chothia defined CDRs. As used herein, "antibody variable domain" refers to the portions of the light and heavy chains of antibody molecules that include amino acid sequences of Complementarity Determining Regions (CDRs; ie., CDR1, CDR2, and CDR3), and Framework Regions (FRs). $V_H$ refers to the variable domain of the heavy chain. $V_L$ refers to the variable domain of the light chain. According to the methods used in this invention, the amino acid positions assigned to CDRS and FRs may be defined according to Kabat (Sequences of Proteins of Immunological Interest (National Institutes of Health, Bethesda, Md., 1987 and 1991)). Amino acid numbering of antibodies or antigen binding fragments is also according to that of Kabat. CDRS can also be described as comprising amino acid residues from a "complementarity determining region" as defined by the IMGT, in some embodiments.

The term "multivalent binding protein" denotes a binding protein comprising two or more antigen binding sites. A multivalent binding protein may be engineered to have three or more antigen binding sites, and is generally not a naturally occurring antibody. The term "multispecific binding protein" refers to a binding protein capable of binding two or more related or unrelated targets.

Similarly, unless indicated otherwise, the expression "multivalent antibody" is used throughout this specification to denote an antibody comprising three or more antigen binding sites. For example, the multivalent antibody is engineered to have the three or more antigen binding sites and is generally not a native sequence IgM or IgA antibody.

In some embodiments, the binding protein is a single chain dual variable domain immunoglobulin protein. The terms "single chain dual variable domain immunoglobulin protein" or "scDVD-Ig protein" or scFvDVD-Ig protein" refer to the antigen binding fragment of a DVD molecule that is analogous to an antibody single chain Fv fragment. scDVD-Ig proteins are described in U.S. Ser. Nos. 61/746,659; 14/141,498 (US application 2014/0243228); and Ser. No. 14/141,500 (US application 2014/0221621), which are incorporated herein by reference in their entireties. In an embodiment, the variable domains of a scDVD-Ig protein are antibody variable domains. In an embodiment, the variable domains are non-immunoglobulin variable domains (e.g., receptor).

In some embodiments, the binding protein is a DVD-Fab. The terms "DVD-Fab" or fDVD-Ig protein" refer to the antigen binding fragment of a DVD-Ig molecule that is analogous to an antibody Fab fragment. fDVD-Ig proteins are described in U.S. Ser. Nos. 61/746,663; 14/141,498 (US Application 2014/0243228); and Ser. No. 14/141,501 (US application US 2014/0235476), incorporated herein by reference in their entireties.

In some embodiments, the binding protein is a receptor DVD-Ig protein. The terms "receptor DVD-Ig protein" constructs, or "rDVD-Ig protein" refer to DVD-Ig™ constructs comprising at least one receptor-like binding domain. rDVD-Ig proteins are described in U.S. Ser. Nos. 61/746,616; and Ser. No. 14/141,499 (US application 2014/0219913), which are incorporated herein by reference in their entireties.

The term "receptor domain" (RD), or receptor binding domain refers to the portion of a cell surface receptor, cytoplasmic receptor, nuclear receptor, or soluble receptor that functions to bind one or more receptor ligands or signaling molecules (e.g., toxins, hormones, neurotransmitters, cytokines, growth factors, or cell recognition molecules).

The terms multi-specific and multivalent IgG-like molecules or "pDVD-Ig" proteins are capable of binding two or more proteins (e.g., antigens). pDVD-Ig proteins are described in U.S. Ser. No. 14/141,502 (US Application 2014/0213771), incorporated herein by reference in its entirety. In certain embodiments, pDVD-Ig™ proteins are disclosed which are generated by specifically modifying and adapting several concepts. These concepts include but are not limited to: (1) forming Fc heterodimer using CH3 "knobs-into-holes" design, (2) reducing light chain missing pairing by using CH1/CL cross-over, and (3) pairing two separate half IgG molecules at protein production stage using "reduction then oxidation" approach.

In certain embodiments, a binding protein disclosed herein is a "half-DVD-Ig" comprised of one DVD-Ig heavy chain and one DVD-Ig light chain. The half-DVD-Ig™ protein preferably does not promote cross-linking observed with naturally occurring antibodies which can result in antigen clustering and undesirable activities. See U.S. Patent Publication No. 2012/0201746 which is incorporated by reference herein in its entirety. In some embodiments, the binding protein is a pDVD-Ig protein. In one embodiment, a pDVD-Ig construct may be created by combining two halves of different DVD-Ig molecules, or a half DVD-Ig protein and half IgG molecule.

In some embodiments, the binding protein is an mDVD-Ig protein. As used herein "monobody DVD-Ig protein" or "mDVD-Ig protein" refers to a class of binding molecules wherein one binding arm has been rendered non-functional. mDVD-Ig proteins are described in U.S. Ser. No. 14/141,503 (US Application 2014/0221622) incorporated herein by reference in its entirety.

The Fc regions of the two polypeptide chains that have a formula of VDH-(X1)n-C-(X2)n may each contain a mutation, wherein the mutations on the two Fc regions enhance heterodimerization of the two polypeptide chains. In one aspect, knobs-into-holes mutations may be introduced into these Fc regions to achieve heterodimerization of the Fc regions. See Atwell et al. (1997) J. Mol. Biol. 270:26-35.

In some embodiments, the binding protein is a cross-over DVD-Ig protein. As used herein "cross-over DVD-Ig" protein or "coDVD-Ig" protein refers to a DVD-Ig protein wherein the cross-over of variable domains is used to resolve the issue of affinity loss in the inner antigen-binding domains of some DVD-Ig molecules. coDVD-Ig proteins are described in U.S. Ser. No. 14/141,504, incorporated herein by reference in its entirety.

In certain embodiments, a binding protein that binds to DEspR (e.g., one or any combination of human, cynomolgus, mouse and rat DEspR) is provided as part of a bispecific antibody. The term "bispecific antibody", as used herein, refers to full-length antibodies that are generated by quadroma technology (see Milstein et al. (1983) Nature 305: 537-540), by chemical conjugation of two different monoclonal antibodies (see Staerz et al. (1985) Nature 314: 628-631), or by knob-into-hole or similar approaches which introduces mutations in the Fc region (see Holliger et al. (1993) Proc. Natl. Acad. Sci. USA 90(14): 6444-6448), resulting in multiple different immunoglobulin species of which only one is the functional bispecific antibody. By molecular function, a bispecific antibody binds one antigen (or epitope) on one of its two binding arms (one pair of HC/LC), and binds a different antigen (or epitope) on its second arm (a different pair of HC/LC). By this definition, a bispecific antibody has two distinct antigen binding arms (in both specificity and CDR sequences), and is monovalent for each antigen it binds.

The term "dual-specific antibody", as used herein, refers to full-length antibodies that can bind two different antigens (or epitopes) in each of its two binding arms (a pair of HC/LC) (see PCT Publication No. WO 02/02773). Accordingly a dual-specific binding protein has two identical antigen binding arms, with identical specificity and identical CDR sequences, and is bivalent for each antigen to which it binds.

A "functional antigen binding site" of a binding protein is one that is capable of binding a target antigen. The antigen binding affinity of the antigen binding site is not necessarily as strong as the parent antibody from which the antigen binding site is derived, but the ability to bind antigen must be measurable using any one of a variety of methods known for evaluating antibody binding to an antigen. Moreover, the antigen binding affinity of each of the antigen binding sites of a multivalent antibody herein need not be quantitatively the same.

As used herein, the terms "donor" and "donor antibody" refer to an antibody providing one or more CDRs. In an exemplary embodiment, the donor antibody is an antibody from a species different from the antibody from which the framework regions are obtained or derived. In the context of a humanized antibody, the term "donor antibody" refers to a non-human antibody providing one or more CDRs.

As used herein, the terms "acceptor" and "acceptor antibody" refer to the antibody providing or nucleic acid sequence encoding at least 80%, at least 85%, at least 90%, at least 95%, at least 98%, or 100% of the amino acid sequences of one or more of the framework regions. In some embodiments, the term "acceptor" refers to the antibody amino acid providing or nucleic acid sequence encoding the constant region(s). In yet another embodiment, the term "acceptor" refers to the antibody amino acid providing or nucleic acid sequence encoding one or more of the framework regions and the constant region(s). In a specific embodiment, the term "acceptor" refers to a human antibody amino acid or nucleic acid sequence that provides or encodes at least 80%, preferably, at least 85%, at least 90%, at least 95%, at least 98%, or 100% of the amino acid sequences of one or more of the framework regions. In accordance with this embodiment, an acceptor may contain at least 1, at least 2, at least 3, least 4, at least 5, or at least 10 amino acid residues that does (do) not occur at one or more specific positions of a human antibody. An acceptor framework region and/or acceptor constant region(s) may be, e.g., derived or obtained from a germline antibody gene, a mature antibody gene, a functional antibody (e.g., antibodies well known in the art, antibodies in development, or antibodies commercially available).

Human heavy chain and light chain acceptor sequences are known in the art. In one embodiment of the disclosure the human heavy chain and light chain acceptor sequences are selected from the sequences listed from V-base (vbase.mrc-cpe.cam.ac.uk/) or from IMGT™ the international ImMunoGeneTics Information System™. (imgt.cines.fr/textes/IMGTrepertoire/LocusGenes/). In another embodiment of the disclosure the human heavy chain and light chain acceptor sequences are selected from the sequences described in Table 3 and Table 4 of U.S. Patent Publication No. 2011/0280800, incorporated by reference herein in their entireties.

As used herein, the term "germline antibody gene" or "gene fragment" refers to an immunoglobulin sequence encoded by non-lymphoid cells that have not undergone the maturation process that leads to genetic rearrangement and mutation for expression of a particular immunoglobulin. (See, e.g., Shapiro et al. (2002) Crit. Rev. Immunol. 22(3): 183-200; Marchalonis et al. (2001) Adv. Exp. Med. Biol. 484:13-30). One of the advantages provided by various embodiments of the present disclosure stems from the recognition that germline antibody genes are more likely than mature antibody genes to conserve essential amino acid sequence structures characteristic of individuals in the species, hence less likely to be recognized as from a foreign source when used therapeutically in that species.

As used herein, the term "key" residues refer to certain residues within the variable domain that have more impact on the binding specificity and/or affinity of an antibody, in particular a humanized antibody. A key residue includes, but is not limited to, one or more of the following: a residue that is adjacent to a CDR, a potential glycosylation site (can be either N- or O-glycosylation site), a rare residue, a residue capable of interacting with the antigen, a residue capable of interacting with a CDR, a canonical residue, a contact residue between heavy chain variable domain and light chain variable domain, a residue within the Vernier zone, and a residue in the region that overlaps between the Chothia definition of a variable heavy chain CDR/and the Kabat definition of the first heavy chain framework.

The term "Framework regions" (hereinafter "FR") refers to the variable domain residues that are not the CDR residues. Because the exact definition of a CDR sequence can be determined by different systems, the meaning of a framework sequence is subject to correspondingly different interpretations. The six CDRS (CDR-L1, -L2, and -L3 of light chain and CDR-H1, -H2, and -H3 of heavy chain) also divide the framework regions on the light chain and the heavy chain into four sub-regions (FR1, FR2, FR3 and FR4)

on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FR's within the variable domain of a single, naturally occurring immunoglobulin chain. As used herein, a FR represents one of the four sub-regions, and FRs represents two or more of the four sub-regions constituting a framework region. Without wishing to be bound by theory, each variable domain typically has four FRs identified as FR1, FR2, FR3 and FR4. If the CDRS are defined according to Kabat, the light chain FR residues are positioned at about residues 1-23 (LCFR1), 35-49 (LCFR2), 57-88 (LCFR3), and 98-107 (LCFR4) and the heavy chain FR residues are positioned about at residues 1-30 (HCFR1), 36-49 (HCFR2), 66-94 (HCFR3), and 103-113 (HCFR4) in the heavy chain residues. If the CDRS comprise amino acid residues from hypervariable loops, the light chain FR residues are positioned about at residues 1-25 (LCFR1), 33-49 (LCFR2), 53-90 (LCFR3), and 97-107 (LCFR4) in the light chain and the heavy chain FR residues are positioned about at residues 1-25 (HCFR1), 33-52 (HCFR2), 56-95 (HCFR3), and 102-113 (HCFR4) in the heavy chain residues. In some instances, when the CDR comprises amino acids from both a CDR as defined by Kabat and those of a hypervariable loop, the FR residues will be adjusted accordingly. For example, when CDRH1 includes amino acids H26-H35, the heavy chain FR1 residues are at positions 1-25 and the FR2 residues are at positions 36-49.

An "isolated antibody" is intended to refer to an antibody that is substantially free of other antibodies having different antigenic specificities (e.g., an isolated antibody that specifically binds DEspR is substantially free of antibodies that specifically bind antigens other than DEspR). An isolated antibody that specifically binds DEspR may, however, have cross-reactivity to other antigens, such as DEspR molecules from other species. In alternative embodiments, an isolated antibody that specifically binds DEspR may specifically bind to the human DEspR molecule. Moreover, an isolated antibody may be substantially free of other cellular material and/or chemicals.

The term "diabodies" refers to small antibody fragments with two antigen-binding sites, which fragments comprise a heavy chain variable domain ($V_H$) connected to a light chain variable domain ($V_L$) in the same polypeptide chain ($V_H$ and $V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-6448 (1993).

The term "linear antibodies" refers to the antibodies described in Zapata et al., Protein Eng., 8(10):1057-1062 (1995). Briefly, these antibodies comprise a pair of tandem Fd segments ($V_H$-$C_H$1-$V_H$-$C_H$1) which, together with complementary light chain polypeptides, form a pair of antigen binding regions. Linear antibodies can be bispecific or monospecific.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)).

The term "humanized antibody" refers to antibodies that comprise heavy and light chain variable domain sequences from a non-human species (e.g., a mouse) but in which at least a portion of the VH and/or VL sequence has been altered to be more "human-like", i.e., more similar to human germline variable sequences. Accordingly, "humanized" antibodies are a form of a chimeric antibody, that are engineered or designed to comprise minimal sequence derived from non-human immunoglobulin. For the most part, humanized antibodies are human immunoglobulins (recipient or acceptor antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies can comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al., Nature 321: 522-525 (1986); Riechmann et al., Nature 332:323-329 (1988); and Presta, Curr. Op. Struct. Biol. 2:593-596 (1992). As used herein, a "composite human antibody" or "deimmunized antibody" are specific types of engineered or humanized antibodies designed to reduce or eliminate T cell epitopes from the variable domains.

One type of humanized antibody is a CDR-grafted antibody, in which human CDR sequences are introduced into non-human VH and VL sequences to replace the corresponding nonhuman CDR sequences. Also "humanized antibody" is an antibody or a variant, derivative, analog or fragment thereof which immunospecifically binds to an antigen of interest and which comprises a framework (FR) region having substantially the amino acid sequence of a human antibody and a complementary determining region (CDR) having substantially the amino acid sequence of a non-human antibody. As used herein, the term "substantially" in the context of a CDR refers to a CDR having an amino acid sequence at least 80%, at least 85%, at least 90%, at least 95%, at least 98% or at least 99% identical to the amino acid sequence of a non-human antibody CDR. A humanized antibody comprises substantially all of at least one, and typically two, variable domains (Fab, Fab', F(ab') .sub.2, FabC, Fv) in which all or substantially all of the CDR regions correspond to those of a non-human immunoglobulin (i.e., donor antibody) and all or substantially all of the framework regions are those of a human immunoglobulin consensus sequence. In an embodiment, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CH1, hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or humanized heavy chain. A humanized antibody may be selected from any class of immunoglobulins, including IgM, IgG, IgD, IgA and IgE, and any isotype including without limitation IgG1, IgG2, IgG3, and IgG4. The humanized antibody may comprise sequences from more than one class or isotype, and particular constant domains may be selected to optimize desired effector functions using techniques well known in the art.

The framework and CDR regions of a humanized antibody need not correspond precisely to the parental sequences, e.g., the donor antibody CDR or the consensus framework may be mutagenized by substitution, insertion and/or deletion of at least one amino acid residue so that the CDR or framework residue at that site does not correspond to either the donor antibody or the consensus framework. In an exemplary embodiment, such mutations, however, will not be extensive. Usually, at least 80%, preferably at least 85%, more preferably at least 90%, and most preferably at least 95% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (see, e.g., Winnaker, From Genes to Clones (Verlagsgesellschaft, Weinheim, Germany 1987)). In a family of immunoglobulins, each position in the consensus sequence is occupied by the amino acid occurring most frequently at that position in the family. If two amino acids occur equally frequently, either can be included in the consensus sequence.

With respect to constructing DVD-Ig or other binding protein molecules, a "linker" is used to denote a single amino acid or a polypeptide ("linker polypeptide") comprising two or more amino acid residues joined by peptide bonds and used to link one or more antigen binding portions. Such linker polypeptides are well known in the art (see, e.g., Holliger et al. (1993) Proc. Natl. Acad. Sci. USA 90: 6444-6448; Poljak (1994) Structure 2: 1121-1123).

As used herein, "Vernier" zone refers to a subset of framework residues that may adjust CDR structure and fine-tune the fit to antigen as described by Foote et al. (1992) J. Mol. Biol., 224: 487-499, which is incorporated herein by reference. Vernier zone residues form a layer underlying the CDRs and may impact on the structure of CDRs and the affinity of the antibody.

A "human antibody," "non-engineered human antibody," or "fully human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art. In one embodiment, the human antibody is selected from a phage library, where that phage library expresses human antibodies (Vaughan et al. Nature Biotechnology 14:309-314 (1996): Sheets et al. Proc. Natl. Acad. Sci. 95:6157-6162 (1998)); Hoogenboom and Winter, J. Mol. Biol., 227:381 (1991); Marks et al., J. Mol. Biol., 222:581 (1991)). Human antibodies can also be made by introducing human immunoglobulin loci into transgenic animals, e.g., mice in which the endogenous mouse immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10: 779-783 (1992); Lonberg et al., Nature 368: 856-859 (1994); Morrison, Nature 368:812-13 (1994); Fishwild et al., Nature Biotechnology 14: 845-51 (1996); Neuberger, Nature Biotechnology 14: 826 (1996); Lonberg and Huszar, Intern. Rev. Immunol. 13:65-93 (1995). Alternatively, the human antibody can be prepared via immortalization of human B lymphocytes producing an antibody directed against a target antigen (such B lymphocytes can be recovered from an individual or can have been immunized in vitro). See, e.g., Cole et al., Monoclonal Antibodies and Cancer Therapy, Alan R. Liss, p. 77 (1985); Boerner et al., J. Immunol., 147 (1):86-95 (1991); and U.S. Pat. No. 5,750,373.

An "affinity matured" antibody is one with one or more alterations in one or more CDRS thereof which result an improvement in the affinity of the antibody for antigen, compared to a parent antibody which does not possess those alteration(s). Exemplary affinity matured antibodies will have nanomolar or even picomolar affinities for the target antigen. A variety of procedures for producing affinity matured antibodies are known in the art. For example, Marks et al. Bio/Technology 10:779-783 (1992) describes affinity maturation by $V_H$ and $V_L$ domain shuffling. Random mutagenesis of CDR and/or framework residues is described by: Barbas et al. Proc Nat. Acad. Sci, USA 91:3809-3813 (1994); Schier et al. Gene 169:147-155 (1995); Yelton et al. J. Immunol. 155:1994-2004 (1995); Jackson et al., J. Immunol. 154(7):3310-9 (1995); and Hawkins et al., J. Mol. Biol. 226:889-896 (1992). Selective mutation at selective mutagenesis positions and at contact or hypermutation positions with an activity enhancing amino acid residue is described in U.S. Pat. No. 6,914,128.

A "functional antigen binding site" of an antibody is one which is capable of binding a target antigen. The antigen binding affinity of the antigen binding site is not necessarily as strong as the parent antibody from which the antigen binding site is derived, but the ability to bind antigen must be measurable using any one of a variety of methods known for evaluating antibody binding to an antigen. Moreover, the antigen binding affinity of each of the antigen binding sites of a multivalent antibody herein need not be quantitatively the same. For multimeric antibodies, the number of functional antigen binding sites can be evaluated using ultracentrifugation analysis as described in Example 2 of U.S. Patent Application Publication No. 20050186208. According to this method of analysis, different ratios of target antigen to multimeric antibody are combined and the average molecular weight of the complexes is calculated assuming differing numbers of functional binding sites. These theoretical values are compared to the actual experimental values obtained in order to evaluate the number of functional binding sites.

As used herein, a "blocking" or "neutralizing" binding protein, antibody, antibody fragment, antigen-binding fragment or an antibody "antagonist" is one which inhibits or reduces the biological activity of the antigen it specifically binds to the antigen. For example, a DEspR-specific antagonist antibody, or binding protein binds DEspR and inhibits the ability of DEspR to, for example, bind VEGFsp and/or optionally inhibits DEspR-induced angiogenesis, and can optionally inhibit DEspR to induce vascular endothelial cell proliferation or to induce vascular permeability. In certain embodiments, blocking or neutralizing antibodies or antagonist antibodies completely inhibit the biological activity of the antigen. A neutralizing binding protein, antibody, antigen-binding fragment thereof as described herein can bind to DEspR resulting in the inhibition of a biological activity of the DEspR or other antigen. The neutralizing binding protein, antibody, antigen-binding fragment thereof can bind DEspR and reduce a biologically activity of the DEspR by at least about 20%, 40%, 60%, 80%, 85%, or more. Inhibition of a biological activity of DEspR by a neutralizing binding protein, antibody or antigen-binding fragment thereof can be assessed by measuring one or more indicators of DEspR biological activity well known in the art; for example, inhibition of DEspR to bind to VEGFsp-17 or VEGFsp-27 and/or optionally inhibits DEspR-induced angiogenesis, or optionally inhibit DEspR to induce vascular endothelial cell proliferation or to induce vascular permeability.

An antibody having a "biological characteristic" or "functional characteristic" of a designated antibody is one which possesses one or more of the biological properties of that antibody which distinguish it from other antibodies that bind to the same antigen, including, for example, binding to a particular epitope, an EC50 value, IC50 value or $K_D$ values, as defined elsewhere herein.

In order to screen for antibodies which bind to an epitope on an antigen bound by an antibody of interest, a routine cross-blocking assay such as that described in Antibodies, A Laboratory Manual, Cold Spring Harbor Laboratory, Ed Harlow and David Lane (1988), can be performed.

A "species-dependent antibody" is one which has a stronger binding affinity for an antigen from a first mammalian species than it has for a homologue of that antigen from a second mammalian species. Normally, the species-dependent antibody "binds specifically" to a human antigen (i.e., has a binding affinity ($K_D$) value of no more than about $1 \times 10^{-7}$ M, preferably no more than about $1 \times 10^{-8}$ M and most preferably no more than about $1 \times 10^{-9}$ M) but has a binding affinity for a homologue of the antigen from a second nonhuman mammalian species which is at least about 50 fold, or at least about 500 fold, or at least about 1000 fold, weaker than its binding affinity for the human antigen. The species-dependent antibody can be any of the various types of antibodies as defined above, but typically is a humanized or human antibody.

As used herein, "antibody mutant" or "antibody variant" refers to an amino acid sequence variant of the species-dependent antibody wherein one or more of the amino acid residues of the species-dependent antibody have been modified. Such mutants necessarily have less than 100% sequence identity or similarity with the species-dependent antibody. In one embodiment, the antibody mutant will have an amino acid sequence having at least 75% amino acid sequence identity or similarity with the amino acid sequence of either the heavy or light chain variable domain of the species-dependent antibody, more preferably at least 80%, more preferably at least 85%, more preferably at least 90%, and most preferably at least 95%. Identity or similarity with respect to this sequence is defined herein as the percentage of amino acid residues in the candidate sequence that are identical (i.e., same residue) or similar (i.e., amino acid residue from the same group based on common side-chain properties, see below) with the species-dependent antibody residues, after aligning the sequences and introducing gaps, if necessary, to achieve the maximum percent sequence identity. None of N-terminal, C-terminal, or internal extensions, deletions, or insertions into the antibody sequence outside of the variable domain shall be construed as affecting sequence identity or similarity.

An "isolated" antibody is one that has been identified and separated and/or recovered from a component of its natural environment. Contaminant components of its natural environment are materials that would interfere with diagnostic or therapeutic uses for the antibody, and can include enzymes, hormones, and other proteinaceous or nonproteinaceous solutes. In certain embodiments, the antibody will be purified (1) to greater than 95% by weight of antibody as determined by, for example, the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, silver stain. Isolated antibody includes the antibody in situ within recombinant cells since at least one component of the antibody's natural environment will not be present. Ordinarily, however, isolated antibody will be prepared by at least one purification step.

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). See also Jonsson U. et al., (1993) Ann. Biol. Clin., 51:19-26; Jonsson U. et al., (1991) BioTechniques, 11:620-627 (1991); Johnsson U. et al., (1995) J. Mol. Recognit., 8:125-131; and Johnsson U. et al., (1991) Anal. Biochem., 198:268-277.

The term "binding protein conjugate" or "antibody conjugate" refers to a binding protein or antibody or antigen-binding fragment thereof as described herein chemically linked to a second chemical moiety, such as a therapeutic or cytotoxic agent. The term "agent" is used herein to denote a chemical compound, a mixture of chemical compounds, a biological macromolecule, or an extract made from biological materials. Preferably the therapeutic or cytotoxic agents include, but are not limited to, anti-cancer therapies as discussed herein, as well as pertussis toxin, taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. When employed in the context of an immunoassay, a binding protein conjugate or antibody conjugate may be a detectably labeled antibody, which is used as the detection antibody.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins such as small molecule toxins or enzymatically active toxins of bacterial, fungal, plant or animal origin, including fragments and/or variants thereof.

The terms "crystal" and "crystallized" as used herein, refer to a binding protein, antibody or antigen-binding protein, or antigen binding portion thereof, that exists in the form of a crystal. Crystals are one form of the solid state of matter that is distinct from other forms such as the amorphous solid state or the liquid crystalline state. Crystals are composed of regular, repeating, three-dimensional arrays of atoms, ions, molecules (e.g., proteins such as DVD-Igs), or molecular assemblies (e.g., antigen/binding protein complexes).

By "fragment" is meant a portion of a polypeptide, such as a binding protein, antibody or antibody fragment, or antigen-binding portion thereof, or nucleic acid molecule that contains, preferably, at least 10%, 20%, 30%, 40%, 50%, 60%, 70%, 80%, 90%, 95%, or more of the entire length of the reference nucleic acid molecule or polypeptide. A fragment can contain 10, 20, 30, 40, 50, 60, 70, 80, 90, or 100, 200, 300, 400, 500, 600, or more nucleotides or 10, 20, 30, 40, 50, 60, 70, 80, 90, 100, 120, 140, 160, 180, 190, 200 amino acids or more.

An "anti-angiogenesis agent" or "angiogenesis inhibitor" refers to a small molecular weight substance, a polynucleotide, a polypeptide, an isolated protein, a recombinant protein, an antibody, or conjugates or fusion proteins thereof, that inhibits angiogenesis, vasculogenesis, or undesirable vascular permeability, either directly or indirectly. It should be understood that the anti-angiogenesis agent includes those agents that bind and block the angiogenic activity of the angiogenic factor or its receptor. For example, an anti-angiogenesis agent is an antibody or other antagonist to an angiogenic agent as defined throughout the specification or known in the art, e.g., but are not limited to, antibodies to VEGF-A or to the VEGF-A receptor (e.g., KDR receptor or Flt-1 receptor), VEGF-trap, anti-PDGFR inhibitors such as GLEEVEC™ (Imatinib Mesylate). Anti-angiogenesis agents also include native angiogenesis inhibitors, e.g., angiostatin, endostatin, etc. See, e.g., Klagsbrun and D'Amore, Annu. Rev. Physiol., 53:217-39 (1991); Streit and Detmar, Oncogene, 22:3172-3179 (2003) (e.g., Table 3 listing anti-angiogenic therapy in malignant melanoma); Ferrara & Alitalo, Nature Medicine 5:1359-1364 (1999); Tonini et al., Oncogene, 22:6549-6556 (2003) (e.g., Table 2 listing known antiangiogenic factors); and Sato. Int. J. Clin. Oncol., 8:200-206 (2003) (e.g., Table 1 lists anti-angiogenic agents used in clinical trials).

The term "anti-cancer therapy" refers to a therapy useful in treating cancer. Examples of anti-cancer therapeutic agents include, but are not limited to, e.g., surgery, chemotherapeutic agents, growth inhibitory agents, cytotoxic agents, agents used in radiation therapy, anti-angiogenesis agents, apoptotic agents, anti-tubulin agents, and other agents to treat cancer, such as anti-HER-2 antibodies (e.g., HERCEPTIN®), anti-CD20 antibodies, an epidermal growth factor receptor (EGFR) antagonist (e.g., a tyrosine kinase inhibitor), HER1/EGFR inhibitor (e.g., erlotinib (TARCEVA®)), platelet derived growth factor inhibitors (e.g., GLEEVEC™ (Imatinib Mesylate)), a COX-2 inhibitor (e.g., celecoxib), interferons, cytokines, antagonists (e.g., neutralizing antibodies) that bind to one or more of the following targets ErbB2, ErbB3, ErbB4, PDGFR-beta, BlyS, APRIL, BCMA or VEGF receptor(s), TRAIL/Apo2, and other bioactive and organic chemical agents, etc. Combinations thereof are also included in the invention.

A "chemotherapeutic agent" is a chemical compound useful in the treatment of cancer. Examples of chemotherapeutic agents include, but are not limited to, alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaI1 (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chlorambucil; GEMZAR® gemcitabine; 6-thioguanine; mercaptopurine; methotrexate; platinum analogs such as cisplatin, oxaliplatin and carboplatin; vinblastine; platinum;

etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (TYKERB); inhibitors of PKC-alpha, Raf, H-Ras, EGFR (e.g., erlotinib (TARCEVA®)) and VEGF-A that reduce cell proliferation and pharmaceutically acceptable salts, acids or derivatives of any of the above. Other chemotherapeutic agents that can be used with compositions and methods described herein are disclosed in US Publication No. 20080171040 or US Publication No. 20080305044 and are incorporated in their entirety by reference.

Also included in this definition are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; and pharmaceutically acceptable salts, acids or derivatives of any of the above.

A "growth inhibitory agent" as used herein refers to a compound or composition which inhibits growth of a cell in vitro and/or in vivo. Thus, the growth inhibitory agent can be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), TAXOL®, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The Molecular Basis of Cancer, Mendelsohn and Israel, eds., Chapter 1, entitled "Cell cycle regulation, oncogenes, and antineoplastic drugs" by Murakami et al. (WB Saunders: Philadelphia, 1995), especially p. 13.

The terms "antibody drug conjugate" or "antibody-drug conjugate," as used herein, refer to an antibody conjugated to a non-proteinaceous agent, typically a chemotherapeutic agent, e.g., a cytotoxic agent, a cytostatic agent, a toxin, or a radioactive agent. A linker molecule can be used to conjugate the drug to the antibody. A wide variety of linkers and drugs useful in ADC technology are known in the art and can be used in embodiments described herein. (See, for example, US20090028856; US2009/0274713; US2007/0031402; WO2005/084390; WO2009/099728; U.S. Pat. Nos. 5,208,020; 5,416,064; 5,475,092; 5,585,499; 6,436,931; 6,372,738; and 6,340,701, all incorporated herein by reference in their entireties). By combining the unique targeting of monoclonal antibodies or fragments thereof with the cancer-killing ability of cytotoxic drugs, antibody drug conjugates allow sensitive and increased discrimination between healthy and diseased tissue.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). The prodrugs described herein include, but are not limited to, phosphate-containing prodrugs, thiophosphate-containing prodrugs, sulfate-containing prodrugs, peptide-containing prodrugs, D-amino acid-modified prodrugs, glycosylated prodrugs, .beta.-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one time administration and typical dosages range from 10 to 200 units (Grays) per day.

The term "intravenous infusion" refers to introduction of a drug into the vein of an animal or human subject over a period of time greater than approximately 5 minutes, preferably between approximately 30 to 90 minutes, although, according to the invention, intravenous infusion is alternatively administered for 10 hours or less. The term "intravenous bolus" or "intravenous push" refers to drug administration into a vein of an animal or human such that the body receives the drug in approximately 15 minutes or less, preferably 5 minutes or less.

The term "subcutaneous administration" refers to introduction of a drug under the skin of an animal or human subject, preferable within a pocket between the skin and underlying tissue, by relatively slow, sustained delivery from a drug receptacle. The pocket can be created by pinching or drawing the skin up and away from underlying tissue.

The term "subcutaneous infusion" refers to introduction of a drug under the skin of an animal or human subject, preferably within a pocket between the skin and underlying tissue, by relatively slow, sustained delivery from a drug receptacle for a period of time including, but not limited to, 30 minutes or less, or 90 minutes or less. Optionally, the infusion can be made by subcutaneous implantation of a drug delivery pump implanted under the skin of the animal or human subject, wherein the pump delivers a predetermined amount of drug for a predetermined period of time, such as 30 minutes, 90 minutes, or a time period spanning the length of the treatment regimen.

The term "subcutaneous bolus" refers to drug administration beneath the skin of an animal or human subject, where bolus drug delivery is preferably less than approximately 15 minutes, more preferably less than 5 minutes, and most preferably less than 60 seconds. Administration is preferably within a pocket between the skin and underlying tissue, where the pocket is created, for example, by pinching or drawing the skin up and away from underlying tissue.

A "disorder" is any condition that would benefit from treatment with, for example, an antibody described herein. This includes chronic and acute disorders or diseases including those pathological conditions which predispose the mammal to the disorder in question. Non-limiting examples of disorders to be treated herein include cancer; benign and malignant tumors; leukemias and lymphoid malignancies; neuronal, glial, astrocytal, hypothalamic and other glandular, macrophagal, epithelial, stromal and blastocoelic disorders; and inflammatory, angiogenic and immunologic disorders.

The word "label" when used herein refers to a detectable compound or composition which is conjugated directly or indirectly to the polypeptide. The label can be itself be detectable (e.g., radioisotope labels or fluorescent labels) or, in the case of an enzymatic label, can catalyze chemical alteration of a substrate compound or composition which is detectable.

By "subject" is meant a mammal, including, but not limited to, a human or non-human mammal, such as a bovine, equine, canine, ovine, or feline. Preferably, the subject is a human. Patients are also subjects herein.

The terms "decrease," "reduce," "reduced", "reduction", "decrease," and "inhibit" are all used herein generally to mean a decrease by a statistically significant amount relative to a reference. However, for avoidance of doubt, "reduce," "reduction" or "decrease" or "inhibit" typically means a decrease by at least 10% as compared to a reference level and can include, for example, a decrease by at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, up to and including, for example, the complete absence of the given entity or parameter as compared to the reference level, or any decrease between 10-99% as compared to the absence of a given treatment. Reduce or inhibit can refer to, for example, the symptoms of the disorder being treated, the presence or size of metastases or micrometastases, the size of the primary tumor, the presence or the size of the dormant tumor, or the size or number of the blood vessels in angiogenic disorders.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

As used herein the term "comprising" or "comprises" is used in reference to compositions, methods, and respective component(s) thereof, that are essential to the method or composition, yet open to the inclusion of unspecified elements, whether essential or not.

As used herein the term "consisting essentially of" refers to those elements required for a given embodiment. The term permits the presence of elements that do not materially affect the basic and novel or functional characteristic(s) of that embodiment.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Other than in the operating examples, or where otherwise indicated, all numbers expressing quantities of ingredients or reaction conditions used herein should be understood as modified in all instances by the term "about." The term "about" when used in connection with percentages can mean±1%.

The term "statistically significant" or "significantly" refers to statistical significance and generally means a two standard deviation (2SD) difference, above or below a reference value. Additional definitions are provided in the text of individual sections below.

BRIEF DESCRIPTION OF THE FIGURES

This patent or application file contains at least one drawing executed in color. Copies of this patent or patent application publication with color drawing(s) will be provided by the Office upon request and payment of the necessary fee.

FIG. 1A. Brain surface showing hemorrhages. FIG. 1B. H&E section confirm hemorrhages. FIG. 1C. H&E section show hemorrhagic infarct.

FIG. 6A. Masson-trichrome stained histology section showing tumor vessels with loss of integrity of endothelial layer. Higher magnification shows loss of endothelial integrity and exposure of tumors cells to vascular lumen—a direct route for metastasis. FIG. 6B. After treatment with anti-rat DEspR monoclonal antibody (mAb) (10A3H10), tumors are smaller, and exhibit normalization of tumor blood vessels as seen in immunohistochemistry staining (DAB) of DEspR expression in tumor endothelial cells and tumor cells.

FIG. 8A. Schematic diagram of human DEspR (SEQ ID NO: 3). FIG. 8B. Western blot of pulldown products.

FIG. 23 shows antiDEspR monoclonal antibodies (mAbs) (7C5B2, 6G8G7) decrease collagen-1 (col1) secretion by Panc1-CSCs. Panc1-CSC peritoneal tumors co-express collagen-1 and DEspR. [human-specific col1/3 mAb; 6G8G7]. Incubation 48 hrs at 37° C. (tissue culture incubator); Collagen measured by ELISA 6G8G7=200 ug/ml; 7C5B2=200 ug/ml. One Way ANOVA+Holm-Sidak MCT; * P<$10^{-3}$; ** P<$10^{-7}$.

FIG. 25 shows anti-DEspR 6G8G7 decreases αSMA expression induced by TNF-α. αSMA expression is a marker of EMT; TNF-α is known to increase tumor growth and invasiveness of pancreatic cancer.

FIG. 35A. Binding of the top 2 6G8-IgG4 candidates shows the candidate with the better Bmax for binding to the antigenic peptide 6G8IgG4 or humab1), compared to 6g8IgG4κh3 or humab2. FIG. 35B. Binding affinity of the original 6G8 mumab. It is noted that the secondary antibody detection systems are different as one is anti-human IgG4 for the candidate 6G8 human monoclonal antibodies (mAbs), and the other is anti-mouse IgG2b for the 6G8 mumab.

FIGS. 39A-39D show testing of functional activity of a 6G8IgG4 humanized monoclonal antibody lead candidate for inhibition of angiogenesis in vitro. FIG. 39A. Representative HUVECs bFGF-mediated, VEGF-independent angiogenesis in non-treated HUVECs control. FIG. 39B. Representative image of angiogenesis assay results with 6G8 humanized monoclonal antibody treatment of HUVECs. FIGS. 39C-39D. Marked inhibition of angiogenesis complex network formation by 6G8 humanized monoclonal antibody lead candidate assessing polygons (FIG. 39C) and branch points (FIG. 39D).

FIG. 40A. % polygons compared to contemporaneous controls, FIG. 40B. % branch points compared to contemporaneous controls.

FIG. 50 shows internalization of anti-human DEspR 7C5-humanized monoclonal antibody (VH5NK1) by DEspR+ Panc1-CSCS. These data regarding stable interaction between anti-DEspR monoclonal antibody and DEspR support their efficacy in inhibiting cancer cells, as well as in targeting of cancer cells and cancer stem-like cells for delivery of therapeutics or for in vivo detection of DEspR+ cancer cells and cancer stem-like cells. Notably, internalization was observed with both anti-humanDEspR murine monoclonal antibody and humanized monoclonal antibody.

DETAILED DESCRIPTION

Figure 1A:
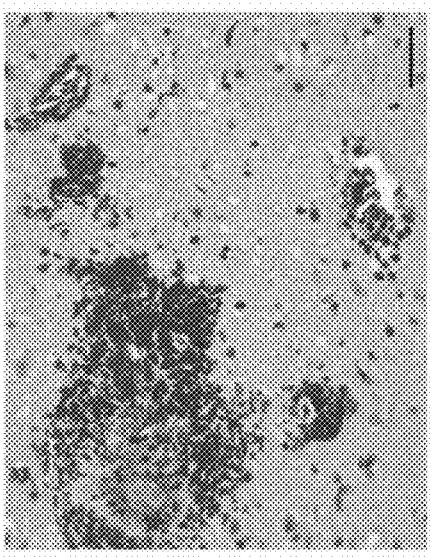
FIGS. 1A-1C show representative brain images at acute onset of stroke using a stroke-prone transgenic-hyperlipidemic, hypertensive rat model.

Provided herein are compositions comprising novel anti-DEspR antibodies and DEspR-binding fragments thereof derived from the 6G8G7 and 7C5B2 anti-DEspR antibodies, and methods of their use in anti-angiogenesis and anti-tumor proliferation and invasiveness therapies, such as the treatment of cancer, as well as the treatment of diseases where pathological angiogenesis plays a role, such as in carotid artery disease, vasa vasorum neovascularization, and stroke, and vulnerable plaque neovascularization and consequent heart disease.

As described herein, peptide GSNEMKSRWNWGS (SEQ ID NO: 1) was used as an antigenic peptide to generate monoclonal antibodies specific for DEspR. A smaller or partial peptide EMKSRWNWGS (SEQ ID NO: 2) was then used to screen for monoclonal antibodies and narrow down the potential epitope for the antibodies generated using the peptide of SEQ ID NO: 1, such as the monoclonal antibody and derivatives thereof termed herein as "6G8G7" or "6G8" or "6g8g7" or "6g8." Such antibodies or antigen-binding fragments thereof or derivatives thereof can also be referred to as an "antibody or antigen-binding fragment specific for and/or directed to SEQ ID NO: 1 or SEQ ID NO: 2." The inventors have discovered that the 6G8G7 anti-DEspR antibody is a neutralizing antibody that inhibits multiple mechanisms contributing to tumor recurrence in vitro and decreases in vivo tumor initiation and progression significantly, thus increasing survival using a pancreatic peritoneal metastasis nude rat model. In addition, the data provided herein demonstrate that the 6G8G7 anti-DEspR antibody and derivatives thereof decreases tumor initiation/tumorigenesis of Panc1-CSCs, decreases collagen-1 (col1) secretion by Panc1-CSCs, and decreases alpha smooth muscle acitn (αSMA) expression induced by the major inflammatory cytokine, TNF-α.

Despite these and other data, DEspR is still annotated as a "pseudogene" in the NCBI database. Accordingly, the compositions comprising antibodies and antigen-binding fragments thereof that bind to DEspR described herein, and the epitopes used to generate these antibodies and antigen-binding fragments, provide novel and unexpected results for treating cancer and other disorders dependent on aberrant angiogenesis, and on DEspR-roles in tumor initiation, recurrence, therapy resistance, microvessel leakiness, microbleeds. Thus, provided herein are compositions and methods comprising isolated antibodies and antigen-binding fragments having one or more functional characteristics and anti-DEspR antibodies and antigen-binding fragments thereof derived from the 6G8G7 and 7C5B2 anti-DEspR antibodies, including chimeric and humanized antibodies, for use in treatment of angiogenesis-dependent diseases or disorders.

Anti-DEspR Antibodies and Antigen-Binding Fragments Thereof

The dual endothelin-1/VEGF signal peptide activated receptor (DEspR), also known as DEAR, was originally cloned from a Dahl salt-sensitive hypertensive rat brain cDNA library and was shown to be a single transmembrane receptor coupled to a Ca2+-mobilizing transduction pathway binding endothelin-1 (ET-1) and angiotensin-II (Ang II) with equivalent affinities (Ruiz-Opazo N. et al. (1998), Molecular characterization of a dual Endothelin-1/Angiotensin II Receptor. Mol Med. 4: 96-108). Subsequent molecular studies elucidated that the mouse ortholog does not interact with AngII but binds ET-1 and the vascular endothelial growth factor signal peptide (VEGFsp) with equal affinities instead.

The role of DEspR in cancer has been deduced, in part, from its embryonic-lethal null mutation phenotype resulting in E10.5-12.5 day embryonic lethality characterized by abnormal vasculogenesis with incomplete dorsal aorta formation, and by absent angiogenesis, and failed endocardial-to-mesenchymal transition/migration resulting in thin-walled hearts. The DEspR null mouse phenotype is similar to, but is distinguished from the heterozygous VEGF+/− knockout mouse phenotype, and from the homozygous knockout mouse phenotype of its overlapping opposite-strand transcript, Fbxw7, a ubiquitin ligase oncosuppressor by the detection of hyperconvoluted neuroepithelium throughout the neural tube, indicating a DEspR-specific role in neuroepithelial stem cell-to-radial cell transition and/or migration. Furthermore, 50% reduction of DEspR expression in heterozygous DEspR+/− knockout mice is not embryonic lethal, in contrast to the embryonic-lethal phenotype of heterozygous VEGF+/− knockout mice, and decreased tumor growth in DEspR+/− male mice, in polar contrast to increased tumorigenesis expected from the loss of Fbxw7-tumor suppressor functions as seen in human cancer and mouse tumor inactivating mutations. Importantly, DEspR inhibition at the protein level via an anti-ratDEspR-specific polyclonal antibody decreased tumor growth, tumor vascularization, and nuclear malignancy-grade in irradiation-induced rat mammary tumors, thereby clarifying DEspR-specific pro-tumorigenic roles in contrast to the tumor suppressor roles of Fbxw7. Confirmatory immunohistochemistry detected DEspR+ expression not only in rat mammary tumor blood vessels, but also in tumor cells and in invading tumor cells. Additionally, DEspR-signaling, studied in human DEspR-positive permanent Cos1-cell transfectants phosphorylates Akt in a dose-response manner. "DEspR roles in tumor vasculo-angiogenesis, invasiveness, CSC-survival and anoikis resistance: a 'common receptor coordinator' paradigm," Herrera V L et al., PLoS One. 2014 Jan. 21; 9(1):e85821.

More recent studies show that DEspR is a common receptor expressed in tumor cells, microvessels, and anchorage-independent cancer stem cells (CSCs), with differential expression in cell- and nuclear-membranes, as well as in the cytoplasm. DEspR is differentially increased in both human pancreatic cancer and glioblastoma in contrast to adjacent normal tissue. DEspR-inhibition at the protein level decreased in vitro angiogenesis, tumor cell invasiveness, CSC-cell anoikis resistance, survival, and promoted pro-apoptosis balance. Concordantly, DEspR-inhibition also decreased in vivo Panc1- and U87-CSC-xenograft tumor volumes, vasculogenesis, invasiveness, and tumor cell survival in the expanding tumor zone.

However, despite these data, DEspR is still annotated as a "pseudogene" in the NCBI database. Accordingly, the compositions comprising antibodies and antigen-binding fragments thereof that bind to DEspR described herein, and the epitopes used to generate these antibodies and antigen-binding fragments, provide novel and unexpected results for treating cancer and other disorders dependent on aberrant angiogenesis.

The term "DEspR," as used herein, refers to the 85-amino acid dual endothelin/VEGF signal peptide receptor (DEspR) having the human amino acid native sequence of: MTMFKGSNEMKSRWNWGSITCI-ICFTCVGSQLSMSSSKASNFSGPLQLYQRELEI-FIVLTDVPNYR LIKENSHLHTTIVDQGRTV (SEQ ID NO: 3), as described by, e.g., Accession Number EF212178.1, Gene ID 102191832, or Glorioso et al. 2007, together with naturally occurring allelic, splice variants, and processed forms thereof. Typically, as used herein, DEspR refers to human DEspR of SEQ ID NO: 3. The term "DEspR" is also used to refer to truncated forms or fragments of the polypeptide comprising specific amino acids sequences of the 85-amino acid human dual endothelin/VEGF signal peptide receptor. Reference to any such forms of DEspR can be identified in the application, e.g., by "DEspR (1-9)" or amino acids 1-9 of SEQ ID NO: 3.

As used herein a DEspR "native sequence" or DEspR "wild-type sequence" polypeptide comprises a polypeptide having the same amino acid sequence as a DEspR polypeptide derived from nature. Thus, a native sequence polypeptide can have the amino acid sequence of naturally-occurring polypeptide from any mammal. Such native sequence polypeptide can be isolated from nature or can be produced by recombinant or synthetic means. The term "native sequence" polypeptide specifically encompasses naturally-occurring truncated or secreted forms of the polypeptide (e.g., an extracellular domain sequence), naturally-occurring variant forms (e.g., alternatively spliced forms) and naturally-occurring allelic variants of the polypeptide.

As used herein, a DEspR polypeptide "variant" means a biologically active DEspR polypeptide having at least about 80% amino acid sequence identity with a native sequence of a DEspR polypeptide. Such variants include, for instance, polypeptides wherein one or more amino acid residues are added, or deleted, at the N- or C-terminus of the polypeptide. Ordinarily, a variant has at least about 80% amino acid sequence identity, more preferably at least about 90% amino acid sequence identity, and even more preferably at least about 95% amino acid sequence identity with the native sequence polypeptide.

Figure 13:
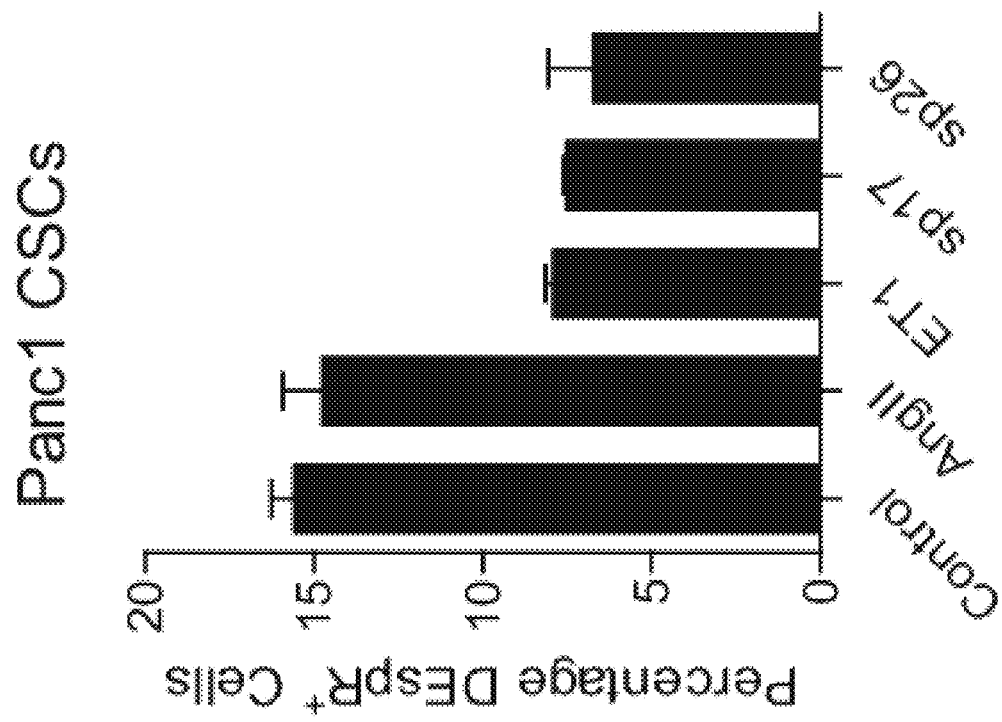
FIG. 13 shows displacement of fluorescently labeled 7C5B2 binding to Panc1 CSCs by different peptide ligands. 50,000 cells were reacted with 10 μg/ml AF568-labelled 7C5B2 monoclonal antibody (mAb) at 4° C. for 20 min in the absence or presence of the different peptides at 100× molar excess. Samples were immediately subjected to FACS analysis for quantification of DEspR+ cells. Samples were run in duplicates. AngII, angiotensinII; ET1, endothelin-1 (DEspR ligand); sp17, VEGFsp17 (DEspR ligand); sp26, VEGFsp26 (DEspR ligand). Data presented as Mean±SD.

DEspR is a cell-membrane receptor that binds to endothelin-1, to VEGF signal peptide signal peptide 26 (VEGFsp-26/sp26, FIG. 13), and to VEGF signal peptide 17 (VEGFsp-17/sp17, FIG. 13). VEGFsp-26 has the human sequence MNFLLSWVHWSLALLLYLHHAKWSQA (SEQ ID NO: 4). VEGFsp-17 has the human sequence MNFLLSWVHWSLALLLY (SEQ ID NO: 48).

Provided herein are compositions and methods comprising antibodies and antigen-binding fragments thereof, such as anti-DEspR antibodies or antigen-binding fragments thereof that are capable of neutralizing, blocking, inhibiting, abrogating, reducing, or interfering with DEspR activities including its binding to endothelin-1 or VEGFsp.

Accordingly, in some aspects, provided herein are anti-DEspR antibodies or antibody fragments thereof that specifically bind human DEspR of SEQ ID NO: 3 and reduce or inhibit DEspR biological activity.

In some aspects, provided herein are anti-DEspR antibodies or antigen-binding fragments thereof specific for an epitope of DEspR comprising, consisting essentially of, or consisting of GSNEMKSRWNWGS (SEQ ID NO: 1).

In some aspects, provided herein are anti-DEspR antibodies or antigen-binding fragments thereof specific for an epitope of DEspR comprising, consisting essentially of, or consisting of EMKSRWNWGS (SEQ ID NO: 2).

In some embodiments of this aspect and all such aspects described herein, the anti-DEspR antibody or antigen-binding fragment thereof that binds to DEspR and inhibits DEspR biological activity blocks or inhibits interaction of DEspR with VEGFsp comprising the sequence of SEQ ID NO: 4.

In some aspects, provided herein are anti-DEspR antibodies or antigen-binding fragments thereof that bind the same or an overlapping epitope of DEspR (e.g., an epitope of human DEspR) as any one of the antibodies produced by hybridomas 6G8G7 and 7C5B2. In some embodiments of this aspect, the anti-DEspR antibodies or antigen-binding fragments thereof bind the same or overlapping epitope of SEQ ID NO: 1 or SEQ ID NO: 2. As known to one of ordinary skill in the art, antibodies that recognize and bind to the same or overlapping epitopes of DEspR (e.g., human DEspR) can be identified using routine techniques such as an immunoassay, for example, by showing the ability of one antibody to block the binding of another antibody to a target antigen, i.e., a competitive binding assay. Competition binding assays also can be used to determine whether two antibodies have similar binding specificity for an epitope. Competitive binding can be determined in an assay in which the immunoglobulin under test inhibits specific binding of a reference antibody to a common antigen, such as DEspR. Numerous types of competitive binding assays are known, for example: solid phase direct or indirect radioimmunoassay (RIA), solid phase direct or indirect enzyme immunoassay (EIA), sandwich competition assay (see Stahli C et al., (1983) Methods Enzymol 9: 242-253); solid phase direct biotin-avidin EIA (see Kirkland T N et al., (1986) J Immunol 137: 3614-9); solid phase direct labeled assay, solid phase direct labeled sandwich assay (see Harlow E & Lane D, (1988) Antibodies: A Laboratory Manual, Cold Spring Harbor Press); solid phase direct label RIA using 1-125 label (see Morel G A et al., (1988) Mol Immunol 25(1): 7-15); solid phase direct biotin-avidin EIA (Cheung R C et al., (1990) Virology 176: 546-52); and direct labeled RIA. (Moldenhauer G et al., (1990) Scand J Immunol 32: 77-82). Typically, such an assay involves the use of purified antigen (e.g., DEspR) bound to a solid surface or cells bearing either of these, an unlabeled test immunoglobulin and a labeled reference immunoglobulin. Competitive inhibition can be measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70% 70-75% or more. A competition binding assay can be configured in a large number of different formats using either labeled antigen or labeled antibody. In a common version of this assay, the antigen is immobilized on a 96-well plate. The ability of unlabeled antibodies to block the binding of labeled antibodies to the antigen is then measured using radioactive or enzyme labels. For further details see, for example, Wagener C et al., (1983) J Immunol 130: 2308-2315; Wagener C et al., (1984) J Immunol Methods 68: 269-274; Kuroki M et al., (1990) Cancer Res 50: 4872-4879; Kuroki Metal., (1992) Immunol Invest 21: 523-538; Kuroki Metal., (1992) Hybridoma 11: 391-407 and Antibodies: A Laboratory Manual, Ed Harlow E & Lane D editors supra, pp. 386-389. A competition assay can be performed, for example, using surface plasmon resonance (BIACORE) e.g., by an 'in tandem approach' such as that described by Abdiche Y N et al., (2009) Analytical Biochem 386: 172-180, whereby DEspR antigen is immobilized on the chip surface, for example, a CMS sensor chip and the anti-DEspR antibodies are then run over the chip. To determine if an antibody competes with a given anti-DEspR antibody or antigen-binding fragment thereof described herein, the anti-DEspR antibody is first run over the chip surface to achieve saturation and then the potential, competing antibody is added. Binding of the competing antibody can then be determined and quantified relative to a non-competing control.

Competition binding assays can be used to determine whether an antibody is competitively blocked, e.g., in a dose dependent manner, by another antibody for example, an antibody that binds essentially the same epitope, or overlapping epitopes, as a reference antibody, when the two antibodies recognize identical or sterically overlapping epitopes in competition binding assays such as competition ELISA assays, which can be configured in all number of different formats, using either labeled antigen or labeled antibody.

Accordingly, in some of the aspects described herein, an antibody or antigen-binding fragment can be generated comprising any of the sequences described herein, including any of the one or more $V_H$ CDRS and/or one or more $V_L$ CDRs of any one of the antibodies produced by hybridomas 6G8G7 and 7C5B2 as described herein, and variants thereof.

Accordingly, in some embodiments of the aspects described herein, an anti-DEspR antibody can be tested in competition binding assays with any one of the antibodies produced by hybridomas 6G8G7 and 7C5B2 described herein, or a chimeric or Fab antibody thereof, or an anti-DEspR antibody comprising one or more $V_H$ CDRS and one or more $V_L$ CDRs of any one of the antibodies produced by hybridomas 6G8G7 and 7C5B2 described herein.

Affinities of anti-DEspR antibodies and antigen-binding fragments thereof can be determined, for example, by a surface plasmon resonance based assay (such as the BIACORE assay described in PCT Application Publication No. WO2005/012359); enzyme-linked immunoabsorbent assay (ELISA); and competition assays (e.g. RIA's), for example. An anti-DEspR antibody for use in the compositions and methods described herein can be subjected to other biological activity assays, e.g., in order to evaluate its effectiveness as a therapeutic, or its effectiveness as a diagnostic aid, etc. Such assays are known in the art and depend on the target antigen and intended use for the antibody. Examples include the HUVEC inhibition assay; tumor cell growth inhibition assays (as described in WO 89/06692, for example); antibody-dependent cellular cytotoxicity (ADCC) and complement-mediated cytotoxicity (CDC) assays (U.S. Pat. No. 5,500,362); and agonistic activity or hematopoiesis assays (see WO 95/27062). Other biological activity assays that can be used to assess an anti-DEspR antibody are described herein in the Examples section and in "DEspR roles in tumor vasculo-angiogenesis, invasiveness, CSC-survival and anoikis resistance: a 'common receptor coordinator' paradigm," Herrera V L et al., PLoS One. 2014 Jan. 21; 9(1):e85821, the contents of which are herein incorporated by reference in their entireties. Thus, anti-DEspR antibodies or antibody fragments thereof that are useful in the compositions and methods described herein include any antibodies or antibody fragments thereof that bind with sufficient affinity and specificity to DEspR, i.e., are specific for DEspR, and can reduce or inhibit the biological activity of DEspR.

While it is preferred that the anti-DEspR antibodies and antigen-binding fragments thereof used in the compositions and methods described herein are monoclonal, in some embodiments, polyclonal antibodies can first be raised or generated in animals by multiple subcutaneous (sc) or intraperitoneal (ip) injections of the relevant antigen, e.g., SEQ ID NO: 1 or SEQ ID NO: 2 and an adjuvant. It can be useful, in some embodiments, to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups. Methods of generating such polyclonal antibodies to a given antigenic sequence, such as SEQ ID NO: 1 or SEQ ID NO:2, are known to one of ordinary skill in the art.

Preferably, anti-DEspR antibodies or antibody fragments thereof for use with the compositions and methods described herein are anti-DEspR monoclonal antibodies or fragments thereof.

In some aspects, the anti-DEspR monoclonal antibody is a monoclonal anti-DEspR antibody 6G8G7 produced or expressed by the hybridoma 6G8G7 described herein, and referred to as a "6G8G7 variant antibody" or "6G8G7 anti-DEspR variant antibody" and derivatives or antigen-binding fragments thereof, including, for example, a "6G8G7 variant variable heavy chain," or a "6G8G7 variant variable light chain." In some aspects, the anti-DEspR monoclonal antibody is a monoclonal anti-DEspR antibody 7C5B2 produced or expressed by the hybridoma 7C5B2 and referred to as a "variant 7C5B2" or "variant 7C5B2 anti-DEspR antibody" and derivatives or antigen-binding fragments thereof, including, for example, a "7C5B2 variant variable heavy chain," or a "7C5B2 variant variable light chain."

As described herein, the 6G8G7 and 7C5B2 hybridomas produce monoclonal antibodies, termed herein as a "6G8G7 variant antibody" or "6G8G7 variant" or a "variant 7C5B2 anti-DEspR antibody" or a "variant 7C5B2 antibody" that is highly specific for DEspR and can potently inhibit DEspR biological activity. The biological characteristics of 6G8G7 and 7C5B2 anti-DEspR variant antibodies, and any chimeric or humanized antibodies or antigen-binding fragments derived or generated therefrom, render them particularly useful for the compositions and methods described herein, including therapeutic and diagnostic applications.

Accordingly, sequence analysis of 6G8G7 hybridoma was performed, as described herein, to identify heavy and light chain variable domain sequences, and complementarity determining region (CDR) sequences, of the antibodies produced by the 6G8G7 hybridoma, and also to identify heavy and light chain variable domain sequences and complementarity determining region (CDR) sequences of the antibodies produced by the 7C5B2 hybridoma for use in the compositions and methods described herein.

The nucleotide sequence encoding a $V_H$ or variable domain of the heavy chain of a 6G8G7 HV1 variant antibody, as obtained by sequence analysis of sequences obtained from a 6G8G7 hybridoma, is:

(SEQ ID NO: 5)
GGATCCCAAGTGCAGCTGCAGGAGTCAGGACCTGGCCTGGTGGCGCCCTC

ACAGAGCCTGTCCATCACATGCACCGTCTCAGGGTTCTCATTAACCGGCT

ATGGTGTAAACTGGGTTCGCCAGCCTCCAGGAAAGGGTCTGGAATGGCTG

GGAATGATTTGGGATGATGGAAGCACAGACTATAATTCAGCTCTCAAATC

CAGACTGATCATCACCAAGGACAACTCCAGGAGCCAAGTTTTCTTAAAAA

TGAACAGTCTGCAAACTGATGACACAGCCAGGTACTACTGTGCCAGAGAC

CCAGTATAGGTCCATTTCTATGCTATGGACTACTGGGGTCAAGGAACCTC

AGTCACCGTCTCCTCAGCCAAAACGACACCCCCATCTGTCTATGGTGGCG

GTGGTTCT.

The amino acid sequence of the $V_H$ domain of a 6G8G7 HV1 variant antibody corresponding to SEQ ID NO: 5 is:

(SEQ ID NO: 6)
GSQVQLQESGPGLVAPSQSLSITCTVSGFSLTGYGVNWVRQPPGKGLEWL
GMIWDDGSTDYNSALKSRLIITKDNSRSQVFLKMNSLQTDDTARYYCARD
PVVHFYAMDYWGQGTSVTVSSAKTTPPSVYGGGGS.

The amino acid sequence of the complementarity determining region 1 or CDR1 of the $V_H$ domain of SEQ ID NO: 6 of the 6G8G7 HV1 variant antibody according to the Kabat sequence numbering is: GYGVN (SEQ ID NO: 7). The amino acid sequence of the CDR2 of the $V_H$ domain of SEQ ID NO: 6 of the 6G8G7 HV1 variant antibody according to the Kabat sequence numbering is: MIWDDGSTDYN-SALKS (SEQ ID NO: 8). The amino acid sequence of the CDR3 of the $V_H$ domain of SEQ ID NO: 6 of the 6G8G7 HV1 variant antibody according to the Kabat sequence numbering is: DPVVHFYAMDY (SEQ ID NO: 9).

The amino acid sequence of the complementarity determining region 1 or CDR1 of the $V_H$ domain of SEQ ID NO: 6 of the 6G8G7 HV1 variant antibody according to the IMGT sequence numbering is: GFSLTGYG (SEQ ID NO: 10). The amino acid sequence of the CDR2 of the $V_H$ domain of SEQ ID NO: 6 of the 6G8G7 HV1 variant antibody according to the IMGT sequence numbering is: IWDDGST (SEQ ID NO: 11).

The nucleotide sequence encoding a $V_H$ or variable domain of the heavy chain of a 6G8G7 HV2 variant antibody, as obtained by sequence analysis of sequences obtained from a 6G8G7 hybridoma, is:

(SEQ ID NO: 12)
GGATCCGAAGTTCAGCTGCAGGAGTCTGGAGGTGGCCTGGTGCAGCCTGG

AGGATCCCTGAAACTCTCCTGTGCAGCCTCAGGATTCGATTTTAGTAGAT

ACTGGATGAGTTGGGTCCGGCAGGCTCCAGGGAAAGGACTAGAATGGATT

GGAGAAATTAATCCAGATAGCAGTACGATAAACTATACGCCATCTCTAAA

GGATAAATTCATCATTTCTAGAGACACCGCCAAAAAAACTCTGTACCTGC

AAATGAGCAAAGTGAGATCAGAGGACACAGCCCTTTATTACTGTGCAAGA

CATGGTAGAGGTATGGACTACTGGAGTCAAGGAACCTCAGTCACCGTCTC

CTCAGCCAAAACGACACCCCCATCTGTCTATGGTGGCGGTGGTTCT.

The amino acid sequence of the $V_H$ domain of a 6G8G7 HV2 variant antibody corresponding to SEQ ID NO: 12 is:

(SEQ ID NO: 13)
GSEVQLQESGGGLVQPGGSLKLSCAASGFDFSRYWMSWVRQAPGKGLEWI
GEINPDSSTINYTPSLKDKFIISRDTAKKTLYLQMSKVRSEDTALYYCAR
HGRGMDYWSQGTSVTVSSAKTTPPSVYGGGGS.

The amino acid sequence of the complementarity determining region 1 or CDR1 of the $V_H$ domain of SEQ ID NO: 13 of the 6G8G7 HV2 variant antibody according to the Kabat sequence numbering is: RYWMS (SEQ ID NO: 14). The amino acid sequence of the CDR2 of the $V_H$ domain of SEQ ID NO: 13 of the 6G8G7HV2 variant antibody according to the Kabat sequence numbering is: EINPDSSTI-NYTPSLKD (SEQ ID NO: 15). The amino acid sequence of the CDR3 of the $V_H$ domain of SEQ ID NO: 13 of the 6G8G7HV2 variant antibody according to the Kabat sequence numbering is: HGRGMDY (SEQ ID NO: 16).

The amino acid sequence of the complementarity determining region 1 or CDR1 of the $V_H$ domain of SEQ ID NO: 13 of the 6G8G7 HV2 variant antibody according to the IMGT sequence numbering is: GFDFSRYW (SEQ ID NO: 17). The amino acid sequence of the CDR2 of the $V_H$ domain of SEQ ID NO: 13 of the 6G8G7 HV2 variant antibody according to the IMGT sequence numbering is: INPDSSTI (SEQ ID NO: 18).

The nucleotide sequence encoding a $V_H$ or variable domain of the heavy chain of the 7C5B2 HV2 variant antibody, as obtained by sequence analysis of sequences obtained from a variant 7C5B2 hybridoma, (SEQ ID NO: 19)
CAGGTGCAGCTGAAGGAGTCAGGACCTGGCCTGGTGGCGCCCTCACAGAG

CCTGTCCATCACATGCACTGTCTCAGGATTCTCATTAAAAAGTTATGCTG

TAAGCTGGGTTCGCCAGCCTCCAGGAAAGGGTCTGGAGTGGCTGGGAGTA

ATCTGGGGTGACGGGAGCACAGATTATCATTCAGCTCTCATATCCAGACT

GAGCATCAGTAAGGATAACTCCAAGAGCCAATTTTTCTTAAGACTGAACA

GTCTGCAAACTGATGACACAGCCACGTATTACTGTGCCAGAGGAACTGGG

ACGGGGTTTGCTTACTGGGGCCAGGGGACTCTGGTCACTGTCTCTGCA.

The amino acid sequence of the $V_H$ domain of the 7C5B2 HV2 variant antibody corresponding to SEQ ID NO: 19 is:

```
                                             (SEQ ID NO: 20)
QVQLKESGPGLVAPSQSLSITCTVSGFSLKSYAVSWVRQPPGKGLEWLGV
IWGDGSTDYHSALISRLSISKDNSKSQFFLRLNSLQTDDTATYYCARGTG
TGFAYWGQGTLVTVSA.
```

The amino acid sequence of the complementarity determining region 1 or CDR1 of the $V_H$ domain of SEQ ID NO: 20 of the 7C5B2 HV2 variant antibody according to the Kabat sequence numbering is: SYAVS (SEQ ID NO: 21). The amino acid sequence of the CDR2 of the $V_H$ domain of SEQ ID NO: 20 of the 7C5B2 HV2 variant antibody according to the Kabat sequence numbering is: VIWGDGSTDYHSALIS (SEQ ID NO: 22). The amino acid sequence of the CDR3 of the $V_H$ domain of SEQ ID NO: 20 of the 7C5B2 HV2 variant antibody according to the Kabat sequence numbering is: GTGTGFAY (SEQ ID NO: 23).

The amino acid sequence of the complementarity determining region 1 or CDR1 of the $V_H$ domain of SEQ ID NO: 20 of the 7C5B2 HV2 variant antibody according to the IMGT sequence numbering is: GFSLKSYA (SEQ ID NO: 24). The amino acid sequence of the CDR2 of the $V_H$ domain of SEQ ID NO: 20 of the 7C5B2 HV2 variant antibody according to the IMGT sequence numbering is: IWGDGSTD (SEQ ID NO: 25).

The nucleotide sequence encoding a $V_L$ or variable domain of the light chain of a 6G8G7 KV1 variant antibody, as obtained by sequence analysis of sequences obtained from a 6G8G7 hybridoma, is:

```
                                             (SEQ ID NO: 26)
GGTGGCGGTGGTTCTGATATTGTGCTCACACAAACTAACCAAATCATGTC

CGCATCAGTAGGAGACCGGGTCAGTGTCACCTGCAAGGCCAGTCAGAATG

TGGATAGTAATGTGGCCTGGTATCAACAGAAACCTGGACATTCTCCCAAA

GCACTAATTTATTCGGCATCCTACCGGTACAGTAGAGTCCCTGATCGCAT

CACAGGCAGTGGATCTGGGACAGATTTCACTCTCACCATCACCAATGTGC

AGTCTAAAGACTTGGCAGACTATTTCTGTCAGCAATATCACAGCTATCCT

CTTCTCGCGTTCGGTGCTGGGACCAAGCTGGAGCTGAAACGGGCTGATGC

TGCACCAACTGTATCCCTCGAG.
```

The amino acid sequence of the $V_L$ domain of a 6G8G7 KV1 variant antibody corresponding to SEQ ID NO: 26 is:

```
                                             (SEQ ID NO: 27)
GGGGSDIVLTQTNQIMSASVGDRVSVTCKASQNVDSNVAWYQQKPGHSPK
ALIYSASYRYSRVPDRITGSGSGTDFTLTITNVQSKDLADYFCQQYHSYP
LLAFGAGTKLELKRADAAPTVSLE.
```

The amino acid sequence of the complementarity determining region 1 or CDR1 of the $V_L$ domain of SEQ ID NO: 27 of the 6G8G7 KV1 variant antibody according to the Kabat sequence numbering is: KASQNVDSNVA (SEQ ID NO: 28). The amino acid sequence of the CDR2 of the $V_L$ domain of SEQ ID NO: 27 of the 6G8G7 KV1 variant antibody according to the Kabat sequence numbering is: SASYRYS (SEQ ID NO: 29). The amino acid sequence of the CDR3 of the $V_L$ domain of SEQ ID NO: 27 of the 6G8G7 KV1 variant antibody according to the Kabat sequence numbering is: QQYHSYP (SEQ ID NO: 30).

The amino acid sequence of the complementarity determining region 1 or CDR1 of the $V_L$ domain of SEQ ID NO: 27 of the 6G8G7 KV1 variant antibody according to the IMGT sequence numbering is: QNVDSN (SEQ ID NO: 31). The amino acid sequence of the CDR2 of the $V_L$ domain of SEQ ID NO: 27 of the 6G8G7 KV1 variant antibody according to the IMGT sequence numbering is: SAS (SEQ ID NO: 32).

The nucleotide sequence encoding a $V_L$ or variable domain of the light chain of a 6G8G7 KV8 variant antibody, as obtained by sequence analysis of sequences obtained from a 6G8G7 hybridoma, is:

```
                                             (SEQ ID NO: 33)
GGTGGCGGTGGTTCTGACATTGTGATCACACAGTCTAACGCAATCATGTC

TGCATCTCCAGGGGAGAAGGTCACCATAACCTGCAGTGCCAGCTCAAGTG

TAAGTTTCATGCACTGGTTCCAGCAGAAGCCAGGCACTTCTCCCAAACTC

TGGATTTATAGCACATCCAACCTGGCTTCTGGAGTCCCTGCTCGCTTCAG

TGGCAGTGGATCTGGGACCTCTTACTCTCTCACAATCAGCCGAATGGAGG

CTGAAGATGCTGCCACTTATTACTGCCAGCAAAGGAGTAGTTACCCACTC

ACGTTCGGTGCTGGGACCAAGCTGGAGCTGAAACGGGCTGATGCTGCACC

AACTGTATCCCTCGAG.
```

The amino acid sequence of the $V_L$ domain of a 6G8G7 KV8 variant antibody corresponding to SEQ ID NO: 33 is:

```
                                             (SEQ ID NO: 34)
GGGGSDIVITQSNAIMSASPGEKVTITCSASSSVSFMHWFQQKPGTSPKL
WIYSTSNLASGVPARFSGSGSGTSYSLTISRMEAEDAATYYCQQRSSYPL
TFGAGTKLELKRADAAPTVSLE.
```

The amino acid sequence of the complementarity determining region 1 or CDR1 of the $V_L$ domain of SEQ ID NO: 34 of the 6G8G7 KV8 variant antibody according to the Kabat sequence numbering is: SASSSVSFMH (SEQ ID NO: 35). The amino acid sequence of the CDR2 of the $V_L$ domain of SEQ ID NO: 34 of the 6G8G7 KV8 variant antibody according to the Kabat sequence numbering is: STSNLAS (SEQ ID NO: 36). The amino acid sequence of the CDR3 of the $V_L$ domain of SEQ ID NO: 34 of the 6G8G7 KV8 variant antibody according to the Kabat sequence numbering is: QQRSSYP (SEQ ID NO: 37).

The amino acid sequence of the complementarity determining region 1 or CDR1 of the $V_L$ domain of SEQ ID NO: 33 of the 6G8G7 KV8 variant antibody according to the IMGT sequence numbering is: SSVSF (SEQ ID NO: 38). The amino acid sequence of the CDR2 of the $V_L$ domain of SEQ ID NO: 34 of the 6G8G7 KV8 variant antibody according to the IMGT sequence numbering is: STS (SEQ ID NO: 39).

The nucleotide sequence encoding a $V_L$ or variable domain of the light chain of a 6G8G7 KV2 variant antibody, as obtained by sequence analysis of sequences obtained from a 6G8G7 hybridoma, is:

```
                                             (SEQ ID NO: 40)
GGTGGCGGTGGTTCTGATATTGTGCTCACACAGACTCACAAATTCCTGCT

TGTATCAGCAGGAGACAGGATTACCATAACCTGCAAGGCCAGTCAGAGTG

TGAGTAATGATGTAGCTTGGTACCAACAGAAGCCAGGGCAGTCTCCTAAA

CTGCTGATATACTATGCATCCAATCGCTACACTGGAGTCCCTGATCGCTT
```

-continued
```
CACTGGCAGTGGATATGGGACGGATTTCACTTTCACCATCAGCACTGTGC

AGGCTGATGACCTGGCAGTTTATTTCTGTCAACAGGATTATAGCTCCCCG

TTCACGTTCGGAGGGGGGACCAAGCTGGAAATAAAACGGGCTGATGCTGC

ACCAACTGTATCCCTCGAG.
```

The amino acid sequence of the $V_L$ domain of a 6G8G7 KV2 variant antibody corresponding to SEQ ID NO: 40 is:

(SEQ ID NO: 41)
```
GGGSDIVLTQTHKFLLVSAGDRITITCKASQSVSNDVAWYQQKPGQSPKL
LIYYASNRYTGVPDRFTGSGYGTDFTFTISTVQADDLAVYFCQQDYSSPF
TFGGGTKLEIKRADAAPTVSLE.
```

The amino acid sequence of the complementarity determining region 1 or CDR1 of the $V_L$ domain of SEQ ID NO: 41 of the 6G8G7 KV2 variant antibody according to the Kabat sequence numbering is: KASQSVSNDVA (SEQ ID NO: 42). The amino acid sequence of the CDR2 of the $V_L$ domain of SEQ ID NO: 41 of the 6G8G7 KV2 variant antibody according to the Kabat sequence numbering is: YASNRYT (SEQ ID NO: 43). The amino acid sequence of the CDR3 of the $V_L$ domain of SEQ ID NO: 41 of the 6G8G7 KV2 variant antibody according to the Kabat sequence numbering is: QQDYSSPFT (SEQ ID NO: 44).

The amino acid sequence of the complementarity determining region 1 or CDR1 of the $V_L$ domain of SEQ ID NO: 41 of the 6G8G7 KV2 variant antibody according to the IMGT sequence numbering is: QSVSND (SEQ ID NO: 45). The amino acid sequence of the CDR2 of the $V_L$ domain of SEQ ID NO: 41 of the 6G8G7 KV2 variant antibody according to the IMGT sequence numbering is: YAS (SEQ ID NO: 46). The amino acid sequence of the CDR3 of the $V_L$ domain of SEQ ID NO: 41 of the 6G8G7 KV2 variant antibody according to the IMGT sequence numbering is: QQDYSSP (SEQ ID NO: 47).

The nucleotide sequence encoding a $V_L$ or variable domain of the light chain of a 7C5B2 KV2 variant antibody, as obtained by sequence analysis of sequences obtained from a 7C5B2 hybridoma, is:

(SEQ ID NO: 49)
```
GATGTTGTGATGACCCAAACTCCACTCTCCCTGCCTGTCAGTCTTGGAGA

TCAAGCCTCCATCTCTTGCAGATCTAGTCAGAGCCTTGTACACAGTAATG

GAAACACCTATTTACATTGGTACCTGCAGAAGCCAGGCCAGTCTCCAAAG

CTCCTGATCTACAAAGTTTCCAACCGATTTTCTGGGGTCCCAGACAGGTT

CAGTGGCAGTGGATCAGGGACAGATTTCACACTCAAGATCAGCCGAGTGG

AGGCTGAGGATCTGGGAATTTATTTCTGCTCTCAATGTACACATATTCCG

TGGACGTTCGGTGGAGGCACCAACCTGGAAATCAAA.
```

The amino acid sequence of the $V_L$ domain of a 7C5B2 KV2 variant antibody corresponding to SEQ ID NO: 49 is:

(SEQ ID NO: 50)
```
DVVMTQTPLSLPVSLGDQASISCRSSQSLVHSNGNTYLHWYLQKPGQSPK
LLIYKVSNRFSGVPDRFSGSGSGTDFTLKISRVEAEDLGIYFCSQCTHIP
WTFGGGTNLEIK.
```

The amino acid sequence of the complementarity determining region 1 or CDR1 of the $V_L$ domain of SEQ ID NO: 50 of the 7C5B2 KV2 variant antibody according to the Kabat sequence numbering is: RSSQSLVHSNGNTYLH (SEQ ID NO: 51). The amino acid sequence of the CDR2 of the $V_L$ domain of SEQ ID NO: 50 of the 7C5B2 KV2 variant antibody according to the Kabat sequence numbering is: KVSNRFS (SEQ ID NO: 52). The amino acid sequence of the CDR3 of the $V_L$ domain of SEQ ID NO: 50 of the 7C5B2 KV2 variant antibody according to the Kabat sequence numbering is: SQCTHIPWT (SEQ ID NO: 53).

Accordingly, in some embodiments of the aspects provided herein, the heavy and/or light chain variable domain(s) sequence(s) of the different 6G8G7 or 7C5B2 variant antibodies, i.e., SEQ ID NO: 6, SEQ ID NO: 13, SEQ ID NO: 20, SEQ ID NO: 27, SEQ ID NO: 34, SEQ ID NO: 41, and/or SEQ ID NO: 50 can be used to generate, for example, chimeric, humanized, or composite human antibodies, as described elsewhere herein.

In some aspects, monoclonal antibodies that specifically bind to DEspR are provided having one or more biological characteristics of a 6G8G7 or 7C5B2 variant antibody. As used herein, an antibody having a "biological characteristic" of a designated antibody, such as a 6G8G7 variant antibody, is one that possesses one or more of the biological characteristics of that antibody which distinguish it from other antibodies that bind to the same antigen. For example, biological characteristics of the 6G8G7 monoclonal antibody includes having an $ED_{50}$ value (i.e., the dose therapeutically effective in 50% of the population) at or around the $ED_{50}$ value of the 6G8G7 antibody for the given population; having an $EC_{50}$ value (i.e., the dose that achieves a half-maximal inhibition of a given parameter or phenotype) at or around the $EC_{50}$ value of the 6G8G7 antibody for a given parameter or phenotype. The effects of any particular dosage can be monitored by a suitable bioassay. For example, in some embodiments of these aspects, the given parameter or phenotype to be inhibited by the antibody that specifically binds to DEspR and has one or more biological characteristics of a 6G8G7 or 7C5B2 variant antibody can include, but is not limited to, the mean total tube number in an in vitro tubulogenesis assay, the mean total tube length in an in vitro tubulogenesis assay, the mean number of branching points in an in vitro tubulogenesis assay, the mean number of vessel connections in an in vitro tubulogenesis assay, and/or tumor cell invasiveness.

In some embodiments of the aspects described herein, anti-DEspR antibodies for use in the compositions and methods described herein include monoclonal antibodies that bind to the same epitope or epitopes of DEspR as a monoclonal anti-DEspR 6G8G7 or 7C5B2 variant antibody. In some embodiments of the aspects described herein, the epitope comprises, consists essentially of, or consists of SEQ ID NO: 1. In some embodiments of the aspects described herein, the epitope comprises, consists essentially of, or consists of SEQ ID NO: 2.

The DNA sequences encoding the antibodies or antibody fragment that specifically bind DEspR described herein can also be modified, for example, by substituting the coding sequence for human heavy- and light-chain constant domains or framework regions in place of the homologous murine sequences (U.S. Pat. No. 4,816,567; Morrison, et al., Proc. Natl. Acad. Sci. USA, 81:6851 (1984)), or by covalently joining to the immunoglobulin coding sequence all or part of the coding sequence for a non-immunoglobulin polypeptide, as also described elsewhere herein.

Such non-immunoglobulin polypeptides can be substituted for the constant domains of an antibody, or they can be substituted for the variable domains of one antigen-combining site of an antibody to create a chimeric bivalent antibody comprising one antigen-combining site having specificity for an antigen and another antigen-combining site having specificity for a different antigen.

Also provided herein, in some aspects, are humanized anti-DEspR antibodies for use in the compositions and methods described herein. Humanized forms of non-human (e.g., murine) antibodies refer to chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some embodiments, Fv framework region (FR) residues of the human immunoglobulin are replaced by corresponding non-human residues. Furthermore, humanized antibodies can comprise residues that are not found in the recipient antibody or in the donor antibody. These modifications are made to further refine antibody performance. In general, a humanized antibody can comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also can comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

A humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody. Accordingly, such humanized antibodies are chimeric antibodies (U.S. Pat. No. 4,816,567) where substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies. In some embodiments, humanized antibodies comprising one or more variable domains comprising the amino acid sequence of the variable heavy (SEQ ID NO: 20) and/or variable light (SEQ ID NO: 49) chain domains of the murine anti-DEspR antibody 7C5B2, are provided, for example.

Accordingly, in some embodiments of the aspects described herein, one or more heavy and/or one or more light chain CDR regions of a humanized anti-DEspR binding protein, binding protein, antibody or antibody fragment, or antigen-binding portion thereof, or antigen-binding portion thereof thereof comprises a sequence of any of the 6G8G7 or 7C5B2 variant antibodies described herein. In some such embodiments, the one or more variable heavy chain CDR regions comprises a sequence selected from the group consisting of SEQ ID NO: 7, SEQ ID NO: 8, SEQ ID NO: 9, SEQ ID NO: 14, SEQ ID NO: 15, SEQ ID NO: 16, SEQ ID NO: 21, SEQ ID NO: 22, and SEQ ID NO: 23. In some such embodiments, the one or more variable light chain CDR regions comprises a sequence selected from the group consisting of SEQ ID NO: 28, SEQ ID NO: 29, SEQ ID NO: 30, SEQ ID NO: 35, SEQ ID NO: 36, SEQ ID NO: 37, SEQ ID NO: 42, SEQ ID NO: 43, SEQ ID NO: 44, SEQ ID NO: 51, SEQ ID NO: 52, and SEQ ID NO: 53. In some such embodiments, the one or more variable heavy chain CDR regions comprises a sequence selected from the group consisting of SEQ ID NO: 7, SEQ ID NO: 8, SEQ ID NO: 9, SEQ ID NO: 14, SEQ ID NO: 15, SEQ ID NO: 16, SEQ ID NO: 21, SEQ ID NO: 22, and SEQ ID NO: 23, and the one or more variable light chain CDR regions comprises a sequence selected from the group consisting of SEQ ID NO: 28, SEQ ID NO: 29, SEQ ID NO: 30, SEQ ID NO: 35, SEQ ID NO: 36, SEQ ID NO: 37, SEQ ID NO: 42, SEQ ID NO: 43, SEQ ID NO: 44, SEQ ID NO: 51, SEQ ID NO: 52, and SEQ ID NO: 53.

Accordingly, in some embodiments of the aspects provided herein, the heavy and/or light chain variable domain(s) sequence(s) of any of the 6G8G7 or 7C5B2 variant antibodies, and their respective variable heavy chain CDR regions SEQ ID NO: 7, SEQ ID NO: 8, SEQ ID NO: 9, SEQ ID NO: 14, SEQ ID NO: 15, SEQ ID NO: 16, SEQ ID NO: 21, SEQ ID NO: 22, and SEQ ID NO: 23, and/or variable light chain CDR regions SEQ ID NO: 28, SEQ ID NO: 29, SEQ ID NO: 30, SEQ ID NO: 35, SEQ ID NO: 36, SEQ ID NO: 37, SEQ ID NO: 42, SEQ ID NO: 43, SEQ ID NO: 44, SEQ ID NO: 51, SEQ ID NO: 52, and SEQ ID NO: 53, can be used to generate, for example, CDR-grafted, chimeric, humanized, or composite human antibodies or antigen-binding fragments, as described elsewhere herein. As understood by one of ordinary skill in the art, any variant, CDR-grafted, chimeric, humanized, or composite antibodies or antigen-binding fragments derived from any of the 6G8G7 or 7C5B2 variant antibodies or any one of the antibodies produced by the 6G8G7 or 7C5B2 hybridomas useful in the compositions and methods described herein will maintain the ability to immunospecifically bind DEspR, such that the variant, CDR-grafted, chimeric, humanized, or composite antibody or antigen-binding fragment thereof has at least 50%, at least 60%, at least 70%, at least 80%, at least 90%, at least 95%, at least 100%, or any amount greater than the binding affinity to DEspR relative to the original antibody from which it is derived.

In some such embodiments of the aspects described herein, the anti-DEspR antibody or antigen-binding fragment thereof comprises one, two, three or four of the framework regions of a light chain variable region sequence which is at least 75%, 80%, 85%, 90%, 95%, or 100% identical to one, two, three or four of the framework regions of the light chain variable region sequence of the 6G8G7 or 7C5B2 variant antibodies from which it is derived. In some embodiments of the aspects described herein, the light chain variable framework region that is derived from said amino acid sequence consists of said amino acid sequence but for the presence of up to 10 amino acid substitutions, deletions, and/or insertions, preferably up to 10 amino acid substitutions. In some embodiments of the aspects described herein, the light chain variable framework region that is derived from said amino acid sequence consists of said amino acid sequence with 1, 2, 3, 4, 5, 6, 7, 8, 9 or 10 amino acid residues being substituted for an amino acid found in an analogous position in a corresponding non-human, primate, or human light chain variable framework region. In some embodiments of the aspects described herein, the antibody or antigen-binding fragment further comprises one, two, three or all four $V_L$ framework regions derived from the $V_L$ of a human or primate antibody. The primate or human light chain framework region of the antibody selected for use with the light chain CDR sequences described herein, can have, for example, at least 70% identity with a light chain framework region of the non-human parent antibody. The primate or human antibody selected can have the same or substantially the same number of amino acids in its light chain complementarity determining regions to that of the light chain complementarity determining regions of any of the 6G8G7 or 7C5B2 variant antibodies. In some embodiments of the aspects described herein, the primate or human light chain framework region amino acid residues are from a natural primate or human antibody light chain framework region having at least 75% identity, at least 80% identity, at least 85% identity (or more) with the light chain framework regions of any of the 6G8G7 or 7C5B2 variant antibodies. In some embodiments, the anti-DEspR antibody or antigen-binding fragment further comprises one, two, three or all four $V_L$ framework regions derived from a human light chain variable kappa subfamily. In some embodiments, the anti-DEspR antibody or antigen-binding fragment further comprises one, two, three or all four VL framework regions derived from a human light chain variable lambda subfamily.

In some embodiments of the aspects described herein, the anti-DEspR antibody or antigen-binding fragment thereof comprises one, two, three or all four of the framework regions of the heavy chain variable region sequence of any of the 6G8G7 or 7C5B2 variant antibodies. In some embodiments of the aspects described herein, the anti-DEspR antibody or antigen-binding fragment thereof comprises one, two, three, or four of the framework regions of a heavy chain variable region sequence which is at least 75%, 80%, 85%, 90%, 95% or 100% identical to one, two, three or four of the framework regions of the heavy chain variable region sequence of any of the 6G8G7 or 7C5B2 variant antibodies. In some embodiments of the aspects described herein, the heavy chain variable framework region that is derived from said amino acid sequence consists of said amino acid sequence but for the presence of up to 10 amino acid substitutions, deletions, and/or insertions, preferably up to 10 amino acid substitutions. In some embodiments of the aspects described herein, the heavy chain variable framework region that is derived from said amino acid sequence consists of said amino acid sequence with 1, 2, 3, 4, 5, 6, 7, 8, 9 or 10 amino acid residues being substituted for an amino acid found in an analogous position in a corresponding non-human, primate, or human heavy chain variable framework region. In some embodiments of the aspects described herein, the anti-DEspR antibody or antigen-binding fragment further comprises one, two, three or all four $V_H$ framework regions derived from the $V_H$ of a human or primate antibody. The primate or human heavy chain framework region of the antibody selected for use with the heavy chain CDR sequences described herein, can have, for example, at least 70% identity with a heavy chain framework region of the non-human parent antibody. Preferably, the primate or human antibody selected can have the same or substantially the same number of amino acids in its heavy chain complementarity determining regions to that of the light chain complementarity determining regions of any of the 6G8G7 or 7C5B2 variant antibodies. In some embodiments of the aspects described herein, the primate or human heavy chain framework region amino acid residues are from a natural primate or human antibody heavy chain framework region having at least 75% identity, at least 80% identity, at least 85% identity (or more) with the heavy chain framework regions of any of the 6G8G7 or 7C5B2 variant antibodies. In specific embodiments, the antibody or antigen-binding fragment further comprises one, two, three or all four $V_H$ framework regions derived from a human heavy chain variable subfamily (e.g., one of subfamilies 1 to 7).

In some embodiments of the aspects described herein, the position of one or more CDRs along the $V_H$ (e.g., CDR1, CDR2, or CDR3) and/or VL (e.g., CDR1, CDR2, or CDR3) region of an antibody described herein can vary, i.e., be shorter or longer, by one, two, three, four, five, or six amino acid positions so long as immunospecific binding to DEspR (e.g., human DEspR) is maintained (e.g., substantially maintained, for example, at least 50%, at least 60%, at least 70%, at least 80%, at least 90%, at least 95% of the binding of the original antibody from which it is derived). For example, in some embodiments, the position defining a CDR of any of the 6G8G7 or 7C5B2 variant antibodies can vary, i.e., be shorter or longer, by shifting the N-terminal and/or C-terminal boundary of the CDR by one, two, three, four, five, or six amino acids, relative to the CDR position of any one of the antibodies described herein, so long as immunospecific binding to DEspR (e.g., human DEspR) is maintained (e.g., substantially maintained, for example, at least 50%, at least 60%, at least 70%, at least 80%, at least 90%, at least 95% of the binding of the original antibody from which it is derived). In another embodiment, the length of one or more CDRs along the $V_H$ (e.g., CDR1, CDR2, or CDR3) and/or $V_L$ (e.g., CDR1, CDR2, or CDR3) region of an antibody described herein can vary (e.g., be shorter or longer) by one, two, three, four, five, or more amino acids, so long as immunospecific binding to DEspR (e.g., human DEspR) is maintained (e.g., substantially maintained, for example, at least 50%, at least 60%, at least 70%, at least 80%, at least 90%, at least 95% of the binding of the original antibody from which it is derived).

With respect to the heavy chain, in some embodiments of the aspects described herein, the heavy chain of an antibody described herein can be an alpha (α), delta (Δ), epsilon (ε), gamma (γ) or mu (μ) heavy chain. In some embodiments of the aspects described herein, the heavy chain of an antibody described can comprise a human alpha (α), delta (Δ), epsilon (ε), gamma (γ) or mu (μ) heavy chain. Non-limiting examples of human constant region sequences have been described in the art, e.g., see U.S. Pat. No. 5,693,780 and Kabat E A et al., (1991) supra.

In some embodiments of the aspects described herein, one, two or more mutations (e.g., amino acid substitutions) are introduced into the Fc region of an any of the 6G8G7 or 7C5B2 variant antibodies described herein or a fragment thereof (e.g., CH2 domain (residues 231-340 of human IgG1) and/or CH3 domain (residues 341-447 of human IgG1) and/or the hinge region, with numbering according to the Kabat numbering system (e.g., the EU index in Kabat)) to alter one or more functional properties of the antibody, such as serum half-life, complement fixation, Fc receptor binding and/or antigen-dependent cellular cytotoxicity.

In some embodiments of the aspects described herein, one, two or more mutations (e.g., amino acid substitutions) are introduced into the hinge region of the Fc region (CH1 domain) such that the number of cysteine residues in the hinge region are altered (e.g., increased or decreased) as described in, e.g., U.S. Pat. No. 5,677,425. The number of cysteine residues in the hinge region of the CH1 domain can be altered to, e.g., facilitate assembly of the light and heavy chains, or to alter (e.g., increase or decrease) the stability of the antibody.

In some embodiments of the aspects described herein, one, two or more mutations (e.g., amino acid substitutions)

are introduced into the Fc region of an anti-DEspR antibody described herein or an antigen-binding fragment thereof (e.g., CH2 domain (residues 231-340 of human IgG1) and/or CH3 domain (residues 341-447 of human IgG1) and/or the hinge region, with numbering according to the Kabat numbering system (e.g., the EU index in Kabat)) to increase or decrease the affinity of the antibody for an Fc receptor (e.g., an activated Fc receptor) on the surface of an effector cell. Mutations in the Fc region of an antibody or fragment thereof that decrease or increase the affinity of an antibody for an Fc receptor and techniques for introducing such mutations into the Fc receptor or fragment thereof are known to one of skill in the art. Examples of mutations in the Fc receptor of an antibody that can be made to alter the affinity of the antibody for an Fc receptor are described in, e.g., Smith P et al., (2012) PNAS 109: 6181-6186, U.S. Pat. No. 6,737,056, and International Publication Nos. WO 02/060919; WO 98/23289; and WO 97/34631, which are incorporated herein by reference.

In some embodiments of the aspects described herein, one, two or more amino acid mutations (i.e., substitutions, insertions or deletions) are introduced into an IgG constant domain, or FcRn-binding fragment thereof (preferably an Fc or hinge-Fc domain fragment) to alter (e.g., decrease or increase) half-life of the antibody in vivo. See, e.g., International Publication Nos. WO 02/060919; WO 98/23289; and WO 97/34631; and U.S. Pat. Nos. 5,869,046, 6,121,022, 6,277,375 and 6,165,745 for examples of mutations that will alter (e.g., decrease or increase) the half-life of an antibody in vivo.

In some embodiments of the aspects described herein, one, two or more amino acid mutations (i.e., substitutions, insertions or deletions) are introduced into an IgG constant domain, or FcRn-binding fragment thereof (preferably an Fc or hinge-Fc domain fragment) to decrease the half-life of the anti-DEspR antibody in vivo. In some embodiments of the aspects described herein, one, two or more amino acid mutations (i.e., substitutions, insertions or deletions) are introduced into an IgG constant domain, or FcRn-binding fragment thereof (preferably an Fc or hinge-Fc domain fragment) to increase the half-life of the antibody in vivo. In some embodiments of the aspects described herein, the antibodies can have one or more amino acid mutations (e.g., substitutions) in the second constant (CH2) domain (residues 231-340 of human IgG1) and/or the third constant (CH3) domain (residues 341-447 of human IgG1), with numbering according to the EU index in Kabat (Kabat E A et al., (1991) supra). In some embodiments of the aspects described herein, the constant region of the IgG1 of an antibody or antigen-binding fragment thereof described herein comprises a methionine (M) to tyrosine (Y) substitution in position 252, a serine (S) to threonine (T) substitution in position 254, and a threonine (T) to glutamic acid (E) substitution in position 256, numbered according to the EU index as in Kabat. See U.S. Pat. No. 7,658,921, which is incorporated herein by reference. This type of mutant IgG, referred to as "YTE mutant" has been shown to display fourfold increased half-life as compared to wild-type versions of the same antibody (see Dall'Acqua W F et al., (2006) J Biol Chem 281: 23514-24). In some embodiments of the aspects described herein, an antibody or antigen-binding fragment thereof comprises an IgG constant domain comprising one, two, three or more amino acid substitutions of amino acid residues at positions 251-257, 285-290, 308-314, 385-389, and 428-436, numbered according to the EU index as in Kabat.

In some embodiments of the aspects described herein, one, two or more amino acid substitutions are introduced into an IgG constant domain Fc region to alter the effector function(s) of the anti-DEspR antibody. For example, one or more amino acids selected from amino acid residues 234, 235, 236, 237, 297, 318, 320 and 322, numbered according to the EU index as in Kabat, can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260. In some embodiments of the aspects described herein, the deletion or inactivation (through point mutations or other means) of a constant region domain can reduce Fc receptor binding of the circulating antibody thereby increasing tumor localization. See, e.g., U.S. Pat. Nos. 5,585,097 and 8,591,886 for a description of mutations that delete or inactivate the constant domain and thereby increase tumor localization. In some embodiments of the aspects described herein, one or more amino acid substitutions may be introduced into the Fc region of an antibody described herein to remove potential glycosylation sites on Fc region, which may reduce Fc receptor binding (see, e.g., Shields R L et al., (2001) J Biol Chem 276: 6591-604). In some embodiments of the aspects described herein, one or more of the following mutations in the constant region of an antibody described herein can be made: an N297A substitution; an N297Q substitution; a L235A substitution and a L237A substitution; a L234A substitution and a L235A substitution; a E233P substitution; a L234V substitution; a L235A substitution; a C236 deletion; a P238A substitution; a D265A substitution; a A327Q substitution; or a P329A substitution, numbered according to the EU index as in Kabat. In some embodiments of the aspects described herein, an antibody or antigen-binding fragment thereof described herein comprises the constant domain of an IgG1 with an N297Q or N297A amino acid substitution.

In some embodiments of the aspects described herein, one or more amino acids selected from amino acid residues 329, 331 and 322 in the constant region of an anti-In some embodiments of the aspects described herein, one or more amino acids selected from amino acid residues 329, 331 and 322 in the constant region of an anti-DEspR antibody described herein, numbered according to the EU index as in Kabat, can be replaced with a different amino acid residue such that the antibody has altered C1q binding and/or reduced or abolished complement dependent cytotoxicity (CDC). This approach is described in further detail in U.S. Pat. No. 6,194,551 (Idusogie et al). In some embodiments of the aspects described herein, one or more amino acid residues within amino acid positions 231 to 238 in the N-terminal region of the CH2 domain of an antibody described herein are altered to thereby alter the ability of the antibody to fix complement. This approach is described further in International Publication No. WO 94/29351. In some embodiments of the aspects described herein, the Fc region of an antibody described herein is modified to increase the ability of the antibody to mediate antibody dependent cellular cytotoxicity (ADCC) and/or to increase the affinity of the antibody for an Fcγ receptor by mutating one or more amino acids (e.g., introducing amino acid substitutions) at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439, numbered according to the EU index as in Kabat. This approach is described further in International Publication No. WO 00/42072.

In some embodiments of the aspects described herein, an anti-DEspR antibody described herein comprises the constant region of an IgG4 antibody and the serine at amino acid residue 228 of the heavy chain, numbered according to the EU index as in Kabat, is substituted for proline.

Antibodies with reduced fucose content have been reported to have an increased affinity for Fc receptors, such as, e.g., FcγRIIIa. Accordingly, in certain embodiments, the anti-DEspR antibodies or antigen-binding fragments thereof described herein have reduced fucose content or no fucose content. Such antibodies can be produced using techniques known to one skilled in the art. For example, the antibodies can be expressed in cells deficient or lacking the ability of fucosylation. In a specific example, cell lines with a knock-out of both alleles of α1,6-fucosyltransferase can be used to produce antibodies with reduced fucose content. The POTELLIGENTR™ system (Lonza) is an example of such a system that can be used to produce antibodies with reduced fucose content. Alternatively, antibodies or antigen-binding fragments with reduced fucose content or no fucose content can be produced by, e.g.: (i) culturing cells under conditions which prevent or reduce fucosylation; (ii) posttranslational removal of fucose (e.g., with a fucosidase enzyme); (iii) post-translational addition of the desired carbohydrate, e.g., after recombinant expression of a non-glycosylated glycoprotein; or (iv) purification of the glycoprotein so as to select for antibodies or antigen-binding fragments thereof which are not fucosylated. See, e.g., Longmore G D & Schachter H (1982) Carbohydr Res 100: 365-92 and Imai-Nishiya H et al., (2007) BMC Biotechnol. 7: 84 for methods for producing antibodies or antigen-binding fragments thereof with no fucose content or reduced fucose content.

In some embodiments of the aspects described herein, anti-DEspR antibodies or antigen-binding fragments thereof described herein have an increased affinity for CD32B (also known as FcγRIIB or FCGR2B), e.g., as compared to an antibody with a wild-type Fc region, e.g., an IgG1 Fc. In some embodiments of the aspects described herein, anti-DEspR antibodies or antigen-binding fragments thereof described herein have a selectively increased affinity for CD32B (FcγRIIB) over both CD32A (FcγRIIA) and CD16 (FcγRIIIA). Sequence alterations that result in increased affinity for CD32B are provided, for example, in Mimoto et al., Protein Engineering, Design & Selection 10: 589-598 (2013), Chu et al., Molecular Immunology 45: 3926-3933 (2008), and Strohl, Current Opinion in Biology 20: 685-691 (2009), each of which is herein incorporated by reference in its entirety. In some embodiments of the aspects described herein, the antibody or antigen-binding fragment with an increased affinity for CD32B comprises a heavy chain constant region, e.g., an IgG1 constant region, or fragment thereof comprising a mutation selected from the group consisting of: G236D, P238D, S239D, S267E, L328F, L328E, an arginine inserted after position 236, and combinations thereof, numbered according to EU index (Kabat et al., Sequences of Proteins of Immunological Interest, U.S. Department of Health and Human Services, Bethesda (1991)). In some embodiments of the aspects described herein, the antibody or antigen-binding fragment with an increased affinity for CD32B comprises a heavy chain constant region, e.g., an IgG1 constant region, or fragment thereof comprising S267E and L328F substitutions. In some embodiments of the aspects described herein, the antibody or antigen-binding fragment with an increased affinity for CD32B comprises a heavy chain constant region, e.g., an IgG1 constant region, or fragment thereof comprising P238D and L328E substitutions. In some embodiments of the aspects described herein, the antibody or antigen-binding fragment with an increased affinity for CD32B comprises a heavy chain constant region, e.g., an IgG1 constant region, or fragment thereof comprising a P238D substitution and substitution selected from the group consisting of E233D, G237D, H268D, P271G, A330R, and combinations thereof. In some embodiments of the aspects described herein, the antibody or antigen-binding fragment with an increased affinity for CD32B comprises a heavy chain constant region, e.g., an IgG1 constant region, or fragment thereof comprising P238D, E233D, G237D, H268D, P271G, and A330R substitutions. In some embodiments of the aspects described herein, the antibody or antigen-binding fragment with an increased affinity for CD32B comprises a heavy chain constant region, e.g., an IgG1 constant region, or fragment thereof comprising G236D and S267E. In some embodiments of the aspects described herein, the antibody or antigen-binding fragment with an increased affinity for CD32B comprises a heavy chain constant region, e.g., an IgG1 constant region, or fragment thereof comprising S239D and S267E. In some embodiments of the aspects described herein, the antibody or antigen-binding fragment with an increased affinity for CD32B comprises a heavy chain constant region, e.g., an IgG1 constant region, or fragment thereof comprising S267E and L328F. In some embodiments of the aspects described herein, the antibody or antigen-binding fragment with an increased affinity for CD32B comprises a heavy chain constant region, e.g., an IgG1 constant region, or fragment thereof comprising an arginine inserted after position 236 and L328R.

The term "CDR-grafted antibody" refers to antibodies which comprise heavy and light chain variable region sequences from one species, but in which the sequences of one or more of the CDR regions of $V_H$ and/or $V_L$ are replaced with CDR sequences of another species, such as antibodies having human heavy and light chain variable regions in which one or more of the human CDRS (e.g., CDR3) has been replaced with mouse CDR sequences. CDR-grafted antibodies described herein comprise heavy and light chain variable region sequences from a human antibody wherein one or more of the CDR regions of $V_H$ and/or $V_L$ are replaced with CDR sequences of the non-human antibodies described herein, such as SEQ ID NO: 7, SEQ ID NO: 8, SEQ ID NO: 9, SEQ ID NO: 14, SEQ ID NO: 15, SEQ ID NO: 16, SEQ ID NO: 21, SEQ ID NO: 22, SEQ ID NO: 23, SEQ ID NO: 28, SEQ ID NO: 29, SEQ ID NO: 30, SEQ ID NO: 35, SEQ ID NO: 36, SEQ ID NO: 37, SEQ ID NO: 42, SEQ ID NO: 43, SEQ ID NO: 44, SEQ ID NO: 51, SEQ ID NO: 52, and SEQ ID NO: 53

In some embodiments of the aspects described herein, a humanized anti-DEspR monoclonal antibody comprises mutated human IgG1, IgG2, IgG3, or IgG4 framework regions and one or more heavy and/or one or more light chain CDR regions from the anti-human DEspR 6G8G7 or 7C5B2 variant antibodies described herein, that blocks binding of human DEspR to its ligands. In some such embodiments, the one or more variable heavy chain CDR regions comprises a sequence selected from the group consisting of SEQ ID NO: 7, SEQ ID NO: 8, SEQ ID NO: 9, SEQ ID NO: 14, SEQ ID NO: 15, SEQ ID NO: 16, SEQ ID NO: 21, SEQ ID NO: 22, and SEQ ID NO: 23. In some such embodiments, the one or more variable light chain CDR regions comprises a sequence selected from the group consisting of SEQ ID NO: 28, SEQ ID NO: 29, SEQ ID NO: 30, SEQ ID NO: 35, SEQ ID NO: 36, SEQ ID NO: 37, SEQ ID NO: 42, SEQ ID NO: 43, SEQ ID NO: 44, SEQ ID NO: 51, SEQ ID NO: 52, and SEQ ID NO: 53. In some such embodiments, the one or more variable heavy chain CDR regions comprises a sequence selected from the group consisting of SEQ ID NO: 7, SEQ ID NO: 8, SEQ ID NO: 9, SEQ ID NO: 14, SEQ ID NO: 15, SEQ ID NO: 16, SEQ ID NO: 21, SEQ ID NO: 22, and SEQ ID NO: 23, and the one or more variable light chain CDR regions comprises a sequence selected from the group consisting of SEQ ID NO: 28, SEQ ID NO: 29, SEQ ID NO: 30, SEQ ID NO: 35, SEQ ID NO: 36, SEQ ID NO: 37, SEQ ID NO: 42, SEQ ID NO: 43, SEQ ID NO: 44, SEQ ID NO: 51, SEQ ID NO: 52, and SEQ ID NO: 53.

The choice of human variable domains, both light and heavy, to be used in making the humanized antibodies is very important to reduce antigenicity. According to the so-called "best-fit" method, the amino acid sequences of the variable heavy and light chain domains of a rodent antibody, such as that of the 6G8G7 or 7C5B2 variant antibodies (SEQ ID NO: 6, SEQ ID NO: 13, and SEQ ID NO: 20, and SEQ ID NO: 27, SEQ ID NO: 34, SEQ ID NO: 41, and SEQ ID NO: 50 respectively), are screened against the entire library of known human variable-domain sequences, especially germline human variable-domain sequences. The human sequence which is closest to that of the rodent is then accepted as the human framework (FR) for the humanized antibody (Sims et al., J. Immunol., 151:2296 (1993); Chothia et al., J. Mol. Biol., 196:901 (1987)). Another method uses a particular framework derived from the consensus sequence of all human antibodies of a particular subgroup of light or heavy chains. The same framework can be used for several different humanized antibodies (Carter et al., Proc. Natl. Acad. Sci. USA, 89:4285 (1992); Presta et al., J. Immunol., 151:2623 (1993)).

In some embodiments of the aspects described herein, the anti-DEspR antibodies or antigen-binding fragments thereof described herein are affinity matured or affinity optimized. Preferably, affinity optimized anti-DEspR antibodies or antigen-binding fragments thereof have affinities that are at least 1-fold, at least 1.5-fold, at least 2-fold higher, at least 5-fold higher, at least 10-fold higher, at least 20-fold higher, at least 50-fold higher, or more than the 6G8G7 or 7C5B2 anti-DEspR variant antibodies from which they are derived.

It is further important that antibodies be humanized with retention of high affinity for the antigen and other favorable biological properties, for example, the anti-angiogenic properties of the 6G8G7 or 7C5B2 anti-DEspR variant antibodies described herein. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

Accordingly, in some embodiments, provided herein is a humanized $V_H$ or variable domain of the heavy chain of a 6G8G7 HV2 variant antibody, termed herein as a "6G8G7 HV2-h1 humanized $V_H$ domain" having a nucleotide sequence of: GAGGTGCAGCTGGTGGAGTCCG GCGGCGGCCTGGTGCAGCCCGGCGGCTCCCTGCGC CTGTCCTGCGCCGCCTCCGGCTTCACCTTCTCCCG CTACTGGATGTCCTGGGTGCGCCAGGCCCCCGGCA AGGGCCTGGAGTGGATCGGCGAGAT-CAACCCCGACTCCTCCACCATCAACTAC ACCCCCTCCCTGAAGGACCGCTTCAC-CATCTCCCGCGACACCGCCAAGAAGTCCCTGTAC CTGCAGATGTC-CAAGGTGCGCTCCGAGGACACCGCCCTGTAC-TACTGCGCCCGCCACGGCCGCGGCATGGACTA CTGGTCCCAGGGCACCTCCGTGACCGTGTCCTCC (SEQ ID NO: 54); and an amino acid sequence of: EVQLVESGGGLVQPGGSLRLS-CAASGFTFSRYWMSWVRQAPGK-GLEWIGEINPDSSTINYTPSLKDRFTISRDTAKKS LYLQMSKVRSEDTALYYCAR-HGRGMDYWSQGTSVTVSS (SEQ ID NO: 55)

In some embodiments, provided herein is a humanized $V_L$ or variable domain of the light chain of a 6G8G7 KV1 variant antibody, termed herein as a "6G8G7 KV1-h2 humanized $V_L$ domain" having a nucleotide sequence of: GACATCGTGCTGACCCAGTCCCCCGA-CATCCTGTCCGTGTCCCTGGGCGAGCGCGCCACC GTGAACTGCAAGGCCTCCCAGAACGTGGACTC-CAACGTGGCCTGGTACCAGCAGAAGCCC GGC-CACCCCCCCAAGCTGCTGATCTACTCCGCCTCC-TACCGCTACTCCCGCGTGCCCGAC CGCATCTCCGGCTCCGGCTCCGGCACCGACTT-CACCCTGACCATCTCCAACCTGCAGGCC GAGGACGTGGCCGTGTACTACTGCCAGCAGTAC-CACTCCTACCCCCTGCTGGCCTTCGGC GCCGGCACCAAGCTGGAGCT-GAAGCGCGCCGACGCCGCCCCC (SEQ ID NO: 56); and an amino acid sequence of: DIVLTQSPDILSVSLGER-ATVNCKASQNVDSN-VAWYQQKPGHPPKLLIYSASYRYSRVPDRISGS GSGTDFTLTISNLQAEDVAVYYCQQYHSYPL-LAFGAGTKLELKRADAAP (SEQ ID NO: 57).

In some embodiments, provided herein is a humanized $V_L$ or variable domain of the light chain of a 6G8G7 KV2 variant antibody, termed herein as a "6G8G7 KV2-h3 humanized $V_L$ domain" having a nucleotide sequence of: GACATCGTGCTGACCCAGTCCCCCGA-CATCCTGTCCGTGTCCCTGGGCGAGCGCGCCACC GTGAACTGCAAGGCCTCCCAGAACGTGGACTC-CAACGTGGCCTGGTACCAGCAGAAGCCC GGC-CACCCCCCCAAGCTGCTGATCTACTCCGCCTCC-TACCGCTACTCCCGCGTGCCCGAC CGCATCTCCGGCTCCGGCTCCGGCACCGACTT-CACCCTGACCATCTCCAACCTGCAGGCC GAGGACCTGGCCGACTACTTCTGCCAGCAGTAC-CACTCCTACCCCCTGCTGGCCTTCGGC GCCGGCACCAAGCTGGAGCT-GAAGCGCGCCGACGCCGCCCCC (SEQ ID NO: 58); and an amino acid sequence of:

(SEQ ID NO: 59)
DIVLTQSPDILSVSLGERATVNCKASQNVDSNVAWYQQKPGHPPKWYSAS
YRYSRVPDRISGSGSGTDFTLTISNLQAEDLADYFCQQYHSYPLLAFGAG
TKLELKRADAAP.

In some embodiments, provided herein is a 6G8G7 HV2-h1 human IgG1 nucleotide sequence: ATGGACCC- CAAGGGCAGCCTGAGCTGGAGAATCCTGCTGTTCCTGAGCCTGGCCTTCGAGCTGAGCTACGGCGAGGTGCAGCTGGTGGAGTCCGGCGGCGGCCTGGTGCAGCCCGGCGGCTCCCTGCGCCTGTCCTGCGCCGCCTCCGGCTTCACCTTCTCCCGCTACTGGATGTCCTGGGTGCGCCAGGCCCCCGGCAAGGGCCTGGAGTGGATCGGCGAGATCAACCCCGACTCCTCCACCATCAACTACACCCCCTCCCTGAAGGACCGCTTCACCATCTCCCGCGACACCGCCAAGAAGTCCCTGTACCTGCAGATGTCCAAGGTGCGCTCCGAGGACACCGCCCTGTACTACTGCGCCCGCCACGGCCGCGGCATGGACTACTGGTCCCAGGGCACCTCCGTGACCGTGTCCTCCGCTAGCACCAAGG GCCCCAGCGTGTTCCCTCTGGCCCCCAGCAGCAAGAGCACCAGCGGCGAACCGCCGCCCT GGGCTGCCTGGTGAAGGACTACTTCCCCGAGCCCGTGACCGTGTCCTGGAACAGCGGCGCTC TGACCAGCGGAGTGCACACCTTCCCTGCCGTGCTGCAGAGCAGCGGCCTGTACTCCCTGAGCAGCGTGGTGACCGTGCCCAGCAGCAGCCTGGGCACCCAGACCTACATCTGCAACGTGAACCACAAGCCCTCCAACAC-CAAGGTGGACAAGAAGGTGGAGCCTAAGAGCTGCGACAAGACCCA CACCTGCCCTCCCTGCCCCGCCCCCGAGCTGCTGGGCGGACCCAGCGTGTTCCTGTTCCCTCCCAAGCCCAAGGACACCCTGAT-GATCAGCCGCACCCCCGAGGTGACCTGCGTGGTGGTGGAC GTGAGCCACGAGGACCCCGAGGT-GAAGTTCAACTGGTACGTGGACGGCGTG-GAGGTGCACA ACGCCAAGACCAAGCCTCGGGAG-GAGCAGTACAACTCCACCTACCGCGTGGTGAGCGTGCT GACCGTGCTGCACCAGGACTGGCT-GAACGGCAAGGAGTACAAGTGCAAGGT-GAGCAACAAG GCCCTGCCCGCTCCCATCGAGAA-GACCATCAGCAAGGCCAAGGGCCAGCCCCGGG AGCCTC AGGTGTA-CACCCTGCCCCCAGCCGCGACGAGCTGAC-CAAGAACCAGGTGAGCCTGACCTG CCTGGT-GAAGGGCTTCTACCCCTCCGACATCGCCGTGGAG TGGGAGAGCAACGGCCAGCCT GAGAACAACTA-CAAGAC-CACCCCTCCCGTGCTGGACAGCGACGGCAGCTTCTTCCTGTACAG CAAGCTGACCGTGGACAAGTCCCGGTGGCAGCAGGGCAACGTGTTCAGCTGCAGCGTGATG CACGAGGCCCTGCACAACCACTA-CACCCAGAAGAGCCTGAGCCTGAGCCCCGGA-TAGTAA (SEQ ID NO: 60), having an amino acid sequence of:

(SEQ ID NO: 61)
MDPKGSLSWRILLFLSLAFELSYGEVQLVESGGGLVQPGGSLRLSCAASG

FTFSRYWMSWVRQAPGKGLEWIGEINPDSSTINYTPSLKDRFTISRDTAK

KSLYLQMSKVRSEDTALYYCARHGRGMDYWSQGTSVTVSSASTKGPSVFP

LAPSSKSTSGGTAALGCLVKDYFPEPVTVSWNSGALTSGVHTFPAVLQSS

GLYSLSSVVTVPSSSLGTQTYICNVNHKPSNTKVDKKVEPKSCDKTHTCP

PCPAPELLGGPSVFLFPPKPKDTLMISRTPEVTCVVVDVSHEDPEVKFNW

YVDGVEVHNAKTKPREEQYNSTYRVVSVLTVLHQDWLNGKEYKCKVSNKA

LPAPIEKTISKAKGQPREPQVYTLPPSRDELTKNQVSLTCLVKGFYPSDI

AVEWESNGQPENNYKTTPPVLDSDGSFFLYSKLTVDKSRWQQGNVFSCSV

MHEALHNHYTQKSLSLSPG.

In some embodiments, provided herein is a 6G8G7 HV2-h1 hinge-stabilized (Kabat S228P) human IgG4 nucleotide sequence: ATGGACCCCAAGGGCAGCCTGAGCTG-GAGAATCCTGCTGTTCCT-GAGCCTGGCCTTCGAGCT GAGC-TACGGCGAGGTGCAGCTGGTGGAGTCCGGCGGCGGCCTGGTGCAGCCCGGCGGCTCC CTGCGCCTGTCCTGCGCCGCCTCCGGCTT-CACCTTCTCCCGCTACTGGATGTCCTGGGTGCGCCAGGCCCCCGGCAAGGGCCTGGAGTG-GATCGGCGAGATCAACCCCGACTCCTCCACCATCAACTACACCCCCTCCCTGAAGGACCGCTTCAC-CATCTCCCGCGACACCGCCAAGAAGTCCCTGTACCTGCAGATGTC-CAAGGTGCGCTCCGAGGACACCGCCCTGTAC-TACTGCGCCCGCCACGG CCGCGGCATGGAC-TACTGGTCCCAGGGCACCTCCGTGACCGTGTCC TCCGCTAGCACCAAGG GCCCCAGCGTGTTTCCTCTCGCTCCCTGCAGCCG-GAGCACATCCGAGAGCACCGCTGCTCTG GGCTGTCTCGTGAAGGACTACTTCCCTGAACCCGT-CACCGTCAGCTGGAATAGCGGCGCCCT GACATCCGGCGTCCACACAT-TCCCCGCTGTCCTGCAGAGCAGCGGCCTGTA-CAGCCTGAGCT CCGTGGT-CACCGTGCCTAGCAGCAGCCTGGGAACAAAGA CCTACACCTGCAACGTGGACCA TAAGCCCTC-CAACACCAAGGTGGACAAGCGGGTGGAATC-CAAGTATGGACCCCCTGTCCTC CTTGCCCTGCTCCTGAATTTCTCG-GAGGCCCCTCCGTCTTCCTGTTTCCCCCAAGCC-CAAGG ACACCCTGAT-GATCTCCCGGACACCCGAAGTCACCTGCGTCGTG GTGGATGTCAGCCAGGAA GATCCCGAGGTGCAGTTCAACTGGTACGTGGACG-GAGTGGAGGTGCATAACGCCAAAACCA AGCCCAGGGAAGAGCAGTTCAACAGCACC-TATCGGGTCGTGTCCGTGCTCACCGTCCTGCAT CAGGATTGGCTCAACGGCAAGGAGTA-CAAGTGCAAGGTGTCCAACAAGGGCCTGCCCTC CT CCATCGAGAAGACCATCTCCAAGGCTAAGGGC-CAACCTCGGGAGCCCCAAGTGTATACCCT CCCTCCCAGCCAGGAGGAGATGACCAAGAAT-CAAGTGAGCCTGACCTGCCTCGTGAAGGGA TTT-TACCCCTCCGACATCGCTGTGGAATGG-GAAAGCAATGGCCAACCTGAGAACAACTACAA GACCACACCCCCGTGCTGGACTCC-GATGGCTCCTTCTTCCTGTA-CAGCAGGCTGACCGTGG ACAAATCCCGGTGGCAAGAGG-GAAACGTGTTCAGCTGCTCCGT-GATGCACGAGGCTCTCCA CAACCACTA-CACCCAGAAGAGCCTCTCCCTGAGCCTCGGCTA GTAA (SEQ ID NO: 62), having an amino acid sequence of:

(SEQ ID NO: 63)
MDPKGSLSWRILLFLSLAFELSYGEVQLVESGGGLVQPGGSLRLSCAASG

FTFSRYWMSWVRQAPGKGLEWIGEINPDSSTINYTPSLKDRFTISRDTAK

KSLYLQMSKVRSEDTALYYCARHGRGMDYWSQGTSVTVSSASTKGPSVFP

-continued
LAPCSRSTSESTAALGCLVKDYFPEPVTVSWNSGALTSGVHTFPAVLQSS

GLYSLSSVVTVPSSSLGTKTYTCNVDHKPSNTKVDKRVESKYGPPCPPCP

APEFLGGPSVFLFPPKPKDTLMISRTPEVTCVVVDVSQEDPEVQFNWYVD

GVEVHNAKTKPREEQFNSTYRVVSVLTVLHQDWLNGKEYKCKVSNKGLPS

SIEKTISKAKGQPREPQVYTLPPSQEEMTKNQVSLTCLVKGFYPSDIAVE

WESNGQPENNYKTTPPVLDSDGSFFLYSRLTVDKSRWQEGNVFSCSVMHE

ALHNHYTQKSLSLSLG.

In some embodiments, provided herein is a 6G8G7 HV2-h1 two amino acid variant of SEQ ID NO: 63 having a nucleotide sequence of: GACATCGTGCTGACCCAGTCCCCCGA-CATCCTGTCCGTGTCCCTGGGCGAGCGCGCCACC GTGAACTGCAAGGCCTCCCAGAACGTGGACTC-CAACGTGGCCTGGTACCAGCAGAAGCCCG GCCACCCCCCAAGCTGCTGATCTACTCCGCCTCC-TACCGCTACTCCCGCGTGCCCGACCGC ATCTCCGGCTCCGGCTCCGGCACCGACTT-CACCCTGACCATCTCCAACCTGCAGGCCGAGGA CCTGGCCGACTACTTCTGCCAGCAGTACCACTCC-TACCCCCTGCTGGCCTTCGGCGCCGGCA CCAAGCTGGAGCTGAAGCGCGCCGACGCCGCCCC-CACCGTGTCCCTGGAG (SEQ ID NO: 66), having an amino acid sequence of:

(SEQ ID NO: 67)
DIVLTQSPDILSVSLGERATVNCKASQNVDSNVAWYQQKPGHPPKWYSAS
YRYSRVPDRISGSGSGTDFTLTISNLQAEDLADYFCQQYHSYPLLAFGAG
TKLELKRADAAPTVSLE.

Additional details concerning the cloning of variable heavy chain domains with either a human IgG1 constant region or a hinge-stabilized (Kabat S228P) human IgG4 can be found in Angal, S., D. J. King, M. W. Bodmer, A. Turner, A. D. G. Lawson, G. Roberts, B. Pedley, and J. R. Adair. 1993. A single amino acid substitution abolishes the heterogeneity of chimeric mouse/human (IgG4) antibody. Mol. Immunol. 30: 105-108), the contents of which are herein incorporated by reference in its entirety.

In some embodiments, provided herein is a 6G8G7 KV1-h2 human kappa constant region nucleotide sequence: ATG-GAGACCGACACCCTGCTGCTCTGGGTGCTGCTG CTCTGGGTGCCCGGCTCCACCGGAGA CATCGTGCTGACCCAGTCCCCCGA-CATCCTGTCCGTGTCCCTGGGCGAGCGCGC-CACCGTGA ACTGCAAGGCCTCCCAGAACGTGGACTC-CAACGTGGCCTGGTACCAGCAGAAGCCCGGCCA CCCCCCCAAGCTGCTGATCTACTCCGCCTCC-TACCGCTACTCCCGCGTGCCCGACCGCATCTC CGGCTCCGGCTCCGGCACCGACTTCACCCTGAC-CATCTCCAACCTGCAGGCCGAGGACGTGG CCGTGTACTACTGCCAGCAGTACCACTCC-TACCCCCTGCTGGCCTTCGGCGCCGGCACCAAG CTGGAGCT-GAAGCGGACCGTGGCCGCCCCAGCGTGTT-CATCTTCCCTCCCAGCGACGAGCA GCT-GAAGTCTGGCACCGCCAGCGTGGTGTGCCTGCT GAACAACTTCTACCCCCGCGAGGCCA AGGTGCAGTG-GAAGGTGGACAACGCCCTGCAGAGCGGCAACA GCCAGGAGAGCGTGACCG AGCAGGACTC-CAAGGACAGCACCTACAGCCT-GAGCAGCACCCTGACCCTGAGCAAGGCCGA CTACGAGAAGCACAAGGTGTACGCCTGCGAGGT GACCCACCAGGGACTGTCTAGCCCCGTG ACCAAGAGCTTCAACCGGGGCGAGTGCTAA (SEQ ID NO: 64), having an amino acid sequence of:

(SEQ ID NO: 65)
METDTLLLWVLLLWVPGSTGDIVLTQSPDILSVSLGERATVNCKASQNVD

SNVAWYQQKPGHPPKWYSASYRYSRVPDRISGSGSGTDFTLTISNLQAED

VAVYYCQQYHSYPLLAFGAGTKLELKRTVAAPSVFIFPPSDEQLKSGTAS

VVCLLNNFYPREAKVQWKVDNALQSGNSQESVTEQDSKDSTYSLSSTLTL

SKADYEKHKVYACEVTHQGLSSPVTKSFNRGEC.

As used herein, "Vernier zone" refers to a subset of framework residues that may adjust CDR structure and fine-tune the fit to antigen as described by Foote and Winter (1992, J. Mol. Biol. 224:487-499, which is incorporated herein by reference). Vernier zone residues form a layer underlying the CDRS and can impact on the structure of CDRS and the affinity of the antibody.

Known human immunoglobulin (Ig) sequences that can be used with the CDR sequences described herein are disclosed, for example, on the worldwide web at ncbi.nlm-.nih.gov/entrez-/query.fcgi; atcc.org/phage/hdb.html; sci-quest.com/; abcam.com/; antibodyresource.com/onlinecomp.html; public.iastate.eduLabout.pedro/researchtools.html; mgen.uniheidelberg.de/SD/IT/IT.html; whfreeman.com/immunology/CH-05/kuby05.htm; library.thinkquest.org/12429/Immune/Antibody.html; hhmi.org/grants/lectures/1996/vlab/; path.cam.ac.uk/.about.mrc7/m-ikei-mages.html; antibodyresource.com/; mcb.harvard.edu/BioLinks/Immunology.html. immunologylink.com/; pathbox.wustl.edu/.about.hcenter/index.-html; biotech.ufl.edu/.about.hcl/; pebio.com/pa/340913/340913.html-; nal.usda.gov/awic/pubs/antibody/; m.ehime-u.acjp/.about.yasuhito-/Elisa.html; biodesign.com/table.asp; icnet.uk/axp/facs/davies/lin-ks.html; biotech.ufl.edu/.about.fccl/protocol.html; isac-net.org/sites_geo.html; aximtl.imt.uni-marburg.de/.about.rek/AEP-Start.html; baserv.uci.kun.nl/.aboutjraats/linksl.html; recab.uni-hd.de/immuno.bme.nwu.edu/; mrc-cpe.cam.a-c.uk/imt-doc/pu-blic/INTRO.html; ibt.unam.mx/virN_ mice.html; imgt.cnusc.fr:8104/; biochem.ucl.ac.uk/.about.martin/abs/index.html; anti-body.bath.ac.uk/; abgen.cvm.tamu.edu/lab/wwwabgen.html; unizh.ch/.about.honegger/AHOsem-inar/Slide01.html; cryst.bbk.ac.uk/.about.ubcg07s/; nimr.mrc.ac.uk/CC/ccaewg/ccaewg.htm; path.cam.ac.ukhabout.mrc7/h-umanisation/TAHHP.html; ibt.unam.na/vir/structure/stat_aim.html; biosci.missou-ri.edu/smithgp/index.html; cryst.bioc.cam.ac.uk/.abo-uti-molina/Web-pages/Pept/spottech.html; jerini.de/fr roduct-s.htm; patents.ibm.com/ibm.html.Kabat et al., Sequences of Proteins of Immunological Interest, U.S. Dept. Health (1983), each entirely incorporated herein by reference. Such imported sequences can be used to reduce immunogenicity or reduce, enhance or modify binding, affinity, on-rate, off-rate, avidity, specificity, half-life, or any other suitable characteristic, as known in the art.

Framework residues in the human framework regions can be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding. Antibodies can be humanized using a variety of techniques known in the art, including, but not limited to, those described in Jones et al., Nature 321:522 (1986); Verhoeyen et al., Science 239:1534 (1988), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), Padlan, Molecular Immunology 28(4/5):489-498 (1991); Studnicka et al., Protein Engineering 7(6):805-814 (1994); Roguska. et al., PNAS 91:969-973 (1994); PCT publication WO 91/09967, PCT/: US98/16280, US96/18978, US91/09630, US91/05939, US94/01234, GB89/01334, GB91/01134, GB92/01755; WO90/14443, WO90/14424, WO90/14430, EP 229246, EP 592,106; EP 519,596, EP 239,400, U.S. Pat. Nos. 5,565,332, 5,723,323, 5,976,862, 5,824,514, 5,817, 483, 5,814,476, 5,763,192, 5,723,323, 5,766,886, 5,714,352, 6,204,023, 6,180,370, 5,693,762, 5,530,101, 5,585,089, 5,225,539; 4,816,567, each entirely incorporated herein by reference.

As used herein, the terms "acceptor" and "acceptor antibody" refer to the antibody or nucleic acid sequence providing or encoding at least 80%, at least 85%, at least 90%, at least 95%, at least 98% or 100% of the amino acid sequences of one or more of the framework regions. In some embodiments, the term "acceptor" refers to the antibody amino acid or nucleic acid sequence providing or encoding the constant region(s). In yet another embodiment, the term "acceptor" refers to the antibody amino acid or nucleic acid sequence providing or encoding one or more of the framework regions and the constant region(s). In a specific embodiment, the term "acceptor" refers to a human antibody amino acid or nucleic acid sequence that provides or encodes at least 80%, preferably, at least 85%, at least 90%, at least 95%, at least 98%, or 100% of the amino acid sequences of one or more of the framework regions. In accordance with this embodiment, an acceptor may contain at least 1, at least 2, at least 3, least 4, at least 5, or at least 10 amino acid residues not occurring at one or more specific positions of a human antibody. An acceptor framework region and/or acceptor constant region(s) may be, e.g., derived or obtained from a germline antibody gene, a mature antibody gene, a functional antibody (e.g., antibodies well-known in the art, antibodies in development, or antibodies commercially available).

As used herein, the term "canonical" residue refers to a residue in a CDR or framework that defines a particular canonical CDR structure as defined by Chothia et al. (J. Mol. Biol. 196:901-907 (1987); Chothia et al., J. Mol. Biol, 227:799 (1992), both are incorporated herein by reference).

According to Chothia et al., critical portions of the CDRs of many antibodies have nearly identical peptide backbone confirmations despite great diversity at the level of amino acid sequence. Each canonical structure specifies primarily a set of peptide backbone torsion angles for a contiguous segment of amino acid residues forming a loop.

As used herein, the terms "donor" and "donor antibody" refer to an antibody providing one or more CDRs. In some embodiments of the compositions and methods described herein, the donor antibody is an antibody from a species different from the antibody from which the framework regions are obtained or derived. In the context of a humanized antibody, the term "donor antibody" refers to a non-human antibody providing one or more CDRs.

As used herein, the term "key" residues refers to certain residues within the variable region that have more impact on the binding specificity and/or affinity of an antibody, in particular a humanized antibody. A key residue includes, but is not limited to, one or more of the following: a residue that is adjacent to a CDR, a potential glycosylation site (which can be either N- or O-glycosylation site), a rare residue, a residue capable of interacting with the antigen, a residue capable of interacting with a CDR, a canonical residue, a contact residue between heavy chain variable region and light chain variable region, a residue within the Vernier zone, and a residue in the region that overlaps between the Chothia definition of a variable heavy chain CDR1 and the Kabat definition of the first heavy chain framework.

Alternatively, it is possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggermann et al., Year in Immuno., 7:33 (1993); and Duchosal et al. Nature 355:258 (1992).

Alternatively, phage display technology (McCafferty et al., Nature 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats; for their review see, e.g., Johnson, Kevin S, and Chiswell, David J., Current Opinion in Structural Biology 3:564-571 (1993). Several sources of V-gene segments can be used for phage display. Clackson et al., Nature, 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222:581-597 (1991), or Griffith et al., EMBO J. 12:725-734 (1993). See, also, U.S. Pat. Nos. 5,565,332 and 5,573,905.

Human antibodies can also be generated by in vitro activated B cells (see U.S. Pat. Nos. 5,567,610 and 5,229, 275).

In some embodiments of the aspects described herein, composite human antibody technology that generates de-immunized 100% engineered human antibodies at the outset can be used to prepare humanized composite anti-DEspR antibodies for use in the compositions and methods described herein, using, for example, a technology as described by Jones, T D, Crompton U, Carr F J, Baker M P. Methods Mol Biol. 2009; 525:405-423.

Briefly, as used herein, "composite human antibodies" comprise multiple sequence segments ("composites") derived from V-regions of unrelated human antibodies that are selected to maintain monoclonal antibody sequences critical for antigen binding of the starting murine precursor anti-human DEspR monoclonal antibody, such as the 6G8G7 or 7C5B2 variant antibodies described herein, and which have all been filtered for the presence of potential T-cell epitopes using "in silico tools" (Holgate & Baker, 2009). The close fit of human sequence segments with all sections of the starting antibody V regions and the elimination of CD4+ T cell epitopes from the outset allow this technology to circumvent immunogenicity in the development of '100% engineered human' therapeutic antibodies while maintaining optimal affinity and specificity through the prior analysis of sequences necessary for antigen-specificity (Holgate & Baker 2009).

As described herein, structural models of mouse anti-hDEspR antibody V regions are produced using Swiss PDB and analyzed in order to identify important "constraining" amino acids in the V regions that are likely to be essential for the binding properties of the antibody. Residues contained within the CDRs (using Kabat definition) together with a number of framework residues are considered to be important. Both the $V_H$ and $V_L$ ($V_\kappa$) sequences of anti-hDEspR, as described herein as SEQ ID NO: 6, SEQ ID NO: 13, and SEQ ID NO: 20, and SEQ ID NO: 27, SEQ ID NO: 34, SEQ ID NO: 41, and SEQ ID NO: 50, respectively, comprise typical framework residues and the CDR1, CDR2, and CDR3 motifs are comparable to many murine antibodies, as described elsewhere herein.

From the above analysis, it is determined that composite human sequences of anti-hDEspR can be created with a wide latitude of alternatives outside of CDRs but with only a narrow menu of possible alternative residues within the CDR sequences. Corresponding sequence segments from several human antibodies can be combined to create CDRs similar or identical to those in the murine sequences. For regions outside of and flanking the CDRs, a wide selection of human sequence segments are identified as possible components of novel anti-DEspR composite human antibody V regions for use with the compositions and methods described herein.

Based upon these analyses, a large preliminary set of sequence segments that can be used to create novel anti-DEspR composite human antibody variants are selected and analysed using ITOPE™ technology for in silico analysis of peptide binding to human MHC class II alleles (Perry et al 2008), and using the TCED™ (T Cell Epitope Database) of known antibody sequence-related T cell epitopes (Bryson et al 2010). Sequence segments that are identified as significant non-human germline binders to human MHC class II or that scored significant hits against the TCED™ are discarded. This results in a reduced set of segments, and combinations of these are again analyzed, as above, to ensure that the junctions between segments do not contain potential T cell epitopes. Selected segments are then combined to produce heavy and light chain V region sequences for synthesis.

Accordingly, provided herein, in some aspects, are variable heavy and light chain sequences for use in anti-DEspR composite human antibody or engineered human antibody production.

In some embodiments of the aspects described herein, an antibody specific for DEspR, such as, for example the anti-DEspR 6G8G7 or 7C5B2 variant antibodies; an anti-DEspR antibody comprising one or more heavy chain CDR regions comprising a sequence selected from the group consisting of SEQ ID NO: 7, SEQ ID NO: 8, SEQ ID NO: 9, SEQ ID NO: 14, SEQ ID NO: 15, SEQ ID NO: 16, SEQ ID NO: 21, SEQ ID NO: 22, and SEQ ID NO: 23; an anti-DEspR antibody comprising one or more light chain CDR regions comprises a sequence selected from the group consisting of SEQ ID NO: 28, SEQ ID NO: 29, SEQ ID NO: 30, SEQ ID NO: 35, SEQ ID NO: 36, SEQ ID NO: 37, SEQ ID NO: 42, SEQ ID NO: 43, SEQ ID NO: 44, SEQ ID NO: 51, SEQ ID NO: 52, and SEQ ID NO: 53; an anti-DEspR composite human antibody comprising a variable heavy ($V_H$) chain amino acid sequence of SEQ ID NO: 6, SEQ ID NO: 13, or SEQ ID NO: 20; an anti-DEspR composite human antibody comprising a variable light ($V_L$) chain amino acid sequence of SEQ ID NO: 27, SEQ ID NO: 34, SEQ ID NO: 41, or SEQ ID NO: 50; an anti-DEspR humanized antibody comprising a variable heavy ($V_H$) chain amino acid sequence of SEQ ID NO: 55; an anti-DEspR humanized antibody comprising a variable light ($V_L$) chain amino acid sequence of SEQ ID NO: 57; an anti-DEspR humanized antibody comprising a variable light ($V_L$) chain amino acid sequence of SEQ ID NO: 59; an anti-DEspR humanized antibody comprising a variable heavy ($V_H$) chain IgG1 amino acid sequence of SEQ ID NO: 61; an anti-DEspR humanized antibody comprising a variable heavy ($V_H$) chain IgG4 amino acid sequence of SEQ ID NO: 63; or an anti-DEspR humanized antibody comprising a variable light ($V_L$) chain kappa amino acid sequence of SEQ ID NO: 65; can be treated or processed into an antibody fragment thereof.

Various techniques have been developed and are available for the production of antibody fragments. Traditionally, these fragments were derived via proteolytic digestion of intact antibodies (see, e.g., Morimoto et al., Journal of Biochemical and Biophysical Methods 24:107-117 (1992) and Brennan et al., Science, 229:81 (1985)). However, these fragments can now be produced directly by recombinant host cells. For example, antibody fragments can be isolated from the antibody phage libraries discussed above. Alternatively, Fab'-SH fragments can be directly recovered from *E. coli* and chemically coupled to form $F(ab')_2$ fragments (Carter et al., Bio/Technology 10:163-167 (1992)). According to another approach, $F(ab')_2$ fragments can be isolated directly from recombinant host cell culture. Other techniques for the production of antibody fragments will be apparent to the skilled practitioner. In other embodiments, the antibody fragment of choice is a single chain Fv fragment (scFv). See WO 93/16185.

In some embodiments of the aspects described herein, a human DEspR-specific antibody fragment is a Fab fragment comprising $V_L$, $C_L$, $V_H$ and $C_H1$ domains. Fab fragments comprise a variable and constant domain of the light chain and a variable domain and the first constant domain ($C_H1$)

of the heavy chain. In some such embodiments, the $V_H$ domain comprises, consists or consists essentially of SEQ ID NO: 6, SEQ ID NO: 13, or SEQ ID NO: 20. In some such embodiments, the $V_H$ domain comprises one or more heavy chain CDR regions comprising a sequence selected from the group consisting of SEQ ID NO: 7, SEQ ID NO: 8, SEQ ID NO: 9, SEQ ID NO: 14, SEQ ID NO: 15, SEQ ID NO: 16, SEQ ID NO: 21, SEQ ID NO: 22, and SEQ ID NO: 23. In some such embodiments, the $V_L$ domain comprises, consists or consists essentially of SEQ ID NO: 27, SEQ ID NO: 34, SEQ ID NO: 41, or SEQ ID NO: 50. In some such embodiments, the $V_L$ domain comprises one or more light chain CDR regions comprising a sequence selected from the group consisting of SEQ ID NO: 28, SEQ ID NO: 29, SEQ ID NO: 30, SEQ ID NO: 35, SEQ ID NO: 36, SEQ ID NO: 37, SEQ ID NO: 42, SEQ ID NO: 43, SEQ ID NO: 44, SEQ ID NO: 51, SEQ ID NO: 52, and SEQ ID NO: 53.

In some embodiments of the aspects described herein, a human DEspR-specific antibody fragment is a Fab' fragment, which is a Fab fragment having one or more cysteine residues at the C-terminus of the $C_H1$ domain.

In some embodiments of the aspects described herein, a human DEspR-specific antibody fragment is a Fd fragment comprising $V_H$ and $C_H1$ domains. In some such embodiments, the $V_H$ domain is comprises, consists or consists essentially of SEQ ID NO: 6, SEQ ID NO: 13, or SEQ ID NO: 20. In some such embodiments, the $V_H$ domain comprises one or more heavy chain CDR regions comprising a sequence selected from the group consisting of SEQ ID NO: 7, SEQ ID NO: 8, SEQ ID NO: 9, SEQ ID NO: 14, SEQ ID NO: 15, SEQ ID NO: 16, SEQ ID NO: 21, SEQ ID NO: 22, and SEQ ID NO: 23.

In some embodiments of the aspects described herein, a human DEspR-specific antibody fragment is a Fd' fragment comprising $V_H$ and $C_H1$ domains and one or more cysteine residues at the C-terminus of the $C_H1$ domain. In some such embodiments, the $V_H$ domain comprises, consists or consists essentially of SEQ ID NO: 6, SEQ ID NO: 13, or SEQ ID NO: 20. In some such embodiments, the $V_H$ domain comprises one or more heavy chain CDR regions comprising a sequence selected from the group consisting of SEQ ID NO: 7, SEQ ID NO: 8, SEQ ID NO: 9, SEQ ID NO: 14, SEQ ID NO: 15, SEQ ID NO: 16, SEQ ID NO: 21, SEQ ID NO: 22, and SEQ ID NO: 23.

Single-chain Fv or scFv antibody fragments comprise the $V_H$ and $V_L$ domains of antibody, such that these domains are present in a single polypeptide chain. Generally, a Fv polypeptide further comprises a polypeptide linker between the $V_H$ and $V_L$ domains, which enables the scFv to form the desired structure for antigen binding. For a review of scFv, see Pluckthun in The Pharmacology of Monoclonal Antibodies, Vol 113, Rosenburg and Moore eds. Springer-Verlag, New York, pp. 269-315 (1994). Accordingly, in some embodiments of the aspects described herein, a human DEspR-specific antibody fragment is a Fv fragment comprising the $V_L$ and $V_H$ domains of a single arm of an antibody. In some such embodiments, the $V_H$ domain comprises, consists or consists essentially of SEQ ID NO: 6, SEQ ID NO: 13, or SEQ ID NO: 20. In some such embodiments, the $V_H$ domain comprises one or more heavy chain CDR regions comprising a sequence selected from the group consisting of SEQ ID NO: 7, SEQ ID NO: 8, SEQ ID NO: 9, SEQ ID NO: 14, SEQ ID NO: 15, SEQ ID NO: 16, SEQ ID NO: 21, SEQ ID NO: 22, and SEQ ID NO: 23. In some such embodiments, the $V_L$ domain comprises, consists or consists essentially of SEQ ID NO: 27, SEQ ID NO: 34, SEQ ID NO: 41, or SEQ ID NO: 50. In some such embodiments, the $V_L$ domain comprises one or more light chain CDR regions comprising a sequence selected from the group consisting of SEQ ID NO: 28, SEQ ID NO: 29, SEQ ID NO: 30, SEQ ID NO: 35, SEQ ID NO: 36, SEQ ID NO: 37, SEQ ID NO: 42, SEQ ID NO: 43, SEQ ID NO: 44, SEQ ID NO: 51, SEQ ID NO: 52, and SEQ ID NO: 53.

The term diabodies refers to small antibody fragments with two antigen-binding sites, which fragments comprise a heavy chain variable domain ($V_H$) connected to a light chain variable domain ($V_L$) in the same polypeptide chain ($V_H$ and $V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-6448 (1993).

Accordingly, in some embodiments of the aspects described herein, a human DEspR-specific antibody fragment is a diabody comprising two antigen binding sites, comprising a heavy chain variable domain ($V_H$) connected to a light chain variable domain ($V_L$) in the same polypeptide chain. In some such embodiments, the $V_H$ domain comprises, consists or consists essentially of SEQ ID NO: 6, SEQ ID NO: 13, or SEQ ID NO: 20. In some such embodiments, the $V_H$ domain comprises one or more heavy chain CDR regions comprising a sequence selected from the group consisting of SEQ ID NO: 7, SEQ ID NO: 8, SEQ ID NO: 9, SEQ ID NO: 14, SEQ ID NO: 15, SEQ ID NO: 16, SEQ ID NO: 21, SEQ ID NO: 22, and SEQ ID NO: 23. In some such embodiments, the $V_L$ domain comprises, consists or consists essentially of SEQ ID NO: 27, SEQ ID NO: 34, SEQ ID NO: 41, or SEQ ID NO: 50. In some such embodiments, the $V_L$ domain comprises one or more light chain CDR regions comprising a sequence selected from the group consisting of SEQ ID NO: 28, SEQ ID NO: 29, SEQ ID NO: 30, SEQ ID NO: 35, SEQ ID NO: 36, SEQ ID NO: 37, SEQ ID NO: 42, SEQ ID NO: 43, SEQ ID NO: 44, SEQ ID NO: 51, SEQ ID NO: 52, and SEQ ID NO: 53.

In some embodiments of the aspects described herein, a human DEspR-specific antibody fragment is a dAb fragment comprising a $V_H$ domain. In some such embodiments, the $V_H$ domain comprises, consists or consists essentially of SEQ ID NO: 6, SEQ ID NO: 13, or SEQ ID NO: 20. In some such embodiments, the $V_H$ domain comprises one or more heavy chain CDR regions comprising a sequence selected from the group consisting of SEQ ID NO: 7, SEQ ID NO: 8, SEQ ID NO: 9, SEQ ID NO: 14, SEQ ID NO: 15, SEQ ID NO: 16, SEQ ID NO: 21, SEQ ID NO: 22, and SEQ ID NO: 23.

In some embodiments of the aspects described herein, a human DEspR-specific antibody fragment comprises isolated CDR regions. In some such embodiments, the isolated CDR region comprises one or more heavy chain CDR regions comprising a sequence selected from the group consisting of SEQ ID NO: 7, SEQ ID NO: 8, SEQ ID NO: 9, SEQ ID NO: 14, SEQ ID NO: 15, SEQ ID NO: 16, SEQ ID NO: 21, SEQ ID NO: 22, and SEQ ID NO: 23. In some such embodiments, the isolated CDR region comprises one or more light chain CDR regions comprising a sequence selected from the group consisting of SEQ ID NO: 28, SEQ ID NO: 29, SEQ ID NO: 30, SEQ ID NO: 35, SEQ ID NO: 36, SEQ ID NO: 37, SEQ ID NO: 42, SEQ ID NO: 43, SEQ ID NO: 44, SEQ ID NO: 51, SEQ ID NO: 52, and SEQ ID NO: 53.

In some embodiments of the aspects described herein, the human DEspR-specific antibody fragment is a F(ab')$_2$ fragment, which comprises a bivalent fragment comprising two Fab' fragments linked by a disulphide bridge at the hinge region.

"Linear antibodies" refer to the antibodies as described in Zapata et al., Protein Eng., 8(10):1057-1062 (1995). Briefly, these antibodies comprise a pair of tandem Fd segments ($V_H$-$C_H$1-$V_H$-$C_H$1) which, together with complementary light chain polypeptides, form a pair of antigen binding regions. Linear antibodies can be bispecific or monospecific.

In some embodiments of the aspects described herein, a human DEspR-specific antibody fragment is a linear antibody comprising a pair of tandem Fd segments ($V_H$-$C_H$1-$V_H$-$C_H$1) which, together with complementary light chain polypeptides, form a pair of antigen binding regions. In some such embodiments, the $V_H$ domain comprises, consists or consists essentially of SEQ ID NO: 6, SEQ ID NO: 13, or SEQ ID NO: 20. In some such embodiments, the $V_H$ domain comprises one or more heavy chain CDR regions comprising a sequence selected from the group consisting of SEQ ID NO: 7, SEQ ID NO: 8, SEQ ID NO: 9, SEQ ID NO: 14, SEQ ID NO: 15, SEQ ID NO: 16, SEQ ID NO: 21, SEQ ID NO: 22, and SEQ ID NO: 23. In some such embodiments, the $V_L$ domain consists or consists essentially of SEQ ID NO: 27, SEQ ID NO: 34, SEQ ID NO: 41, or SEQ ID NO: 50. In some such embodiments, the $V_L$ domain comprises one or more light chain CDR regions comprising a sequence selected from the group consisting of SEQ ID NO: 28, SEQ ID NO: 29, SEQ ID NO: 30, SEQ ID NO: 35, SEQ ID NO: 36, SEQ ID NO: 37, SEQ ID NO: 42, SEQ ID NO: 43, SEQ ID NO: 44, SEQ ID NO: 51, SEQ ID NO: 52, and SEQ ID NO: 53.

In some embodiments of these aspects, a human DEspR-specific antibody fragment has specificity for the same epitope as a monoclonal anti-DEspR antibody 6G8G7 variant, described herein, and produced by hybridoma 6G8G7, or alternatively the specificity for the same epitope as a monoclonal anti-DEspR antibody 7C5B2 variant, described herein, and produced by hybridoma 7C5B2. In some embodiments of these aspects, a human DEspR-specific antigen-binding fragment has specificity for an epitope comprising, consisting essentially of, or consisting of SEQ ID NO: 1. In some embodiments of these aspects, a human DEspR-specific antigen-binding fragment has specificity for an epitope comprising, consisting essentially of, or consisting of SEQ ID NO: 2.

Examples of DEspR-inhibiting antibodies are described in PCT/US2005/041594, PCT/US2011/045056, and PCT/US2013/022537, the contents of each of which are incorporated herein by reference in their entireties.

In some embodiments of the aspects described herein, a DEspR binding protein, an isolated antibody or antigen-binding fragment thereof, or anti-DEspR antibody or antigen-binding fragment thereof as disclosed herein binds to DEspR present on intact cells or an antigenic-peptide containing a DEspR epitope, such as an epitope of SEQ ID NOs: 1 or 2, with a EC50 of 12 µg/ml or less, 10 µg/ml or less, 7 µg/ml or less, 5 µg/ml or less, 3 µg/ml or less, 1.5 µg/ml or less, 1.2 µg/ml or less, 1 µg/ml or less, 0.7 µg/ml or less, or 0.64 µg/ml or less (see, e.g., Tables 2 and 5). Preferably, the antibody or antigen-binding fragment thereof is a neutralizing antibody or a DEspR antagonist. In some embodiments of the aspects described herein, a DEspR binding protein, isolated antibody or antigen-binding fragment thereof, or anti-DEspR antibody or antigen-binding fragment thereof as disclosed herein binds to DEspR present on intact cells or an antigenic-peptide containing a DEspR epitope, such as an epitope of SEQ ID NOs: 1 or 2, with an EC50 of 30 nM or less, an EC50 of 25 nM or less, an EC50 of 24 nM or less, an EC50 of 23 nM or less, an EC50 of 21 nM or less, an EC50 of 20 nM or less, or an EC50 of 15 nM or less (see, e.g., see Table 2 and 5). Preferably, the antibody or antigen-binding fragment thereof is a neutralizing antibody or a DEspR antagonist. The EC50 can be determined, for example, by measuring the binding of one of the described DEspR antibodies or antigen-binding fragments thereof to an antigenic peptide containing the epitope such as SEQ ID NO. 1 or SEQ ID NO: 2, by, for example, ELISA (see, e.g., Table 1) or to the receptor on an intact human cell (e.g. that is positive for DEspR by FACS (see e.g. Table 2, FIG. 37).

Figure 3:
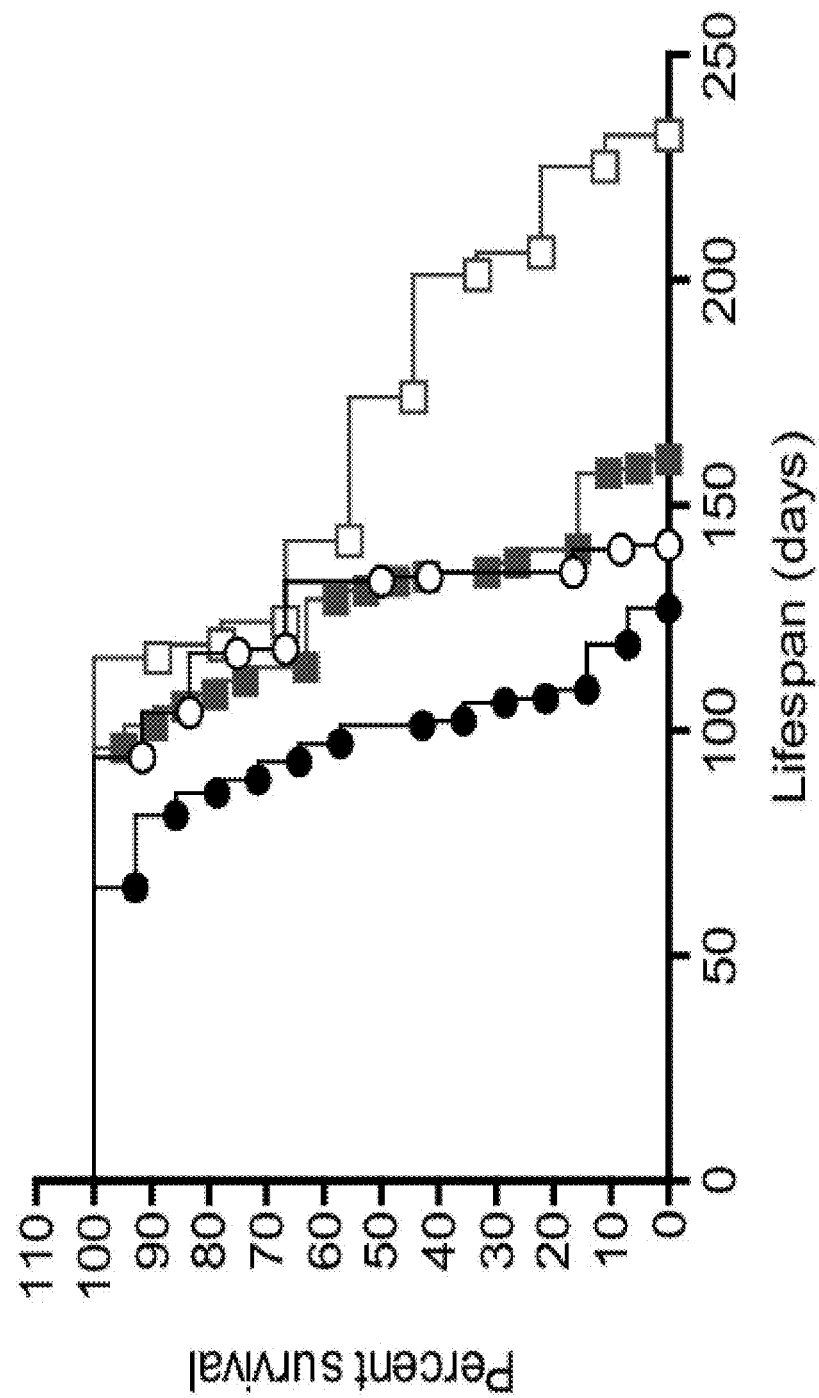
FIG. 3 demonstrates that survival analysis reveals significant shortening of life-span due to early stroke onset in transgenic females (black dots)>transgenic males (black open circles)/non-transgenic females (filled squares)>non-transgenic males (open squares).
Figures 40A, 40B:
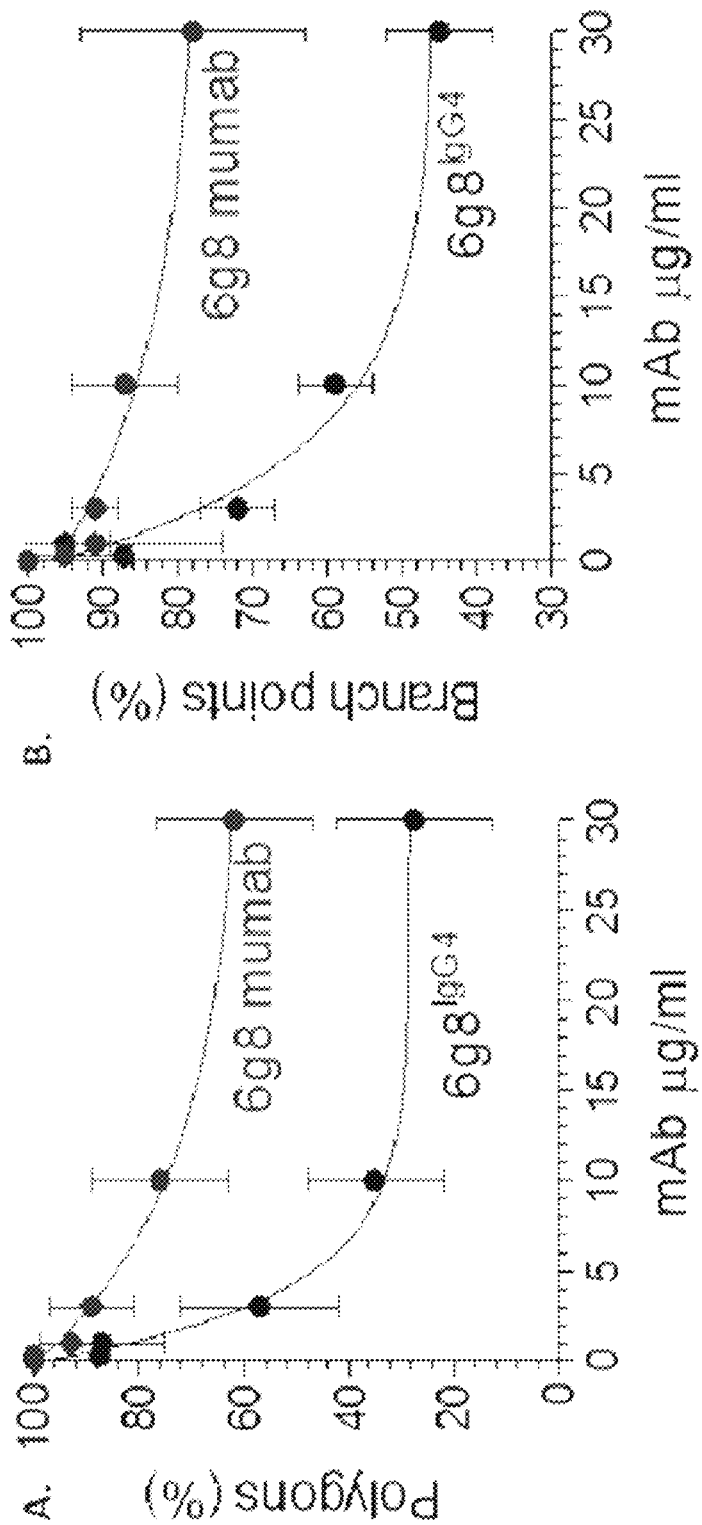
FIGS. 40A-40B show dose-dependent inhibition of HUVECs angiogenesis in bFGF-mediated/VEGF-independent angiogenesis assay. Measurement of complex network formation was done using the following parameters.
Figure 41A:
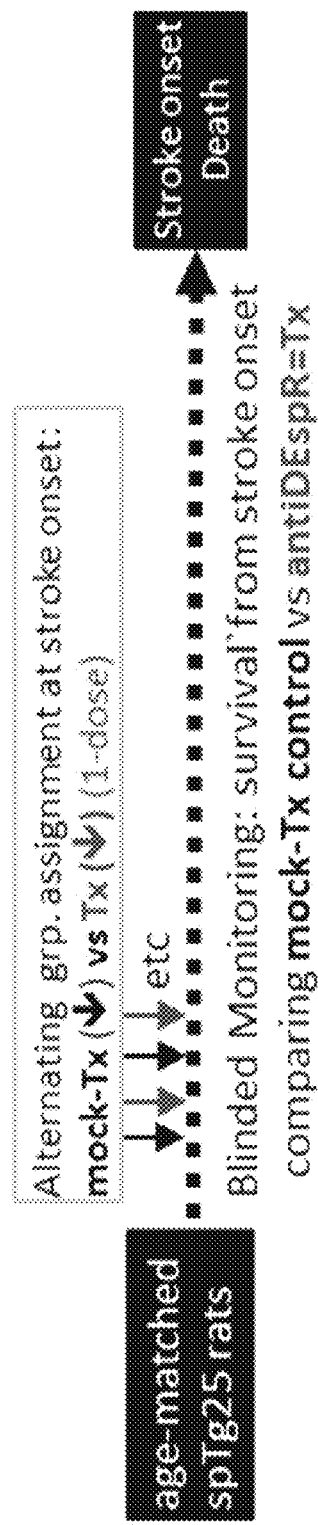
FIGS. 41A-41B demonstrate that a one-time treatment with an anti-rat DEspR 10A3 IgG1 antibody at 40 μg/kg/dose intravenously administered via tail vein injection prevents cerebral edema/microbleed progression at the acute stroke stage. Survival analysis: Log Rank (Mantel-Cox) Test: p=0.0001; Control: n=10; Treated: n=7. Median survival for control animals was 0.5 days, while median survival for treated animals was 22 days.
Figure 41B:
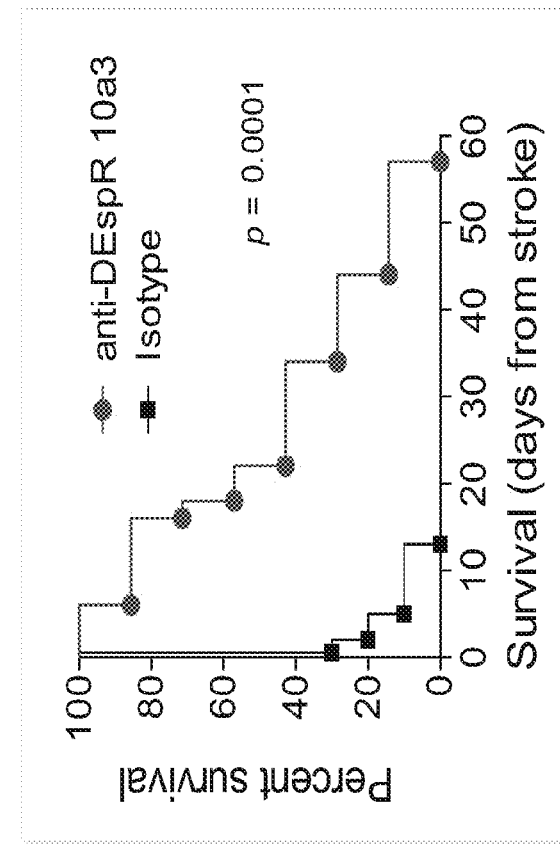
Figure 42:
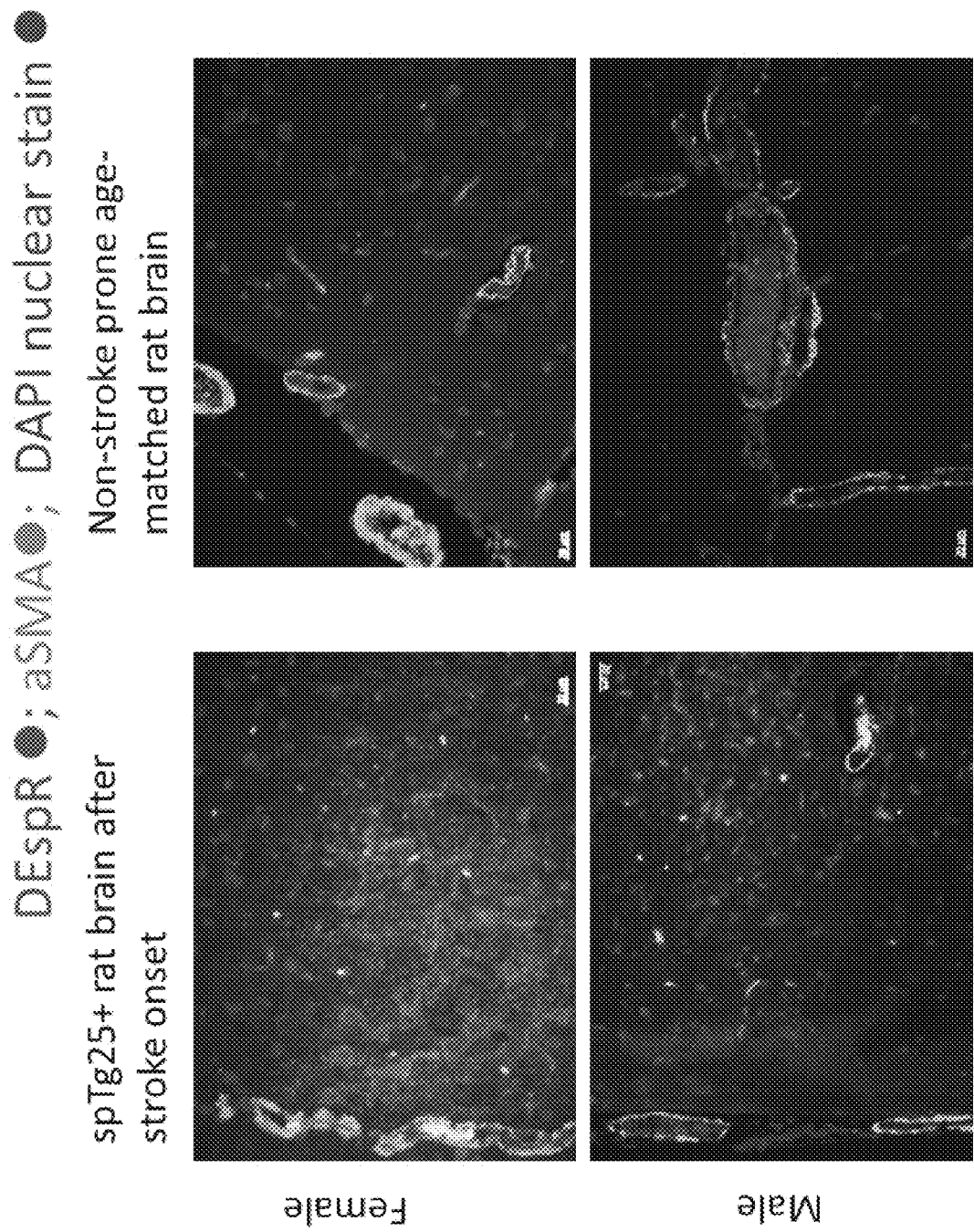
FIG. 42 shows immunofluorescence staining of brains tissue sections at stroke onset where increased DEspR expression compared to minimal to no expression in normal age-matched brains. Immunostaining was done with a 10A3 murine monoclonal antibody on fixed (PBS-buffered paraformaldehyde, pH 7.4), paraffin embedded 5 micron sections after antigen retrieval. Antibodies are labeled: Anti-DEspR: AF568; Anti-alpha smooth muscle actin: AF488 as + control.
Figure 43A:
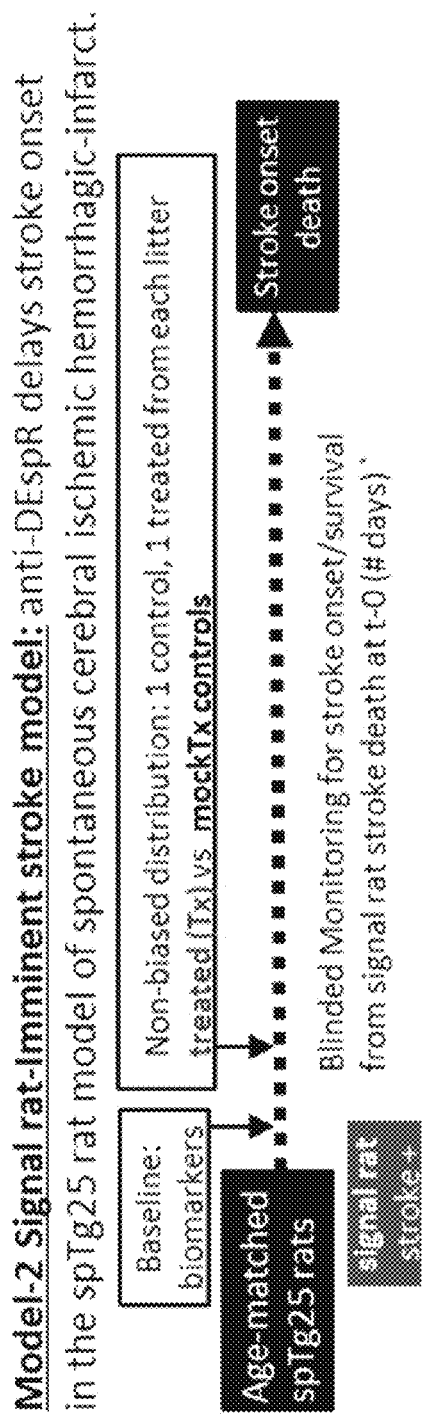
FIGS. 43A-43B demonstrate that treatment with an anti-rat DEspR 10Aa3 IgG1 antibody, at 1 mg/kg/dose intravenously administered via tail vein injection for 1 time per week for six weeks, delays stroke onset in the spTg25 rat model of spontaneous cerebral ischemic hemorrhagic-infarct. Survival analysis: Log Rank Test: p=0.0017; Control: n=5; Treated: n=6. Median survival for control animals was 13 days, while median survival for treated animals was 120 days.
Figure 43B:
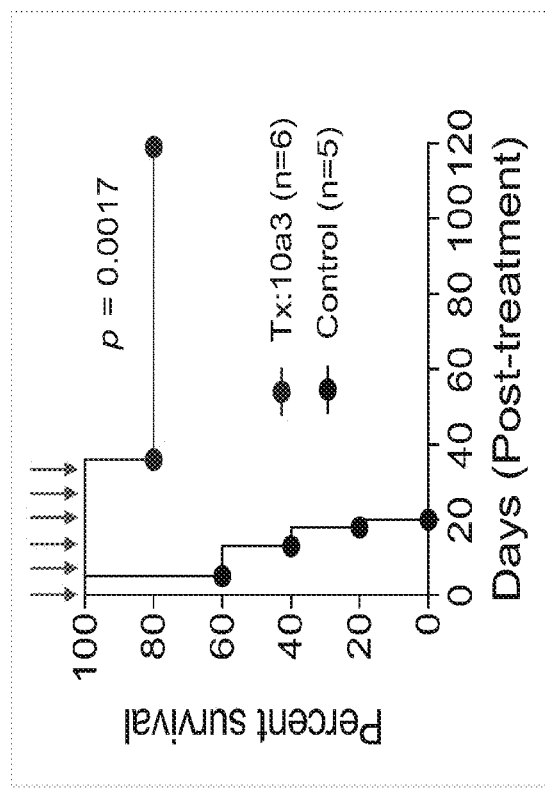
Figure 44A:
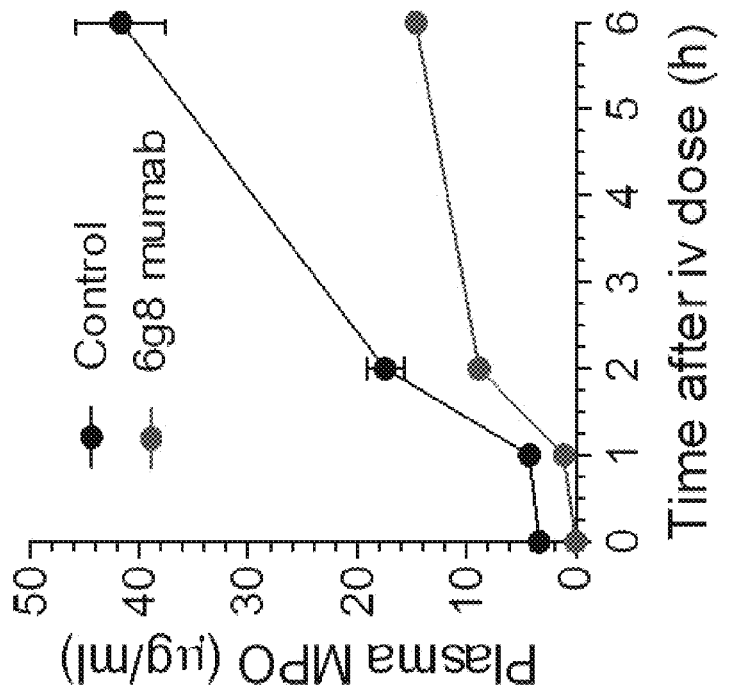
FIGS. 44A-44B show PK evidence for in vivo efficacy. Plasma dose-concentration and target bioeffects of a prototype murine monoclonal antibody in a stroke-prone rat model are shown.
Figure 44B:
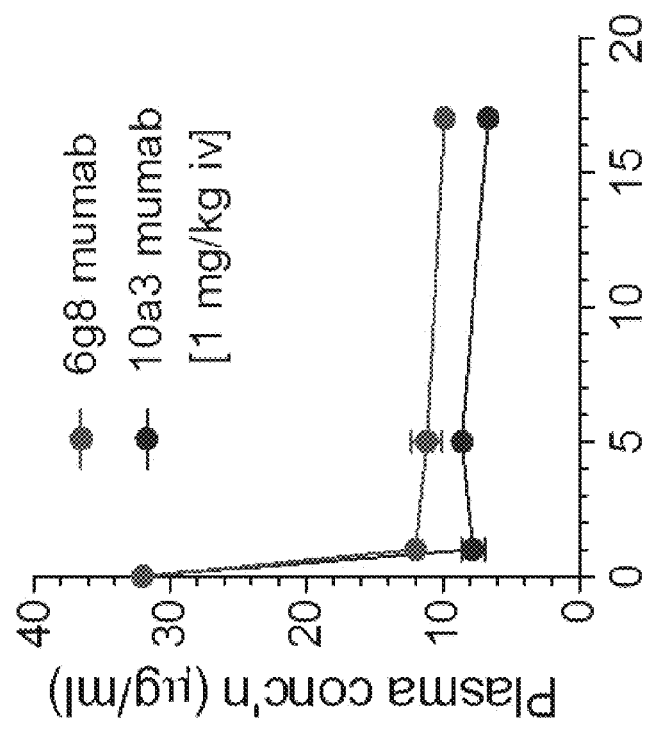
Figure 45A:
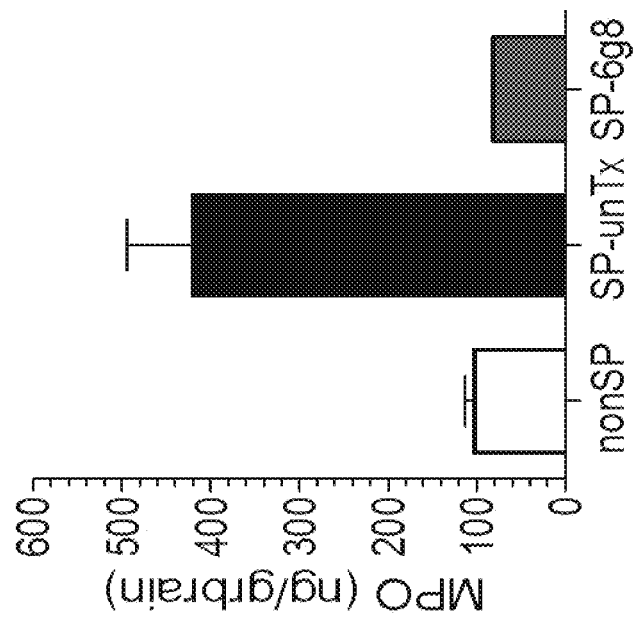
FIGS. 45A-45B show PD evidence for in vivo efficacy. Brain target-engagement and target-bioeffects of a prototype 6g8 murine monoclonal antibody in a stroke-prone rat model are shown.
Figure 45B:
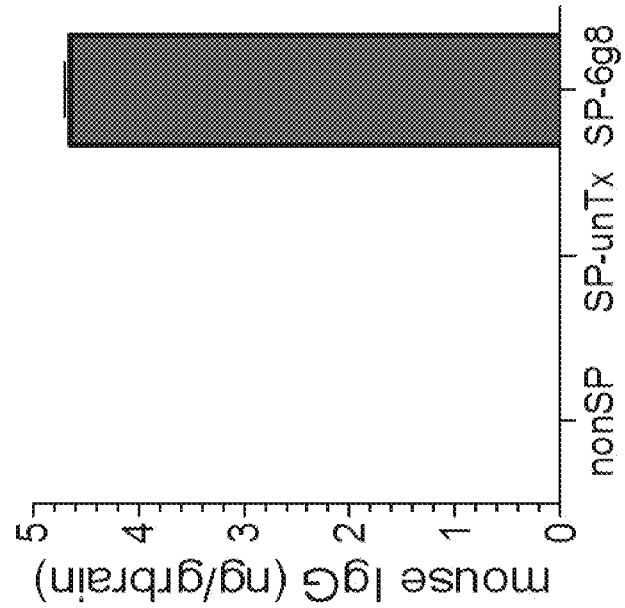
Figure 46:
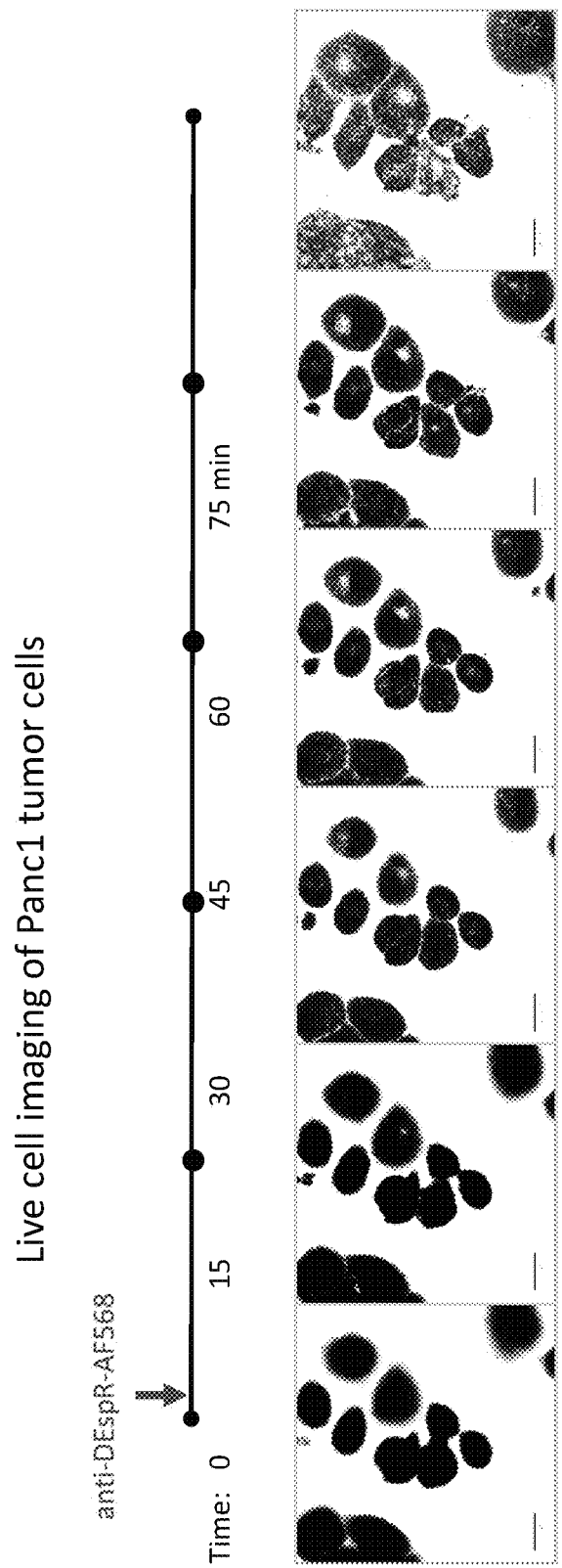
FIG. 46 shows that anti-DEspR monoclonal antibody-receptor interaction results in internalization of fluorescently-labeled anti-human DEspR 7C5-murine monoclonal antibody, transport to nucleus, and induction of apoptosis. Representative time series of internalization of fluorescently labeled (AF568) anti-DEspR monoclonal antibody by Panc1 tumor cells within 1.5 hours is shown. Confocal images showing representative Panc1 tumor cells from baseline (t-0) prior to addition of AF568-labeled antibody, up to 1 hour, 15 minutes from addition of fluorescently labeled anti-DEspR 7C5 murine monoclonal antibody. Increasing intracellular fluorescence is detected in multiple Panc1 cells.
Figure 47:
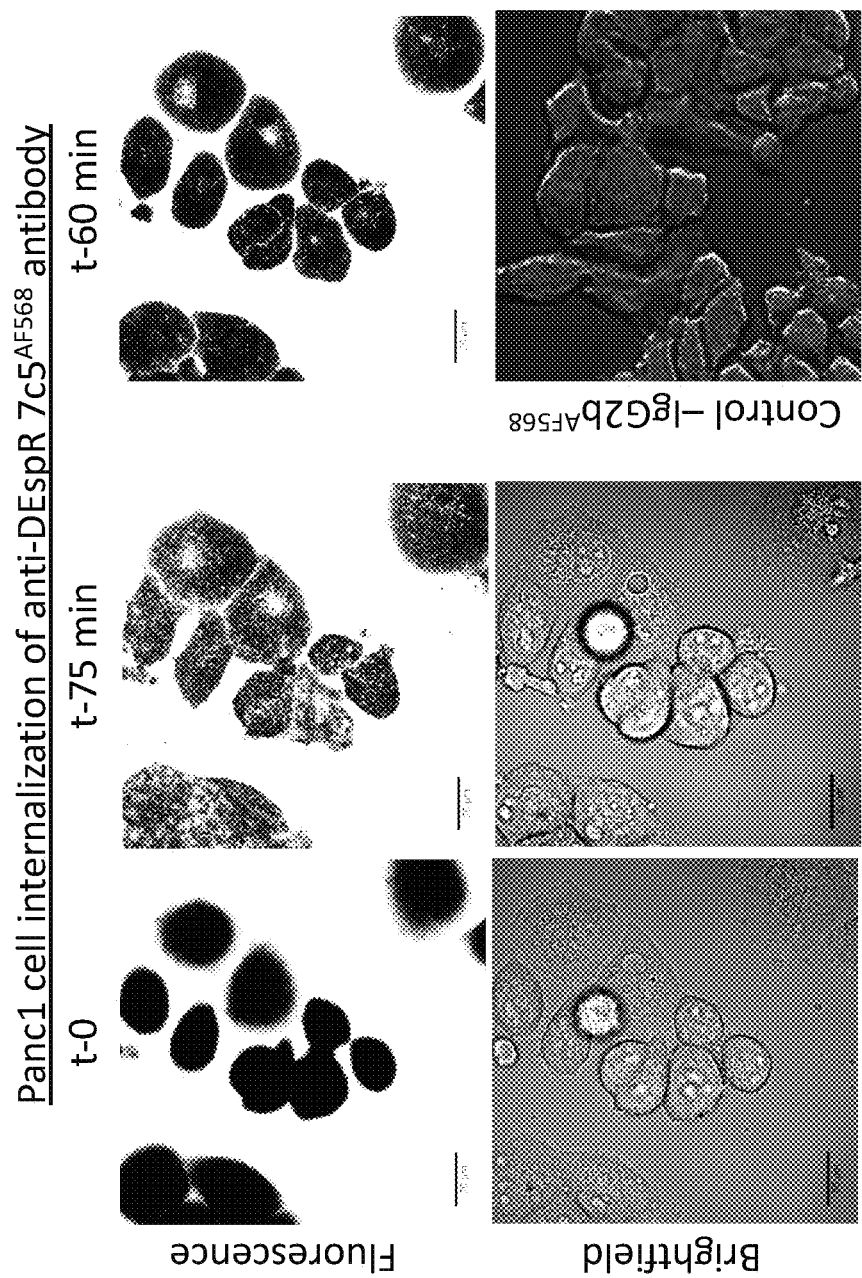
FIG. 47 shows that anti-DEspR monoclonal antibody-receptor interaction results in internalization of fluorescently-labeled anti-human DEspR 7C5-monoclonal antibody, transport to nucleus and induction of apoptosis. Representative time series of internalization of fluorescently labeled (AF568) anti-DEspR monoclonal antibody by Panc1 tumor cells within 1.5 hours at higher magnification of Panc1 tumor cells at baseline and t-75 minutes with corresponding brightfield images of Panc1 cells. At t-60 minutes, representative image of Panc1 tumor cells exposed to control AF568-labeled IgG2b isotype, with DAPI stained nuclei to mark cells, demonstrate no intracellular AF568 fluorescence uptake.
Figure 48:
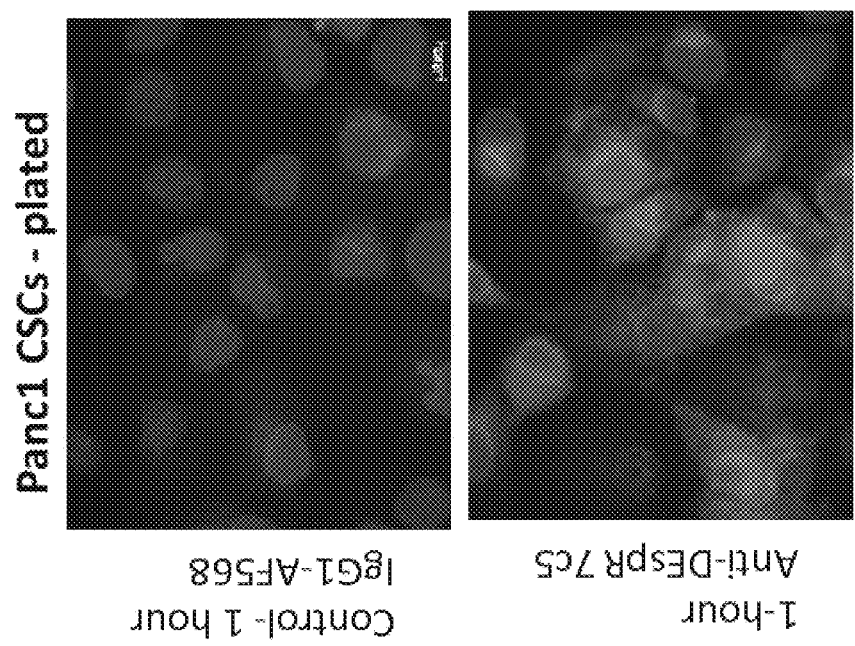
FIG. 48 shows that internalization of anti-DEspR monoclonal antibody in Panc1 tumor cell is associated with nuclear changes consistent with early phase of apoptosis. For comparison, see MORPHOLOGICAL ASPECTS OF APOPTOSIS. Walter Malorni, Stefano Faisl, and Carla Fiorentini Laboratory of Ultrastructures and (1) Virology, Istituto Superiore di Sanita', viale Regina Elena 299, 00161, Rome, Italy.
Figure 49:
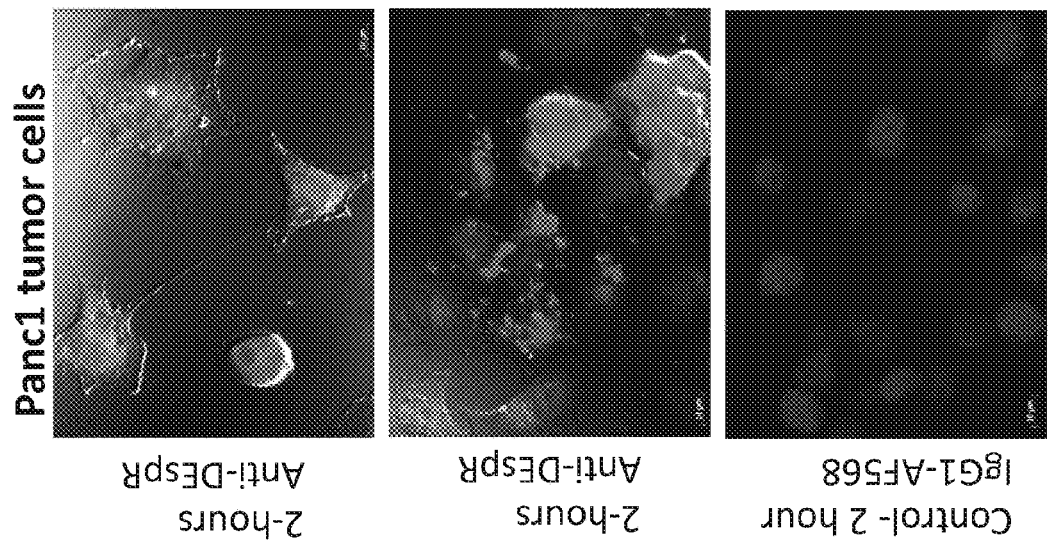
FIG. 49 shows that internalization of anti-DEspR monoclonal antibody in Panc1 tumor cell is associated with nuclear changes consistent with early phase of apoptosis. For comparison, see Indian Journal of Cancer, Vol. 50, No. 3, July-September, 2013, pp. 274-283, "Various methods available for detection of apoptotic cells."
Figure 51:
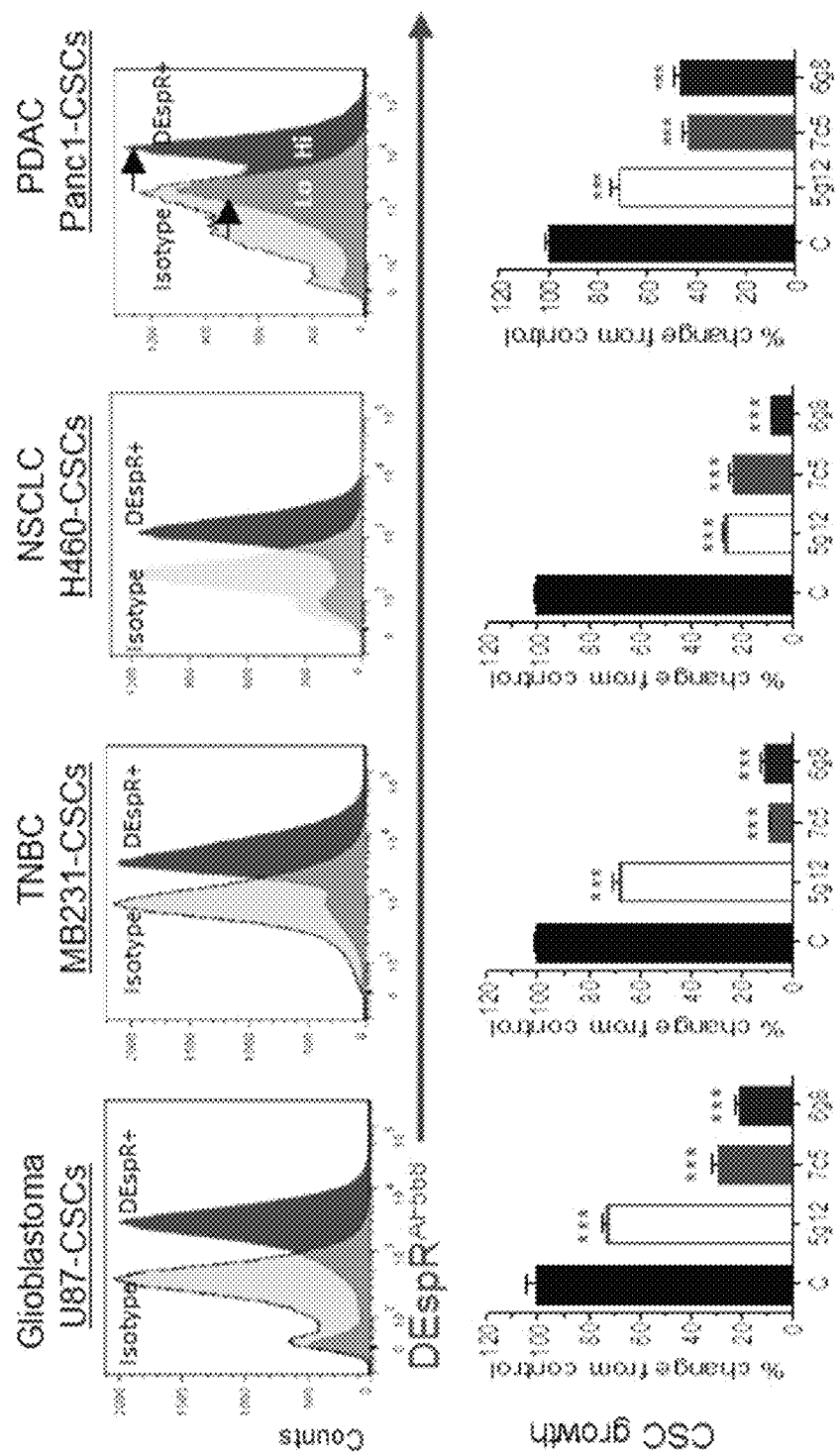
FIG. 51 demonstrates that FACS analyses detect DEspR expression in CSCs in multiple cancers and that multiple anti-human DEspR monoclonal antibodies targeting 2 different DEspR epitopes, namely 5G12E8 and 7C5B2 for epitope 1, and 6G8 for epitope 2, inhibit CSC growth.
Figure 52:
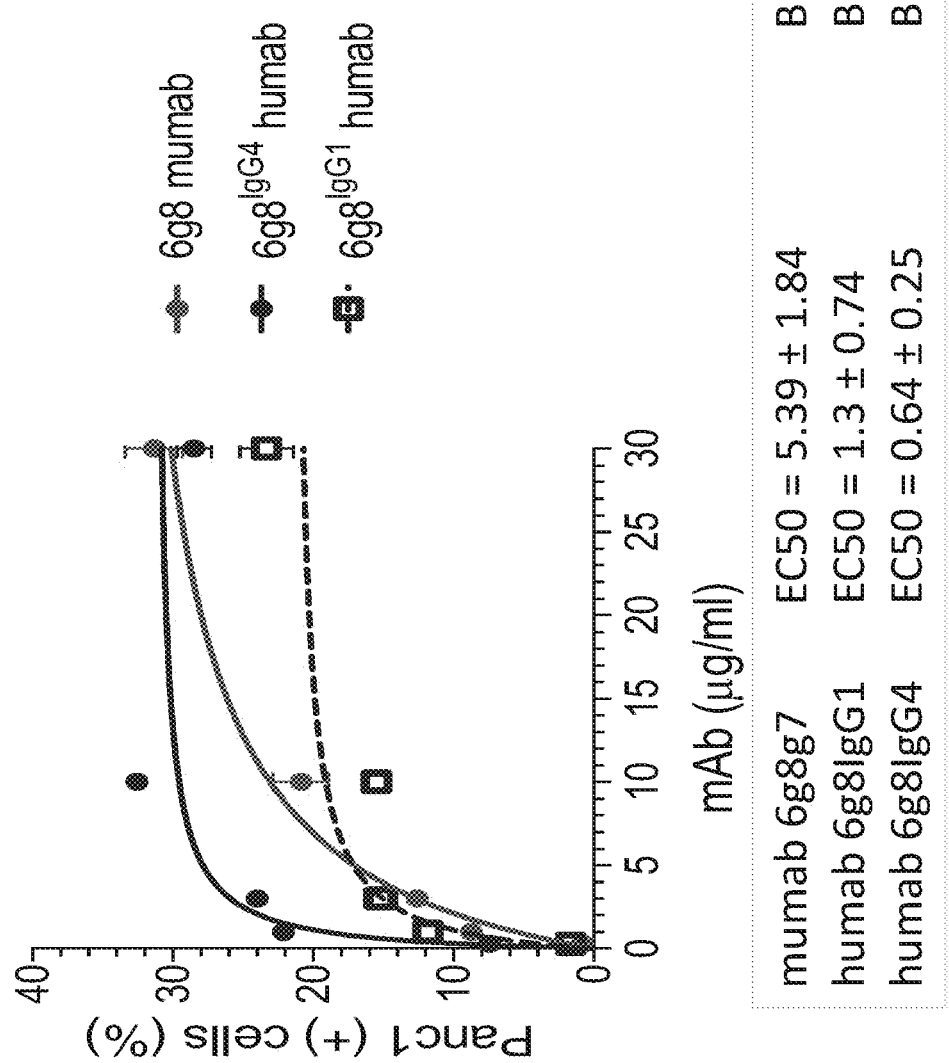
FIG. 52 demonstrates a comparison of a prototype 6G8 murine monoclonal antibody with 6G8 humanized monoclonal antibodies: binding to DEspR on intact DEspR+ cells (Panc1 tumor cells). Binding of AF-568-labeled monoclonal antibodies to Panc1 cells at 4° C. for 20 minutes was analyzed. Binding was quantified by FACS with corresponding isotype labeled antibodies as background controls. These data demonstrate high-affinity binding of 6G8 humanized monoclonal antibodies to DEspR on intact cells having a native target, not just the antigenic peptide. Furthermore, 6G8 humanized monoclonal antibodies were developed using two different human IgG Fc regions—human IgG1 and hinge-stabilized human IgG4, thus affirming high-affinity binding.
Figure 53:
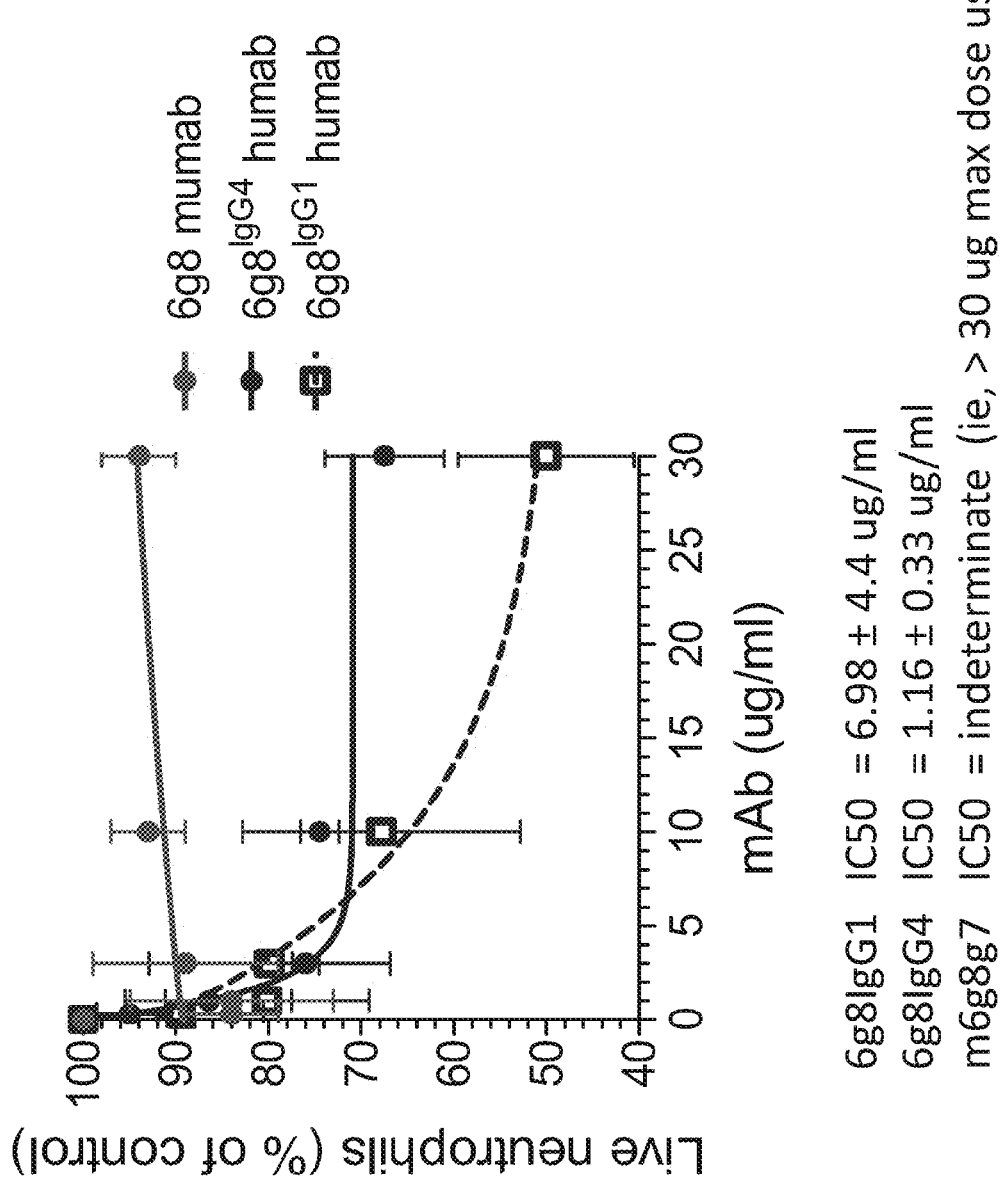
FIG. 53 shows a comparison of functional activities of 6G8 humanized monoclonal antibodies and 6G murine monoclonal antibody on inhibition of rat neutrophil survival. Neutrophil survival assays were performed with freshly isolated rat neutrophils. Neutrophils (50,000/well) were incubated in the absence or presence of monoclonal antibodies at 37° C. for 4 hrs and live cells counted by using Trypan blue. Each point was done in triplicates.
Figure 54:
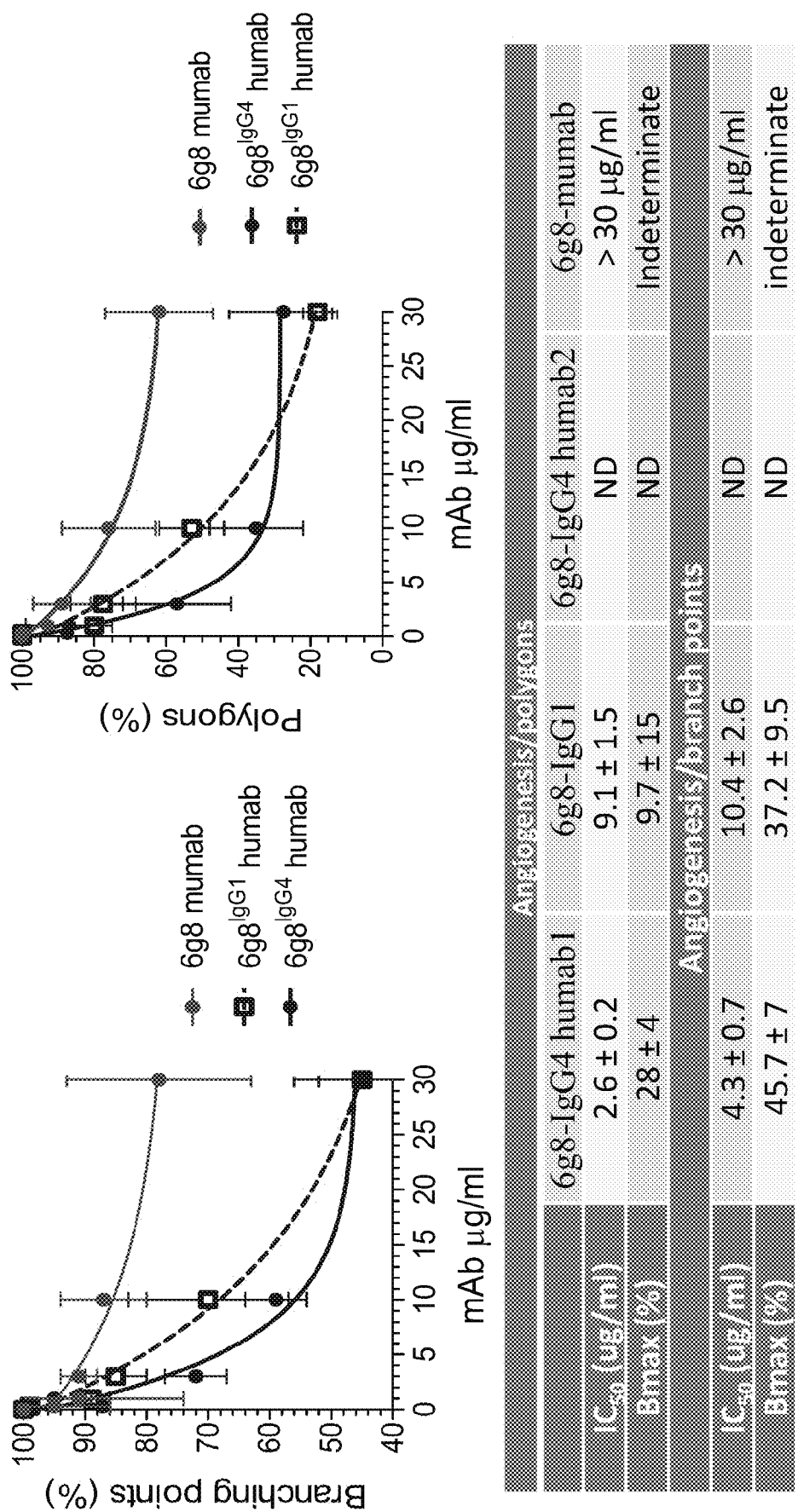
FIG. 54 shows a comparison of functional activities of 6G8 humanized monoclonal antibodies and 6G murine monoclonal antibody on inhibition of HUVECs angiogenesis. HUVEC-tube formation (angiogenesis) assay (20,000 cells/well) was performed in the presence or absence of monoclonal antibodies. Number of polygons, number of branch points (standard parameters of complex network formation) were determined after 14 hrs of incubation at 37° C. ND, not determined.

In some embodiments of the aspects described herein, a DEspR binding protein, an isolated antibody or antigen-binding fragment thereof, or anti-DEspR antibody or antigen-binding fragment thereof as disclosed herein has an IC50 of 3.0 µg/ml or less, an IC50 of 2.8 µg/ml or less, an IC50 of 2.6 µg/ml or less, an IC50 of 2.5 µg/ml or less, an IC50 of 2.0 µg/ml or less, an IC50 of 1.5 µg/ml or less, an IC50 of 1.2 µg/ml or less, or an IC50 of 1.0 µg/ml or less, as determined by, for example, inhibition of activated neutrophil survival or human angiogenesis assays as described herein (see, for example, Tables 3-5 herein). IC50 can be determined, for example, by measuring the ability of one of the described DEspR antibodies or antigen-binding fragments thereof to inhibit neutrophil survival (see, e.g., Tables 3, 5) or in inhibiting bFGF-medicated NEGF-independent angiogenesis of human umbilical vein cells (see, e.g., Table 4, FIGS. 3, 9 and 40). Neutrophil survival can be performed with freshly isolated rat neutrophils. For example, neutrophils (e.g., 50,000/well) are incubated in the presence or absence of the antibody at 37° C. for 4 hours and live cells counted by using, for example, Tryphan blue. Any of the standard HUVEC angiogenesis assays known to one of ordinary skill in the art can be used.

In some embodiments of the aspects described herein, a DEspR binding protein, an isolated antibody or antigen-binding fragment thereof, or anti-DEspR antibody or antigen-binding fragment thereof as disclosed herein has a $K_D$ of less than 5.0 µg/ml, less than 4.0 µg/ml, less than 3 µg/ml, less than 2.5 µg/ml, less than 2.0 µg/ml, less than 1.5 µg/ml, or less than 1.0 µg/ml, for binding to DEspR+ pancreatic cancer cells. In some embodiments, a DEspR binding protein, an isolated antibody or antigen-binding fragment thereof, or anti-DEspR antibody or antigen-binding fragment thereof as disclosed herein has a $K_D$ of less than 35 nM, less than 33 nM, less than 30 nM, or between 15-35 nM for binding to DEspR+ pancreatic cancer cells. In some embodiments of the aspects described herein, a DEspR binding protein, an isolated antibody or antigen-binding fragment thereof, or anti-DEspR antibody or antigen-binding fragment thereof as disclosed herein has a of less than 5.0 µg/ml, less than 4.0 µg/ml, less than 3 µg/ml, less than 2.5 µg/ml, less than 2.0 µg/ml, less than 1.5 µg/ml, or less than 1.0 µg/ml, for binding to DEspR+ pancreatic cancer cells, or binding to SEQ ID NO: 2 and is a neutralizing antibody or DEspR antagonist.

In some embodiments of the aspects described herein, a DEspR binding protein, an isolated antibody or antigen-binding fragment thereof, or anti-DEspR antibody or antigen-binding fragment thereof as disclosed herein has at least of a EC50 of 12 µg/ml less, an IC50 of 3.0 µg/ml, or less, or a $K_D$ of 5.2 µg/ml or less. In some embodiments, a DEspR binding protein, an isolated antibody or antigen-binding fragment thereof, or anti-DEspR antibody or antigen-binding fragment thereof as disclosed herein has a EC50 of 12

µg/ml or less, and an IC50 of 3.0 µg/ml or less, and a $K_D$ of 5.2 µg/ml or less and is a neutralizing antibody or DEspR antagonist.

In some embodiments of the aspects described herein, amino acid sequence modification(s) of the antibodies or antigen-binding fragments thereof specific for DEspR, such as the 6G8G7 or 7C5B2 variant antibodies or an antigen-binding fragments thereof described herein are contemplated. For example, it can be desirable to improve the binding affinity and/or other biological properties of the antibody. Amino acid sequence variants of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics, e.g., binding specificity, inhibition of biological activity. The amino acid changes also can alter post-translational processes of the antibody, such as changing the number or position of glycosylation sites.

A useful method for identification of certain residues or regions of the antibody that are preferred locations for mutagenesis is called "alanine scanning mutagenesis" as described by Cunningham and Wells Science, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include antibody with an N-terminal methionyl residue or the antibody fused to a cytotoxic polypeptide. Other insertional variants of the antibody molecule include the fusion to the N- or C-terminus of the antibody to an enzyme (e.g. for ADEPT) or a polypeptide which increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated for use in the antibodies or antigen-binding fragments thereof specific for DEspR described herein.

Substantial modifications in the biological properties of the antibodies or antigen-binding fragments thereof specific for DEspR are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H).

Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class.

Any cysteine residue not involved in maintaining the proper conformation of the antibodies or antigen-binding fragments thereof specific for DEspR also can be substituted, generally with serine, to improve the oxidative stability of the molecule and prevent aberrant crosslinking Conversely, cysteine bond(s) can be added to the antibody to improve its stability (particularly where the antibody is an antigen-binding fragment such as an Fv fragment).

A particularly preferred type of substitutional variant involves substituting one or more hypervariable region residues of a parent antibody (e.g., the monoclonal 6G8G7 or 7C5B2 anti-DEspR variant antibodies, or a humanized or human antibody or antigen-binding fragment thereof specific for DEspR, as provided herein). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding.

Alternatively, or additionally, it can be beneficial to analyze a crystal structure of the antigen-antibody complex to identify contact points between the antibody or antigen-binding fragments thereof specific for DEspR and human DEspR. Such contact residues and neighboring residues are candidates for substitution according to the techniques elaborated herein. Once such variants are generated, the panel of variants is subjected to screening as described herein and antibodies or antigen-binding fragments thereof with superior properties in one or more relevant assays can be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine can also be used.

Addition of glycosylation sites to the antibodies or antigen-binding fragments thereof specific for DEspR is accomplished by altering the amino acid sequence such that it contains one or more of the above-described tripeptide sequences (for N-linked glycosylation sites). The alteration can also be made by the addition of, or substitution by, one or more serine or threonine residues to the sequence of the original antibody (for O-linked glycosylation sites).

Where the antibody comprises an Fc region, the carbohydrate attached thereto can be altered. For example, antibodies with a mature carbohydrate structure that lacks fucose attached to an Fc region of the antibody are described in US Pat Appl No US 2003/0157108 A1, Presta, L. See also US 2004/0093621 A1 (Kyowa Hakko Kogyo Co., Ltd). Antibodies with a bisecting N-acetylglucosamine (GlcNAc) in the carbohydrate attached to an Fc region of the antibody are referenced in WO03/011878, Jean-Mairet et al. and U.S. Pat. No. 6,602,684, Umana et al. Antibodies with at least one galactose residue in the oligosaccharide attached to an Fc region of the antibody are reported in WO97/30087, Patel et al. See, also, WO98/58964 (Raju, S.) and WO99/22764 (Raju, S.) concerning antibodies with altered carbohydrate attached to the Fc region thereof.

In some embodiments, it can be desirable to modify the antibodies or antigen-binding fragments thereof specific for DEspR described herein with respect to effector function, e.g., so as to enhance antigen-dependent cell-mediated cytotoxicity (ADCC) and/or complement dependent cytotoxicity (CDC) of the antibody. This can be achieved by introducing one or more amino acid substitutions in an Fc region of the antibody or antigen-binding fragment thereof. Alternatively or additionally, cysteine residue(s) can be introduced in the Fc region, thereby allowing interchain disulfide bond formation in this region. The homodimeric antibody thus generated can have improved internalization capability and/or increased complement-mediated cell killing and antibody-dependent cellular cytotoxicity (ADCC). See Caron et al., J. Exp Med. 176:1191-1195 (1992) and Shopes, B. J. Immunol. 148:2918-2922 (1992). Homodimeric antibodies with enhanced anti-tumor activity can also be prepared using heterobifunctional cross-linkers as described in Wolff et al. Cancer Research 53:2560-2565 (1993). Alternatively, an antibody can be engineered which has dual Fc regions and can thereby have enhanced complement lysis and ADCC capabilities. See Stevenson et al. Anti-Cancer Drug Design 3:219-230 (1989).

For example, WO00/42072 (Presta, L.) describes antibodies with improved ADCC function in the presence of human effector cells, where the antibodies comprise amino acid substitutions in the Fc region thereof. Preferably, the antibody with improved ADCC comprises substitutions at positions 298, 333, and/or 334 of the Fc region (Eu numbering of residues). Preferably the altered Fc region is a human IgG1 Fc region comprising or consisting of substitutions at one, two or three of these positions. Such substitutions are optionally combined with substitution(s) which increase C1q binding and/or CDC.

Antibodies with altered C1q binding and/or complement dependent cytotoxicity (CDC) are described in WO99/51642, U.S. Pat. No. 6,194,551B1, U.S. Pat. No. 6,242,195B1, U.S. Pat. No. 6,528,624B1 and U.S. Pat. No. 6,538,124 (Idusogie et al.). The antibodies comprise an amino acid substitution at one or more of amino acid positions 270, 322, 326, 327, 329, 313, 333 and/or 334 of the Fc region thereof (Eu numbering of residues).

To increase the serum half life of the antibody specific for DEspR described herein, one can incorporate a salvage receptor binding epitope into the antibody (especially an antigen-binding fragment) as described in U.S. Pat. No. 5,739,277, for example. As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule.

Antibodies with improved binding to the neonatal Fc receptor (FcRn), and increased half-lives, are described in WO00/42072 (Presta, L.) and US2005/0014934A1 (Hinton et al.). These antibodies comprise an Fc region with one or more substitutions therein which improve binding of the Fc region to FcRn. For example, the Fc region can have substitutions at one or more of positions 238, 250, 256, 265, 272, 286, 303, 305, 307, 311, 312, 314, 317, 340, 356, 360, 362, 376, 378, 380, 382, 413, 424, 428 or 434 (EU numbering of residues). The preferred Fc region-comprising antibody variant with improved FcRn binding comprises amino acid substitutions at one, two or three of positions 307, 380 and 434 of the Fc region thereof (EU numbering of residues). In one embodiment, the antibody has 307/434 mutations.

Engineered antibodies specific for DEspR with three or more (preferably four) functional antigen binding sites are also contemplated (US Appln No. US2002/0004587 A1, Miller et al.).

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

In some embodiments of the aspects described herein, antibody and antigen-binding fragments specific for DEspR described herein are incorporated together with one or more other antibody and antigen-binding fragments specific for other targets to produce "dual targeting" or multi-targeting molecules which bind to one or more targets additional to DEspR. Examples of dual targeting strategies are reviewed in Kontermann (MAbs. 2012 March-April; 4(2): 182-197).

DEspR Binding Proteins

In various embodiments, provided herein are DEspR Binding Proteins, e.g., DVD-Ig binding proteins that bind one or more epitopes of DEspR polypeptide. An exemplary embodiment of such DVD-Ig molecules comprises a heavy chain that comprises the structural formula VD1-(X1)n-VD2-C-(X2)n, wherein VD1 is a first heavy chain variable domain, VD2 is a second heavy chain variable domain, C is a heavy chain constant domain, X1 is a linker, X2 is an Fc region on the first polypeptide chain and X2 does not comprise an Fc region on the second polypeptide chain; n is independently 0 or 1 on the first and second chains; and a light chain that comprises the structural formula VD1-(X1)n-VD2-C-(X2)n, wherein VD1 is a first light chain variable domain, VD2 is a second light chain variable domain, C is a light chain constant domain, X1 is a linker, and X2 is an Fc region on the first polypeptide chain and X2 does not comprise an Fc region on the second polypeptide chain; n is independently 0 or 1 on the first and second chains. Such a DVD-Ig may comprise two such heavy chains and two such light chains, wherein each chain comprises variable domains linked in tandem without an intervening constant region between the variable domains, wherein a heavy chain and a light chain associate to form two tandem antigen binding sites, and a pair of heavy and light chains may associate with another pair of heavy and light chains to form a tetrameric binding protein with four antigen binding sites. In another embodiment, a DVD-Ig molecule may comprise heavy and light chains that each comprise three variable domains, e.g., VD1, VD2, VD3, linked in tandem without an intervening constant region between variable domains, wherein a pair of heavy and light chains may associate to form three antigen binding sites, and wherein a pair of heavy and light chains may associate with another pair of heavy and light chains to form a tetrameric binding protein with six antigen binding sites.

Each variable domain (VD) in a DVD-Ig may be obtained from one or more "parent" monoclonal antibodies that bind one or more desired antigens or epitopes, such as LRP-8 antigens or epitopes. General methods of making DVD-Ig and properties associated with DVD-Igs are described in U.S. Pat. No. 8,841,417, incorporated by reference herein in its entirety.

Antibody and Binding-Protein Conjugates:

In some embodiments of the aspects described herein, immunoconjugates comprising a DEspR-binding protein, or anti-DEspR antibody or antigen-binding fragments specific for DEspR described herein are conjugated to an agent such as a chemotherapeutic agent, toxin (e.g. an enzymatically active toxin of bacterial, fungal, plant or animal origin, or fragments thereof), a small molecule, an siRNA, a nanoparticle, a targeting agent (e.g., a microbubble), or a radioactive isotope (i.e., a radioconjugate) can be used. Such immunoconjugates can be used, for example, in diagnostic, theranostic, or targeting methods.

In some embodiments, antibody or binding-protein drug conjugates comprising DEspR-binding protein, or anti-DEspR antibody or antigen-binding fragments specific for DEspR described herein are provided. The terms "antibody drug conjugate" or "antibody-drug conjugate," as used herein, refer to an antibody conjugated to a non-proteinaceous agent, typically a chemotherapeutic agent, e.g., a cytotoxic agent, a cytostatic agent, a toxin, or a radioactive agent. A linker molecule can be used to conjugate the drug to the antibody. A wide variety of linkers and drugs useful in ADC technology are known in the art and can be used in embodiments described herein. (See, for example, US20090028856; US2009/0274713; US2007/0031402; WO2005/084390; WO2009/099728; U.S. Pat. Nos. 5,208,020; 5,416,064; 5,475,092; 5,585,499; 6,436,931; 6,372,738; and 6,340,701, all incorporated herein by reference in their entireties). By combining the unique targeting of monoclonal antibodies or fragments thereof with the cancer-killing ability of cytotoxic drugs, antibody drug conjugates allow sensitive and increased discrimination between healthy and diseased tissue.

Chemotherapeutic agents useful in the generation of such immunoconjugates are described herein. Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin and the tricothecenes. A variety of radionuclides are available for the production of radioconjugate antibodies. Examples include $^{212}$Bi, $^{131}$I, $^{131}$In, $^{90}$Y and $^{186}$Re.

Conjugates of the antibodies specific for DEspR described herein and a cytotoxic agent can be made using any of a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al. Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In some embodiments, the DEspR-specific antibody or antigen-binding fragment thereof, such as the 6G8G7 or 7C5B2 variant antibodies or antigen-binding fragments thereof, or a humanized or composite antibody or antigen-binding fragment thereof derived or obtained from the 6G8G7 or 7C5B2 variant antibodies, can be conjugated to a "receptor" (such as, for example, streptavidin) for utilization in tumor pretargeting wherein the antibody-receptor conjugate is administered to the subject, followed by removal of unbound conjugate from the circulation using a clearing agent and then administration of a "ligand" (e.g. avidin) which is conjugated to a cytotoxic agent (e.g. a radionucleotide). In some embodiments, the DEspR-specific antibody or antigen-binding fragment thereof can be conjugated to biotin, and the biotin conjugated antibody or antigen-binding fragment thereof can be further conjugated or linked to a streptavidin-bound or -coated agent, such as a streptavidin-coated microbubble, for use in, for example, molecular imaging of angiogenesis.

The antibodies and antigen-binding fragments thereof specific for DEspR described herein, such as the 6G8G7 or 7C5B2 variant antibodies or antigen-binding fragments thereof, or a humanized or composite antibody or antigen-binding fragment thereof derived or obtained from the 6G8G7 or 7C5B2 variant antibodies, can also be formulated as immunoliposomes. Liposomes containing the antibody are prepared by methods known in the art, such as described in Epstein et al., Proc. Natl. Acad. Sci. USA, 82:3688 (1985); Hwang et al., Proc. Natl. Acad. Sci. USA, 77:4030 (1980); and U.S. Pat. Nos. 4,485,045 and 4,544,545. Liposomes with enhanced circulation time are disclosed in U.S. Pat. No. 5,013,556.

Particularly useful liposomes can be generated, for example, by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the invention can be conjugated to the liposomes as described in Martin et al. J. Biol. Chem. 257: 286-288 (1982) via a disulfide interchange reaction. A chemotherapeutic agent is optionally contained within the liposome. See Gabizon et al. J. National Cancer Inst. 81(19) 1484 (1989).

The hybridoma cell lines 6G8G7 and 7C5B2 are being maintained and stored.

Therapeutic & Diagnostic Uses of DEsR Binding Proteins, Anti-DEspR Antibodies and Fragments Thereof As described herein, the inventors have discovered that both the 7C5B2 and 6G8G7 anti-DEspR variant antibodies, and fully humanized antibody derivatives thereof inhibit cancer stem cell growth and anoikis resistance in multiple human cancer cell lines and decreases tumor progression and increases survival using a pancreatic peritoneal metastasis nude rat model. In addition, the data provided herein demonstrate that the 6G8G7 anti-DEspR antibody decreases tumor initiation/tumorigenesis of Panc1-CSCs, decreases collagen-1 (col1) secretion by Panc1-CSCs, and decreases αSMA expression induced by TNF-α.

Accordingly, provided herein, in some aspects, are methods of treating an angiogenesis-dependent disease or disorder comprising administering a therapeutically effective amount of an antibody or antigen-binding specific for DEspR. Such methods can comprise administering, for example, a chimeric, humanized, deimmunized, or composite human anti-DEspR antibody derived from the 6G8G7 or 7C5B2 variant antibodies; an anti-DEspR antibody comprising one or more heavy chain CDR regions comprising a sequence selected from the group consisting of SEQ ID NO: 7, SEQ ID NO: 8, SEQ ID NO: 9, SEQ ID NO: 14, SEQ ID NO: 15, SEQ ID NO: 16, SEQ ID NO: 21, SEQ ID NO: 22, and SEQ ID NO: 23; an anti-DEspR antibody comprising one or more light chain CDR regions comprising a sequence selected from the group consisting of SEQ ID NO: 28, SEQ ID NO: 29, SEQ ID NO: 30, SEQ ID NO: 35, SEQ ID NO: 36, SEQ ID NO: 37, SEQ ID NO: 42, SEQ ID NO: 43, SEQ ID NO: 44, SEQ ID NO: 51, SEQ ID NO: 52, and SEQ ID NO: 53; an anti-DEspR composite human antibody comprising a variable heavy (VH) chain amino acid sequence consisting of SEQ ID NO: 6, SEQ ID NO: 13, or SEQ ID NO: 20; an anti-DEspR composite human antibody comprising a variable light (VL) chain amino acid sequence consisting of SEQ ID NO: 27, SEQ ID NO: 34, or SEQ ID NO: 41; an anti-DEspR antibody comprising one or more CDRs, e.g. 1 CDR, 2 CDRs, 3 CDRs, 4 CDRs, 5 CDRs, or 6 CDRs, selected from the group consisting of (a) a heavy chain CDR1 having the amino acid sequence of SEQ ID NO: 7, SEQ ID NO: 14, or SEQ ID NO: 21; (b) a heavy chain CDR2 having the amino acid sequence of SEQ ID NO: 8, SEQ ID NO: 15, or SEQ ID NO: 22; (c) a heavy chain CDR3 having the amino acid sequence of SEQ ID NO: 9; SEQ ID NO: 16, or SEQ ID NO: 22; (d) a light chain CDR1 having the amino acid sequence of SEQ ID NO: 28, SEQ ID NO: 35, or SEQ ID NO: 42; (e) a light chain CDR2 having the amino acid sequence of SEQ ID NO: 29, SEQ ID NO: 36, or SEQ ID NO: 43; and (f) a light chain CDR3 having the amino acid sequence of SEQ ID NO: 30, SEQ ID NO: 37, or SEQ ID NO: 44; an anti-DEspR antibody comprising a heavy chain or a fragment thereof, comprising one or more CDRs, e.g., 1 CDR, 2 CDRs, or 3 CDRs, selected from the group consisting of a heavy chain CDR1 having the amino acid sequence of SEQ ID NO: 7, SEQ ID NO: 14, or SEQ ID NO: 21; a heavy chain CDR2 having the amino acid sequence of SEQ ID NO: 8, SEQ ID NO: 15, or SEQ ID NO: 22; and a heavy chain CDR3 having the amino acid sequence of SEQ ID NO: 9; SEQ ID NO: 16, or SEQ ID NO: 22; an anti-DEspR antibody comprising a light chain or a fragment thereof, comprising one or more CDRs, e.g., 1 CDR, 2 CDRs, or 3 CDRs selected from the group consisting of a light chain CDR1 having the amino acid sequence of SEQ ID NO: 28, SEQ ID NO: 35, or SEQ ID NO: 42; a light chain CDR2 having the amino acid sequence of SEQ ID NO: 29, SEQ ID NO: 36, or SEQ ID NO: 43; and a light chain CDR3 having the amino acid sequence of SEQ ID NO: 30, SEQ ID NO: 37, or SEQ ID NO: 44.

These antiangiogenic therapies can be used as cancer treatment strategies aimed at inhibiting existing tumor blood vessels and development of tumor blood vessels required for providing nutrients to support tumor growth. Because angiogenesis is involved in both primary tumor growth and metastasis, the antiangiogenic treatments using the antibodies and antigen-binding fragments specific for DEspR described herein are capable of inhibiting the neoplastic growth of tumor at the primary site, as well as preventing micro- and macro-metastasis of tumors at the secondary sites, therefore allowing attack of the tumors by other therapeutics. Angiogenesis-dependent diseases and disorders that can be treated using the methods and compositions described herein are those diseases and disorders affected by vascular growth. In other words, an "angiogenesis-dependent disease or disorder" refers to those diseases or disorders that are dependent on a rich blood supply and blood vessel proliferation for the diseases' pathological progression (e.g., metastatic tumors), or diseases or disorders that are the direct result of aberrant blood vessel proliferation (e.g., diabetic retinopathy and hemangiomas).

In some aspects, also provided herein, are methods of treating cancer or tumor metastasis comprising administering a therapeutically effective amount of an antibody or antigen-binding fragment thereof specific for DEspR. Such methods can comprise administering, for example, a chimeric, humanized, deimmunized, or composite human anti-DEspR antibody derived from the 6G8G7 or variant 7C5B2 antibody; an anti-DEspR antibody comprising one or more heavy chain CDR regions comprising a sequence selected from the group consisting of SEQ ID NO: 7, SEQ ID NO: 8, SEQ ID NO: 9, SEQ ID NO: 14, SEQ ID NO: 15, SEQ ID NO: 16, SEQ ID NO: 21, SEQ ID NO: 22, and SEQ ID NO: 23; an anti-DEspR antibody comprising one or more light chain CDR regions comprises a sequence selected from the group consisting of SEQ ID NO: 28, SEQ ID NO: 29, SEQ ID NO: 30, SEQ ID NO: 35, SEQ ID NO: 36, SEQ ID NO: 37, SEQ ID NO: 42, SEQ ID NO: 43,SEQ ID NO: 44, SEQ ID NO: 51, SEQ ID NO: 52, and SEQ ID NO: 53; an anti-DEspR composite human antibody comprising a variable heavy ($V_H$) chain amino acid sequence of SEQ ID NO: 6, SEQ ID NO: 13, or SEQ ID NO: 20; an anti-DEspR composite human antibody comprising a variable light ($V_L$) chain amino acid sequence of SEQ ID NO: 27, SEQ ID NO: 34, SEQ ID NO: 41, or SEQ ID NO: 50; an anti-DEspR antibody comprising one or more CDRs, e.g. 1 CDR, 2 CDRs, 3 CDRs, 4 CDRs, 5 CDRs, or 6 CDRs, selected from the group consisting of (a) a heavy chain CDR1 having the amino acid sequence of SEQ ID NO: 7, SEQ ID NO: 14, or SEQ ID NO: 21; (b) a heavy chain CDR2 having the amino acid sequence of SEQ ID NO: 8, SEQ ID NO: 15, or SEQ ID NO: 22; (c) a heavy chain CDR3 having the amino acid sequence of SEQ ID NO: 9; SEQ ID NO: 16, or SEQ ID NO: 23; (d) a light chain CDR1 having the amino acid sequence of SEQ ID NO: 28, SEQ ID NO: 35, SEQ ID NO: 42, or SEQ ID NO: 51; (e) a light chain CDR2 having the amino acid sequence of SEQ ID NO: 29, SEQ ID NO: 36, SEQ ID NO: 43, or SEQ ID NO: 52; and (f) a light chain CDR3 having the amino acid sequence of SEQ ID NO: 30, SEQ ID NO: 37, SEQ ID NO: 44, or SEQ ID NO: 53; an anti-DEspR antibody comprising a heavy chain or a fragment thereof, comprising one or more CDRs, e.g., 1 CDR, 2 CDRs, or 3 CDRs, selected from the group consisting of a heavy chain CDR1 having the amino acid sequence of SEQ ID NO: 7, SEQ ID NO: 14, or SEQ ID NO: 21; a heavy chain CDR2 having the amino acid sequence of SEQ ID NO: 8, SEQ ID NO: 15, or SEQ ID NO: 22; and a heavy chain CDR3 having the amino acid sequence of SEQ ID NO: 9; SEQ ID NO: 16, or SEQ ID NO: 22; an anti-DEspR antibody comprising a light chain or a fragment thereof, comprising one or more CDRs, e.g., 1 CDR, 2 CDRs, or 3 CDRs selected from the group consisting of a light chain CDR1 having the amino acid sequence of SEQ ID NO: 28, SEQ ID NO: 35, SEQ ID NO: 42, or SEQ ID NO: 51; a light chain CDR2 having the amino acid sequence of SEQ ID NO: 29, SEQ ID NO: 36, SEQ ID NO: 43, or SEQ ID NO: 52; and a light chain CDR3 having the amino acid sequence of SEQ ID NO: 30, SEQ ID NO: 37, SEQ ID NO: 44, or SEQ ID NO: 53; an anti-DEspR humanized antibody comprising a variable heavy ($V_H$) chain amino acid sequence of SEQ ID NO: 55; an anti-DEspR humanized antibody comprising a variable light ($V_L$) chain amino acid sequence of SEQ ID NO: 57; an anti-DEspR humanized antibody comprising a variable light ($V_L$) chain amino acid sequence of SEQ ID NO: 59; an anti-DEspR humanized antibody comprising a variable heavy ($V_H$) chain IgG1 amino acid sequence of SEQ ID NO: 61; an anti-DEspR humanized antibody comprising a variable heavy ($V_H$) chain IgG4 amino acid sequence of SEQ ID NO: 63; or an anti-DEspR humanized antibody comprising a variable light ($V_L$) chain kappa amino acid sequence of SEQ ID NO: 65. Such anti-metastasis therapies provide cancer treatment strategies aimed at inhibiting concurrent inhibition of tumor vascularization and tumor cell invasiveness for treatment and/or inhibition of micrometastasis and macrometastasis, as further described herein. Furthermore, since DEspR is also expressed in tumor cells, including cancer stem cells, as demonstrated herein, immunoconjugates of DEspR specific antibodies or antigen-binding fragments thereof, as described herein, can be generated by conjugation to any agent such as a toxin, cytotoxic or pro-apoptotic agent, and can further inhibit tumor growth by directly targeting/killing tumor cells and cancer stem cells.

Angiogenesis is a process of tissue vascularization that involves both the growth of new developing blood vessels into a tissue (neo-vascularization) and co-opting of existing blood vessels to a target site. Blood vessels are the means by which oxygen and nutrients are supplied to living tissues and waste products are removed from living tissue. Angiogenesis can be a critical biological process. For example, angiogenesis is essential in reproduction, development and wound repair. Conversely, inappropriate angiogenesis can have severe negative consequences. For example, it is only after solid tumors are vascularized as a result of angiogenesis that the tumors have a sufficient supply of oxygen and nutrients that permit it to grow rapidly and metastasize.

Where the growth of new blood vessels is the cause of, or contributes to, the pathology associated with a disease, inhibition of angiogenesis, using the compositions and methods described herein, can reduce the deleterious effects of the disease. Non-limiting examples include tumors, carotid artery disease, rheumatoid arthritis, diabetic retinopathy, inflammatory diseases, restenosis, and the like. Where the growth of new blood vessels is required to support growth of a deleterious tissue, inhibition of angiogenesis, using the compositions and methods described herein, can reduce the blood supply to the tissue and thereby contribute to reduction in tissue mass based on blood supply requirements. Non-limiting examples include growth of tumors where neovascularization is a continual requirement in order that the tumor growth beyond a few millimeters in thickness, and for the establishment of solid tumor metastases. Another example is coronary plaque enlargement.

There are a variety of diseases or disorders in which angiogenesis is believed to lead to negative consequences, referred to herein as "angiogenesis-dependent disease or disorder," "pathological angiogenesis," or "diseases or disorders dependent or modulated by angiogenesis," including but not limited to, inflammatory disorders such as immune and non-immune inflammation, chronic articular rheumatism and psoriasis, disorders associated with inappropriate or inopportune invasion of vessels such as diabetic retinopathy, neovascular glaucoma, restenosis, capillary proliferation in atherosclerotic plaques and osteoporosis, and cancer associated disorders, such as solid tumors, solid tumor metastases, angiofibromas, retrolental fibroplasia, hemangiomas, Kaposi sarcoma and the like cancers which require neovascularization to support tumor growth. In some embodiments of the aspects described herein, the methods are directed to inhibiting angiogenesis in a subject with cancer.

Non-limiting examples of angiogenesis-dependent diseases or disorders that can be treated using the compositions and methods described herein include abnormal vascular proliferation, ascites formation, psoriasis, age-related macular degeneration, thyroid hyperplasia, preeclampsia, rheumatoid arthritis and osteoarthritis, carotid artery disease, vaso vasorum neovascularization, vulnerable plaque neovascularization, neurodegenerative disorders, Alzheimer's disease, obesity, pleural effusion, atherosclerosis, endometriosis, diabetic/other retinopathies, ocular neovascularizations, such as neovascular glaucoma and corneal neovascularization, disorders associated with inappropriate or inopportune invasion of vessels such as diabetic retinopathy, macular degeneration, neovascular glaucoma, restenosis, capillary proliferation in atherosclerotic plaques and osteoporosis, and cancer associated disorders, such as solid tumors, solid tumor metastases, angiofibromas, retrolental fibroplasia, hemangiomas, Kaposi sarcoma, cancers which require neovascularization to support tumor growth, etc.

Accordingly, described herein are methods of inhibiting angiogenesis in a tissue of a subject or individual having a disease or disorder dependent or modulated by angiogenesis, where the disease or disorder can be treated by the inhibition of angiogenesis. Generally, the methods comprise administering to the subject a therapeutically effective amount of a composition comprising an angiogenesis-inhibiting amount of an anti-DEspR antibody or antigen-binding fragment thereof, as described herein. In some embodiments of the methods described herein, the methods further comprises selecting or diagnosing a subject having or at risk for a disease or disorder dependent on angiogenesis.

In some embodiments of these methods, the DEspR is human DEspR. In some embodiments of these methods, the DEspR target has a sequence comprising SEQ ID NO: 3 or an allelic variant thereof. In some embodiments of these methods, an antibody or antigen-binding fragment thereof that specifically binds to DEspR and inhibits DEspR biological activity blocks interaction of DEspR with VEGFsp. In some embodiments of these methods, the VEGFsp has a sequence comprising the sequence of SEQ ID NO: 4. In some embodiments of these methods, the antibody or antigen-binding fragment thereof is specific for an epitope of DEspR comprising an extracellular portion of DEspR. In some embodiments of these methods, the antibody or antigen-binding fragment thereof is specific for an epitope of DEspR comprising, consisting essentially of, or consisting of SEQ ID NO: 1. In some embodiments of these methods, the antibody or antigen-binding fragment thereof is specific for an epitope of DEspR comprising, consisting essentially of, or consisting of SEQ ID NO: 2.

In some embodiments of these methods for inhibiting angiogenesis or treating an angiogenesis-dependent disease or disorder, the antibody or antigen-binding fragment thereof specific for DEspR is a chimeric, humanized, deimmunized, or composite human anti-DEspR antibody derived from the 6G8G7 or variant 7C5B2 antibody; an anti-DEspR antibody comprising one or more heavy chain CDR regions comprising a sequence selected from the group consisting of SEQ ID NO: 7, SEQ ID NO: 8, SEQ ID NO: 9, SEQ ID NO: 14, SEQ ID NO: 15, SEQ ID NO: 16, SEQ ID NO: 21, SEQ ID NO: 22, and SEQ ID NO: 23; an anti-DEspR antibody comprising one or more light chain CDR regions comprises a sequence selected from the group consisting of SEQ ID NO: 28, SEQ ID NO: 29, SEQ ID NO: 30, SEQ ID NO: 35, SEQ ID NO: 36, SEQ ID NO: 37, SEQ ID NO: 42, SEQ ID NO: 43,SEQ ID NO: 44, SEQ ID NO: 51, SEQ ID NO: 52, and SEQ ID NO: 53; an anti-DEspR composite human antibody comprising a variable heavy ($V_H$) chain amino acid sequence of SEQ ID NO: 6, SEQ ID NO: 13, or SEQ ID NO: 20; an anti-DEspR composite human antibody comprising a variable light ($V_L$) chain amino acid sequence of SEQ ID NO: 27, SEQ ID NO: 34, SEQ ID NO: 41, or SEQ ID NO: 50; an anti-DEspR antibody comprising one or more CDRs, e.g. 1 CDR, 2 CDRs, 3 CDRs, 4 CDRs, 5 CDRs, or 6 CDRs, selected from the group consisting of (a) a heavy chain CDR1 having the amino acid sequence of SEQ ID NO: 7, SEQ ID NO: 14, or SEQ ID NO: 21; (b) a heavy chain CDR2 having the amino acid sequence of SEQ ID NO: 8, SEQ ID NO: 15, or SEQ ID NO: 22; (c) a heavy chain CDR3 having the amino acid sequence of SEQ ID NO: 9; SEQ ID NO: 16, or SEQ ID NO: 23; (d) a light chain CDR1 having the amino acid sequence of SEQ ID NO: 28, SEQ ID NO: 35, SEQ ID NO: 42, or SEQ ID NO: 51; (e) a light chain CDR2 having the amino acid sequence of SEQ ID NO: 29, SEQ ID NO: 36, SEQ ID NO: 43, or SEQ ID NO: 52; and (f) a light chain CDR3 having the amino acid sequence of SEQ ID NO: 30, SEQ ID NO: 37, SEQ ID NO: 44, or SEQ ID NO: 53; an anti-DEspR antibody comprising a heavy chain or a fragment thereof, comprising one or more CDRs, e.g., 1 CDR, 2 CDRs, or 3 CDRs, selected from the group consisting of a heavy chain CDR1 having the amino acid sequence of SEQ ID NO: 7, SEQ ID NO: 14, or SEQ ID NO: 21; a heavy chain CDR2 having the amino acid sequence of SEQ ID NO: 8, SEQ ID NO: 15, or SEQ ID NO: 22; and a heavy chain CDR3 having the amino acid sequence of SEQ ID NO: 9; SEQ ID NO: 16, or SEQ ID NO: 22; an anti-DEspR antibody comprising a light chain or a fragment thereof, comprising one or more CDRs, e.g., 1 CDR, 2 CDRs, or 3 CDRs selected from the group consisting of a light chain CDR1 having the amino acid sequence of SEQ ID NO: 28, SEQ ID NO: 35, SEQ ID NO: 42, or SEQ ID NO: 51; a light chain CDR2 having the amino acid sequence of SEQ ID NO: 29, SEQ ID NO: 36, SEQ ID NO: 43, or SEQ ID NO: 52; and a light chain CDR3 having the amino acid sequence of SEQ ID NO: 30, SEQ ID NO: 37, SEQ ID NO: 44, or SEQ ID NO: 53; an anti-DEspR humanized antibody comprising a variable heavy ($V_H$) chain amino acid sequence of SEQ ID NO: 55; an anti-DEspR humanized antibody comprising a variable light ($V_L$) chain amino acid sequence of SEQ ID NO: 57; an anti-DEspR humanized antibody comprising a variable light ($V_L$) chain amino acid sequence of SEQ ID NO: 59; an anti-DEspR humanized antibody comprising a variable heavy ($V_H$) chain IgG1 amino acid sequence of SEQ ID NO: 61; an anti-DEspR humanized antibody comprising a variable heavy ($V_H$) chain IgG4 amino acid sequence of SEQ ID NO: 63; or an anti-DEspR humanized antibody comprising a variable light ($V_L$) chain kappa amino acid sequence of SEQ ID NO: 65.

In some embodiments of the methods described herein, the antigen-binding fragment is a Fab fragment. In some embodiments, the anti-DEspR antigen-binding fragment is a Fab' fragment. In some embodiments, the anti-DEspR antigen-binding fragment is a Fd fragment. In some embodiments, the anti-DEspR antigen-binding fragment is a Fd' fragment. In some embodiments, the antigen-binding fragment is a Fv fragment. In some embodiments, the anti-DEspR antigen-binding fragment is a dAb fragment. In some embodiments, the anti-DEspR antigen-binding fragment comprises isolated CDR regions. In some embodiments, the anti-DEspR antigen-binding fragment is a $F(ab)_2$ fragment. In some embodiments, the anti-DEspR antigen-binding fragment is a single chain antibody molecule. In some embodiments, the anti-DEspR antigen-binding fragment is a diabody comprising two antigen binding sites. In some embodiments, the anti-DEspR antigen-binding fragment is a linear antibody comprising a pair of tandem Fd segments ($V_H$-$C_H$1-$V_H$-$C_H$1).

Accordingly, in some aspects, the disease or disorder dependent or modulated by angiogenesis is cancer, where the rapidly dividing neoplastic cancer cells require an efficient blood supply to sustain their continual growth of the tumor. Inhibition of angiogenesis or tumor cell invasiveness or a combination thereof using the compositions and therapeutic methods described herein at the primary tumor site and secondary tumor site serve to prevent and limit metastasis and progression of disease.

Accordingly, in some aspects, provided herein are methods to treat a subject having or at risk for a cancer or tumor comprising administering a therapeutically effective amount of an anti-DEspR antibody or antigen-binding fragment thereof, such as a chimeric, humanized, deimmunized, or composite human anti-DEspR antibody derived from the 6G8G7 or variant 7C5B2 antibody; an anti-DEspR antibody comprising one or more heavy chain CDR regions comprising a sequence selected from the group consisting of SEQ ID NO: 7, SEQ ID NO: 8, SEQ ID NO: 9, SEQ ID NO: 14, SEQ ID NO: 15, SEQ ID NO: 16, SEQ ID NO: 21, SEQ ID NO: 22, and SEQ ID NO: 23; an anti-DEspR antibody comprising one or more light chain CDR regions comprises a sequence selected from the group consisting of SEQ ID NO: 28, SEQ ID NO: 29, SEQ ID NO: 30, SEQ ID NO: 35, SEQ ID NO: 36, SEQ ID NO: 37, SEQ ID NO: 42, SEQ ID NO: 43,SEQ ID NO: 44, SEQ ID NO: 51, SEQ ID NO: 52, and SEQ ID NO: 53; an anti-DEspR composite human antibody comprising a variable heavy ($V_H$) chain amino acid sequence of SEQ ID NO: 6, SEQ ID NO: 13, or SEQ ID NO: 20; an anti-DEspR composite human antibody comprising a variable light ($V_L$) chain amino acid sequence of SEQ ID NO: 27, SEQ ID NO: 34, SEQ ID NO: 41, or SEQ ID NO: 50; an anti-DEspR antibody comprising one or more CDRs, e.g. 1 CDR, 2 CDRs, 3 CDRs, 4 CDRs, 5 CDRs, or 6 CDRs, selected from the group consisting of (a) a heavy chain CDR1 having the amino acid sequence of SEQ ID NO: 7, SEQ ID NO: 14, or SEQ ID NO: 21; (b) a heavy chain CDR2 having the amino acid sequence of SEQ ID NO: 8, SEQ ID NO: 15, or SEQ ID NO: 22; (c) a heavy chain CDR3 having the amino acid sequence of SEQ ID NO: 9; SEQ ID NO: 16, or SEQ ID NO: 23; (d) a light chain CDR1 having the amino acid sequence of SEQ ID NO: 28, SEQ ID NO: 35, SEQ ID NO: 42, or SEQ ID NO: 51; (e) a light chain CDR2 having the amino acid sequence of SEQ ID NO: 29, SEQ ID NO: 36, SEQ ID NO: 43, or SEQ ID NO: 52; and (f) a light chain CDR3 having the amino acid sequence of SEQ ID NO: 30, SEQ ID NO: 37, SEQ ID NO: 44, or SEQ ID NO: 53; an anti-DEspR antibody comprising a heavy chain or a fragment thereof, comprising one or more CDRs, e.g., 1 CDR, 2 CDRs, or 3 CDRs, selected from the group consisting of a heavy chain CDR1 having the amino acid sequence of SEQ ID NO: 7, SEQ ID NO: 14, or SEQ ID NO: 21; a heavy chain CDR2 having the amino acid sequence of SEQ ID NO: 8, SEQ ID NO: 15, or SEQ ID NO: 22; and a heavy chain CDR3 having the amino acid sequence of SEQ ID NO: 9; SEQ ID NO: 16, or SEQ ID NO: 22; an anti-DEspR antibody comprising a light chain or a fragment thereof, comprising one or more CDRs, e.g., 1 CDR, 2 CDRs, or 3 CDRs selected from the group consisting of a light chain CDR1 having the amino acid sequence of SEQ ID NO: 28, SEQ ID NO: 35, SEQ ID NO: 42, or SEQ ID NO: 51; a light chain CDR2 having the amino acid sequence of SEQ ID NO: 29, SEQ ID NO: 36, SEQ ID NO: 43, or SEQ ID NO: 52; and a light chain CDR3 having the amino acid sequence of SEQ ID NO: 30, SEQ ID NO: 37, SEQ ID NO: 44, or SEQ ID NO: 53; an anti-DEspR humanized antibody comprising a variable heavy ($V_H$) chain amino acid sequence of SEQ ID NO: 55; an anti-DEspR humanized antibody comprising a variable light ($V_L$) chain amino acid sequence of SEQ ID NO: 57; an anti-DEspR humanized antibody comprising a variable light ($V_L$) chain amino acid sequence of SEQ ID NO: 59; an anti-DEspR humanized antibody comprising a variable heavy ($V_H$) chain IgG1 amino acid sequence of SEQ ID NO: 61; an anti-DEspR humanized antibody comprising a variable heavy ($V_H$) chain IgG4 amino acid sequence of SEQ ID NO: 63; or an anti-DEspR humanized antibody comprising a variable light ($V_L$) chain kappa amino acid sequence of SEQ ID NO: 65.

In some embodiments of the methods described herein, the methods can further comprise first selecting or diagnosing the subject having or at risk for a cancer or tumor. In some such embodiments, the diagnosis of the subject can comprise administering to the subject an anti-DEspR antibody or antigen-binding fragment thereof coupled to a label, for example, a radioactive label, or a label used for molecular imaging, as described elsewhere herein. In such embodiments, detection of the labeled anti-DEspR antibody or antigen-binding fragment is indicative of the subject having a cancer or tumor.

The terms "cancer" and "cancerous" refer to or describe the physiological condition in mammals that is typically characterized by unregulated cell growth. Accordingly, the terms "cancer" or "tumor" as used herein refers to an uncontrolled growth of cells which interferes with the normal functioning of the bodily organs and systems, including cancer stem cells and tumor vascular niches. A subject that has a cancer or a tumor is a subject having objectively measurable cancer cells present in the subject's body. Cancers which migrate from their original location and seed vital organs can eventually lead to the death of the subject through the functional deterioration of the affected organs. Hematopoietic cancers, such as leukemia, are able to outcompete the normal hematopoietic compartments in a subject, thereby leading to hematopoietic failure (in the form of anemia, thrombocytopenia and neutropenia) ultimately causing death.

By "metastasis" is meant the spread of cancer from its primary site to other places in the body. Cancer cells can break away from a primary tumor, penetrate into lymphatic and blood vessels, circulate through the bloodstream, and grow in a distant focus (metastasize) in normal tissues elsewhere in the body. Metastasis can be local or distant. Metastasis is a sequential process, contingent on tumor cells breaking off from the primary tumor, traveling through the bloodstream, and stopping at a distant site. At the new site, the cells establish a blood supply and can grow to form a life-threatening mass. Both stimulatory and inhibitory molecular pathways within the tumor cell regulate this behavior, and interactions between the tumor cell and host cells in the distant site are also significant.

Metastases are most often detected through the sole or combined use of magnetic resonance imaging (MRI) scans, computed tomography (CT) scans, blood and platelet counts, liver function studies, chest X-rays and bone scans in addition to the monitoring of specific symptoms.

Examples of cancer include but are not limited to, carcinoma, lymphoma, blastoma, sarcoma, and leukemia. More particular examples of such cancers include, but are not limited to, basal cell carcinoma, biliary tract cancer; bladder cancer; bone cancer; brain and CNS cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; glioblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

In other aspects, the methods described herein are used in the treatment or inhibition or imaging of artherosclerotic plaques and atherosclerosis. The process of atherosclerosis involves inflammation, and white blood cells (e.g., lymphocytes, monocytes, and macrophages) are often present throughout the development of atherosclerosis. Atherosclerosis begins when monocytes are activated and move out of the bloodstream into the wall of an artery. There, they are transformed into foam cells, which collect cholesterol and other fatty materials. In time, these fat-laden foam cells accumulate and form atheromas in the lining of the artery's wall, causing a thickening and hardening of the wall. Atheromas can be scattered throughout medium-sized and large arteries, but usually form where the arteries branch. Treatment of and diagnosis of atherosclerosis is important because it often leads to heart disease and can also cause stroke or other vascular problems such as claudication.

Accordingly, in some embodiments of the aspects described herein, pathological angiogenesis in atherosclerotic plaques and in the vasa vasorum of atherosclerotic arteries (coronary and carotid artery disease) is considered a risk and/or causal factor for vulnerable plaque progression and disruption. Thus, in some such embodiments, a subject having an angiogenic disorder to be treated using the compositions and methods described herein can have or be at risk for atherosclerosis. As used herein, "atherosclerosis" refers to a disease of the arterial blood vessels resulting in the hardening of arteries caused by the formation of multiple atheromatous plaques within the arteries. Atherosclerosis can be associated with other disease conditions, including but not limited to, coronary heart disease events, cerebrovascular events, acute coronary syndrome, and intermittent claudication. For example, atherosclerosis of the coronary arteries commonly causes coronary artery disease, myocardial infarction, coronary thrombosis, and angina pectoris. Atherosclerosis of the arteries supplying the central nervous system frequently provokes strokes and transient cerebral ischemia. In the peripheral circulation, atherosclerosis causes intermittent claudication and gangrene and can jeopardize limb viability. Atherosclerosis of an artery of the splanchnic circulation can cause mesenteric ischemia. Atherosclerosis can also affect the kidneys directly (e.g., renal artery stenosis). Also, persons who have previously experienced one or more non-fatal atherosclerotic disease events are those for whom the potential for recurrence of such an event exists.

Sometimes these other diseases can be caused by or associated with other than atherosclerosis. Therefore, in some embodiments, one first diagnoses that atherosclerosis is present prior to administering the compositions described herein to the subject. A subject is "diagnosed with atherosclerosis" or "selected as having atherosclerosis" if at least one of the markers of symptoms of atherosclerosis is present. In one such embodiment, the subject is "selected" if the person has a family history of atherosclerosis or carries a known genetic mutation or polymorphism for high cholesterol. In one embodiment, a subject is diagnosed by measuring an increase level of C-reactive protein (CRP) in the absence of other inflammatory disorders. In other embodiments, atherosclerosis is diagnosed by measuring serum levels of homocysteine, fibrinogen, lipoprotein (a), or small LDL particles. Alternatively a computed tomography scan, which measures calcium levels in the coronary arteries, can be used to select a subject having atherosclerosis. In one embodiment, atherosclerosis is diagnosed by an increase in inflammatory cytokines. In one embodiment, increased interleukin-6 levels are used as an indicator to select an individual having atherosclerosis. In other embodiments, increased interleukin-8 and/or interleukin-17 level is used as an indicator to select an individual having atherosclerosis.

In other aspects, the compositions and methods described herein are used in blocking or inhibiting angiogenesis that occurs in age-related macular degeneration. It is known, for example, that VEGF contributes to abnormal blood vessel growth from the choroid layer of the eye into the retina, similar to what occurs during the wet or neovascular form of age-related macular degeneration. Macular degeneration, often called AMD or ARMD (age-related macular degeneration), is the leading cause of vision loss and blindness in Americans aged 65 and older. New blood vessels grow (neovascularization) beneath the retina and leak blood and fluid. This leakage causes permanent damage to light-sensitive retinal cells, which die off and create blind spots in central vision or the macula. Accordingly, encompassed in the methods disclosed herein are subjects treated for age-related macular degeneration with anti-angiogenic therapy.

In other aspects, the compositions and methods described herein are used in blocking or inhibiting angiogenesis that occurs in a subject having diabetic retinopathy, where abnormal blood vessel growth is associated with diabetic eye diseases and diabetic macular edema. When normal blood vessels in the retina are damaged by tiny blood clots due to diabetes, a chain reaction is ignited that culminates in new blood vessel growth. However, the backup blood vessels are faulty; they leak (causing edema), bleed and encourage scar tissue that detaches the retina, resulting in severe loss of vision. Such growth is the hallmark of diabetic retinopathy, the leading cause of blindness among young people in developed countries. Therefore, encompassed in the methods disclosed herein are subjects treated for diabetic retinopathy and/or diabetic macular edema.

In other aspects, the compositions and methods described herein are used in blocking or inhibiting angiogenesis that occurs in a subject having rheumatoid arthritis. Rheumatoid arthritis (RA) is characterized by synovial tissue swelling, leukocyte ingress and angiogenesis, or new blood vessel growth. The expansion of the synovial lining of joints in rheumatoid arthritis (RA) and the subsequent invasion by the pannus of underlying cartilage and bone necessitate an increase in the vascular supply to the synovium, to cope with the increased requirement for oxygen and nutrients. Angiogenesis is now recognized as a key event in the formation and maintenance of the pannus in RA (Paleolog, E. M., Arthritis Res. 2002; 4 Suppl 3:S81-90; Afuwape A O, Histol Histopathol. 2002; 17(3):961-72). Even in early RA, some of the earliest histological observations are blood vessels. A mononuclear infiltrate characterizes the synovial tissue along with a luxuriant vasculature. Angiogenesis is integral to formation of the inflammatory pannus and without angiogenesis, leukocyte ingress could not occur (Koch, A. E., Ann. Rheum. Dis. 2000, 59 Suppl 1:i65-71). Disruption of the formation of new blood vessels would not only prevent delivery of nutrients to the inflammatory site, it could also reduce joint swelling due to the additional activity of VEGF, a potent proangiogenic factor in RA, as a vascular permeability factor. Anti-VEGF hexapeptide RRKRRR (dRK6) can suppress and mitigate the arthritis severity (Seung-Ah Yoo, et. al., 2005, supra). Accordingly, encompassed in the methods disclosed herein are subjects having or being treated for rheumatoid arthritis.

In other aspects, the compositions and methods described herein are used in blocking or inhibiting angiogenesis that occurs in Alzheimer's disease. Alzheimer's disease (AD) is the most common cause of dementia worldwide. AD is characterized by an excessive cerebral amyloid deposition leading to degeneration of neurons and eventually to dementia. The exact cause of AD is still unknown. It has been shown by epidemiological studies that long-term use of non-steroidal anti-inflammatory drugs, statins, histamine H2-receptor blockers, or calcium-channel blockers, all of which are cardiovascular drugs having anti-angiogenic effects, seem to prevent Alzheimer's disease and/or influence the outcome of AD patients. Therefore, AD angiogenesis in the brain vasculature can play an important role in AD. In Alzheimer's disease, the brain endothelium secretes the precursor substrate for the beta-amyloid plaque and a neurotoxic peptide that selectively kills cortical neurons.

Moreover, amyloid deposition in the vasculature leads to endothelial cell apoptosis and endothelial cell activation which leads to neovascularization. Vessel formation could be blocked by the VEGF antagonist SU 4312 as well as by statins, indicating that anti-angiogenesis strategies can interfere with endothelial cell activation in AD (Schultheiss C., el. al., 2006; Grammas P., et. al., 1999) and can be used for preventing and/or treating AD. Accordingly, encompassed in the methods disclosed herein are subjects being treated for Alzheimer's disease.

In other aspects, the compositions and methods described herein are used in blocking or inhibiting angiogenesis that occurs in ischemic regions in the brain, which can contribute to edema, leaky neovessels, and predispose a subject to hemorrhagic transformation after an ischemic stroke event, thus worsening the morbidity and mortality risk from the stroke event. Inhibition of leaky angiogenic neovessels using the compositions and methods described herein can reduce neurologic deficits from an ischemic stroke event, as well as prevent the progression to hemorrhagic stroke. Currently, there is no therapy for ischemic hemorrhagic transformation nor effective therapies to reduce the neurologic deficits from stroke.

In other aspects, the compositions and methods described herein are used in blocking or inhibiting angiogenesis that occurs in obesity. Adipogenesis in obesity involves interplay between differentiating adipocytes, stromal cells, and blood vessels. Close spatial and temporal interrelationships between blood vessel formation and adipogenesis, and the sprouting of new blood vessels from preexisting vasculature was coupled to adipocyte differentiation. Adipogenic/angiogenic cell clusters can morphologically and immunohistochemically be distinguished from crown-like structures frequently seen in the late stages of adipose tissue obesity. Administration of anti-vascular endothelial growth factor (VEGF) antibodies inhibited not only angiogenesis but also the formation of adipogenic/angiogenic cell clusters, indicating that the coupling of adipogenesis and angiogenesis is essential for differentiation of adipocytes in obesity and that VEGF is a key mediator of that process. (Satoshi Nishimura et. al., 2007, Diabetes 56:1517-1526). It has been shown that the angiogenesis inhibitor, TNP-470 was able to prevent diet-induced and genetic obesity in mice (Ebba Bräkenhielm et. al., Circulation Research, 2004; 94:1579). TNP-470 reduced vascularity in the adipose tissue, thereby inhibiting the rate of growth of the adipose tissue and obesity development. Accordingly, encompassed in the methods disclosed herein are subjects suffering from obesity.

In other aspects, the compositions and methods described herein are used in blocking or inhibiting angiogenesis that occurs in endometriosis. Excessive endometrial angiogenesis is proposed as an important mechanism in the pathogenesis of endometriosis (Healy, D L., et. al., Hum Reprod Update. 1998 September-October; 4(5):736-40). The endometrium of patients with endometriosis shows enhanced endothelial cell proliferation. Moreover there is an elevated expression of the cell adhesion molecule integrin vß3 in more blood vessels in the endometrium of women with endometriosis when compared with normal women. The U.S. Pat. No. 6,121,230 described the use of anti-VEGF agents in the treatment of endometriosis and is Patent is incorporated hereby reference. Accordingly, encompassed in the methods disclosed herein are subjects having or being treated for endometriosis.

As described herein, any of a variety of tissues, or organs comprised of organized tissues, can support angiogenesis in disease conditions including skin, muscle, gut, connective tissue, joints, bones and the like tissue in which blood vessels can invade upon angiogenic stimuli.

The individual or subject to be treated as described herein in various embodiments is desirably a human patient, although it is to be understood that the methods are effective with respect to all mammals, which are intended to be included in the term "patient" or "subject". In this context, a mammal is understood to include any mammalian species in which treatment of diseases associated with angiogenesis is desirable. The terms "subject" and "individual" are used interchangeably herein, and refer to an animal, for example a human, recipient of the DEspR-specific antibodies and antigen-binding fragments described herein. For treatment of disease states which are specific for a specific animal such as a human subject, the term "subject" refers to that specific animal. The terms "non-human animals" and "non-human mammals" are used interchangeably herein, and include mammals such as rats, mice, rabbits, sheep, cats, dogs, cows, pigs, and non-human primates. The term "subject" also encompasses any vertebrate including but not limited to mammals, reptiles, amphibians and fish. However, advantageously, the subject is a mammal such as a human, or other mammals such as a domesticated mammal, e.g. dog, cat, horse, and the like, or production mammal, e.g. cow, sheep, pig, and the like are also encompassed in the term subject.

The DEspR-specific antagonist agents, such as anti-DEspR antibodies or antigen-binding fragments thereof, described herein can be administered to a subject in need thereof by any appropriate route which results in an effective treatment in the subject. As used herein, the terms "administering," and "introducing" are used interchangeably and refer to the placement of an anti-DEspR antibody or antigen-binding fragment thereof into a subject by a method or route which results in at least partial localization of such agents at a desired site, such as a site of inflammation or cancer, such that a desired effect(s) is produced.

In some embodiments, the anti-DEspR antibody or antigen-binding fragment thereof is administered to a subject having an angiogenic disorder to be inhibited by any mode of administration that delivers the agent systemically or to a desired surface or target, and can include, but is not limited to, injection, infusion, instillation, and inhalation administration. To the extent that anti-DEspR antibodies or antigen-binding fragments thereof can be protected from inactivation in the gut, oral administration forms are also contemplated. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments, the anti-DEspR antibodies or anti-gen-binding fragments thereof for use in the methods described herein are administered by intravenous infusion or injection.

The phrases "parenteral administration" and "administered parenterally" as used herein, refer to modes of administration other than enteral and topical administration, usually by injection. The phrases "systemic administration," "administered systemically", "peripheral administration" and "administered peripherally" as used herein refer to the administration of the bispecific or multispecific polypeptide agent other than directly into a target site, tissue, or organ, such as a tumor site, such that it enters the subject's circulatory system and, thus, is subject to metabolism and other like processes.

The anti-DEspR antibodies or antigen-binding fragments thereof described herein are administered to a subject, e.g., a human subject, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. In some embodiments of the methods described herein, local administration, for example, to a tumor or cancer site where angiogenesis is occurring, can be used to increase effectiveness of the anti-DEspR antibody or antigen-binding fragment thereof and/or to help reduce side effects or toxicity.

In some embodiments, the anti-DEspR antibody or antigen-binding fragment thereof is administered by any suitable means, including parenteral, subcutaneous, intraperitoneal, intrapulmonary, and intranasal, and, if desired for local immunosuppressive treatment, intralesional administration. Parenteral infusions include intramuscular, intravenous, intraarterial, intraperitoneal, or subcutaneous administration. In some embodiments, the antibody or antigen-binding fragment thereof is suitably administered by pulse infusion, particularly with declining doses of the antibody. Preferably the dosing is given by injections, most preferably intravenous or subcutaneous injections, depending in part on whether the administration is brief or chronic.

In some embodiments, the anti-DEspR antibody or antigen-binding fragment thereof is administered locally, e.g., by direct injections, when the disorder or location of the tumor permits, and the injections can be repeated periodically. The DEspR-specific antagonist can also be delivered systemically to the subject or directly to the tumor cells, e.g., to a tumor or a tumor bed following surgical excision of the tumor, in order to prevent or reduce local recurrence or metastasis, for example of a dormant tumor or micrometastases.

Antibody-targeted sonoporation methods are contemplated for use in some embodiments of the methods for inhibiting angiogenesis described herein, in order to enhance the efficacy and potency of the therapeutic compositions comprising anti-DEspR antibodies and antigen-binding fragments thereof provided herein. Accordingly, in some embodiments of the methods of inhibiting angiogenesis described herein, anti-DEspR antibodies and antigen-binding fragments thereof are administered to a subject in need thereof by sonoporation.

As used herein, "sonoporation" refers to the use of sound, preferably at ultrasonic frequencies, or the interaction of ultrasound with contrast agents (e.g., stabilized microbubbles) for temporarily modifying the permeability of cell plasma membranes, thus allowing uptake of large molecules, such as therapeutic agents. The membrane permeability caused by the sonoporation is transient, leaving the agents trapped inside the cell after the ultrasound exposure. Sonoporation employs acoustic cavitation of microbubbles to enhance delivery of large molecules.

Accordingly, in some embodiments of the methods, the anti-DEspR antibodies and antigen-binding fragments thereof described herein, mixed with ultrasound contrast agents, such as microbubbles, can be injected locally or systemically into a subject in need of treatment for an angiogenic disorder, and ultrasound can be coupled and even focused into the defined area, e.g., tumor site, to achieve targeted delivery of the anti-DEspR antibodies and antigen-binding fragments thereof described herein. In addition to the operator-determined focused ultrasound, anti-DEspR targeting of a microbubble can be used to target the sonoporation-mediated enhanced entry of any therapeutic agent, including antiDEspR monoclonal antibody per se, into said targeted cancerous areas.

In some embodiments, the methods use focused ultrasound methods to achieve targeted delivery of the anti-DEspR antibodies and antigen-binding fragments thereof described herein. As used herein, HIFU or "High Intensity Focused Ultrasound" refers to a non-invasive therapeutic method using high-intensity ultrasound to heat and destroy malignant or pathogenic tissue without causing damage to overlying or surrounding health tissue. Typically, HIFU has been used in tissue ablation techniques, whereby the biological effects of HIFU treatment, including coagulative necrosis and structural disruption, can be induced in a tissue requiring ablation, such as a solid tumor site. However, as described in Khaibullina A. et al., J Nucl Med. 2008 February; 49(2):295-302, and WO2010127369, the contents of which are herein incorporated in their entireties by reference, HIFU can also be used as a means of delivery of therapeutic agents, such as antibodies or antigen-binding fragments thereof.

Methods using contrast-enhanced ultrasound (CEUS) are also contemplated for use with anti-DEspR inhibiting agents described herein. Contrast-enhanced ultrasound (CEUS) refers to the application of ultrasound contrast medium and ultrasound contrast agents to traditional medical sonography. Ultrasound contrast agents refer to agents that rely on the different ways in which sound waves are reflected from interfaces between substances. This can be the surface of a small air bubble or a more complex structure. Commercially available contrast media include gas-filled microbubbles that are administered intravenously to the systemic circulation. Microbubbles have a high degree of echogenicity, i.e., the ability of an object to reflect the ultrasound waves. The echogenicity difference between the gas in the microbubbles and the soft tissue surroundings of the body is immense, and enhances the ultrasound backscatter, or reflection of the ultrasound waves, to produce a unique sonogram with increased contrast due to the high echogenicity difference. Contrast-enhanced ultrasound can be used with the compositions and methods described herein to image a variety of conditions and disorders, such as angiogenesis dependent disorders, as described herein A variety of microbubble contrast agents are available for use with the compositions and methods described herein. Microbubbles can differ in their shell makeup, gas core makeup, and whether or not they are targeted.

The microbubble shell material determines how easily the microbubble is taken up by the immune system. A more hydrophilic shell material tends to be taken up more easily, which reduces the microbubble residence time in the circulation. This reduces the time available for contrast imaging. The shell material also affects microbubble mechanical elasticity. The more elastic the material, the more acoustic energy it can withstand before bursting. Example of materials used in current microbubble shells include albumin, galactose, lipid, and polymers, as described in Lindner, J. R. 2004. Microbubbles in medical imaging: current applications and future directions. Nat Rev Drug Discov. 3: 527-32, the contents of which are herein incorporated by reference in their entireties.

The microbubble gas core is an important part of the ultrasound contrast microbubble because it determines the echogenicity. When gas bubbles are caught in an ultrasonic frequency field, they compress, oscillate, and reflect a characteristic echo—this generates the strong and unique sonogram in contrast-enhanced ultrasound. Gas cores can be composed of, for example, air, or heavy gases like perfluorocarbon, or nitrogen. Heavy gases are less water-soluble so they are less likely to leak out from the microbubble to impair echogenicity. Therefore, microbubbles with heavy gas cores are likely to last longer in circulation.

Regardless of the shell or gas core composition, microbubble size are typically fairly uniform. They can lie within in a range of 1-4 micrometres in diameter. That makes them smaller than red blood cells, which allows them to flow easily through the circulation as well as the microcirculation.

Targeting ligands that bind to receptors characteristic of angiogenic disorders, such as DEspR, can be conjugated to microbubbles, enabling the microbubble complex to accumulate selectively in areas of interest, such as diseased or abnormal tissues. This form of molecular imaging, known as targeted contrast-enhanced ultrasound, will only generate a strong ultrasound signal if targeted microbubbles bind in the area of interest. Targeted contrast-enhanced ultrasound has many applications in both medical diagnostics and medical therapeutics. Microbubbles targeted with an anti-DEspR antibody or antigen-binding fragment thereof are injected systemically in a small bolus. These DEspR-targeted microbubbles can travel through the circulatory system, eventually finding their respective targets and binding specifically. Ultrasound waves can then be directed on the area of interest. If a sufficient number of DEspR-targeted microbubbles have bound in the area, their compressible gas cores oscillate in response to the high frequency sonic energy field. The DEspR-targeted microbubbles also reflect a unique echo that is in stark contrast to the surrounding tissue due to the orders of magnitude mismatch between microbubble and tissue echogenicity. The ultrasound system converts the strong echogenicity into a contrast-enhanced image of the area of interest, revealing the location of the bound DEspR-targeted microbubbles. Detection of bound microbubbles can then show that the area of interest is expressing DEspR, which can be indicative of a certain disease state, or identify particular cells in the area of interest. In addition, targeted sonoporation can be done at the site where DEspR-targeted microbubbles are attached, thus achieving targeted delivery of any therapeutic agent (drug, siRNA, DNA, small molecule) encapsulated in or carried on the echogenic microbubble.

Accordingly, in some embodiments of the methods described herein, an anti-DEspR antibody or antigen-binding fragment thereof, such as a chimeric, humanized, deimmunized, or composite human anti-DEspR antibody derived from the 6G8G7 or variant 7C5B2 antibody; an anti-DEspR antibody comprising one or more heavy chain CDR regions comprising a sequence selected from the group consisting of SEQ ID NO: 7, SEQ ID NO: 8, SEQ ID NO: 9, SEQ ID NO: 14, SEQ ID NO: 15, SEQ ID NO: 16, SEQ ID NO: 21, SEQ ID NO: 22, and SEQ ID NO: 23; an anti-DEspR antibody comprising one or more light chain CDR regions comprises a sequence selected from the group consisting of SEQ ID NO: 28, SEQ ID NO: 29, SEQ ID NO: 30, SEQ ID NO: 35, SEQ ID NO: 36, SEQ ID NO: 37, SEQ ID NO: 42, SEQ ID NO: 43, SEQ ID NO: 44, SEQ ID NO: 51, SEQ ID NO: 52, and SEQ ID NO: 53; an anti-DEspR composite human antibody comprising a variable heavy ($V_H$) chain amino acid sequence of SEQ ID NO: 6, SEQ ID NO: 13, or SEQ ID NO: 20; an anti-DEspR composite human antibody comprising a variable light ($V_L$) chain amino acid sequence of SEQ ID NO: 27, SEQ ID NO: 34, SEQ ID NO: 41, or SEQ ID NO: 50; an anti-DEspR antibody comprising one or more CDRs, e.g. 1 CDR, 2 CDRs, 3 CDRs, 4 CDRs, 5 CDRs, or 6 CDRs, selected from the group consisting of (a) a heavy chain CDR1 having the amino acid sequence of SEQ ID NO: 7, SEQ ID NO: 14, or SEQ ID NO: 21; (b) a heavy chain CDR2 having the amino acid sequence of SEQ ID NO: 8, SEQ ID NO: 15, or SEQ ID NO: 22; (c) a heavy chain CDR3 having the amino acid sequence of SEQ ID NO: 9; SEQ ID NO: 16, or SEQ ID NO: 23; (d) a light chain CDR1 having the amino acid sequence of SEQ ID NO: 28, SEQ ID NO: 35, SEQ ID NO: 42, or SEQ ID NO: 51; (e) a light chain CDR2 having the amino acid sequence of SEQ ID NO: 29, SEQ ID NO: 36, SEQ ID NO: 43, or SEQ ID NO: 52; and (f) a light chain CDR3 having the amino acid sequence of SEQ ID NO: 30, SEQ ID NO: 37, SEQ ID NO: 44, or SEQ ID NO: 53; an anti-DEspR antibody comprising a heavy chain or a fragment thereof, comprising one or more CDRs, e.g., 1 CDR, 2 CDRs, or 3 CDRs, selected from the group consisting of a heavy chain CDR1 having the amino acid sequence of SEQ ID NO: 7, SEQ ID NO: 14, or SEQ ID NO: 21; a heavy chain CDR2 having the amino acid sequence of SEQ ID NO: 8, SEQ ID NO: 15, or SEQ ID NO: 22; and a heavy chain CDR3 having the amino acid sequence of SEQ ID NO: 9; SEQ ID NO: 16, or SEQ ID NO: 22; an anti-DEspR antibody comprising a light chain or a fragment thereof, comprising one or more CDRs, e.g., 1 CDR, 2 CDRs, or 3 CDRs selected from the group consisting of a light chain CDR1 having the amino acid sequence of SEQ ID NO: 28, SEQ ID NO: 35, SEQ ID NO: 42, or SEQ ID NO: 51; a light chain CDR2 having the amino acid sequence of SEQ ID NO: 29, SEQ ID NO: 36, SEQ ID NO: 43, or SEQ ID NO: 52; and a light chain CDR3 having the amino acid sequence of SEQ ID NO: 30, SEQ ID NO: 37, SEQ ID NO: 44, or SEQ ID NO: 53; an anti-DEspR humanized antibody comprising a variable heavy ($V_H$) chain amino acid sequence of SEQ ID NO: 55; an anti-DEspR humanized antibody comprising a variable light ($V_L$) chain amino acid sequence of SEQ ID NO: 57; an anti-DEspR humanized antibody comprising a variable light ($V_L$) chain amino acid sequence of SEQ ID NO: 59; an anti-DEspR humanized antibody comprising a variable heavy ($V_H$) chain IgG1 amino acid sequence of SEQ ID NO: 61; an anti-DEspR humanized antibody comprising a variable heavy ($V_H$) chain IgG4 amino acid sequence of SEQ ID NO: 63; or an anti-DEspR humanized antibody comprising a variable light ($V_L$) chain kappa amino acid sequence of SEQ ID NO: 65, is administered to a subject in need of treatment for an angiogenic disorder, such as for example, cancer, using a targeted ultrasound delivery. In some such embodiments, the targeted ultrasound delivery comprises using microbubbles as contrast agents to which an anti-DEspR antibody or antigen-binding fragment thereof. In some such embodiments, the targeted ultrasound is HIFU.

For the clinical use of the methods described herein, administration of the anti-DEspR antibodies or antigen-binding fragments thereof described herein, can include formulation into pharmaceutical compositions or pharmaceutical formulations for parenteral administration, e.g., intravenous; mucosal, e.g., intranasal; ocular, or other mode of administration. In some embodiments, the anti-DEspR antibodies or antigen-binding fragments thereof described herein can be administered along with any pharmaceutically acceptable carrier compound, material, or composition which results in an effective treatment in the subject. Thus, a pharmaceutical formulation for use in the methods described herein can contain an anti-DEspR antibody or antigen-binding fragment thereof as described herein in combination with one or more pharmaceutically acceptable ingredients.

The phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" as used herein means a pharmaceutically acceptable material, composition or vehicle, such as a liquid or solid filler, diluent, excipient, solvent, media, encapsulating material, manufacturing aid (e.g., lubricant, talc magnesium, calcium or zinc stearate, or steric acid), or solvent encapsulating material, involved in maintaining the stability, solubility, or activity of, an anti-DEspR antibody or antigen-binding fragment thereof. Each carrier must be "acceptable" in the sense of being compatible with the other ingredients of the formulation and not injurious to the patient. The terms "excipient", "carrier", "pharmaceutically acceptable carrier" or the like are used interchangeably herein.

The anti-DEspR antibodies or antigen-binding fragments thereof described herein can be specially formulated for administration of the compound to a subject in solid, liquid or gel form, including those adapted for the following: (1) parenteral administration, for example, by subcutaneous, intramuscular, intravenous or epidural injection as, for example, a sterile solution or suspension, or sustained-release formulation; (2) topical application, for example, as a cream, ointment, or a controlled-release patch or spray applied to the skin; (3) intravaginally or intrarectally, for example, as a pessary, cream or foam; (4) ocularly; (5) transdermally; (6) transmucosally; or (79) nasally. Additionally, an anti-DEspR antibody or antigen-binding fragment thereof can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 35 3,270,960.

Therapeutic formulations of the anti-DEspR antibodies or antigen-binding fragments thereof described herein can be prepared for storage by mixing the anti-DEspR antibodies or antigen-binding fragments having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Exemplary lyophilized anti-VEGF antibody formulations are described in WO 97/04801, expressly incorporated herein be reference.

Optionally, but preferably, the formulations comprising the compositions described herein contain a pharmaceutically acceptable salt, typically, e.g., sodium chloride, and preferably at about physiological concentrations. Optionally, the formulations of the invention can contain a pharmaceutically acceptable preservative. In some embodiments the preservative concentration ranges from 0.1 to 2.0%, typically v/v. Suitable preservatives include those known in the pharmaceutical arts. Benzyl alcohol, phenol, m-cresol, methylparaben, and propylparaben are examples of preservatives. Optionally, the formulations of the invention can include a pharmaceutically acceptable surfactant at a concentration of 0.005 to 0.02%.

The therapeutic formulations of the compositions comprising anti-DEspR antibodies and antigen-binding fragments thereof described herein can also contain more than one active compound as necessary for the particular indication being treated, preferably those with complementary activities that do not adversely affect each other. For example, in some embodiments, it can be desirable to further provide antibodies which bind to EGFR, VEGF (e.g. an antibody which binds a different epitope on VEGF), VEGFR, or ErbB2 (e.g., Herceptin™). Alternatively, or in addition, the composition can comprise a cytotoxic agent, cytokine, growth inhibitory agent, and/or VEGFR antagonist. Such molecules are suitably present in combination in amounts that are effective for the purpose intended.

The active ingredients of the therapeutic formulations of the compositions comprising the anti-DEspR antibodies or antigen-binding fragments described herein can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

In some embodiments, sustained-release preparations can be used. Suitable examples of sustained-release preparations include semipermeable matrices of solid hydrophobic polymers containing the anti-DEspR antibodies or antigen-binding fragments in which the matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they can denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization can be achieved by modifying sulfhydryl residues, lyophilizing from acidic solutions, controlling moisture content, using appropriate additives, and developing specific polymer matrix compositions.

The therapeutic formulations to be used for in vivo administration, such as parenteral administration, in the methods described herein can be sterile, which is readily accomplished by filtration through sterile filtration membranes, or other methods known to those of skill in the art.

The anti-DEspR antibodies and antigen-binding fragments thereof, are formulated, dosed, and administered in a fashion consistent with good medical practice. Factors for consideration in this context include the particular disorder being treated, the particular subject being treated, the clinical condition of the individual subject, the cause of the disorder, the site of delivery of the agent, the method of administration, the scheduling of administration, and other factors known to medical practitioners. The "therapeutically effective amount" of the anti-DEspR antibodies and antigen-binding fragments thereof to be administered will be governed by such considerations, and refers to the minimum amount necessary to ameliorate, treat, or stabilize, the cancer; to increase the time until progression (duration of progression free survival) or to treat or prevent the occurrence or recurrence of a tumor, a dormant tumor, or a micrometastases. The anti-DEspR antibodies and antigen-binding fragments thereof are optionally formulated with one or more additional therapeutic agents currently used to prevent or treat cancer or a risk of developing a cancer. The effective amount of such other agents depends on the amount of anti-DEspR antibodies and antigen-binding fragments thereof present in the formulation, the type of disorder or treatment, and other factors discussed above. These are generally used in the same dosages and with administration routes as used herein before or about from 1 to 99% of the heretofore employed dosages.

The dosage ranges for the agent depend upon the potency, and encompass amounts large enough to produce the desired effect e.g., slowing of tumor growth or a reduction in tumor size. The dosage should not be so large as to cause unacceptable adverse side effects. Generally, the dosage will vary with the age, condition, and sex of the patient and can be determined by one of skill in the art. The dosage can also be adjusted by the individual physician in the event of any complication. In some embodiments, the dosage ranges from 0.001 mg/kg body weight to 100 mg/kg body weight. In some embodiments, the dose range is from 5 µg/kg body weight to 100 µg/kg body weight. Alternatively, the dose range can be titrated to maintain serum levels between 1 µg/mL and 1000 µg/mL. For systemic administration, subjects can be administered a therapeutic amount, such as, e.g., 0.1 mg/kg, 0.5 mg/kg, 1.0 mg/kg, 2.0 mg/kg, 2.5 mg/kg, 5 mg/kg, 7.5 mg/kg, 10 mg/kg, 15 mg/kg, 20 mg/kg, 25 mg/kg, 30 mg/kg, 40 mg/kg, 50 mg/kg, or more. These doses can be administered by one or more separate administrations, or by continuous infusion. For repeated administrations over several days or longer, depending on the condition, the treatment is sustained until, for example, the cancer is treated, as measured by the methods described above or known in the art. However, other dosage regimens can be useful.

In some embodiments, the anti-DEspR antibody or antigen-binding fragment thereof is administered once every week, every two weeks, or every three weeks, at a dose range from about 2 mg/kg to about 15 mg/kg, including, but not limited to 5 mg/kg, 7.5 mg/kg, 10 mg/kg or 15 mg/kg. The progress of using the methods described herein can be easily monitored by conventional techniques and assays. In some embodiments the dose can be administered about weekly. In some embodiments, the dose can be administered weekly. In some embodiments, the dose can be administered weekly for from about 12 weeks to about 18 weeks. In some embodiments the dose can be administered about every 2 weeks. In some embodiments the dose can be administered about every 3 weeks. In some embodiments, the dose can be from about 2 mg/kg to about 15 mg/kg administered about every 2 weeks. In some embodiments, the dose can be from about 2 mg/kg to about 15 mg/kg administered about every 3 weeks. In some embodiments, the dose can be from about 2 mg/kg to about 15 mg/kg administered intravenously about every 2 weeks. In some embodiments, the dose can be from about 2 mg/kg to about 15 mg/kg administered intravenously about every 3 weeks. In some embodiments, a total of from about 2 to about 10 doses are administered. In some embodiments, a total of 4 doses are administered. In some embodiments, a total of 5 doses are administered. In some embodiments, a total of 6 doses are administered. In some embodiments, a total of 7 doses are administered. In some embodiments, a total of 8 doses are administered. In some embodiments, the administration occurs for a total of from about 4 weeks to about 12 weeks. In some embodiments, the administration occurs for a total of about 6 weeks. In some embodiments, the administration occurs for a total of about 8 weeks. In some embodiments, the administration occurs for a total of about 12 weeks. In some embodiments, the initial dose can be from about 1.5 to about 2.5 fold greater than subsequent doses.

The duration of a therapy using the methods described herein will continue for as long as medically indicated or until a desired therapeutic effect (e.g., those described herein) is achieved. In certain embodiments, the administration of the DEspR-specific antibody or antigen-binding fragment described herein is continued for 1 month, 2 months, 4 months, 6 months, 8 months, 10 months, 1 year, 2 years, 3 years, 4 years, 5 years, 10 years, 20 years, or for a period of years up to the lifetime of the subject.

The efficacy of the treatment methods for cancer comprising therapeutic formulations of the compositions comprising anti-DEspR antibodies or antigen-binding fragments thereof described herein can be measured by various endpoints commonly used in evaluating cancer treatments, including but not limited to, tumor regression, tumor weight or size shrinkage, time to progression, duration of survival, progression free survival, overall response rate, duration of response, and quality of life. Because the anti-DEspR antibodies and antigen-binding fragments thereof described herein target the tumor vasculature, cancer cells, and some cancer stem cell subsets, they represent a unique class of multi-targeting anticancer drugs, and therefore can require unique measures and definitions of clinical responses to drugs. For example, tumor shrinkage of greater than 50% in a 2-dimensional analysis is the standard cut-off for declaring a response. However, the anti-DEspR-antibodies or antigen-binding fragments thereof described herein can cause inhibition of metastatic spread without shrinkage of the primary tumor, or can simply exert a tumoristatic effect. Accordingly, novel approaches to determining efficacy of an anti-angiogenic therapy should be employed, including for example, measurement of plasma or urinary markers of angiogenesis, and measurement of response through molecular imaging, using, for example, an DEspR-antibody or antigen-binding fragment conjugated to a label, such as a microbubble. In the case of cancers, the therapeutically effective amount of the DEspR-antibody or antigen-binding fragment thereof can reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the DEspR-antibody or antigen-binding fragment thereof can prevent growth and/or kill existing cancer cells, it can be cytostatic and/or cytotoxic. For cancer therapy, efficacy in vivo can, for example, be measured by assessing the duration of survival, duration of progression free survival (PFS), the response rates (RR), duration of response, and/or quality of life.

In other embodiments, described herein are methods for increasing progression free survival of a human subject susceptible to or diagnosed with a cancer. Time to disease progression is defined as the time from administration of the drug until disease progression or death. In a preferred embodiment, the combination treatment using an anti-DEspR antibody or antigen-binding fragment thereof, and one or more chemotherapeutic agents significantly increases progression free survival by at least about 1 month, 1.2 months, 2 months, 2.4 months, 2.9 months, 3.5 months, preferably by about 1 to about 5 months, when compared to a treatment with chemotherapy alone. In another embodiment, the methods described herein significantly increase response rates in a group of human subjects susceptible to or diagnosed with a cancer who are treated with various therapeutics. Response rate is defined as the percentage of treated subjects who responded to the treatment. In one embodiment, the combination treatment described herein using a DEspR-specific antagonist, such as an anti-DEspR antibody or antigen-binding fragment thereof, and one or more chemotherapeutic agents significantly increases response rate in the treated subject group compared to the group treated with chemotherapy alone.

As used herein, the terms "treat," "treatment," "treating," or "amelioration" refer to therapeutic treatments, wherein the object is to reverse, alleviate, ameliorate, inhibit, slow down or stop the progression or severity of a condition associated with, a disease or disorder. The term "treating" includes reducing or alleviating at least one adverse effect or symptom of a condition, disease or disorder associated with a chronic immune condition, such as, but not limited to, a chronic infection or a cancer. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of at least slowing of progress or worsening of symptoms that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. The term "treatment" of a disease also includes providing relief from the symptoms or side-effects of the disease (including palliative treatment).

For example, in some embodiments, the methods described herein comprise administering an effective amount of the anti-DEspR antibodies or antigen-binding fragments thereof described herein to a subject in order to alleviate a symptom of a cancer, or other such disorder characterized by excess or unwanted angiogenesis. As used herein, "alleviating a symptom of a cancer" is ameliorating or reducing any condition or symptom associated with the cancer. As compared with an equivalent untreated control, such reduction or degree of prevention is at least 5%, 10%, 20%, 40%, 50%, 60%, 80%, 90%, 95%, or 100% as measured by any standard technique. Ideally, the cancer is completely cleared as detected by any standard method known in the art, in which case the cancer is considered to have been treated. A patient who is being treated for a cancer is one who a medical practitioner has diagnosed as having such a condition. Diagnosis can be by any suitable means. Diagnosis and monitoring can involve, for example, detecting the level of cancer cells in a biological sample (for example, a tissue or lymph node biopsy, blood test, or urine test), detecting the level of a surrogate marker of the cancer in a biological sample, detecting symptoms associated with the specific cancer, or detecting immune cells involved in the immune response typical of such a cancer.

The term "effective amount" as used herein refers to the amount of an anti-DEspR antibody or antigen-binding fragment thereof needed to alleviate at least one or more symptom of the disease or disorder, and relates to a sufficient amount of pharmacological composition to provide the desired effect, i.e., inhibit the formation of new blood vessels. The term "therapeutically effective amount" therefore refers to an amount of an anti-DEspR antibody or antigen-binding fragment thereof using the methods as disclosed herein, that is sufficient to effect a particular effect when administered to a typical subject. An effective amount as used herein would also include an amount sufficient to delay the development of a symptom of the disease, alter the course of a symptom disease (for example but not limited to, slow the progression of a symptom of the disease), or reverse a symptom of the disease. Thus, it is not possible to specify the exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dosage can vary depending upon the dosage form employed and the route of administration utilized. The dose ratio between toxic and therapeutic effects is the therapeutic index and can be expressed as the ratio $LD_{50}/ED_{50}$. Compositions and methods that exhibit large therapeutic indices are preferred. A therapeutically effective dose can be estimated initially from cell culture assays. Also, a dose can be formulated in animal models to achieve a circulating plasma concentration range that includes the $IC_{50}$ (i.e., the concentration of the anti-DEspR antibody or antigen-binding fragment thereof), which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay. The dosage can be determined by a physician and adjusted, as necessary, to suit observed effects of the treatment.

In other embodiments, the methods provided for inhibiting angiogenesis in a tissue of a subject or individual having a disease or disorder dependent or modulated by angiogenesis by administering to the subject a therapeutically effective amount of a composition comprising an angiogenesis-inhibiting amount of an anti-DEspR antibody or antigen-binding fragment thereof, can further comprise administration one or more additional treatments such as angiogenic inhibitors, chemotherapy, radiation, surgery, or other treatments known to those of skill in the art to inhibit angiogenesis.

In some embodiments, the methods described herein further comprise administration of a combination of an anti-DEspR antibody or antigen-binding fragment thereof, with one or more additional anti-cancer therapies. Examples of additional anti-cancer therapies include, without limitation, surgery, radiation therapy (radiotherapy), biotherapy, immunotherapy, chemotherapy, or a combination of these therapies. In addition, cytotoxic agents, anti-angiogenic and anti-proliferative agents, targeted therapies like Erlotinib or immunotherapy like OPDIVA®, can be used in combination with the anti-DEspR antibody or antigen-binding fragment thereof.

In certain aspects of any of the methods and uses, the invention provides treating cancer by administering effective amounts of an anti-DEspR antibody or antigen-binding fragment thereof and one or more chemotherapeutic agents to a subject susceptible to, or diagnosed with, locally recurrent or previously untreated cancer. A variety of chemotherapeutic agents can be used in the combined treatment methods and uses of the invention. An exemplary and non-limiting list of chemotherapeutic agents contemplated for use in the methods described herein is provided under "Definition," or described herein.

In some embodiments, the methods described herein comprise administration of an anti-DEspR antibody or antigen-binding fragment thereof with one or more chemotherapeutic agents (e.g., a cocktail) or any combination thereof. In some embodiments, the methods described herein comprise administration of an anti-DEspR antibody or antigen-binding fragment thereof with a chemotherapeutic agent(s) as an antibody drug conjugate. Examples of chemotherapeutic agents include alkylating agents, such as thiotepa and cyclophosphamide (CYTOXAN™); alkyl sulfonates such as busulfan, improsulfan and piposulfan; aziridines, such as benzodopa, carboquone, meturedopa, and uredopa; ethylenimines and methylamelamines including altretamine, triethylenemelamine, trietylenephosphoramide, triethylenethiophosphaoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics, such as the enediyne antibiotics (e.g. calicheamicin, especially calicheamicin .gamma1 and calicheamicin theta I, see, e.g., Angew Chem. Intl. Ed. Engl. 33:183-186 (1994); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin; chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, nitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites, such as methotrexate and 5-fluorouracil (5-FU); folic acid analogues, such as denopterin, methotrexate, pteropterin, trimetrexate; purine analogs, such as fludarabine, 6-mercaptopurine, thiamiprine, thioguanine; pyrimidine analogs such as, ancitabine, azacitidine, 6-azauridine, carmofur, cytarabine, dideoxyuridine, doxifluridine, enocitabine, floxuridine, 5-FU; androgens, such as calusterone, dromostanolone propionate, epitiostanol, mepitiostane, testolactone; anti-adrenals, such as aminoglutethimide, mitotane, trilostane; folic acid replenisher, such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidamine; maytansinoids, such as maytansine and ansamitocins; mitoguazone; mitoxantrone; mopidamol; nitracrine; pentostatin; phenamet; pirarubicin; podophyllinic acid; 2-ethylhydrazide; procarbazine; PSK®; razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL™, Bristol-Myers Squibb Oncology, Princeton, N.J.) and doxetaxel (TAXOTERE®, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid; capecitabine; and pharmaceutically acceptable salts, acids or derivatives of any of the above. Also included in this definition are anti-hormonal agents that act to regulate or inhibit hormone action on tumors, such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens, such as flutamide, nilutamide, bicalutamide, leuprolide, and goserelin; siRNA and pharmaceutically acceptable salts, acids or derivatives of any of the above. Other chemotherapeutic agents that can be used with the compositions and methods described herein are disclosed in US Publication No. 20080171040 or US Publication No. 20080305044 and are incorporated in their entirety by reference. In certain embodiments, the chemotherapeutic agent is for example, capecitabine, taxane, anthracycline, paclitaxel, docetaxel, paclitaxel protein-bound particles (e.g., ABRAXANE™), doxorubicin, epirubicin, 5-fluorouracil, cyclophosphamide or combinations thereof therapy. As used herein, combined administration includes simultaneous administration, using separate formulations or a single pharmaceutical formulation, and consecutive administration in either order, wherein preferably there is a time period while both (or all) active agents simultaneously exert their biological activities. Preparation and dosing schedules for such chemotherapeutic agents can be used according to manufacturers' instructions or as determined empirically by the skilled practitioner. Preparation and dosing schedules for chemotherapy are also described in Chemotherapy Service Ed., M. C. Perry, Williams & Wilkins, Baltimore, Md. (1992). Accordingly, in some embodiments, the chemotherapeutic agent can precede, or follow administration of the anti-DEspR antibody or antigen-binding fragment thereof or can be given simultaneously therewith.

In some other embodiments of the methods described herein, other therapeutic agents useful for combination tumor therapy with the anti-DEspR antibodies or antigen-binding fragments thereof described herein include antagonists of other factors that are involved in tumor growth, such as EGFR, ErbB2 (also known as Her2), ErbB3, ErbB4, or TNF. In some embodiments, it can be beneficial to also administer one or more cytokines to the subject. In some embodiments, the anti-DEspR antibody or antigen-binding fragment thereof is co-administered with a growth inhibitory agent. For example, the growth inhibitory agent can be administered first, followed by the anti-DEspR antibody or antigen-binding fragment thereof. However, simultaneous administration or administration of the anti-DEspR antibody or antigen-binding fragment thereof first is also contemplated. Suitable dosages for the growth inhibitory agent are those presently used and can be lowered due to the combined action (synergy) of the growth inhibitory agent and the anti-DEspR antibody or antigen-binding fragment thereof.

Examples of additional angiogenic inhibitors that can be used in combination with the DEspR inhibitors, such as anti-DEspR antibodies and antigen-binding fragments thereof, described herein include, but are not limited to: direct angiogenesis inhibitors, Angiostatin, Bevacizumab (AVASTIN®), Arresten, Canstatin, Combretastatin, Endostatin, NM-3, Thrombospondin, Tumstatin, 2-methoxyestradiol, cetuximab (ERBITUX®), panitumumab (VECTIBIX™), trastuzumab (HERCEPTIN®) and Vitaxin; and indirect angiogenesis inhibitors: ZD1839 (Iressa), ZD6474, OS1774 (Tarceva), CI1033, PKI1666, IMC225 (Erbitux), PTK787, SU6668, SU11248, Herceptin, and IFN-α, CELEBREX® (Celecoxib), THALOMID® (Thalidomide), and IFN-α.

In some embodiments, the additional angiogenesis inhibitors for use in the methods described herein include but are not limited to small molecule tyrosine kinase inhibitors (TKIs) of multiple pro-angiogenic growth factor receptors. The three TKIs that are currently approved as anti-cancer therapies are erlotinib (TARCEVA®), sorafenib (NEXAVAR®), and sunitinib (SUTENT®).

In some embodiments, the angiogenesis inhibitors for use in the methods described herein include but are not limited to inhibitors of mTOR (mammalian target of rapamycin) such as temsirolimus (TORICEL™), bortezomib (VELCADE®), thalidomide (THALOMID®), and Doxycyclin, In other embodiments, the angiogenesis inhibitors for use in the methods described herein include one or more drugs that target the VEGF pathway. Bevacizumab (AVASTIN®) was the first drug that targeted new blood vessels to be approved for use against cancer. It is a monoclonal antibody that binds to VEGF, thereby blocking VEGF from reaching the VEGF receptor (VEGFR). Other drugs, such as sunitinib (SUTENT®) and sorafenib (NEXAVAR®), are small molecules that attach to the VEGF receptor itself, preventing it from being turned on. Such drugs are collectively termed VEGF inhibitors. As the VEGF/VPF protein interacts with the VEGFRs, inhibition of either the ligand VEGF, e.g. by reducing the amount that is available to interact with the receptor; or inhibition of the receptor's intrinsic tyrosine kinase activity, blocks the function of this pathway. This pathway controls endothelial cell growth, as well as permeability, and these functions are mediated through the VEGFRs.

Accordingly, as described herein, "VEGF inhibitors" for use as angiogenesis inhibitors include any compound or agent that produces a direct or indirect effect on the signaling pathways that promote growth, proliferation and survival of a cell by inhibiting the function of the VEGF protein, including inhibiting the function of VEGF receptor proteins. These include any organic or inorganic molecule, including, but not limited to modified and unmodified nucleic acids such as antisense nucleic acids, RNAi agents such as siRNA or shRNA, peptides, peptidomimetics, receptors, ligands, and antibodies that inhibit the VEGF signaling pathway. The siRNAs are targeted at components of the VEGF pathways and can inhibit the VEGF pathway. Preferred VEGF inhibitors, include for example, AVASTIN® (bevacizumab), an anti-VEGF monoclonal antibody of Genentech, Inc. of South San Francisco, Calif., VEGF Trap (Regeneron/Aventis). Additional VEGF inhibitors include CP-547,632 (3-(4-Bromo-2,6-difluoro-benzyloxy)-5-[3-(4-pyrrolidin 1-yl-butyl)-ureido]-isothiazole-4-carboxylic acid amide hydrochloride; Pfizer Inc., NY), AG13736, AG28262 (Pfizer Inc.), SU5416, SU11248, & SU6668 (formerly Sugen Inc., now Pfizer, New York, N.Y.), ZD-6474 (AstraZeneca), ZD4190 which inhibits VEGF-R2 and -R1 (AstraZeneca), CEP-7055 (Cephalon Inc., Frazer, Pa.), PKC 412 (Novartis), AEE788 (Novartis), AZD-2171), NEXAVAR® (BAY 43-9006, sorafenib; Bayer Pharmaceuticals and Onyx Pharmaceuticals), vatalanib (also known as PTK-787, ZK-222584: Novartis & Schering: AG), MACUGEN® (pegaptanib octasodium, NX-1838, EYE-001, Pfizer Inc./Gilead/Eyetech), IM862 (glufanide disodium, Cytran Inc. of Kirkland, Wash., USA), VEGFR2-selective monoclonal antibody DC101 (ImClone Systems, Inc.), angiozyme, a synthetic ribozyme from Ribozyme (Boulder, Colo.) and Chiron (Emeryville, Calif.), Sirna-027 (an siRNA-based VEGFR1 inhibitor, Sirna Therapeutics, San Francisco, Calif.) Caplostatin, soluble ectodomains of the VEGF receptors, Neovastat (Æterna Zentaris Inc; Quebec City, Calif.), ZM323881 (CalBiochem. CA, USA), pegaptanib (Macugen) (Eyetech Pharmaceuticals), an anti-VEGF aptamer and combinations thereof.

VEGF inhibitors are also disclosed in U.S. Pat. Nos. 6,534,524 and 6,235,764, both of which are incorporated in their entirety. Additional VEGF inhibitors are described in, for example in WO 99/24440 (published May 20, 1999), International Application PCT/IB99/00797 (filed May 3, 1999), in WO 95/21613 (published Aug. 17, 1995), WO 99/61422 (published Dec. 2, 1999), U.S. Pat. Publ. No. 20060094032 "siRNA agents targeting VEGF", U.S. Pat. No. 6,534,524 (discloses AG13736), U.S. Pat. No. 5,834,504 (issued Nov. 10, 1998), WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), U.S. Pat. No. 6,653,308 (issued Nov. 25, 2003), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), WO 01/02369 (published Jan. 11, 2001); U.S. Provisional Application No. 60/491,771 piled Jul. 31, 2003); U.S. Provisional Application No. 60/460,695 (filed Apr. 3, 2003); and WO 03/106462A1 (published Dec. 24, 2003). Other examples of VEGF inhibitors are disclosed in International Patent Publications WO 99/62890 published Dec. 9, 1999, WO 01/95353 published Dec. 13, 2001 and WO 02/44158 published Jun. 6, 2002.

In other embodiments, the angiogenesis inhibitors for use in the methods described herein include anti-angiogenic factors such as alpha-2 antiplasmin (fragment), angiostatin (plasminogen fragment), antiangiogenic antithrombin III, cartilage-derived inhibitor (CDI), CD59 complement fragment, endostatin (collagen XVIII fragment), fibronectin fragment, gro-beta (a C-X-C chemokine), heparinases heparin hexasaccharide fragment, human chorionic gonadotropin (hCG), interferon alpha/beta/gamma, interferon inducible protein (IP-10), interleukin-12, kringle 5 (plasminogen fragment), beta-thromboglobulin, EGF (fragment), VEGF inhibitor, endostatin, fibronectin (45 kD fragment), high molecular weight kininogen (domain 5), NK1, NK2, NK3 fragments of HGF, PF-4, serpin proteinase inhibitor 8, TGF-beta-1, thrombospondin-1, prosaposin, p53, angioarrestin, metalloproteinase inhibitors (TIMPs), 2-Methoxyestradiol, placental ribonuclease inhibitor, plasminogen activator inhibitor, prolactin 16 kD fragment, proliferin-related protein (PRP), retinoids, tetrahydrocortisol-S transforming growth factor-beta (TGF-b), vasculostatin, and vasostatin (calreticulin fragment). pamidronate thalidomide, TNP470, the bisphosphonate family such as amino-bisphosphonate zoledronic acid. bombesin/gastrin-releasing peptide (GRP) antagonists such as RC-3095 and RC-3940-II (Bajol A M, et. al., British Journal of Cancer (2004) 90, 245-252), anti-VEGF peptide RRKRRR (dRK6) (Seung-Ah Yoo, J. Immuno, 2005, 174: 5846-5855).

Thus, in connection with the administration of anti-DEspR antibodies and antigen-binding fragments thereof, a compound which inhibits angiogenesis indicates that administration in a clinically appropriate manner results in a beneficial effect for at least a statistically significant fraction of patients, such as improvement of symptoms, a cure, a reduction in disease load, reduction in tumor mass or cell numbers, extension of life, improvement in quality of life, or other effect generally recognized as positive by medical doctors familiar with treating the particular type of disease or condition.

Examples of additional DEspR inhibitors include, but are not limited to, molecules which block the binding of VEGFsp (sp26, sp17), ET-1 and/or other ET-1 or VEGFsp-like ligands to DEspR, compounds which interfere with downstream signaling events of DEspR, or other compounds or agents that inhibit activation of the receptor. Such compounds can bind to DEspR and prevent binding of VEGFsp (sp26, sp17), ET-1 or other mimetic ligands. Other inhibitors including small molecules that bind to the DEspR domain that binds to VEGFsp, soluble DEspR receptors, peptides containing the DEspR ET-1 and/or VEGFsp binding domains, etc. are also contemplated. For example, in some aspects, provided herein are VEGFsp-26 peptides with one or more modifications that stabilize the peptide in vivo to be used in methods of inhibiting DEspR expression and/or function.

The compositions described herein can also contain more than one active compound as necessary for the particular indication being treated, and these active compounds are preferably those with complementary activities that do not adversely affect each other. For example, it can be desirable to further provide antibodies or antagonists that bind to EGFR, VEGF, VEGFR, or ErbB2 (e.g., Herceptin™). Alternatively, or in addition, the composition can comprise a cytotoxic agent, cytokine, growth inhibitory agent and/or VEGFR antagonist. Such molecules are suitably present in combination in amounts that are effective for the purpose intended.

In certain aspects of any of the methods and uses described herein, other therapeutic agents useful for combination cancer therapy with the antibody of the invention include other anti-angiogenic agents. Many anti-angiogenic agents have been identified and are known in the arts, including those listed by Carmeliet and Jain (2000). In some embodiments, the DEspR antagonist, such as a humanized anti-DEspR antibody or antigen-binding fragment thereof described herein is used in combination with a VEGF antagonist or a VEGF receptor antagonist such as VEGF variants, soluble VEGF receptor fragments, aptamers capable of blocking VEGF or VEGFR, neutralizing anti-VEGFR antibodies, low molecule weight inhibitors of VEGFR tyrosine kinases and any combinations thereof. Alternatively, or in addition, two or more anti-DEspR antagonists can be co-administered to the subject.

For the treatment of diseases, as described herein, the appropriate dosage of an anti-DEspR antibody or antigen-binding fragment thereof will depend on the type of disease to be treated, as defined above, the severity and course of the disease, whether the anti-DEspR antibody or antigen-binding fragment thereof is administered for preventive or therapeutic purposes, previous therapeutic indications, the subject's clinical history and response to the anti-DEspR antibody or antigen-binding fragment thereof, and the discretion of the attending physician. The anti-DEspR antibody or antigen-binding fragment thereof is suitably administered to the subject at one time or over a series of treatments. In a combination therapy regimen, the anti-DEspR antibody or antigen-binding fragment thereof and the one or more anti-cancer therapeutic agents described herein are administered in a therapeutically effective or synergistic amount. As used herein, a therapeutically effective amount is such that co-administration of an anti-DEspR antibody or antigen-binding fragment thereof and one or more other therapeutic agents, or administration of a composition described herein, results in reduction or inhibition of the cancer as described herein. A therapeutically synergistic amount is that amount of an anti-DEspR antibody or antigen-binding fragment thereof and one or more other therapeutic agents necessary to synergistically or significantly reduce or eliminate conditions or symptoms associated with a particular disease. In some cases, the anti-DEspR antibody or antigen-binding fragment thereof can be co-administered with one or more additional therapeutically effective agents to give an additive effect resulting in a significantly reduction or elimination of conditions or symptoms associated with a particular disease, but with a much reduced toxicity profile due to lower dosages of one or more of the additional therapeutically effective agents.

The anti-DEspR antibody or antigen-binding fragment thereof and the one or more other therapeutic agents can be administered simultaneously or sequentially in an amount and for a time sufficient to reduce or eliminate the occurrence or recurrence of a tumor, a dormant tumor, or a micrometastases. The anti-DEspR antibody or antigen-binding fragment thereof and the one or more other therapeutic agents can be administered as maintenance therapy to prevent or reduce the likelihood of recurrence of the tumor.

As will be understood by those of ordinary skill in the art, the appropriate doses of chemotherapeutic agents or other anti-cancer agents will be generally around those already employed in clinical therapies, e.g., where the chemotherapeutics are administered alone or in combination with other chemotherapeutics or targeted therapies. Variation in dosage will likely occur depending on the condition being treated. The physician administering treatment will be able to determine the appropriate dose for the individual subject.

In addition to the above therapeutic regimes, the subject can be subjected to radiation therapy.

In certain embodiments of any of the methods, uses and compositions described herein, the administered DEspR antibody is an intact, naked antibody. However, in some embodiments, the anti-DEspR antibody can be conjugated with a cytotoxic agent. In certain embodiments of any of the methods and uses, the conjugated anti-DEspR antibody and/or DEspR antigen-binding fragment thereof is/are internalized by the cell, resulting in increased therapeutic efficacy of the conjugate in killing the cancer cell to which it binds. In some embodiments, the cytotoxic agent conjugated to the DEspR antibody and/or DEspR antigen-binding fragment thereof targets or interferes with nucleic acid in the cancer cell. Examples of such cytotoxic agents include maytansinoids, calicheamicins, ribonucleases and DNA endonucleases, and are further described elsewhere herein.

This invention is further illustrated by the following examples which should not be construed as limiting. It is understood that the foregoing description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

EXAMPLES

Example 1

Peptide GSNEMKSRWNWGS (SEQ ID NO: 1) was used as antigenic peptide to generate monoclonal antibodies directed to DEspR. A smaller or partial peptide EMKSRWNWGS (SEQ ID NO: 2) was then used to screen (by ELISA) for monoclonal antibodies and narrow down the potential epitope for 6G8G7.

Figure 1B:
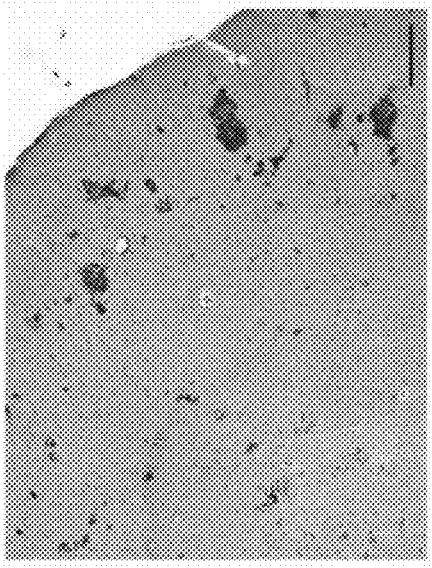
Figure 1C:
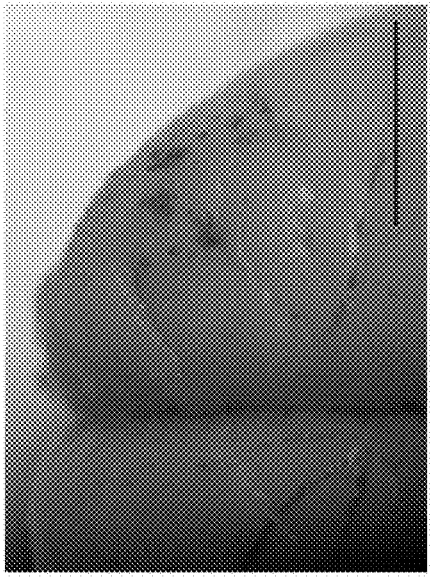

The stroke prone Tg25+ rat model was developed in the polygenic Dahl Salt-sensitive hypertensive strain, transgenic for human cholesteryl ester transfer protein conveying a hyperlipidemic profile (Herrera et al. 1999). These rats were made stroke prone by early life Na-exposure during gestation to PURINA 5001 regular rat chow with 0.3% NaCl (Decano et al. 2009). Anatomical and histological analysis revealed that Tg25+ stroke prone rats exhibited parenchymal hemorrhages (FIGS. 1A-1B) and hemorrhagic infarctions (FIG. 1C).

Figures 2A, 2B, 2C, 2D, 2E:
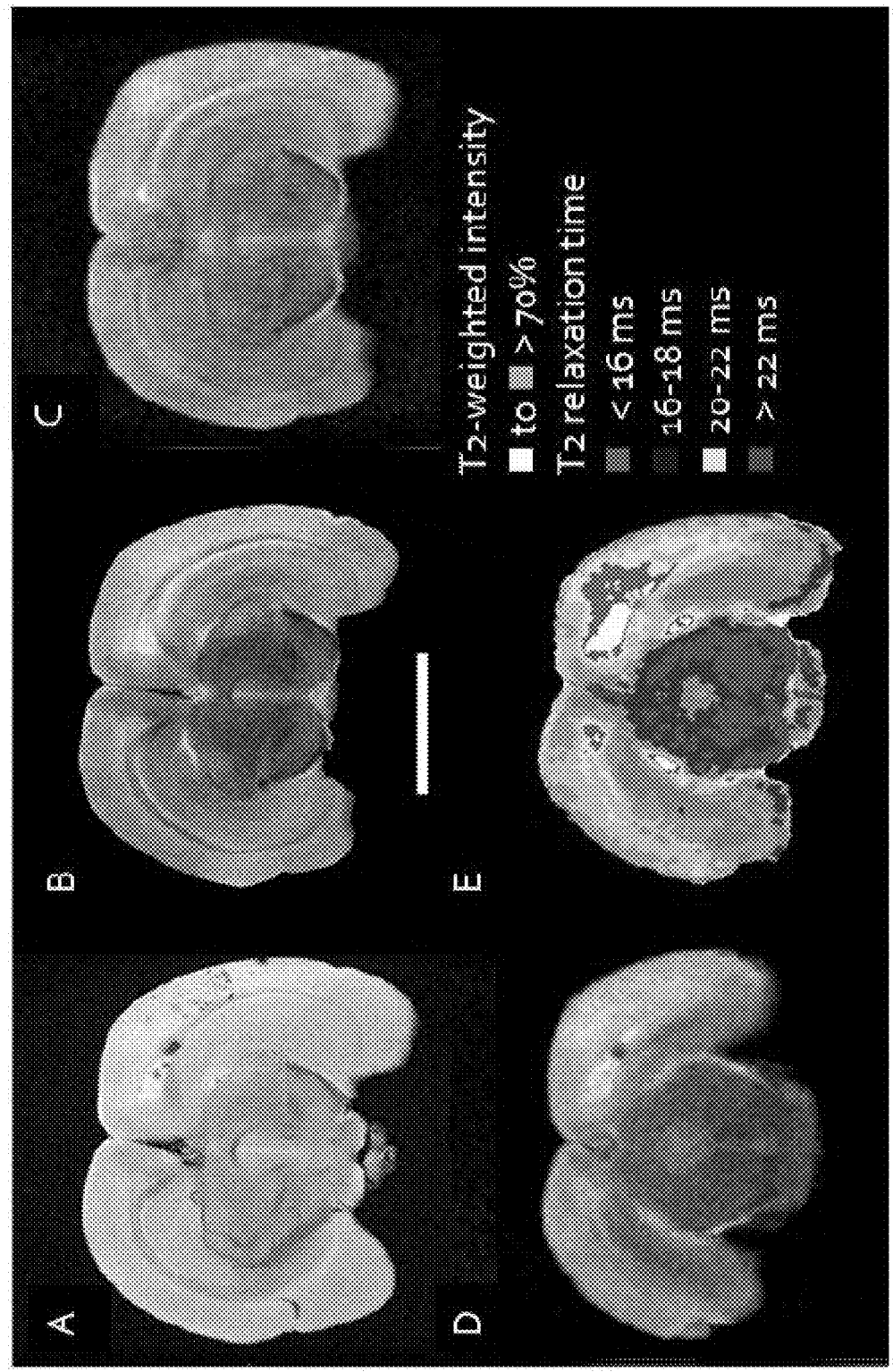
FIGS. 2A-2E show that a rat stroke model exhibits stroke-pathology lesions seen in humans. These lesions were detectable on ex vivo 11.7T MR-imaging using gradient echo sequences (FIG. 2A) and T2 weighted MRI (FIGS. 2B-C). Ischemia surrounding microhemorrhages were noted on T2-weighted intensity analysis (FIG. 2C) and on analysis of T2 relaxation time (FIGS. 2D-2E).

The rat stroke model exhibits stroke-pathology lesions seen in humans. These lesions were detectable on ex vivo 11.7T MR-imaging using gradient echo sequences (FIG. 2A) and T2 weighted MRI (FIGS. 2B-2C). Ischemia surrounding microhemorrhages were noted on T2-weighted intensity analysis (FIG. 2C) and on analysis of T2 relaxation time (FIGS. 2D-2E).

As observed in humans, stroke-prone Tg25+ females exhibited earlier onset of ischemic-hemorrhagic strokes compared to male Tg25+ rats (FIG. 3) (Decano et al. 2009).

Figure 4:
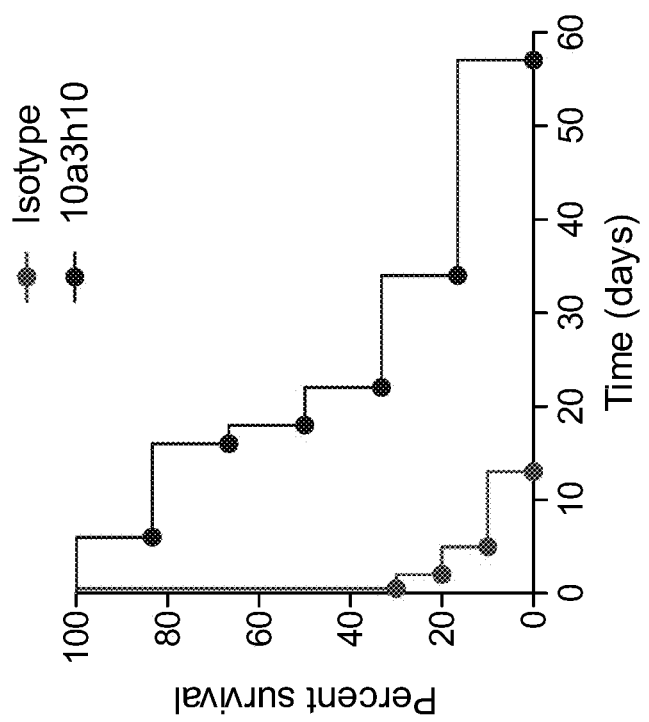
FIG. 4 shows effect of anti-DEspR treatment on stroke survival in Tg25 stroke-prone Dahl S rat model (Dahl S rats transgenic for human cholesteryl ester transfer protein). Tg25 female rats were treated (IV infusion) with a single dose of either 10 μg of Isotype control (IgG1, n=10) or 10 μg of anti-DEspR 10A3H10 monoclonal antibody (mAb) (n=6) at stroke onset (rats were 4-6 months of age with documented neurological deficits). Rats were allowed to proceed to recovery up to eventual death. As shown below, there is a significant increase in post-stroke survival upon anti-DEspR treatment (Mean post-stroke survival time for controls=2.35±1.27 days versus Mean post-stroke survival time for anti-DEspR treated group=25.5±7.3 days; P=0.0002, Log-Rank Test) extending post-stroke survival>ten fold compared with controls.
Figure 5A:
FIG. 5A. At stroke onset, a rat presented with dystonic head movements, which resolved completely after 3 days (FIG. 5B). Only 1 treatment was given. The rat was then monitored until repeat stroke onset (thus demonstrating stroke-prone phenotype).
Figure 5B:
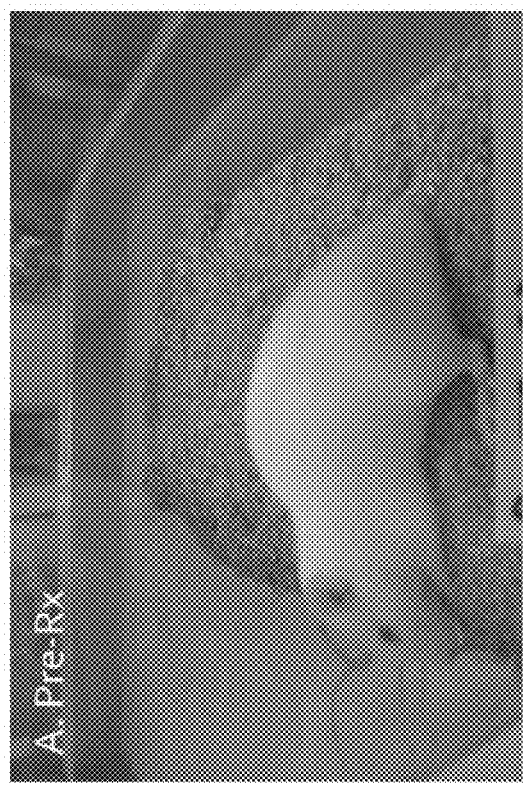

At onset of acute stroke, rats exhibit neurologic deficits such as seizures, paresis or paralysis, or dystonic movements, or lethargy. When these neurologic deficits appear, rats are assigned to either the anti-DEspR (anti-rat DESpR monoclonal antibody, 10a3h10) treatment group or the control isotype antibody group. One dose of 30 µg/kg is administered intravenously. Rats were then monitored and aided to have adequate food and water until they recover or needed to be euthanized. As shown in FIG. 4, early anti-DEspR mAb therapy at acute stroke resolves presenting neurologic deficits and increases survival of spTg25+ female rats.

Without wishing to be bound or limited by theory, a putative mechanism for the results described herein includes stabilizing leaky microvessels or microvascular disruption in stroke ischemic sites, as seen in cancer.

Treatment of rats with spontaneous breast tumors with anti-DEspR therapy (10a3h10 antibody) resulted not just in decreased tumor growth, but also stabilization of 'tumor leaky neovessels.' As seen in FIG. 6A, pretreatment, rat tumor vessels are eroded, with red blood cells encroaching into the tumor, and tumor cells encroaching into the vessel lumen. After a 4-dose therapy over several weeks, tumors from treated rats exhibited smaller sizes as well as tumor blood vessels with intact endothelium (FIG. 6B).

As demonstrated herein, DEspR is a membrane bound receptor that is glycosylated, and 'pulled down' with galectin-1 as identified by Mass Spectronomy peptide signature analysis. Galectin-1 has recently been implicated to "tie-up" the key receptor for VEGF, VEGF-R2, in the membrane as a mechanism for VEGF-resistance, (Croci et al 2014. Cell 156(4):744-58), however, no pulldown experiments were reported by Croci et al 2014. Anti-human DEspR mAb, 5g12e8 monoclonal antibody, was used for pulldown of DEspR from membrane proteins isolated from glioblastoma u87 CSCs and from Cos1-DEspR permanent cell transfectants.

Figure 7:
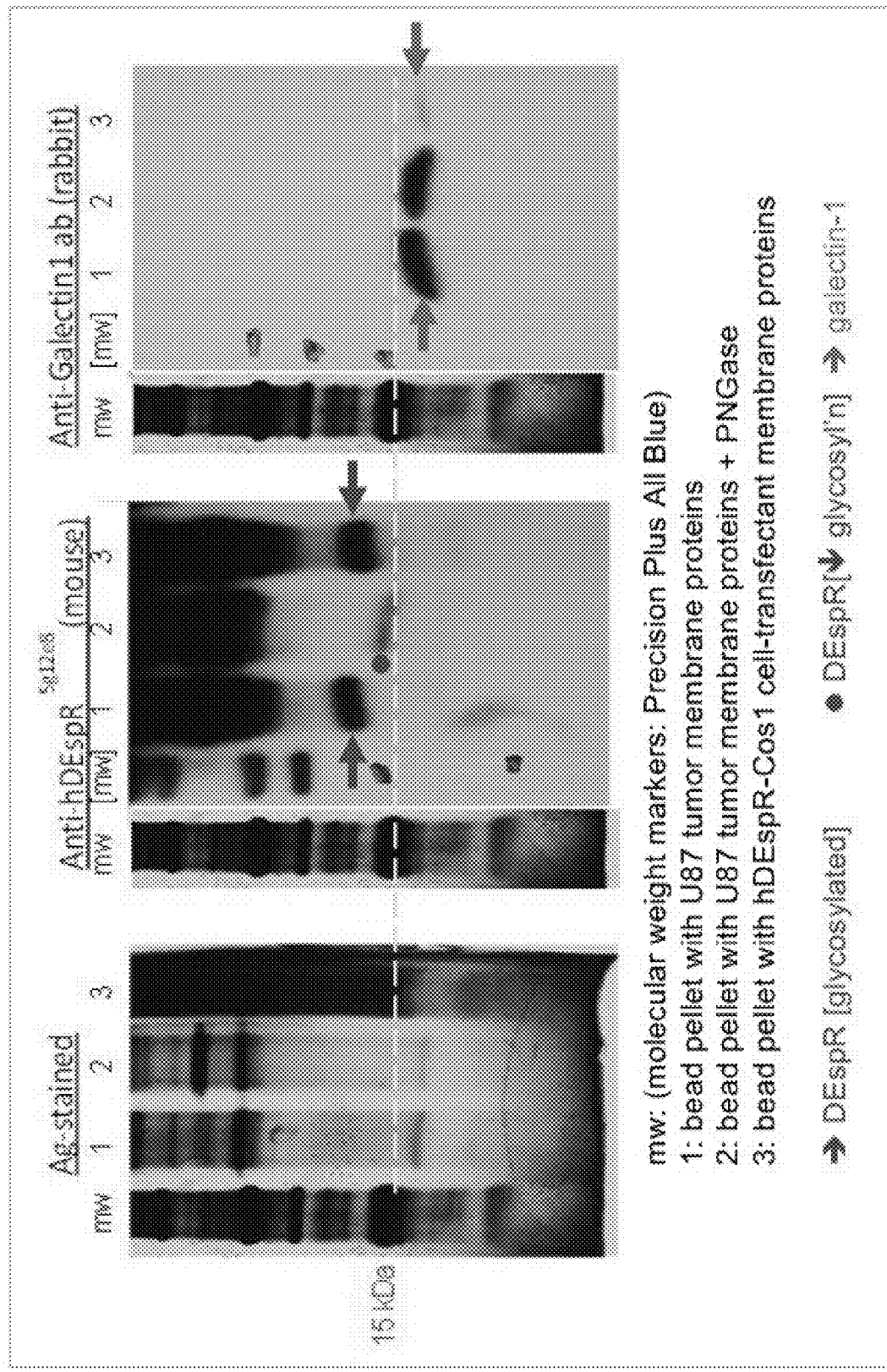
FIG. 7 shows Western blot analysis of pulldown proteins from membrane proteins isolated from human glioblastoma tumor cells (U87), PNGase-F treated U87 pulldown proteins, and from hDEspR-Cos1 permanent transfectant cells.

As shown in FIG. 7, hDEspR Cos-1 cell permanent transfectants express the DEspR protein produced by a recombinant DEspR-unspliced minigene construct, which automated sequencing reports to contain the purported 'stop codon sequence of TGA' at amino acid #14 position. The minigene construct contains the unspliced cDNA construct. As demonstrated herein, detection of protein products >10 kDa by anti-DEspR monoclonal antibody 5g12e8 indicates unequivocally that the stop codon is not present. A stop codon would produce only a 13-aa long peptide which is only 1.547 kDa. Detection of identical pulldown DEspR products (band detected by anti-DEspR mAb) in human glioblastoma U87 cells and DEspR+ Cos1-cell transfectants indicates that the unspliced hDEspR minigene construct is transcribed, spliced, translated and undergoes post-translational glycosylation. There is less galectin-1 in Cos1 cells than U87 cells; non-transfected Cos1 cells have no detectable DEspR by western blot and binding assays. The consistent pulldown of DEspR-Galectin1 complex (n>5) indicates that DEspR could underlie the persistent angiogenesis observed in so called "VEGF-resistance" with galectin-1 serving as the scaffold and linker for different glycosylated proteins.

Figure 8A:
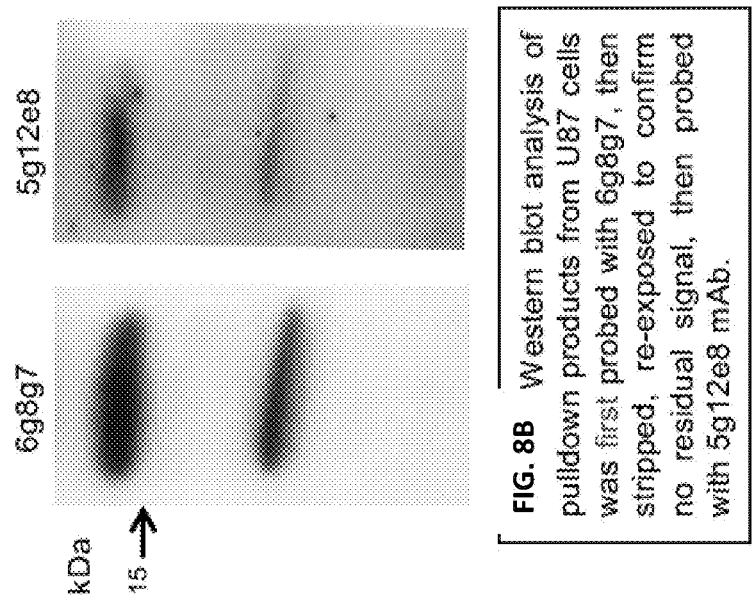
FIGS. 8A-8B shows that two different monoclonal antibodies (mAbs) raised against different domains in the DEspR protein bind to the identical protein bands on a Western blot of pull-down proteins (FIGS. 8A, 8B), thus refuting the existence of a stop codon at amino acid #14 position and indicating DEspR protein in human cancer cells.
Figure 8B:
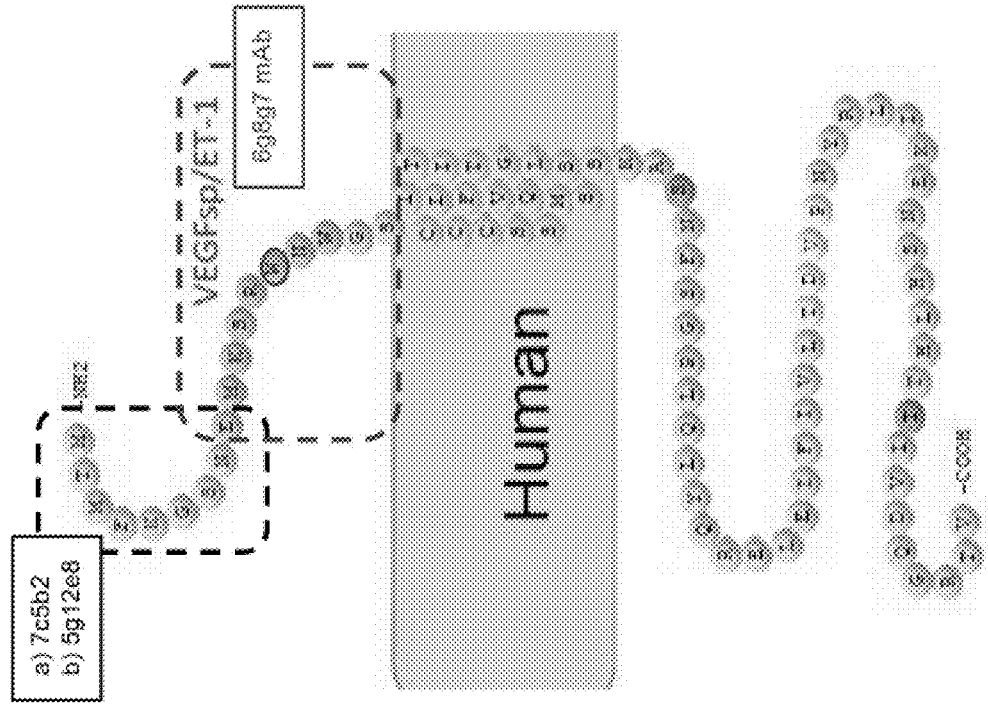

5G12E8 and 6G8G7 monoclonal antibodies work in western blots and were used to confirm DEspR protein in pulldown (FIGS. 8A and 8B: ~17 kDa protein band is DEspR-glycosylated (as shown by PNGase digest, and ~12.5 kDa protein is DEspR with less glycosylation. Two different monoclonal antibodies raised against different domains in the DEspR protein bind to the identical protein bands on Western blot of pull-down proteins (FIGS. 8A, 8B), thus refuting the existence of a stop codon at amino acid #14 position and demonstrating DEspR protein expression in human cancer cells.

Western blot 'walking' with the 5G12E8 monoclonal antibody binding to amino terminal end, and 6G8G7 binding to the predicted ligand-binding domain demonstrate the existence of DEspR. If the stop codon were indeed present at position amino acid 14 W (□), then 6G8G7 should not bind to the identical 17 kDa and 12.5 kDa bands, or any protein. In addition, 7C5B2 monoclonal antibody does not 'work' in Western Blot analysis indicating that conformation plays a role in its epitope in the 9-aa N-terminal peptide antigen. It is to be noted that the peptide used to generate 6G8G7 is 100% identical in Human-Rat-Mouse (unlike peptide for 7C5B2 and 5G12E8), thus facilitating FDA-required 2-species toxicity studies.

DEspR, a single transmembrane integral membrane protein, was not detectable by peptide mass fingerprinting methods using techniques such as MALDI-TOF Mass Spectrometry analysis (c/o D. Pappin, Cold Spring Harbor, do CRO). This is not surprising given that majority (87-97%) of integral membrane proteins are not identifiable on Mass Spectrometry, and only >150 kDa integral membrane proteins (with e2 transmembrane domains) were detected by MS.

Bensalem et al. 2006: Peptide mass fingerprinting of membrane proteins, using techniques such as MALDI-TOF MS, remains a 'real challenge for at least 3 reasons: 1. Membrane proteins are naturally present at low levels. 2. Most of the detergents strongly inhibit proteases and have deleterious effects on MALDI spectra. 3. Despite the presence of detergent, membrane proteins are unstable and often aggregate [Bensalem N, et al., High sensitivity identification of membrane proteins by MALDI TOF-MASS Spectrometry using polystyrene beads. J Proteome Res 2007, 6:1595-1602.] Mirza et al 2007 at the National Center for Proteomics Research, Medical College of Wisconsin, detected only 204 (3% of 6718) integral membrane proteins from rat endothelial cells even after their chloroform-extraction method. Notably, no VEGFR2 was identified on MS-like DEspR. [Mirza S P Halligan B D, Greene A S, Olivier M. 2007. Improved method for the analysis of membrane proteins by mass spectrometry. Physiol Genomics 30:89-94, 2007. Peng et al 2011 detected only 301 (4.5% of 6718) integral membrane proteins via SDS-PAGE shotgun proteomics. [Peng L, Kapp E A, McLauhlan D Jordan T W. Characterization of the Asia Oeania human proteome organization membrane proteomics initiative standard using SDS-PAGE shotgun proteomics. Proteomics 11:4376-4384.]. Fagerberd et al 2010: range of integral membrane proteins 5508 to 7651 depending on the method used. Based on a majority decision method, estimate is 5539 human genes code for membrane proteins or 26% of human genome. Highest count using SCX-RPLC-MS/MS (MudPIT) strategy detected 876 integral membrane proteins or 13% of 6718 integral membrane proteins in murine NK cells [Fagerberd L, Jonasson K, vonHeijne G, Uhlen M, Berglund L. 2010. Prediction of the human membrane proteome. Proteomics 10:1141-1149; Blonder J et al., J Proteome Res 2004, 3, 862-870.] Almen et al 2009, mined the human proteome and identified the membrane proteome subset using 3 prediction tools for alpha-helices: Phobius, TMHMM, and SOSUI. This data set was reduced to a non-redundant set by aligning it to the human genome and then clustered using the ISODATA algorithm. 6,718 human membrane proteins were identified (32% of all human proteins—estimated at 21,000 proteins)—901 are GPCRs and 7-transmembrane domain receptors, 88% of the rest are single-transmembrane domain receptors. [Almen 2009, Fagerbered et al 2010.] DEspR has single transmembrane domain. This is concordant with the most recent and reliable set of genes in the human genome which lists 5,359 validated protein coding α-helical transmembrane proteins ~27% of the entire human proteome.

Single transmembrane proteins—like DEspR and VEGF-R2—are not detected on Mass Spectrometry analysis of membrane proteins. Zhou et al 2011. Moreover, of the ones detected by Mass Spectrometry using an improved method that detects more membrane proteins using a centrifugal proteomic reactor, all membrane proteins detected by Mass Spectrometry were >150 kDa and contained e 2 transmembrane domains. [Zhou H, Wang F, Wang Y, Ning Z, Hou W, Wright T G, Sundaram M, Zong S, Yao Z, Figeys D. 2011. Improved recovery and identification of membrane proteins from rat hepatic cells using a centrifugal proteomic reactor. Mol Cell. Proteomics 10.10 (2011). Cao et al, 2013: "Deglycosylation of plasma membrane proteins by treatment with PNGase-F did not yield detection of additional hydrophobic proteins" (by MS with in-gel proteolytic predigestion) (Cao L, Clifton J G, Reutter W, Josic D. 2013. Mass spectrometry-based analysis of rat liver and hepatocellular carcinoma Morris hepatoma 7777 plasma membrane proteome. Analytical Chem 85:8112-8120, 2013.) Therefore, peptide mass fingerprinting mass spectrometry analysis of PNGase-treated pulldown proteins, which did not identify DespR, does not negate the existence of DEspR protein.

Based on UNIPROT criteria for determining a protein's existence, the demonstration of protein-protein interactions (as in the DEspR-galectin 1 complex) and the antibody detection of DEspR protein in human tumor cells and endothelial cells in vitro using multiple techniques (immunofluorescence analysis of cells and tumor tissue arrays—breast cancer, pancreatic cancer, glioblastoma, stomach, colon, ovarian cancers)—each fulfill established criteria for documenting the existence of DEspR protein in human cells. Together, these date provide multiple lines of evidence for DEspR protein at the highest criterion-level of protein determination.

Figure 9:
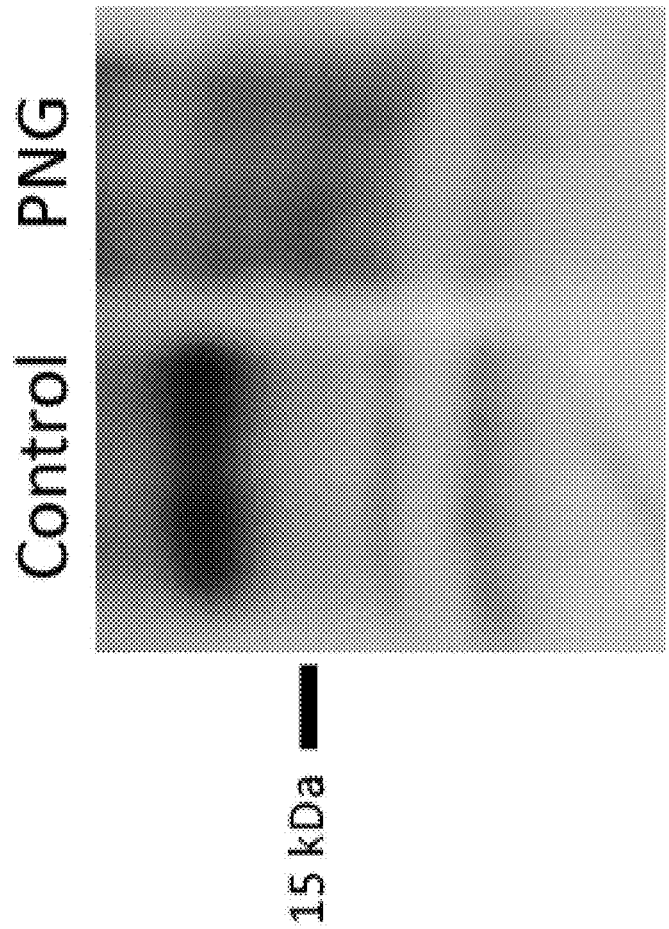
FIG. 9 shows Western blot (wb) analysis of 5G12E8 anti-DEspR monoclonal antibody (mAb) pulldown proteins: control non-digested (Control) and PNGase (PNG) digested pulldown proteins show loss of major 17 kDa protein band and appearance of smaller-size bands indicating deglycosylation. WB probed with 5G12E8 mAb; 15 kDa molecular weight (mw) marker.
Figures 10A, 10B:
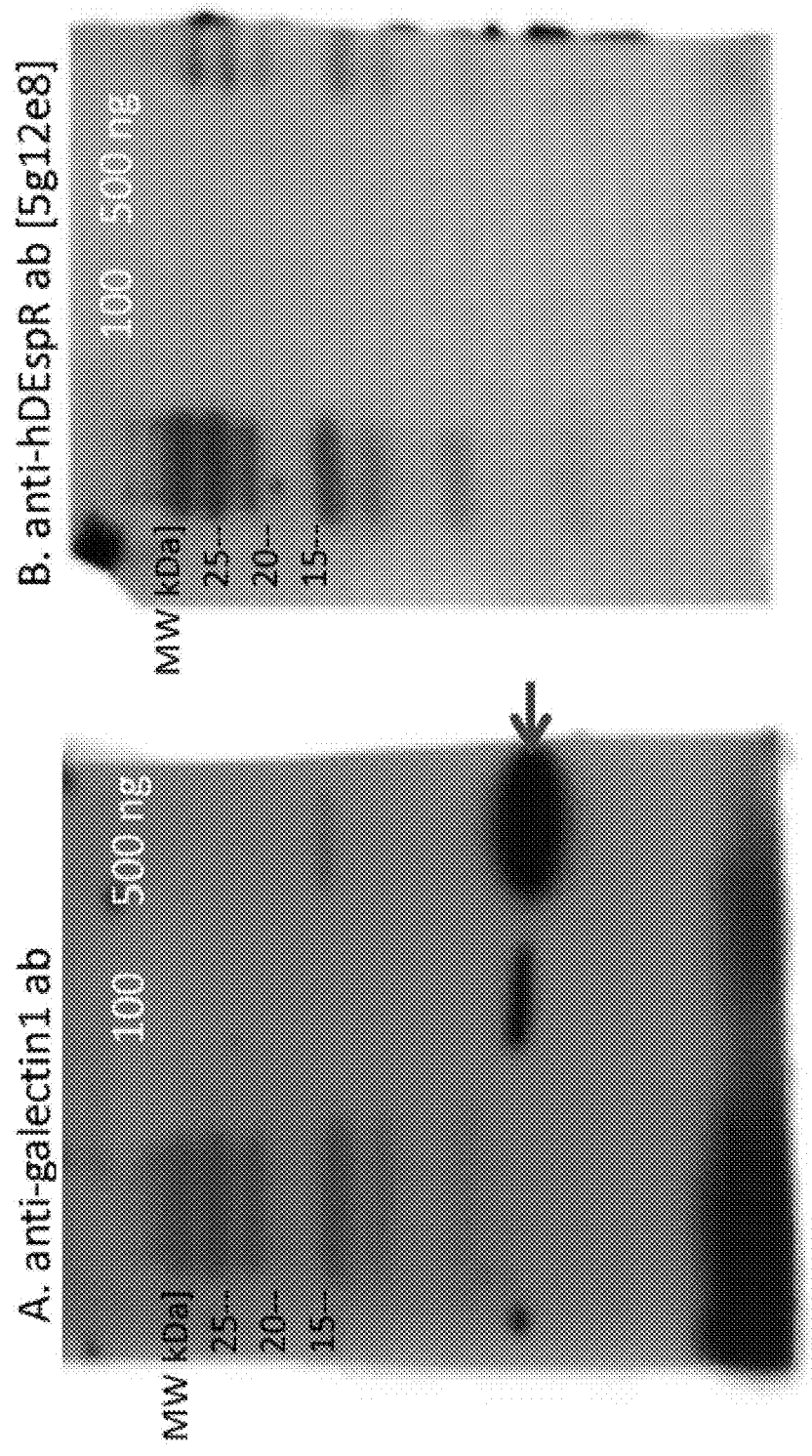
FIGS. 10A-10B show Western blot analysis of recombinant galectin-1 protein probed with FIG. 10A anti-human galectin1 monoclonal antibody (mAb), and FIG. 10B anti-humanDEspR monoclonal antibody (mAb) 5G12E8.
Figure 11:
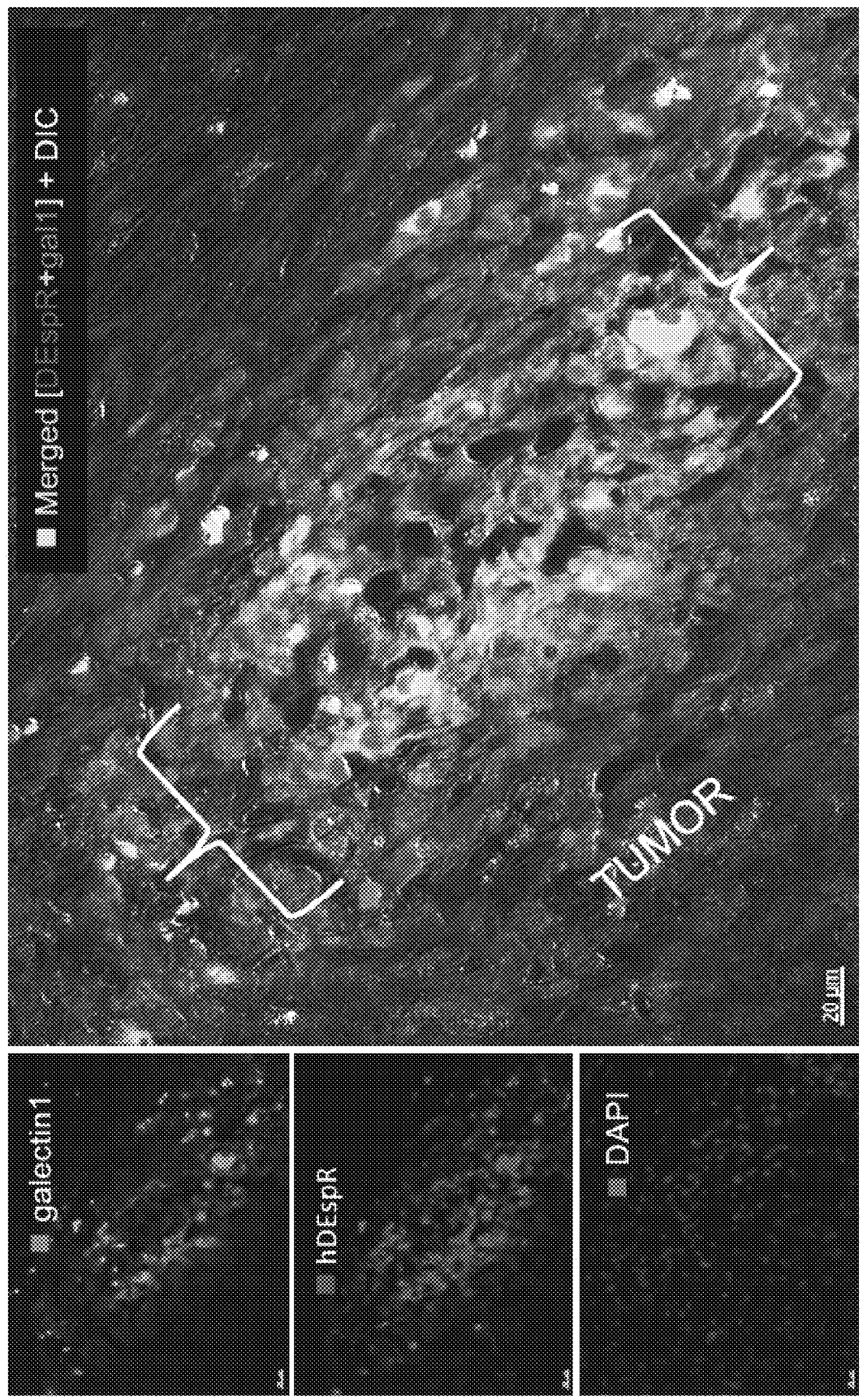
FIG. 11 shows that concordant with pulldown of a DEspR-galectin1 complex, DEspR and galectin1 colocalize in tumor cells at the invasive front { } of a human glioblastoma (U87-csc) xenograft subQ tumor. Immunofluorescence analysis of DEspR and galectin1; DAPI nuclear DNA stain; colocalized DEspR+galectin1. U87 glioblastoma CSC xenograft tumor in nude rats.
Figure 12:
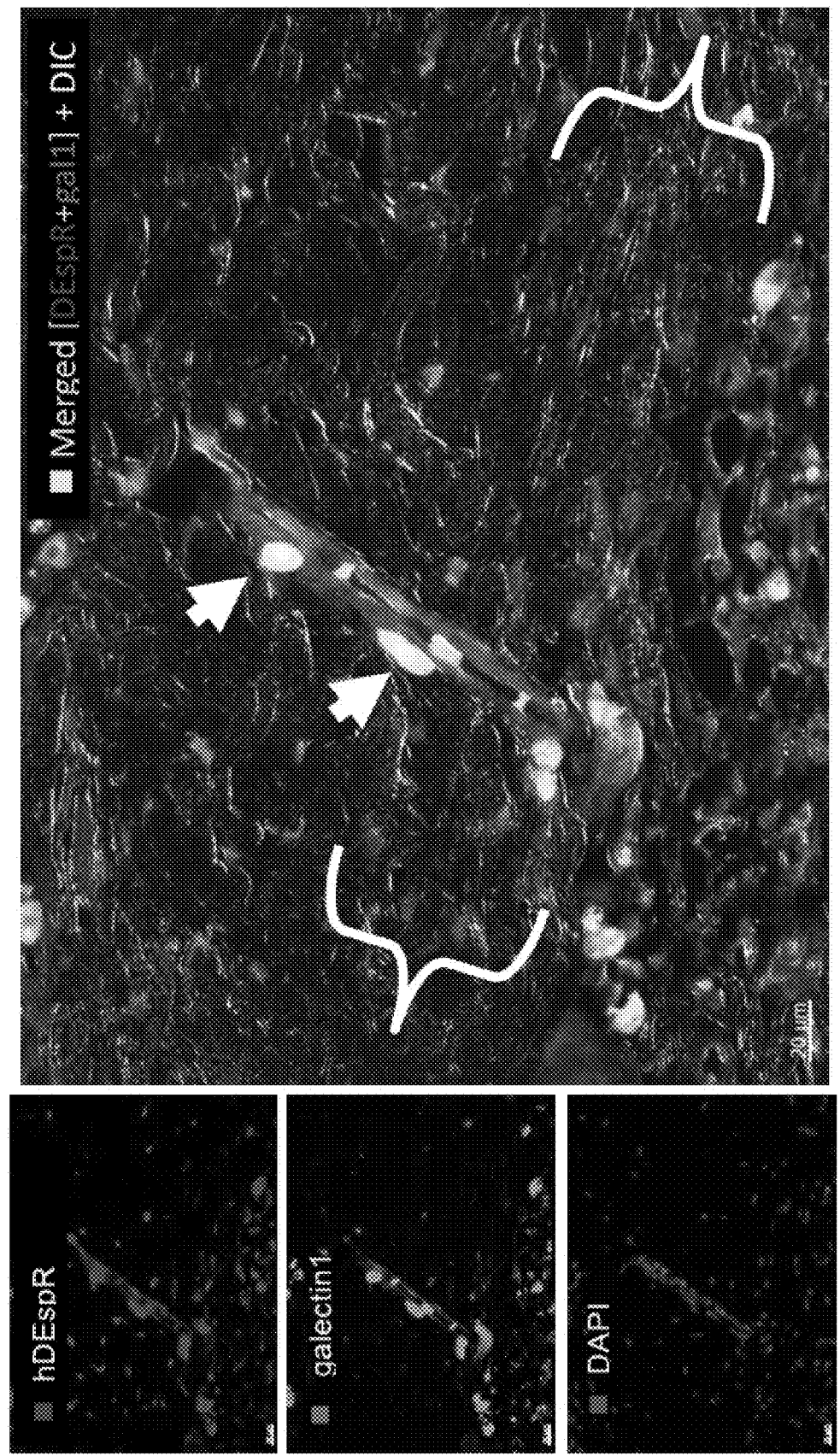
FIG. 12 shows invasive tumor cells (□) have invaded through the xenograft tumor's fibrous cap { }, through the overlying loose connective tissue and aligned with a blood vessel in the tissue surrounding the xenograft tumor cap. Representative photomicrograph of a glioblastoma U87-csc xenograft tumor (subcutaneous, 2 cm diameter) showing immunofluorescence detection of DEspR and galectin-1 colocalization in invasive tumor cells. Using human-specific antibodies for both DEspR, Galectin-1, only human U87-tumor cells exhibit expression. Co-localization (merged) is detected in invasive tumor cells (arrow) which are deduced to have invaded through the xenograft tumor's fibrous cap { }, through the overlying loose connective tissue and aligned with a blood vessel in the tissue surrounding the xenograft tumor cap. hDEspR, galectin1, DAPI, Merged [DEspR+gal1]+DIC (differential interference contrast).

Immunostaining of human tissue using 7C5B2 monoclonal antibody has been done. Furthermore, based on UNIPROT criteria, functional consequences of inhibition of DEspR by anti-DEspR antibody indicate the existence of a functional protein. Demonstration of DEspR protein is concordant with demonstration of spliced and unspliced DEspR-mRNA by ARMS (Herrera et al 2014). DEspR (17K glycosylated) and Galectin-1 (14.5 kDa) are distinct proteins. The consistent pulldown of galectin1 does not suggest that the anti-DEspR monoclonal antibody detects Galectin1 and that there is no DEspR protein. No cross reactivity of antibodies has been detected. While both DEspR and galectin-1 are found at the plasma membrane, in the cytosol and nucleus concordant with colocalization for complexing, galectin1 is secreted from the cell into the ECM, but not DEspR. DEspR is 17 kDa (glycosylated) and 12.5 kDa (non or minimal glycosylation). PNGase digest shows decreasing MW of DEspR 17 kDa band (FIG. 9). While DEspR is glycosylated, galectin1 is not glycosylated. "Galectin-1 is not a glycosylated protein" (Cherch et al 2006. Glycobiolgy 16:137R-157R)—hence the 17 kDa glycosylated protein detected on WB analysis proven by PNG-ase digestion cannot be galectin1. Anti-DEspR 5G12E8 monoclonal antibody does not bind galectin-1 on western blot analysis of pulldown proteins, and does not bind recombinant galectin-1 protein on western blot (FIGS. 10A-10B).

Concordant with pulldown of a DEspR-galectin1 complex, DEspR and galectin1 colocalize in tumor cells at the invasive front of a human glioblastoma (U87-csc) xenograft subcutaneous tumor. Detection of colocalization confirms pulldown data identifying a DEspR-galectin1 complex. Since Croci et al. identified galectin-1 as a mechanism for anti-VEGF (Avastin) resistance, the DEspR-galectin-1 complex defines a mechanism for the observed resistance through DEspR-mediated angiogenesis. Since galectin-1 is increased in cancers, and has been implicated in metastasis and tumor angiogenesis, inhibition of DEspR could then impact the DEspR-galectin-1 complex, thus expanding the mechanisms for efficacy from solo-DEspR-mediated to also include DEspR-galectin1 complex-mediated mechanisms. Hsu et al. 2013. Galectin-1 promotes lung cancer tumor metastasis by potentiating integrin a6r34 and Notch1/Jagged2 signaling pathway. Carcinogenesis Feb. 6, 2013.

Protein-glycan interactions play important functions in several aspects of cancer biology, including cancer transformation, growth, metastasis, angiogenesis and immune response. Galectin-1, the first protein discovered in the family, has been shown to be overexpressed in many malignancies, including lymphoma, oral, colon, bladder, ovarian, astrocytoma, liver, pancreatic and melanoma carcinomas. Dysregulation of galectin-1 in cancer has also been correlated with the aggressiveness of these tumors. Rek, A. et al. (2009) Therapeutically targeting protein-glycan interactions. Br. J. Pharmacol., 157, 686-694; Yamamoto-Sugitani, M. et al. (2011) Galectin-3 (Gal-3) induced by leukemia microenvironment promotes drug resistance and bone marrow lodgment in chronic myelogenous leukemia. Proc. Natl. Acad. Sci. U.S.A., 108, 17468-17473; Wu, H. et al. (2012) Overexpression of galectin-1 is associated with poor prognosis in human hepatocellular carcinoma following resection. J. Gastroenterol. Hepatol., 27, 1312-1319; Xue, X. et al. (2011) Galectin-1 secreted by activated stellate cells in pancreatic ductal adenocarcinoma stroma promotes proliferation and invasion of pancreatic cancer cells: an in vitro study on the microenvironment of pancreatic ductal adenocarcinoma. Pancreas, 40, 832-839; Watanabe, M. et al. (2011) Clinical significance of circulating galectins as colorectal cancer markers. Oncol. Rep., 25, 1217-1226; Kamper, P. et al. (2011) Proteomic analysis identifies galectin-1 as a predictive biomarker for relapsed/refractory disease in classical Hodgkin lymphoma. Blood, 117, 6638-6649.

A lead mouse prototype anti-human DEspR monoclonal antibody (7C5B2 or 7c5b2) has been characterized to inhibit pancreatic ductal adenocarcinoma (PDAC) and glioblastoma U87 cancer stem cells in vitro and in vivo in CSC-derived xenograft tumors in nude rats. DEspR-inhibition in vivo and in vitro inhibit CSC anoikis resistance, tumor growth, tumor vasculo-angiogenesis (Herrera et al 2014, PloS One). A lead mouse prototype anti-humanDEspR monoclonal antibody (7c5b2) is "competed out" by the known ligands for human DEspR: endothelin-1 (ET1) and VEGFsp17, and VEGFsp26. (FIG. 13). This shows specificity for 7c5b2-antibody binding to human DEspR such that the antibody blocks the binding of DEspR-ligands, ET1 and VEGFsp. Two peptides of differing lengths: VEGFsp26 with anti-angiogenic function, and VEGFsp17 with pro-angiogenic function.

These observations indicate that 7c5b2 binds DEspR and blocks ligand engagement of DEspR for both its ligands—ET1 and VEGFsp (VEGFsp17-aa and VEGFsp26-aa). 7c5b2 has been sequenced and a fully human composite antibody developed (Antitope, UK; Lake Pharma, USA). ELISA and growth capabilities selected several candidates: vh5/vk1, vh3/vk2, and humanized forms of HV2KV2 (SEQ ID NOs: 20 and 50).

Figure 14:
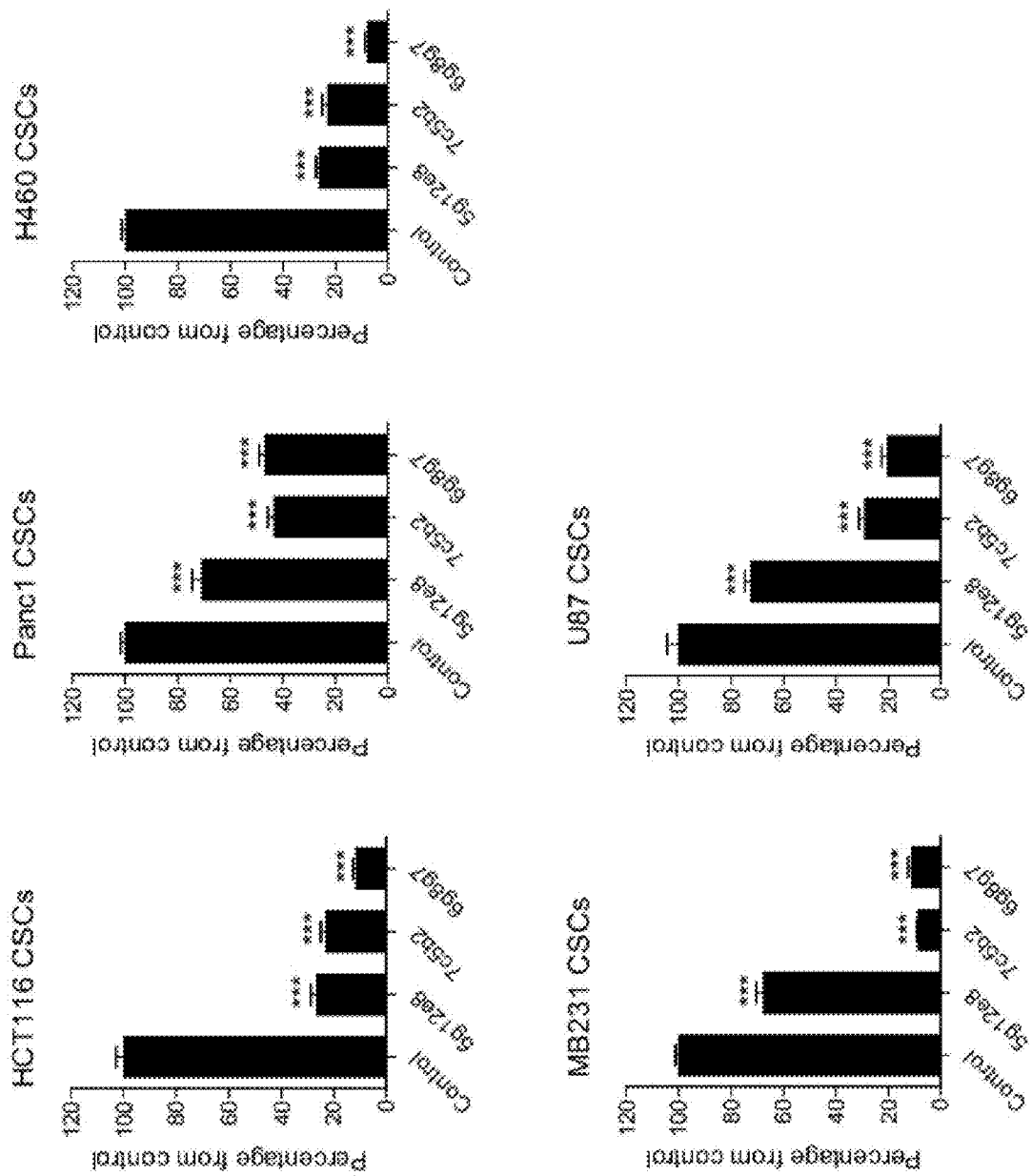
FIG. 14 shows testing of 5G12E8, 7C5B2 and 6G8G7 anti-hDEspR monoclonal antibodies (mAbs) on CSC-growth. 2,000 CSCs were seeded in 200 μL of complete MammoCult media in an ultra-low attachment 96-well plate. Cells were either not treated (control) or treated with mAbs (200 μg/ml) at days 0, 2 and 4. Live cells were counted using Trypan Blue at day 5. Each experiment was run in five replicates. Data is presented as Mean±SEM. ***P<0.001 (One Way ANOVA followed by Holm-Sidak Multiple Comparisons Testing).
Figure 15:
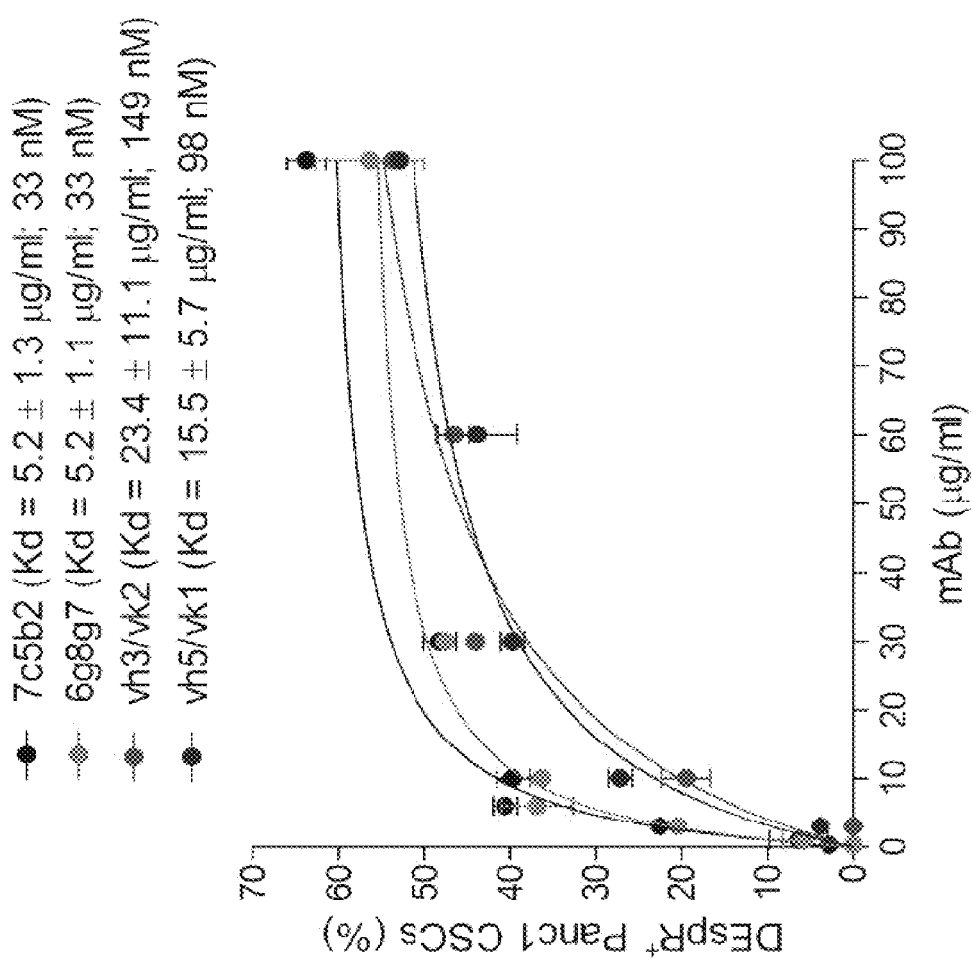
FIG. 15 shows comparative analysis of 7C5B2, 6G8G7, vh5/vk1 and vh3/vk2 antibodies using the identical assay and following identical experimental conditions. Saturation binding curves of monoclonal antibody (mAb) binding to DEspR on Panc1 CSCs. Each mAb was labeled with Alexa Flour 568 using the Alexa Fluor 568 Monoclonal Antibody Labeling Kit (Invitrogen). Specific binding was determined by FACS analysis using 100,000 cells in 0.25 ml containing increasing concentrations of mAbs. Incubations were done at 4° C. for 20 min and immediately subjected to FACS analysis on a BD™ LSRII Flow cytometer. Each data point was performed in duplicate.

Mouse monoclonal anti-hDEspR antibodies, 7C5B2, 5G12E8 (N-terminal peptide antigen), and 6G8G7 (binding domain peptide antigen) have comparable in vitro inhibition of CSC growth in suspension cultures (FIG. 14). Growth in suspension cultures requires anoikis resistance, and is a stem cell characteristic. Anti-hDEspR inhibition results in decreased CSC growth in different human tumor cell lines: colon cancer (HCT116), pancreatic ductal adenocarcinoma (Panc1), lung cancer (H460), triple negative breast cancer (MB231) and glioblastoma (U87).

Efficacy in different tumor cell line-derived CSCs indicates that DEspR plays a key role in CSC growth in suspension cultures, ie, unattached—which then indicates key roles in metastasis as metastatic cancer cells need to survive detachment or be anoikis resistant.

Figure 16:
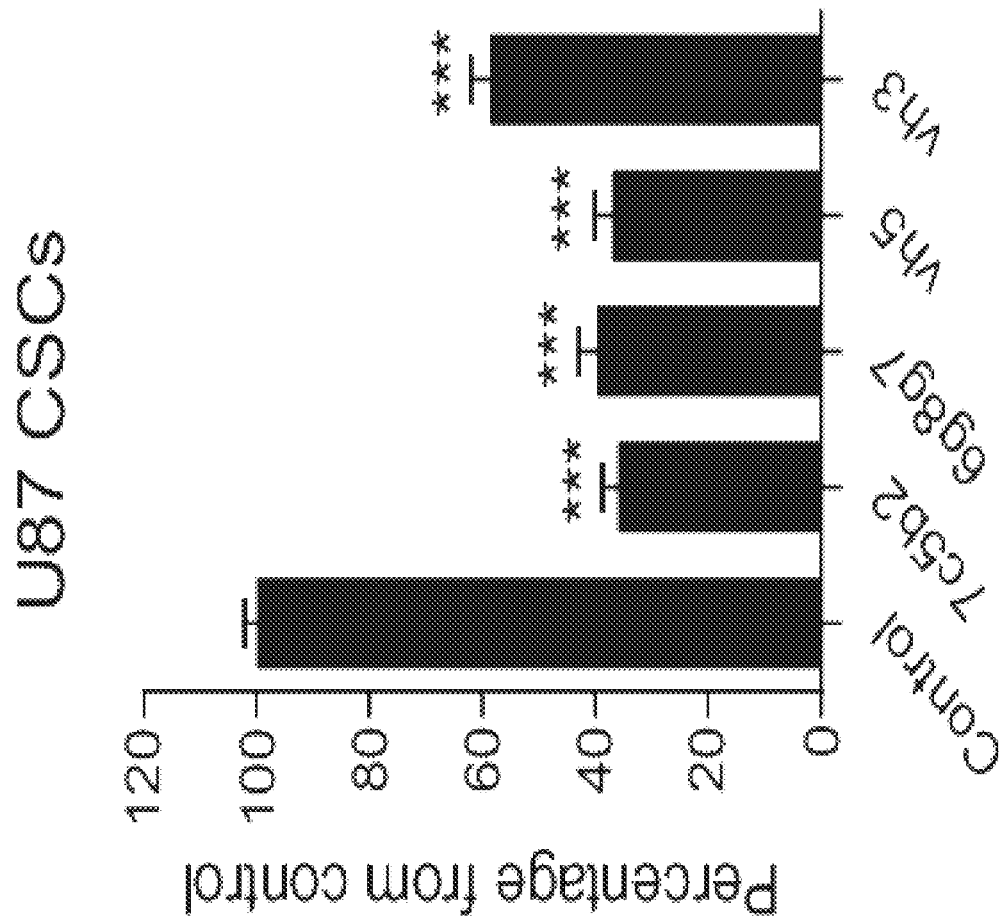
FIG. 16 shows in vitro inhibition of CSC growth by vh3/vk2 (vh3), vh5/vk1 (vh5), 6G8G7 and 7C5B2 mAbs. 2000 CSCs were seeded in 200 μL of complete MammoCult media in an ultralow attachment 96-well plate in absence (control) or presence (treated) of 100 μg/ml (7C5B2, 6G8G7), 300 μg/ml (vh5/vk1) and 450 μg/ml (vh3/vk2) of corresponding monoclonal antibodies (mAbs). Cells were treated at days 0, 2 and 4. After 5 days in culture live cells were counted using Trypan Blue. Each condition was performed in six replicates. Data is presented as Mean±SEM. ***, P<0.001 (One-way ANOVA followed by Holm-Sidak test for multiple comparisons).

Comparative analysis of mouse prototype 7C5B2 (amino terminal end antibody) and 6G8G7 (binding domain antibody) have comparable Kd 5.2 ug/ml or 33 nM for binding to DEspR+ pancreatic cancer Panc1 cells. Fully human VH5NK1 has a slightly better Kd than VH3/VK2 fully human composite antibodies. When adjusted for Kd, equivalent dosing of anti-DEspR antibodies shows equivalent efficacy of VH5NK1 [fully human composite antibody] to mouse prototype monoclonal variant antibodies 7C5B2 and 6G8G7. In vitro assays show that VH5NK1 inhibits glioblastoma CSC survival and growth in detached suspension culture conditions better than VH3/VK1. Notably, VH3/VK1 also exhibits inhibitory functionality (P<0.001). (FIG. 16).

Figure 17:
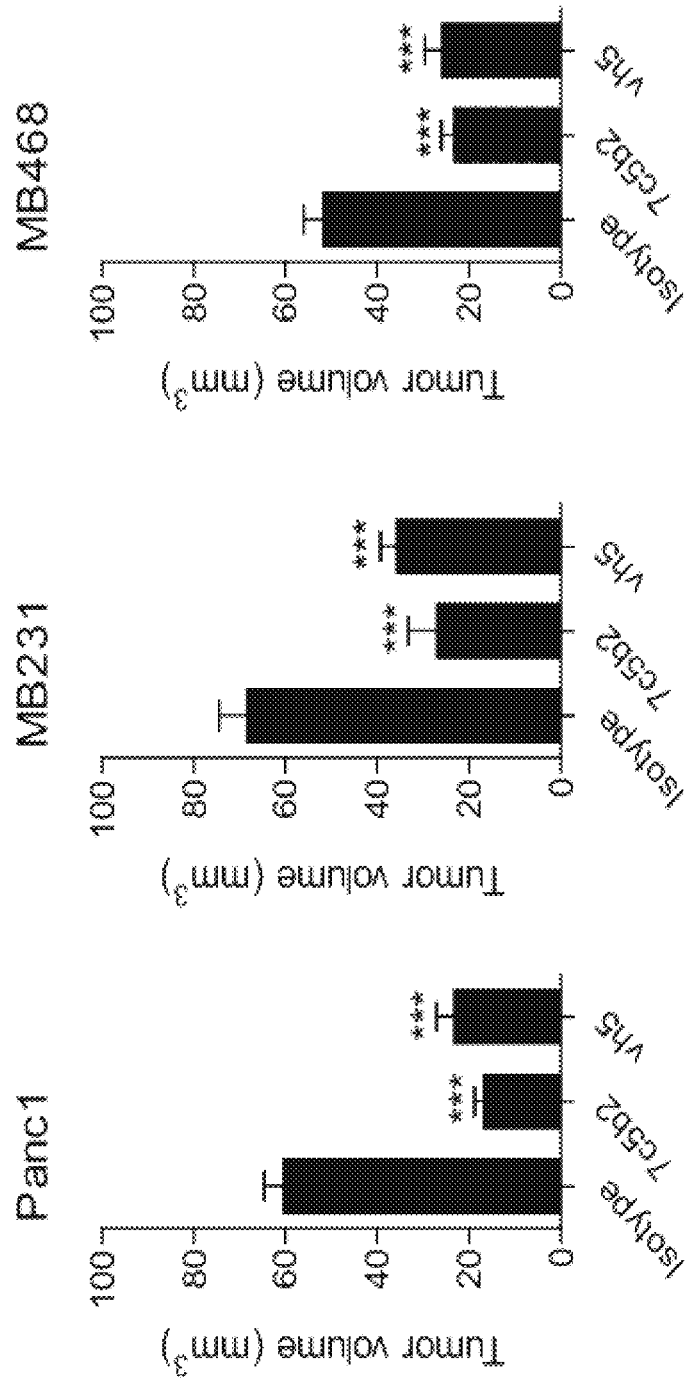
FIG. 17 shows inhibition of Panc1, MB231 and MB468 CSC-dependent in vivo tumour initiation by 7C5B2 and vh5/vk1 monoclonal antibodies (mAbs). 2×10$^6$ CSCs in 200 μL of M2 media were incubated at 4° C. for 60 min in the presence of 100 μg/ml of IgG2b (Isotype control), 100 μg/ml of 7C5B2 mAb and 300 μg/ml of vh5/vk1 Ab and immediately injected subcutaneously (two injection sites per nude rat). Each condition was performed in 8-10 replicates for CSCs subcutaneous tumour initiation. Subcutaneous tumour volumes [Volume=4/3pi(a/2×b/2×c/2)] were measured 10 days after cell injections. A significant inhibition of MB468, MB231, Panc1 CSC derived subcutaneous tumour formation was observed (7C5B2 55%, vh5 50% for MB468; 7C5B2 60%, vh5 48% for MB231; 7C5B2 72%, vh5 61% for Panc1). *** P<0.001 (One Way ANOVA followed by Holm-Sidak Test for multiple comparisons).
Figure 18:
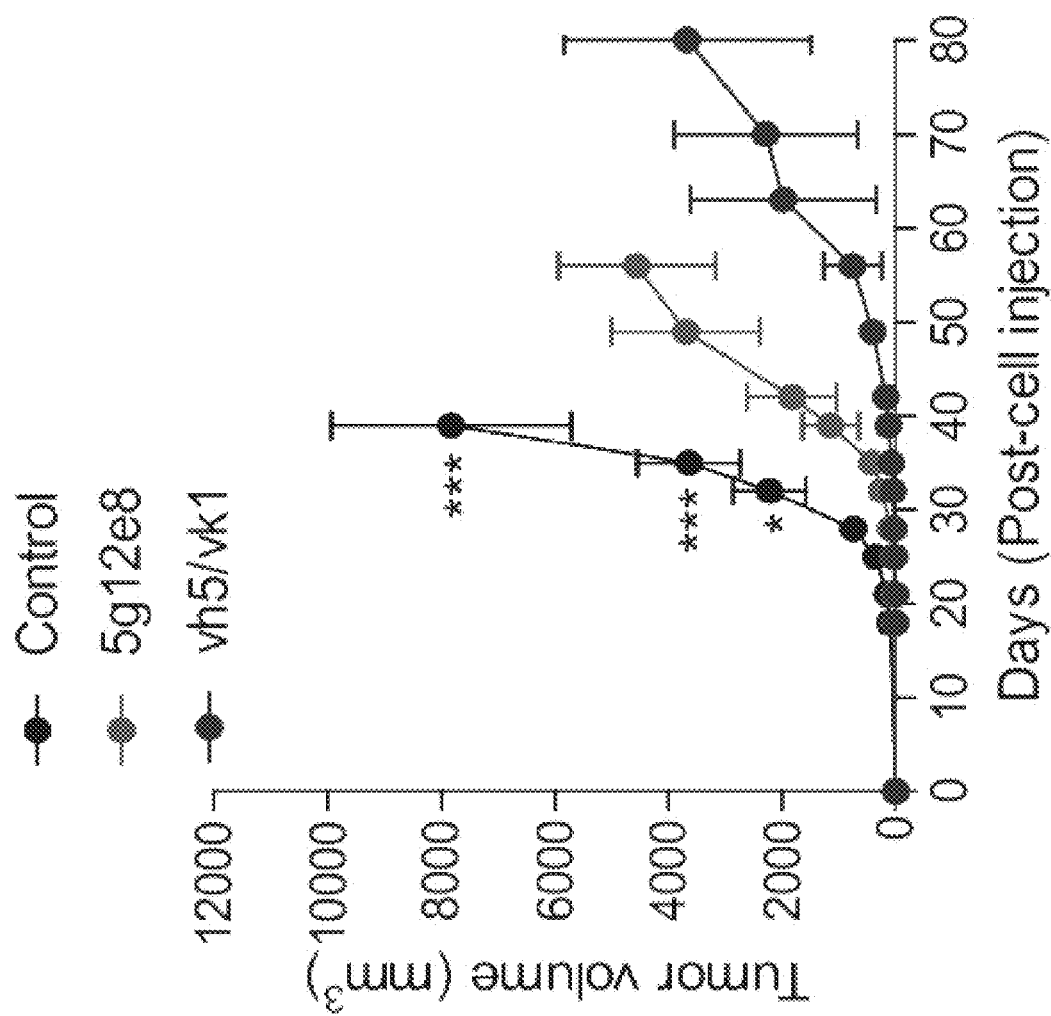
FIG. 18 shows inhibition of U87 CSC-dependent tumour initiation and progression in vivo by 5G12E8 and vh5/vk1 monoclonal antibodies (mAbs). $3 \times 10^5$ CSCs in 200 µL of M2 media were incubated at 4° C. for 60 min in the absence (control) and presence of 300 µg/ml of 5G12E8 and 900 µg/ml of vh5/vk1 mAb and immediately injected subcutaneously (two injection sites per nude rat). Each condition was performed in 8 replicates for subcutaneous tumour initiation. Tumour volume was calculated as Volume=4/3 pi (a/2xb/2xc/2).
Figures 19A, 19B, 19C:
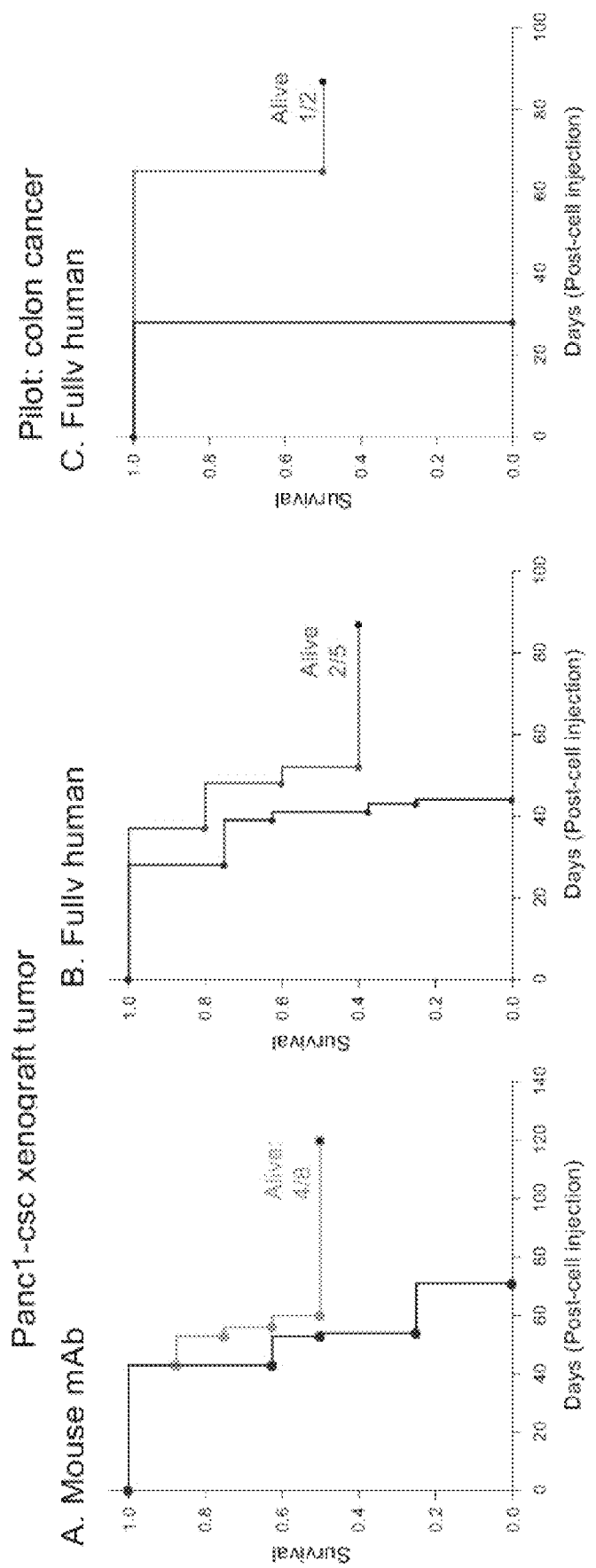
FIGS. 19A-19C show testing efficacy in vivo of 5G12E8 and VH5NK1 pre-treatment of Panc1 and HCT116 CSCs on survival of nude rats harbouring Panc1 and HCT116 peritoneal tumours. $2 \times 10^6$ Panc1 (FIG. 19A, FIG. 19B) and HCT116 (FIG. 19C) CSCs in 200 µL of M2 media were incubated at 4° C. for 60 min in the absence (control, in FIG. 19A, FIG. 19B and FIG. 19C) and presence of 200 µg/ml of 5G12E8 (FIG. 19A) and 1 mg/ml of VH5NK1 Ab (FIG. 19B and FIG. 19C). Cells were immediately injected intra-peritoneally. For FIG. 19A: controls n=8, 5G12E8-treated n=8. For FIG. 19B: controls n=8, VH5NK1-treated n=5; For FIG. 19 C: controls n=2, VH5NK1-treated n=2 (pilot).

In vivo analyses of inhibition of tumour growth in a heterotopic xenograft glioblastoma tumour model indicate that mouse prototype lead 7C5B2 and its corresponding fully human anti-hDEspR monoclonal antibody VH5NK1 show that both inhibit tumour growth of different xenograft heterotopic (subQ) tumour models significantly developed from pancreatic cancer Panc1-CSCs, and triple negative breast cancer MB231-CSCs and MB468-CSCs (FIG. 17). Notably, VH5NK1 performs equivalently to 7C5B2 mouse prototype anti-DEspR monoclonal antibody. Data support VH5NK1 as a therapeutic lead for anti-DEspR therapy. In vivo analyses of anti-hDEspR-mediated inhibition of tumour growth in a heterotopic xenograft glioblastoma tumour model indicate that mouse prototype 5G12E8 (used for pulldowns) and fully human anti-hDEspR lead VH5NK1 inhibit tumour growth from glioblastoma U87 CSCs significantly. (FIG. 18). SubQ xenograft tumour models allow analysis of tumour progression to larger tumour sizes and for longer duration compared to the orthotopic intracranial xenograft glioblastoma tumour models wherein nude rats with brain tumors need to be euthanized within 30 days or less due to neurologic deficits and tumour masses of only 1000 mm3. Notably, VH5NK1 performs better than 5G12E8 monoclonal antibody (used for pulldown) in inhibiting tumour growth in the xenograft human glioblastoma U87 heterotic tumour model. Thus, the data described herein support VH5NK1 as a therapeutic lead for anti-DEspR therapy Significant inhibition of U87 CSC-derived subcutaneous tumour progression by 5G12E8 and VH5NK1 monoclonal antibodies was observed. * P<0.05; *** P<0.001 (Two Way ANOVA followed by Student-Newman-Keuls Test for multiple comparisons). In vivo analyses of inhibition of tumour initiation in xenograft peritoneal metastatic models of pancreatic cancer (Panc1-CSCs) and of colon cancer (pilot data on HCT-116) indicate that mouse prototype 5G12E8 (used for pulldowns) and fully human anti-hDEspR lead VH5NK1 monoclonal antibody inhibit tumour initiation of peritoneal metastasis seeding and progression in at least 50% of animals seeded with 2×10$^6$ CSCs. (FIGS. 19A-19C)

Data indicate clinical application of adjuvant therapy to prevent peritoneal metastasis for PDAC and colon cancer. Data demonstrate inhibition of tumor initiation in vivo by VH5NK1-Rx, experimental modelling of clinical application as adjuvant anti-DEspR therapy. We observed a significant increase in survival of nude rats injected with 5G12E8-treated Panc1 CSCs (A, P=0.042); VH5NK1-treated Panc1 CSCs (B, P=0.041) and VH5NK1-treated HCT116 CSCs (C, P=0.08). P values from Kaplan-Meier Survival Analysis, Log-Rank Test. Note: 4/8 5G12E8-treated rats were still alive after 120 days post-cell injection in experiment A (no tumours at euthanasia); 2/5 VH5NK1-treated rats were still alive after 87 days post-cell injection in experiment B (no tumours at euthanasia); half VH5NK1-treated rats were still alive after 87 days post-cell injection in experiment C, and were electively euthanized Post-mortem analysis revealed few tumours at euthanasia (FIGS. 19A-19C).

Figures 20A, 20B:
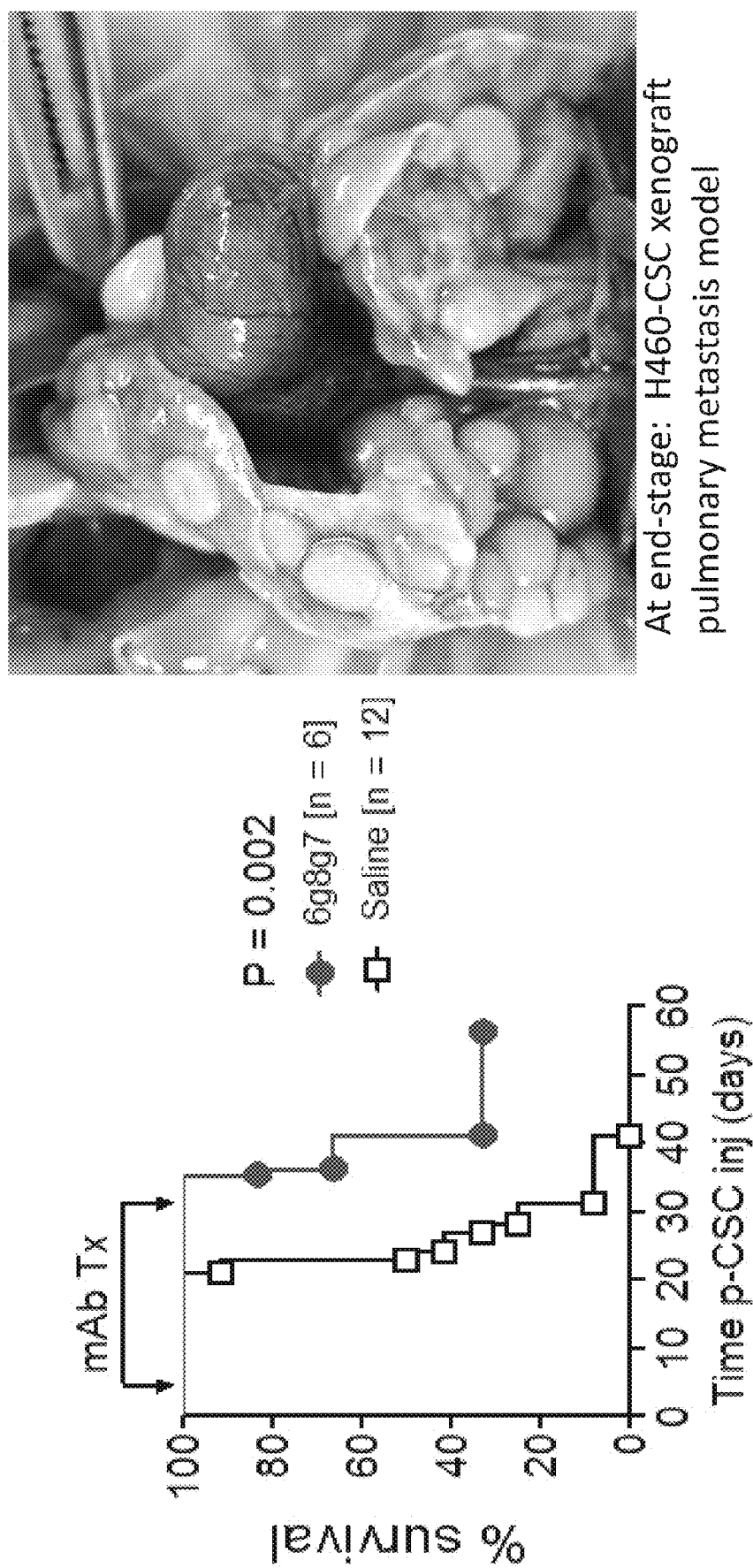
FIGS. 20A-20B show anti-hDEspR monoclonal antibody (mAb) treatment decreases NSCLC (H460-csc) tumor progression resulting in increased survival. H460 cancer stem-like cells (CSCs) xenograft tumors in nude rats (iv-infused). Post-cell injection (PCI)-in days. CSC injection of H460-CSCs via tail vein: 100,000 CSCs mAb Tx: anti-hDEspR 6G8G7 mAb onset: 4 days PCI, 2x per week×4 weeks: 1 mg/kg body weight.
Figures 21A, 21B:
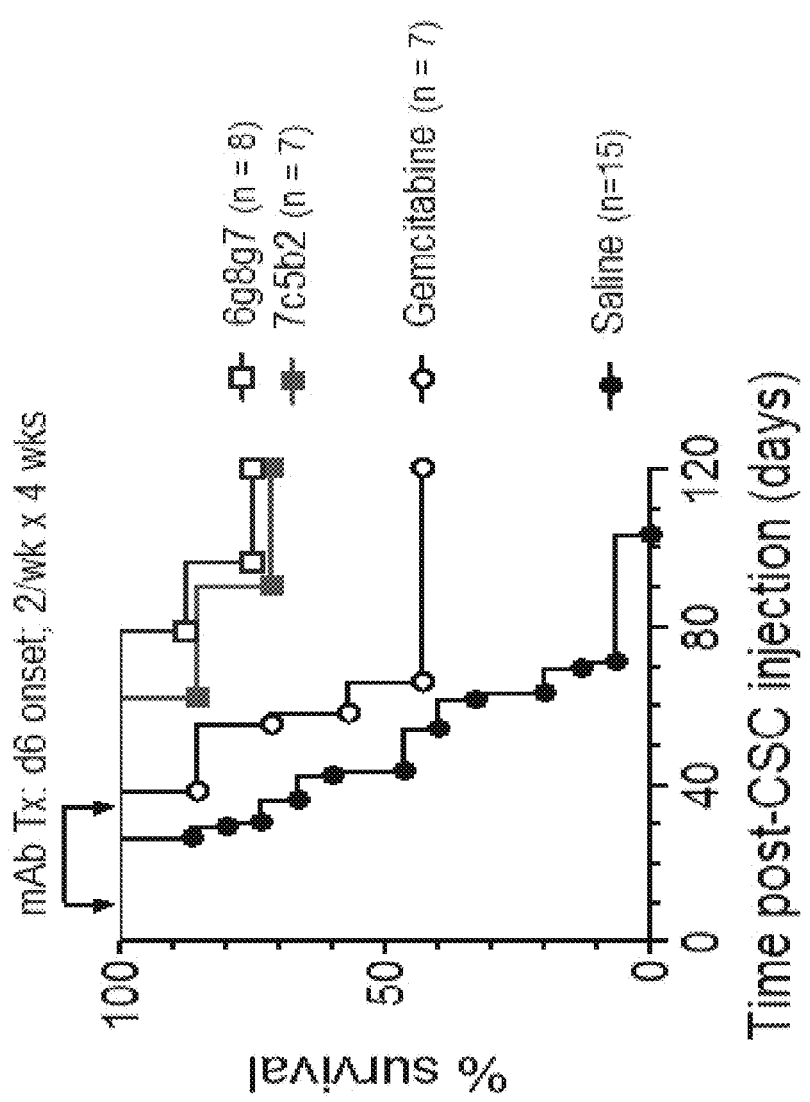
FIGS. 21A-21B show anti-hDEspR monoclonal antibody (mAb) decreases tumor progression, and increases survival: pancreatic peritoneal metastasis nude rat model. mAb dose: 1 mg/kg ip; One Way ANOVA followed by Holm Sidak Multiple Comparisons Test: p=0.002 (7C5B2 vs saline); p=0.0002 (6g8g7 vs Saline); Gemcitabine (max dose: 26 mg/kg×4) vs saline: not significant.
Figure 22:
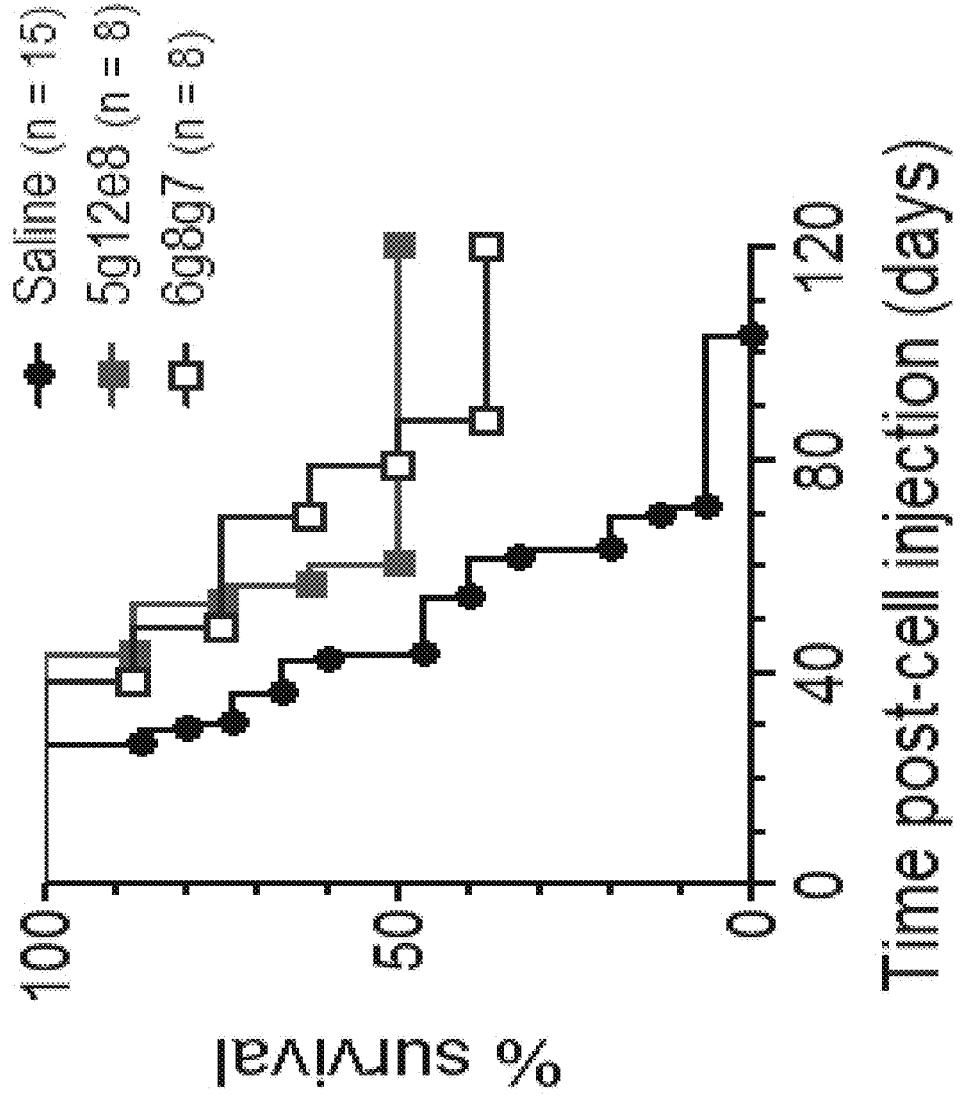
FIG. 22 shows anti-hDEspR monoclonal antibody (mAb) decreases tumor initiation/tumorigenesis in the pancreatic peritoneal metastasis nude rat model resulting in increased survival. 2,000,000 Panc1 CSCs in 200 µL of M2 media were incubated at 4° C. for 60 min in the absence (control, Saline in FIG. 22) and presence of 200 µg/ml of 5G12E8 (FIG. 22) and 200 µg/ml of 6G8G7 mAb (FIG. 22). Cells were immediately injected intra-peritoneally. 6G8G7 vs saline P=0.02; 5G12E8 vs saline P=0.03 (Log-Rank test followed by Holm-Sidak MCT).
Figure 24:
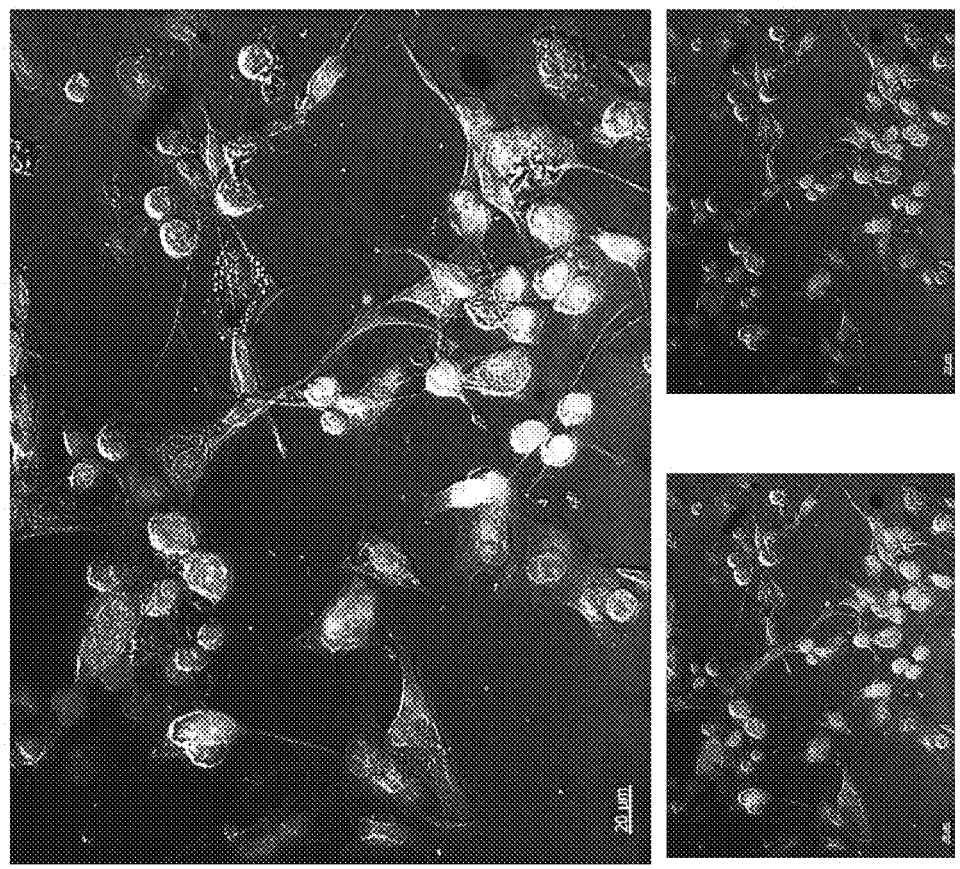
FIG. 24 shows Panc1-CSC s co-express collagen-1 and αSMA, a marker for EMT.
Figure 26:
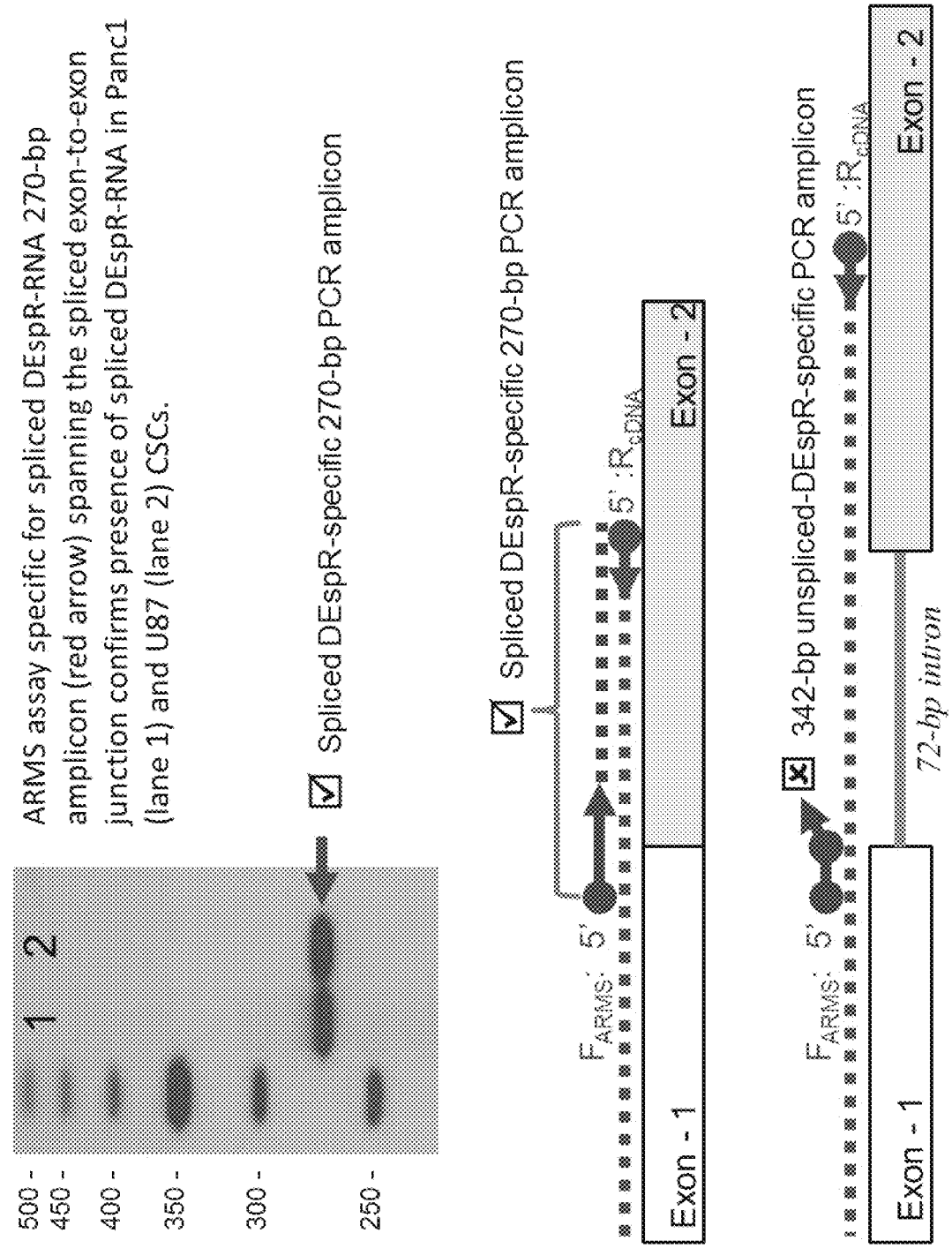
FIG. 26 shows detection of spliced DEspR RNA in human cancer cells (CSCs) by ARMS. ARMS assay specific for spliced DEspR-RNA 270-bp amplicon (arrow) spanning the spliced exon-to-exon junction confirms presence of spliced DEspR-RNA in Panc1 (lane 1) and U87 (lane 2) CSCs.
Figure 27:
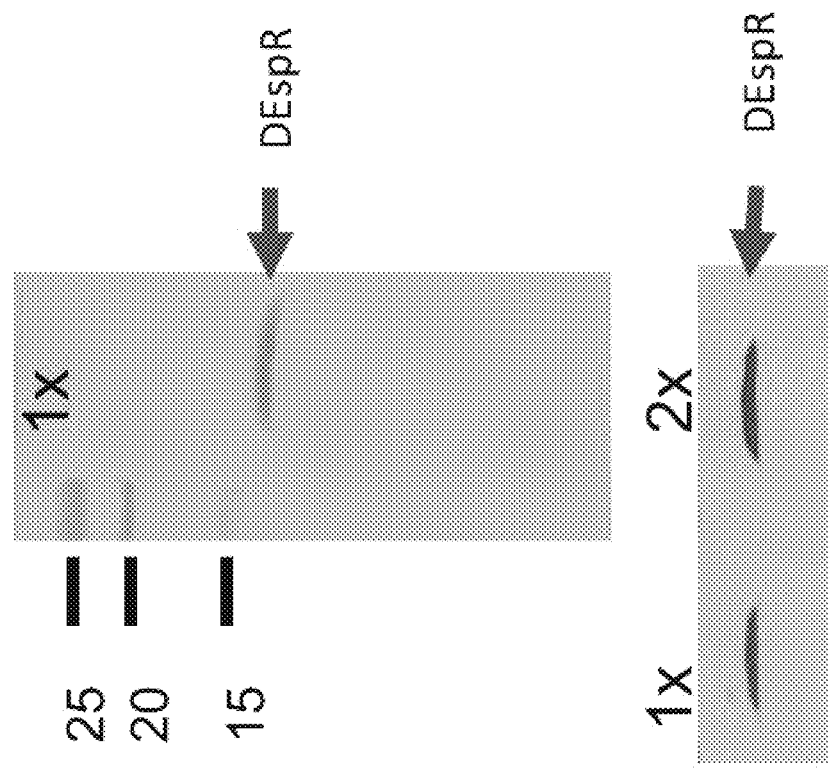
FIG. 27 shows that Western blot analysis detects DEspR ~10 kDa protein in human cancer cells. Using 5G12E8 monoclonal antibody (mAb), two different detection systems, two concentrations of mAb (1×, 2×) two independent Western blot analyses detected the predicted size for DEspR protein in U87 CSC membrane protein isolates.
Figure 28:
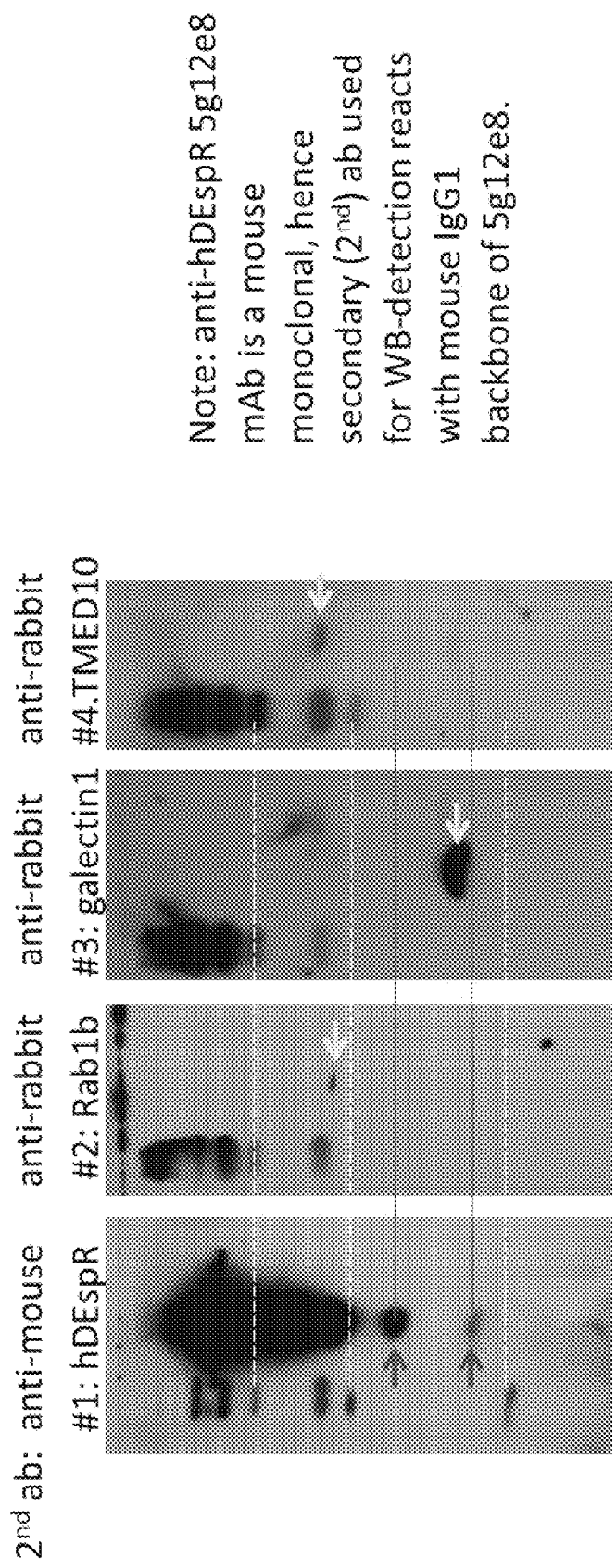
FIG. 28 shows Western Blot analysis of DEspR-galectin1, Rab1b, TMED10-complex. No antibody-cross reactivity observed. Anti-hDEspR 5G12E8 monoclonal antibody (mAb) is a mouse monoclonal, hence secondary (2nd) Ab used for WB-detection reacts with mouse IgG1 backbone of 5G12E8.
Figure 29:
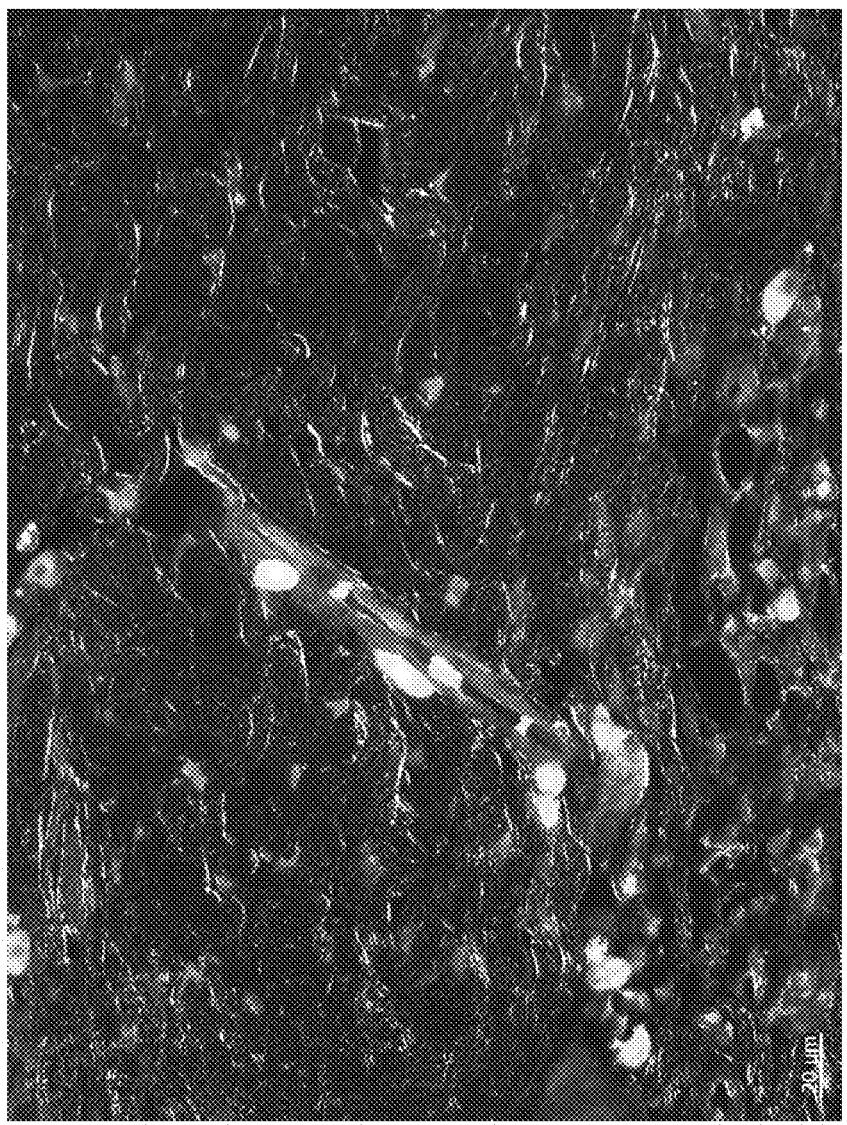
FIG. 29 shows immunohisto fluorescence analysis of heterotopic (subQ) xenograft U87-csc tumors in nude rats. Detection of hDEspR+/galectin+ invading human tumor U87 cells along a blood vessel outside the xenograft tumor capsule (below). Anti-hDEspR and anti-hGalectin1 detect human proteins only respectively.
Figure 30:
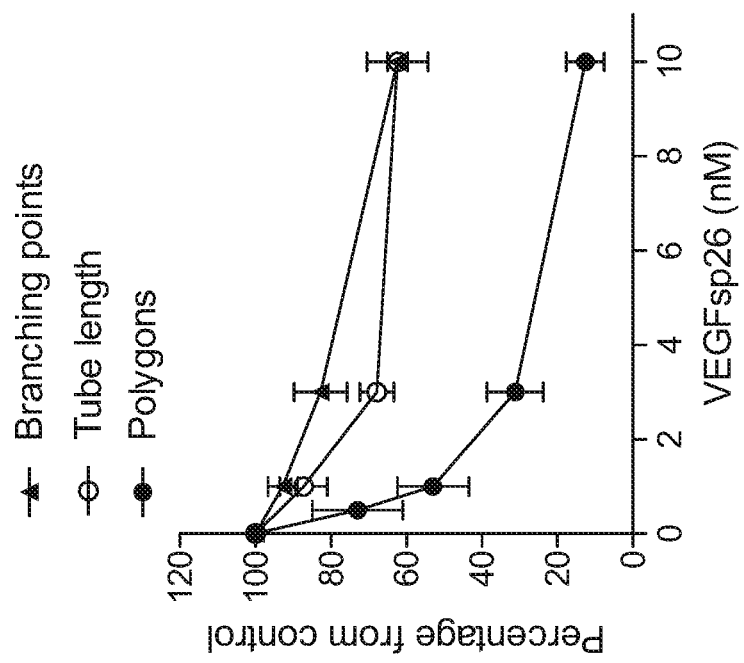
FIG. 30 shows inhibition of angiogenesis by VEGFsp26. 10000 HUVECs were seeded on P96 wells containing Matrigel. Cells were incubated overnight at 37° C. in M200 complete media in the absence (control) or presence of VEGFsp26 (0.5-10 nM). Number of polygons, total tube length and branching points was measured after 16 hours of incubation. Each data point was run in four replicates. Data is presented as mean percentage from control ±SEM. VEGFsp26 IC50=1.185±0.1 nM based on number of polygons; VEGFsp26 $IC_{50}$=1.897±0.82 nM based on total tube length.
Figure 31:
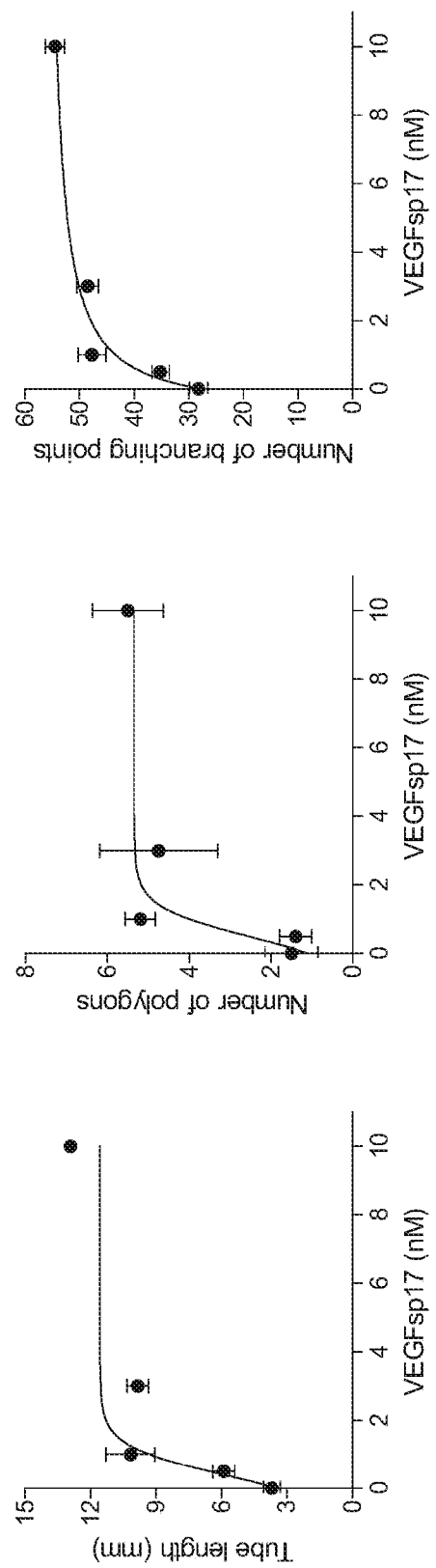
FIG. 31 shows stimulation of angiogenesis by VEGFsp17. 10000 HUVECs were seeded on P96 wells containing Matrigel. Cells were incubated overnight at 37° C. in M200 media (without supplements) in the absence (control) or presence of VEGFsp17 (0.5-10 nM). Total tube length, number of polygons and number of branching points was measured after 16 hours of incubation. Data is presented as Mean±SEM. Each data point was run in 4-5 replicates. Curve fitting and $EC_{50}$ values were obtained by using a Sigmoidal dose-response model (GraphPad Prism 5.04). VEGFsp17 $EC_{50}$=2.63±0.83 nM based on number of polygons; VEGFsp17 $EC_{50}$=1.98±1.19 nM based on total tube length.
Figure 32:
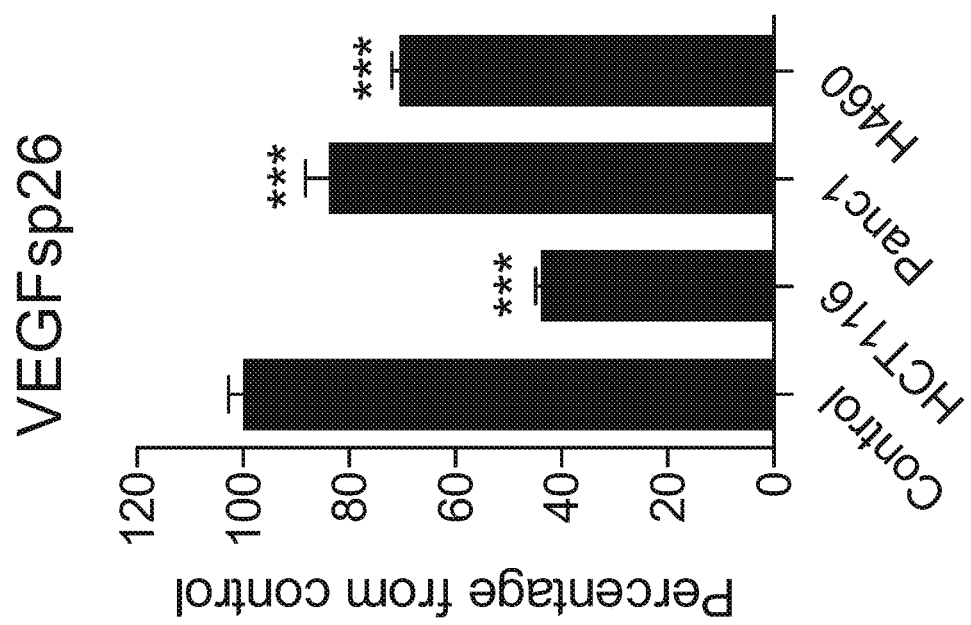
FIG. 32 shows inhibition of CSC-growth by VEGFsp26. 2000 CSCs were seeded in 200 µL of complete MammoCult media in an ultra-low attachment 96-well plate. Cells were either not treated (control) or treated with VEGFsp26 peptide (100 nM) at days 0, 2 and 4. Live cells were counted using Trypan Blue at day 5. Data is presented as Mean±SEM. Each experiment was run in five replicates. *** P<0.001 (One Way ANOVA followed by Holm-Sidak MCT).
Figure 33:
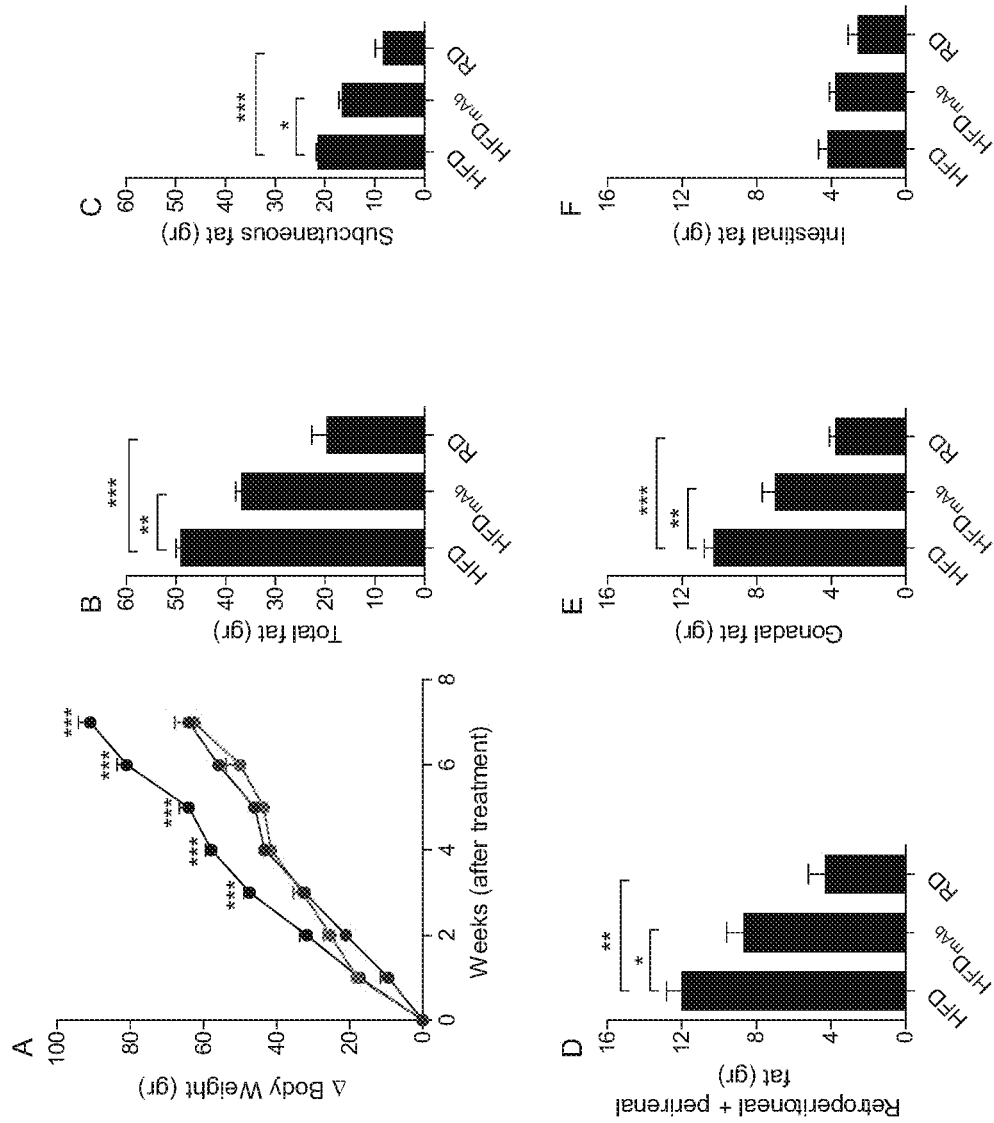
FIG. 33 shows inhibition of high fat diet-induced obesity by 10A3H10 monoclonal antibody (mAb). Seven male Sprague Dawley rats were fed a High Fat Diet (HFD) starting at 9 weeks of age along with 4 male Sprague Dawley rats maintained on a regular rat chow as controls (FIG. 33A, circle). After 6 weeks on the HFD (15 weeks of age, Week 0 on treatment period) 3 HFD-rats were maintained on the HFD for the specified time as controls (FIG. 33A, circle) and 4 HFD-rats began treatment with anti-rat DEspR mAb (10A3H10): 50 ug/rat IV (T-F, 2×week) for 6 weeks (FIG. 33A, circle). Data is presented as Mean±SEM. For panel A * P<0.001 (HFD vs 10a3h10/reg diet), Two Way ANOVA followed by Student-Newman-Keuls test for MC. For panels B-F, * P<0.001; ** P<0.01; * P<0.05 (One Way ANOVA followed by Holm-Sidak test for MC).
Figure 34:
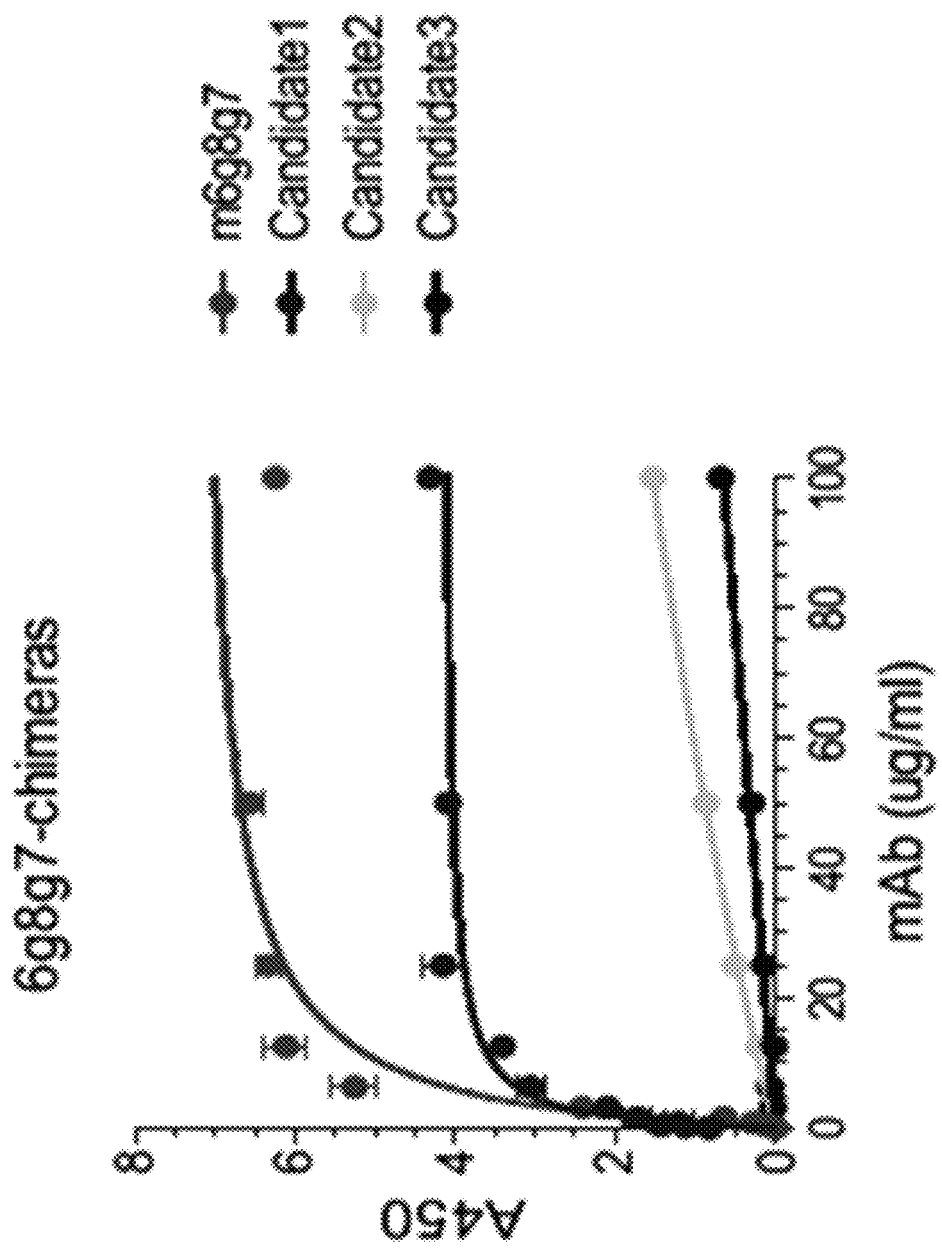
FIG. 34 shows ELISA data from 6G8 monoclonal antibody (mAb)-derived candidate chimeric antibodies. Candidate 1 chimeric antibody was selected for humanization based on ELISA testing of binding affinity to the antigenic peptide: EMKSRWNWGS (SEQ ID NO: 2). Briefly, Candidate 1 exhibited an EC50=1.87±0.6 ug/ml, which is a 2-fold improvement over the 6g8 murine mAb with an EC50=4.96±1.4 ug/ml.

Additional data on survival analysis further indicate clinical application to inhibit NSCLC (non-small cell lung cancer) tumor progression (FIGS. 20A-20B, anti-DEspR treated subjects vs controls, P=0.002) and pancreatic peritoneal metastatic tumor progression (FIGS. 21A-21B, anti-DEspR subjects vs Controls, P<0.01). Of note, anti-DEspR inhibition was significantly more efficacious than Gemcitabine treatment (Gemcitabine vs Controls, P=not significant), the gold standard for treatment of pancreatic cancer.

Example 2

As described herein, variable heavy ($V_H$) and variable light ($V_L$) chains sequences were obtained from the hybridoma 6g8g7 both at the DNA level by PCR and by Mass Spectrometry sequencing from 2 independent CROs. It was found that there were two variable heavy ($V_H$) and three variable light ($V_L$) chains sequences.

Humanized chimeric sequences were made of the 6g8g7 murine monoclonal antibody CDR sequences with human IgG1/kappa Fc region.

Several 6g8g7-derived human monoclonal antibody candidates were next designed with the following specifications:

a) CDR sequences from 6G8G7 HV2 (SEQ ID NOs: 14, 15, and 16) and 6G8G7 KV1 (SEQ ID NOs: 28, 29, and 30) that retain 6G8G7 binding to rat and human DEspR.

b) Sequence modifications in variable regions were made to exclude or reduce the following sites for optimal biotherapeutic properties for efficacy, safety and manufacture: 1) potential CD4+ T-cell epitopes for low immunogenicity; 2) acid-labile sites for antibody stability during processing requiring low pH; 3) destabilizing post-translational modification sites predisposed to deamidation and oxidation for structural stability of humabs and to retain functionality in adverse metabolic conditions such as in hypoxic tumors; and 4) post-translational modification sites predisposed to inappropriate N-glycosylation, isomerization, and pyroglutamate formation for reproducible production and efficacious performance.

c) Human IgG4 constant region was used to avail of IgG4 Fc's property of insignificant effector functions (i.e., minimal antibody-dependent cell cytotoxicity (ADCC) and complement-dependent cytotoxicity (CDC)), but with the S228P hinge-stabilizing mutation in order to minimize Fab arm exchange (FAE) in vivo which would result in loss of therapeutic efficacy (Silva et al. 2015). The S228P mutation confers stability properties to human IgG4. It is further noted that this S228P hinge-stabilized IgG4 is used in FDA-approved PD1 receptor inhibitor Keytruda, consistent with the S228P IgG4 as being suitable for biotherapeutic applications. (Yang X et al. 2015).

Multiple 6G8G7-$V_H$ (n=2) and 6G8G7-$V_L$ (n=3) recombinant clones were constructed, sequenced to confirm the different constructs, and transiently expressed in HEK293. Humanized antibodies were tested by ELISA for binding to the antigenic peptide (representing the human/monkey/rat DEspR epitope). Some did not show significant binding, but others showed binding to the 6G8G7 antigenic peptide. The top two were selected and then grown in 0.3 L medium to generate sufficient amounts for further characterization.

Figures 35A, 35B:
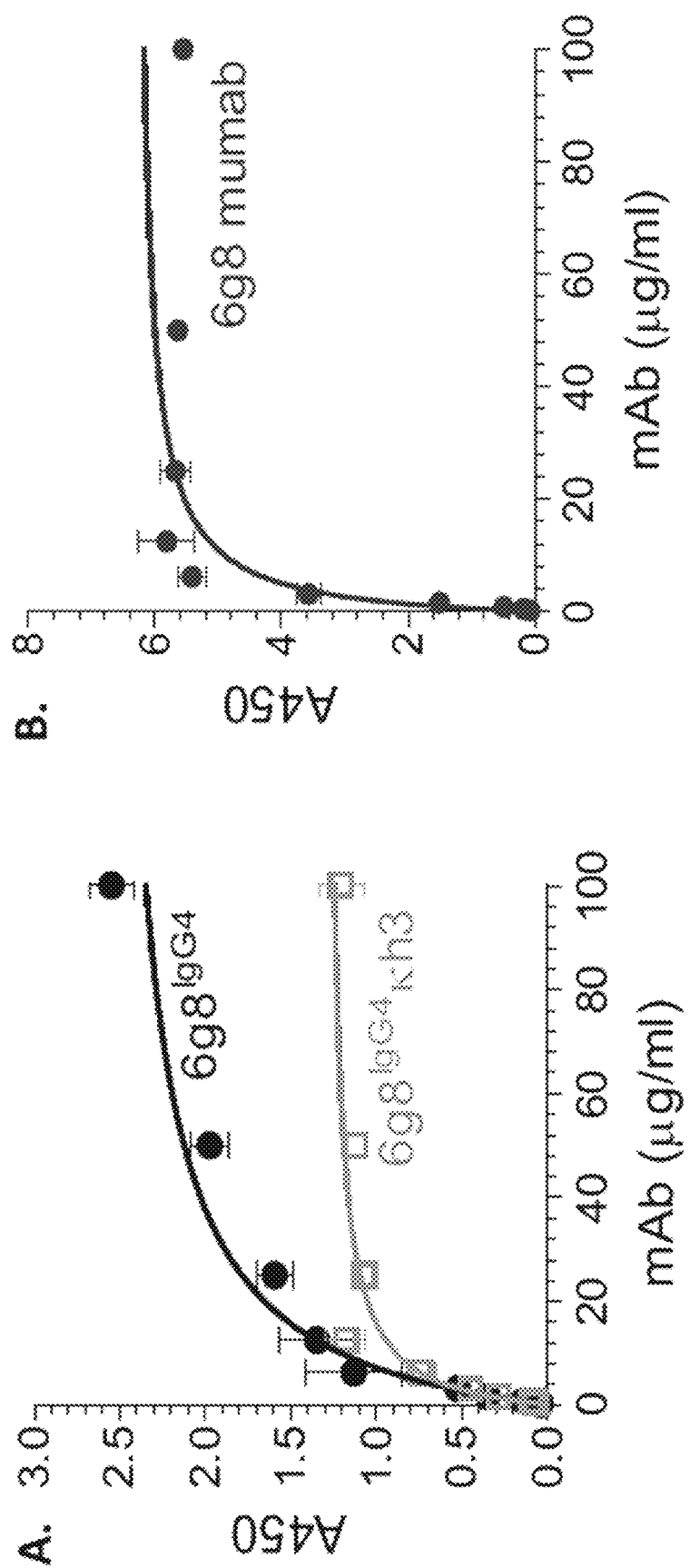
FIGS. 35A-35B show comparative binding affinity analysis.

Next, the EC50 of binding to the antigenic peptide was determined by ELISA, as shown in FIGS. 35A-35B, comparing two IgG4 6g8g7 humanized antibody candidates (including humab1 comprising SEQ ID NOs: 63 and 65 and humab2 comprising SEQ ID NO: 65 with substitutions in SEQ ID NO: 26 at Kabat residues 83V and 85Y to give 83D and 85Y), and the IgG1 6G8G7 humanized monoclonal antibody (comprising SEQ ID NOs: 61 and 65), and 6G8G7 murine monoclonal antibody ("6g8 mumab").

These studies showed the following EC50 and Bmax for binding to the antigenic peptide detected on ELISA (Table 1). As shown in Table 1, based on Bmax, a 6g8g7-derived IgG4 humanized monoclonal antibody 1 ("6g8$^{IgG4}$ humab1") is better than a 6g8g7-derived IgG4 humanized monoclonal antibody 2 ("6g8$^{IgG4}$ humab2") in binding to the antigenic peptide on ELISA. Hence 6g8$^{IgG4}$ humab1 was expressed in 0.5 L medium for further study and demonstration of functional activity of 6g8$^{IgG4}$ humab as a lead candidate. This 0.5 L transient expression of transfectants produced 110 mg of 6g8$^{IgG4}$ humab.

TABLE 1

| Table 1. | 6g8$^{IgG4}$ humab1 | 6g8$^{IgG1}$ humab1 | 6g8$^{IgG4}$ humab2 | 6g8-mumab |
|---|---|---|---|---|
| | ELISA (AP) | | | |
| EC$_{50}$ (ug/ml) | 11.7 ± 2.2 | 13.4 ± 2.5 | 4.8 ± 1.2 | 2.96 ± 0.93 |
| Bmax (A$_{450}$) | 2.62 ± 0.16 | 3.09 ± 0.2 | 1.31 ± 0.08 | 6.36 ± 0.48 |

Figure 36:
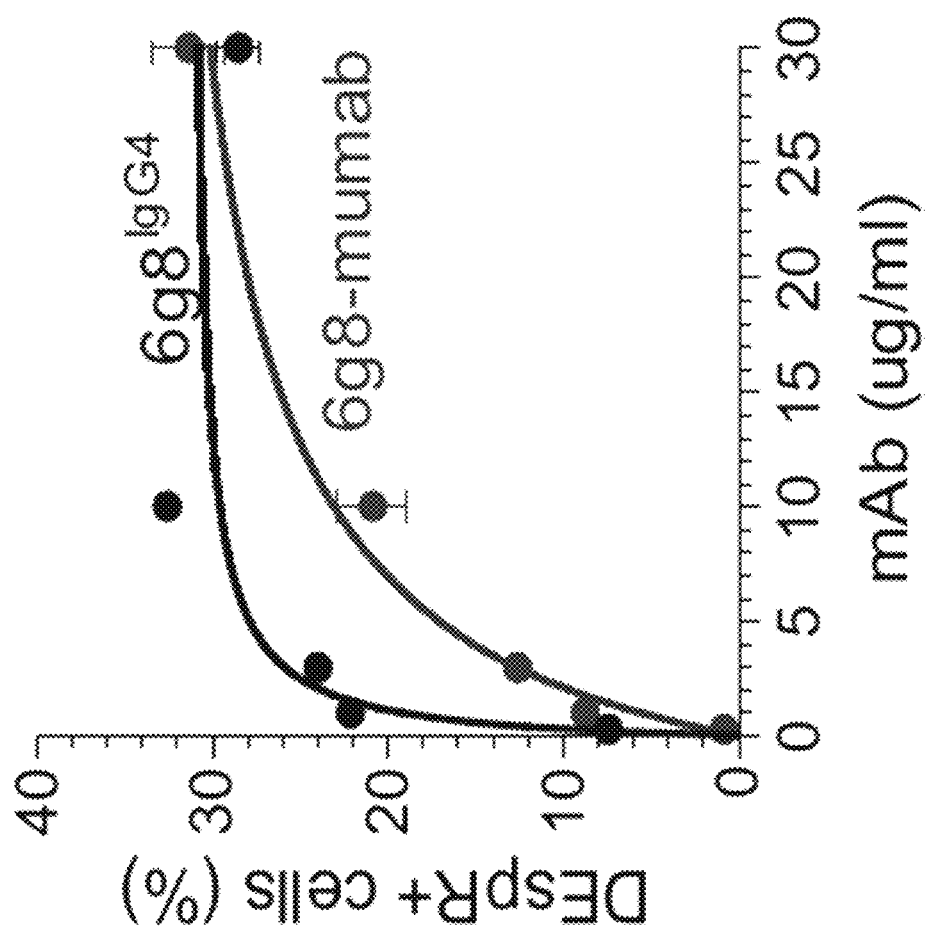
FIG. 36 shows studies of binding affinity to intact DEspR+ cells of 6G8IgG4 humanized monoclonal antibody 1 (mAb 1) compared to 6G8-murine monoclonal antibody (mAb).

Next, the EC50 binding to DEspR on intact cells at 4° C. was determined to eliminate non-specific endocytosis. Binding was determined by FACS analysis. As shown in FIG. 36, the 6g8$^{IgG4}$ humab1 exhibited better binding affinity to intact DEspR+ human cells than the original 6g8g7 murine monoclonal antibody.

These studies show the following EC50 for binding to intact DEspR+ cells. (Table 2) As shown in Table 2, the 6g8$^{IgG4}$ humab1 shows better EC50 binding to intact cells than 6g8g7 murine monoclonal antibody from which it is derived.

TABLE 2

Table-2. Binding to DEspR on intact human cells (FACS)

| | 6g8$^{IgG4}$ humab1 | 6g8$^{IgG1}$ humab | 6g8$^{IgG4}$ humab2 | 6g8 mumab |
|---|---|---|---|---|
| EC50 (ug/ml) | 0.64 ± 0.25 | 1.3 ± 0.74 | ND | 5.39 ± 1.84 |
| EC50 (nM) | 21.1 ± 8.3 | 42.9 ± 24 | ND | 177.9 ± 60 |
| Bmax (% + cells) | 31.5 ± 2.6 | 21.6 ± 3.0 | ND | 35.6 ± 4.0 |

Figure 37:
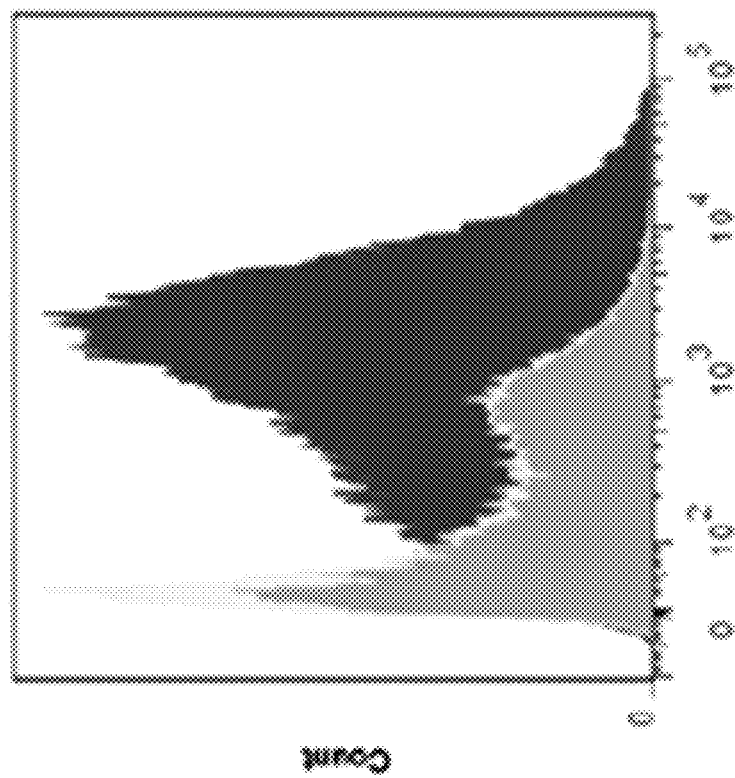
FIG. 37 shows a representative fluorescence intensity plot. FACS analysis of DEspR+ human cells was done using a red-fluorophore labeled anti-DEspR 6G8IgG4 humanized monoclonal antibody 1 (mAb 1) lead candidate probing DEspR+ human cells. The peak is shifted to the right indicating binding of fluorescently-labeled antibody to cells. The lightest peak indicates the control isotype background.

To confirm binding, we obtained a FACS fluorescence intensity plot of 6g8$^{IgG4}$ humab1 binding to DEspR on intact human cells (FIG. 37). The 6g8$^{IgG4}$ humab1 lead candidate was labeled with a 'red' fluorophore, AF568, and used for FACS analysis of DEspR+ human cells compared to control IgG4 isotype.

Figure 38:
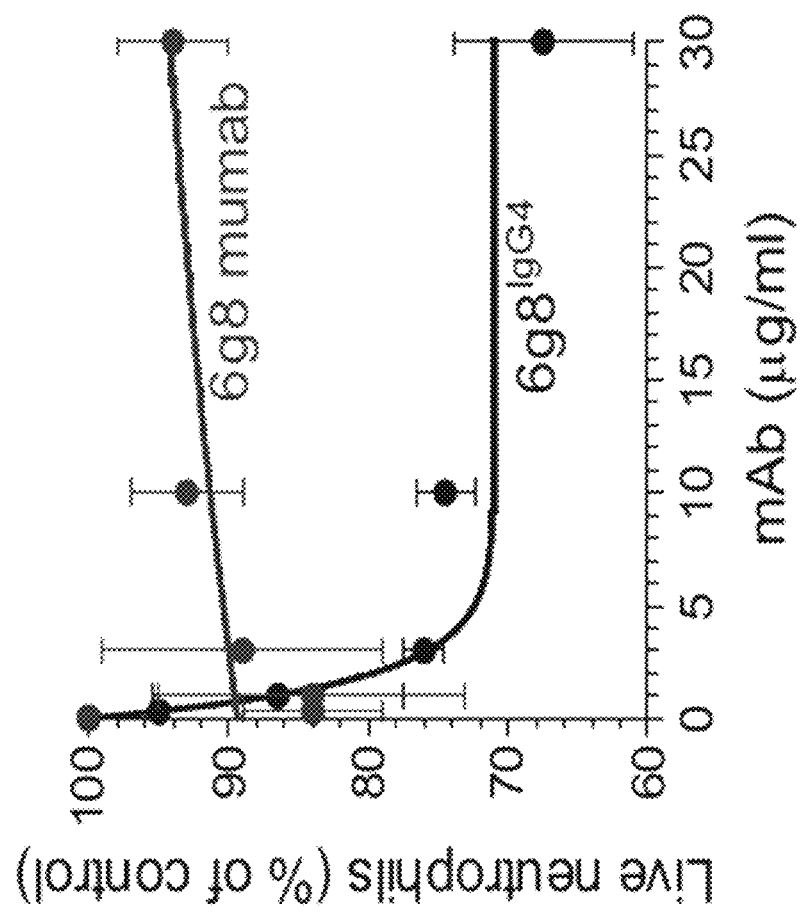
FIG. 38 shows comparative analysis of 6G8 murine monoclonal antibody and lead candidate 6G8IgG4 humanized monoclonal antibody in inhibiting rat neutrophil survival. Neutrophils were isolated from stroke-prone rats and incubated with the test and control antibodies at 37° C. for 4 hours. Afterwards, live/dead cells were then counted and expressed as % of control.

Functionality of the lead candidate humab, 6g8$^{IgG4}$ humab1 comprising SEQ ID NOs: 63 and 65, was next determined. It was first tested whether anti-DEspR 6g8$^{IgG4}$ humab1 can inhibit neutrophil survival pertinent to stopping neutrophil-mediated blood brain barrier disruption that contributes to hemorrhagic conversion in stroke. Rat neutrophils were obtained from stroke-prone rats. As shown in FIG. 38, the lead candidate humab, 6g8$^{IgG4}$ exhibited greater efficacy in vitro in inhibiting neutrophil survival compared to the original 6g8 mumab control.

The EC50 values shown in Table 3 demonstrate superior functional activity of the lead candidate 6g8$^{IgG4}$ humab1 in the inhibition of neutrophil survival compared to the 6g8 mumab. Notably, 6g8$^{IgG1}$ humab (serving as reference) also exhibited better functional activity in inhibiting neutrophil survival than the 6g8 mumab.

TABLE 3

Table 3. Rat Neutrophil survival

| | 6g8$^{IgG4}$ humab1 | 6g8$^{IgG1}$ humab | 6g8$^{IgG4}$ humab2 | 6g8 mumab |
|---|---|---|---|---|
| IC$_{50}$ (ug/ml) | 1.16 ± 0.3 | 6.98 ± 4.4 | ND | >30 µg/ml |
| Bmax (% live cells) | 70.9 ± 2.0 | 48.78 ± 10 | ND | indeterminate |

Functional activity in inhibiting bFGF-mediated/VEGF-independent (Falcon et al. 2013) angiogenesis of human umbilical vein cells (HUVECs), the standard in angiogenesis assays, was next tested (FIGS. 39A-39D). Parameters for complex formation were first measured—polygons (ability to form a closed interconnected loop of neovessels (tube polygon), and branch points (ability for angiogenic endothelial cells to initiate network formation from a node).

After a pilot study of inhibition of angiogenesis, dose-dependent inhibition of angiogenesis experiments were performed using 6g8$^{IgG4}$ humab1 lead candidate (FIGS. 40A-40B) to obtain IC50 values to ascertain functional activity.

These data demonstrate that the 6g8IgG4 humab1 exhibits more robust functional activity than the 6g8 mumab as shown in the IC50 values (Table 4), concordant with observations for inhibition of neutrophil-survival.

TABLE 4

| | 6g8$^{IgG4}$ humab1 | 6g8$^{IgG1}$ humab1 | 6g8$^{IgG4}$ humab2 | 6g8 mumab |
|---|---|---|---|---|
| Table 4. Human Angiogenesis assay: complex network formation parameter = polygons | | | | |
| IC$_{50}$ (ug/ml) | 2.6 ± 0.2 | 9.1 ± 1.5 | ND | >30 µg/ml |
| Bmax (%) | 28 ± 4 | 9.7 ± 15 | ND | indeterminate |
| Human Angiogenesis assay: complex network formation parameter = branch points | | | | |
| IC$_{50}$ (ug/ml) | 4.3 ± 0.7 | 10.4 ± 2.6 | ND | >30 µg/ml |
| Bmax (%) | 45.7 ± 7 | 37.2 ± 9.5 | ND | indeterminate |

Accordingly, described herein is the successful development and characterization of a lead candidate for a humanized anti-DEspR monoclonal antibody through recombinant technology with a human S228P IgG4-framework, referred to herein as "6g8$^{IgG4}$ humab" or 6g8g7-derived IgG4 humanized antibody. This humanized antibody has robust transient expression in HEK293 cells and has improved binding to DEspR compared to 6g8 murine monoclonal antibody on intact cells and functional activity, including inhibition of activated neutrophil survival and angiogenesis, which are two mechanisms of blood brain barrier disruption in stroke. These results are summarized in Table 5.

TABLE 5

Table 5. Binding characteristics and effector activities of candidate 6g8-humabs.

| | 6g8$^{IgG4}$ humab1 | 6g8$^{IgG1}$ humab1 | 6g8$^{IgG4}$ humab2 | m6g8 |
|---|---|---|---|---|
| ELISA (Antigenic Peptide) | | | | |
| EC$_{50}$ (ug/ml) | 11.7 ± 2.2 | 13.4 ± 2.5 | 4.8 ± 1.2 | 2.96 ± 0.93 |
| Bmax (A$_{450}$) | 2.62 ± 0.16 | 3.09 ± 0.2 | 1.31 ± 0.08 | 6.36 ± 0.48 |
| Binding to DEspR on intact human cells (FACS) | | | | |
| EC$_{50}$ (ug/ml) | 0.64 ± 0.25 | 1.3 ± 0.74 | ND | 5.39 ± 1.84 |
| EC$_{50}$ (nM) | 21.1 ± 8.3 | 42.9 ± 24 | ND | 177.9 ± 60 |
| Bmax (% + cells) | 31.5 ± 2.6 | 21.6 ± 3.0 | ND | 35.6 ± 4.0 |
| Rat activated Neutrophil survival | | | | |
| IC$_{50}$ (ug/ml) | 1.16 ± 0.3 | 6.98 ± 4.4 | ND | >30 µg/ml |
| Bmax (% live cells) | 70.9 ± 2.0 | 48.78 ± 10 | ND | indeterminate |
| Human Angiogenesis assay: complex network formation parameter = polygons | | | | |
| IC$_{50}$ (ug/ml) | 2.6 ± 0.2 | 9.1 ± 1.5 | ND | >30 µg/ml |
| Bmax (%) | 28 ± 4 | 9.7 ± 15 | ND | indeterminate |
| Human Angiogenesis assay: complex network formation parameter = branch points | | | | |
| IC$_{50}$ (ug/ml) | 4.3 ± 0.7 | 10.4 ± 2.6 | ND | >30 µg/ml |
| Bmax (%) | 45.7 ± 7 | 37.2 ± 9.5 | ND | indeterminate |

ELISA was performed with antigenic peptide (AP): EMKSRWNWGS (SEQ ID NO: 2); binding of AF-568-labeled mAbs to Panc1 cells was quantified by FACS with corresponding isotype labeled antibodies as background controls; Neutrophil survival assays were performed with freshly isolated rat neutrophils. Neutrophils (50000/well) were incubated in the absence or presence of mAbs at 37° C. x 4 hrs and live cells counted by using Trypan blue. HUVEC-dependent angiogenesis (20,000 cells/well) was performed as described in the presence or absence of mAbs. Number of polygons and number of branch points were determined after 14 hrs of incubation at 37° C.
ND, not done, indeterminate, value greater than upper limit of max dose used in these experiments.

Next, IC50 of anti-DEspR 6g8IgG4 humab1 inhibition of angiogenic tube length is measured, which represents the ability of angiogenic endothelial cells to proliferate, migrate and align, and subsequently fuse together to form tubes (in vitro neovessels).

Further, in vitro efficacy (IC50) of the lead candidate, 6g8IgG4 humab1 in inhibiting myeloperoxidase (MPO)

release by activated neutrophils is measured. MPO is a mediator of neutrophil-mediated injury to the blood brain barrier during ischemic stroke.

REFERENCES

Yang X, Ambrogelly A. 2014. Enlarging the repertoire of therapeutic monoclonal antibodies platforms: domesticating half molecule exchange to produce stable IgG4 and IgG1 bispecific antibodies. Current Opinion in Biotechnology 30: 225-229.

Yang X, Wang F, Zhang Y, Wang L, Antonenko S, Zhang S, Zhang Y W, Tabrizifard M, Emakov G, Wiswell D, Beaumnt M, Liu L, Richardson D, Shameem M, Ambrogelly A. 2015. Comprehensive Analysis of the Therapeutic IgG4 Antibody Pembrolizumab: Hinge Modification Blocks Half Molecule Exchange In Vitro and In Vivo. J Pharm Sci 104:4002-4014.

Silva J P, Vetterlein O, Jose J, Peters S, Kirby H. 2015. The S228P mutation prevents in vivo and in vitro IgG4 Fab-arm exchange as demonstrated using a combination of novel quantitative immunoassays and physiological matrix preparation. J Biol Chem 290:5462-5469.

Methodology

Each gene for heavy and light chain expression was synthesized and cloned into a mammalian expression using standard methods. Each complete construct was sequence verified by DNA sequencing. Plasmid DNA was produced for transfection into suspension HEK293 cells grown in serum-free chemically-defined medium. Antibodies from conditioned media were purified by binding to and elution from Protein A columns with subsequent filtration through 0.2 µm membrane filters. Buffer exchange was either into HEPES: 200 mM HEPES, 100 mM NaCl, 50 mM NaOAc, pH 7.0 or PBS pH 7.4. Protein concentrations were calculated from OD280. CE-SDS analysis of antibodies were performed using LABCHIP GXII (Perkin Elmer).

The sequences of the variable heavy and variable light chains of the 6G8G7 variant antibodies are disclosed elsewhere herein as SEQ ID NOs: 6 (variable heavy 1), 13 (variable heavy 2), 27 (variable light 1), 34 (variable light 8), and 41 (variable light 2). The sequences of the variable heavy and light chain of the 7C5B2 variant antibodies are disclosed elsewhere herein as SEQ ID NO: 20 (variable heavy 2) and SEQ ID NO: 50 (variable light 2).

The invention claimed is:

1. A method of inhibiting angiogenesis in a subject having a disease or disorder dependent or modulated by angiogenesis, the method comprising administering to a subject in need thereof a therapeutically effective amount of a pharmaceutical composition comprising: (i) a pharmaceutically acceptable carrier and (ii) an isolated anti-DEspR antibody or antigen-binding fragment thereof that specifically binds DEspR (dual endothelin/VEGF signal peptide receptor) of SEQ ID NO: 3 and that has an EC50 for binding to DEspR of SEQ ID NO: 3 of 12 μg/ml or less and comprising heavy and light chain sequences comprising complementarity determining regions (CDRs) of a heavy chain CDR1 having the amino acid sequence of SEQ ID NO: 14; a heavy chain CDR2 having the amino acid sequence of SEQ ID NO: 15; a heavy chain CDR3 having the amino acid sequence of SEQ ID NO: 16; a light chain CDR1 having the amino acid sequence of SEQ ID NO: 28; a light chain CDR2 having the amino acid sequence of SEQ ID NO: 29; and a light chain CDR3 having the amino acid sequence of SEQ ID NO: 30.

2. The method of claim 1, wherein the antibody is a chimeric, humanized, or composite human antibody or dual antibody.

3. The method of claim 1, wherein the antigen-binding fragment is a Fab fragment, a Fab' fragment, a Fd fragment, a Fd' fragment, a Fv fragment, a dAb fragment, a $F(ab')_2$ fragment, a single chain fragment, a diabody, or a linear antibody.

4. The method of claim 1, wherein the isolated anti-DEspR antibody or antigen-binding fragment thereof specifically binds to an epitope of DEspR (dual endothelin/VEGF signal peptide receptor) of SEQ ID NO: 1 or SEQ ID NO: 2.

5. The method of claim 1, wherein the antibody is a humanized antibody comprising a humanized variable heavy chain amino acid sequence of SEQ ID NO: 55, a humanized variable heavy chain IgG1 amino acid sequence of SEQ ID NO: 61, a humanized variable heavy chain IgG4 amino acid sequence of SEQ ID NO: 63, a humanized variable light chain amino acid sequence of SEQ ID NO: 57, a humanized variable light chain amino acid sequence of SEQ ID NO: 59, a humanized variable kappa light chain amino acid sequence of SEQ ID NO: 67, or any combination thereof.

6. The method of claim 1, wherein the disease or disorder dependent or modulated by angiogenesis is a cancer or a tumor.

7. The method of claim 1, wherein the disease or disorder dependent or modulated by angiogenesis is selected from the group consisting of age-related macular degeneration, carotid artery disease, diabetic retinopathy, rheumatoid arthritis, neurodegenerative disorder, Alzheimer's disease, obesity, endometriosis, psoriasis, atherosclerosis, ocular neovascularization, neovascular glaucoma, osteoporosis, and restenosis.

8. A method of inhibiting angiogenesis in a subject having a disease or disorder dependent or modulated by angiogenesis, the method comprising administering to a subject in need thereof a therapeutically effective amount of a pharmaceutical composition comprising: (i) a pharmaceutically acceptable carrier, and (ii) an isolated antibody or antigen-binding fragment thereof capable of binding to DEspR (dual endothelin-1/VEGF signal peptide receptor) of SEQ ID NO: 3 and comprising heavy and light chain sequences comprising complementarity determining regions (CDRs) of a heavy chain CDR1 having the amino acid sequence of SEQ ID NO: 14; a heavy chain CDR2 having the amino acid sequence of SEQ ID NO: 15; a heavy chain CDR3 having the amino acid sequence of SEQ ID NO: 16; a light chain CDR1 having the amino acid sequence of SEQ ID NO: 28; a light chain CDR2 having the amino acid sequence of SEQ ID NO: 29; and a light chain CDR3 having the amino acid sequence of SEQ ID NO: 30.

9. The method of claim 1, wherein the antibody or antigen binding fragment thereof has one or more of the following characteristics: a) an IC50 for inhibiting activated neutrophil survival or human angiogenesis of 3.0 μg/ml or less; or b) a $K_D$ for binding DEspR of SEQ ID NO: 3 of 2.5 μg/ml or less.

* * * * *